US 10,294,228 B2

(12) United States Patent
Dax et al.

(10) Patent No.: US 10,294,228 B2
(45) Date of Patent: May 21, 2019

(54) BREATHING CONTROL MODULATING COMPOUNDS, AND METHODS OF MAKING AND USING SAME

(71) Applicant: NEURAD LTD., Tel-Aviv (IL)

(72) Inventors: Scott L. Dax, Landenberg, PA (US); James Joseph Mencel, North Wales, PA (US); Vita Ozola, Adazu nov. (LV); Edgars Suna, Riga (LV); Kirill Shubin, Riga (LV)

(73) Assignee: NEURAD LTD., Tel-Aviv (IL)

( * ) Notice: Subject to any disclaimer, the term of this patent is extended or adjusted under 35 U.S.C. 154(b) by 16 days.

(21) Appl. No.: 15/737,431

(22) PCT Filed: Jun. 23, 2016

(86) PCT No.: PCT/US2016/039032
§ 371 (c)(1),
(2) Date: Dec. 18, 2017

(87) PCT Pub. No.: WO2017/003822
PCT Pub. Date: Jan. 5, 2017

(65) Prior Publication Data
US 2018/0141953 A1 May 24, 2018

Related U.S. Application Data

(60) Provisional application No. 62/328,277, filed on Apr. 27, 2016, provisional application No. 62/186,468, filed on Jun. 30, 2015.

(51) Int. Cl.
C07D 487/04 (2006.01)
A61K 9/00 (2006.01)
(Continued)

(52) U.S. Cl.
CPC .......... C07D 487/04 (2013.01); A61K 9/0053 (2013.01); A61K 31/485 (2013.01);
(Continued)

(58) Field of Classification Search
CPC .... C07D 487/04; A61K 9/0053; A61K 45/06; A61K 31/485; A61K 31/519; A61P 11/00
See application file for complete search history.

(56) References Cited

U.S. PATENT DOCUMENTS

2014/0051684 A1 2/2014 Agarwal et al.
2014/0371224 A1 12/2014 Mannion et al.
2016/0046635 A1 2/2016 Dax et al.

FOREIGN PATENT DOCUMENTS

WO 2014151462 A1 9/2014

OTHER PUBLICATIONS

International Search Report cited in PCT/US2016/039032, dated Sep. 2, 2016, 3 pages.

Primary Examiner — Trevor Love
(74) Attorney, Agent, or Firm — Rothwell, Figg, Ernst & Manbeck, P.C.

(57) ABSTRACT

The present invention includes compounds that are useful in the prevention and/or treatment of breathing control diseases or disorders in a subject in need thereof. The present invention also includes a method of preventing and/or treating a respiratory disease or disorder in a subject in need thereof, comprising administering to the subject a therapeutically effective amount of a compound and/or composition of the invention. The present invention further includes a method of preventing destabilization or stabilizing breathing rhythm in a subject in need thereof, comprising administering to the subject a therapeutically effective amount of a compound and/or composition of the invention.

52 Claims, 48 Drawing Sheets

(51) Int. Cl.
*A61P 11/00* (2006.01)
*A61K 45/06* (2006.01)
*A61K 31/485* (2006.01)
*A61K 31/519* (2006.01)

(52) U.S. Cl.
CPC ............ *A61K 31/519* (2013.01); *A61K 45/06* (2013.01); *A61P 11/00* (2018.01)

FIG. 1A

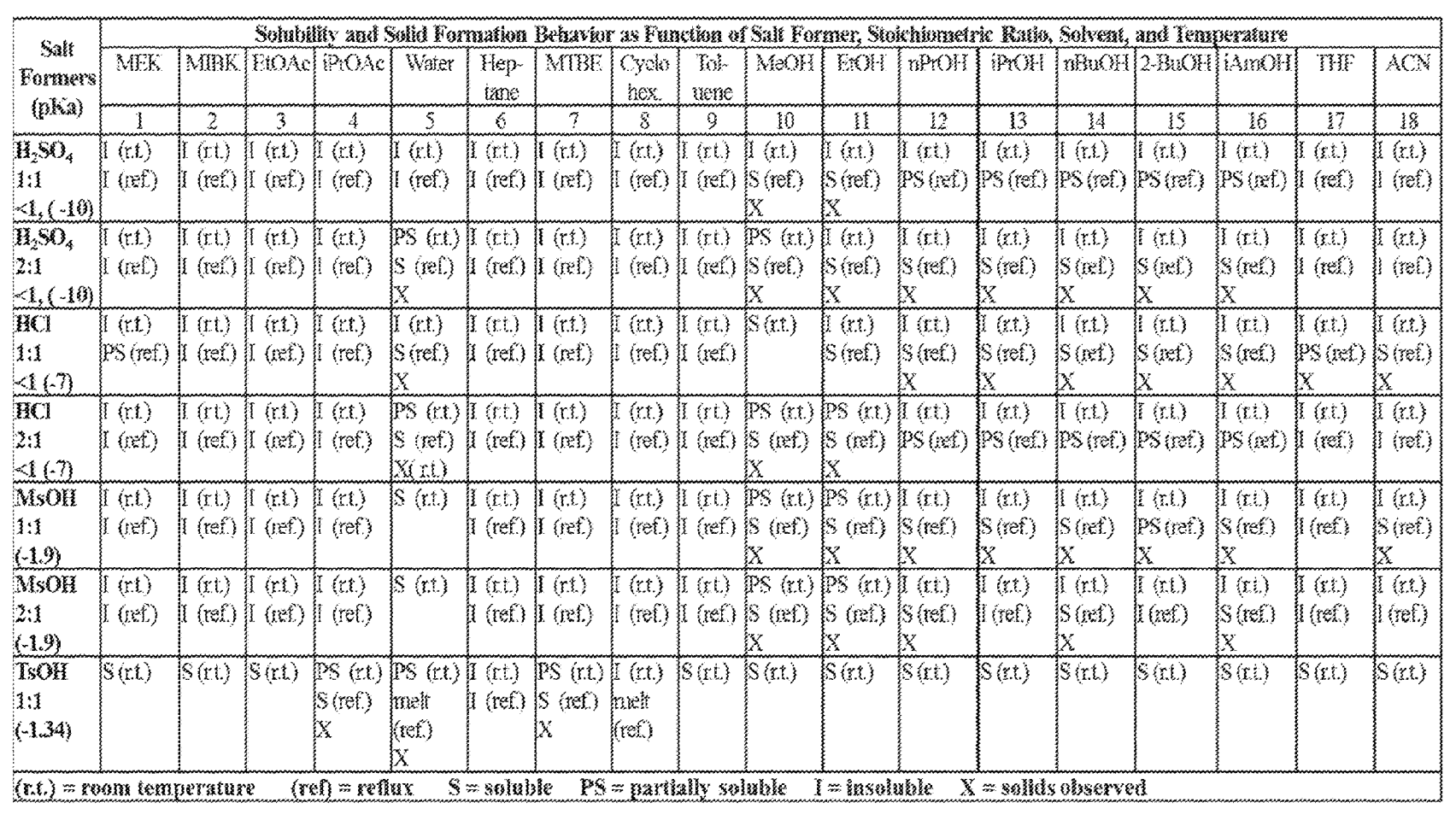

Solubility and Solid Formation Behavior as Function of Salt Former, Stoichiometric Ratio, Solvent, and Temperature (r.t.) = room temperature   (ref) = reflux   S = soluble   PS = partially soluble   I = insoluble   X = solids observed

FIG. 1B

Solubility and Solid Formation Behavior as Function of Salt Former, Stoichiometric Ratio, Solvent, and Temperature

| Salt Formers (pKa) | MEK | MIBK | EtOAc | iPrOAc | Water | Hep-tane | MTBE | Cyclo hex. | Tol-uene | MeOH | EtOH | nPrOH | iPrOH | nBuOH | 2-BuOH | iAm OH | THF | ACN |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Saccharin 1:1 (1.6) | I (r.t.) S (ref.) X | I (r.t.) S (ref.) X | I (r.t.) S (ref.) X | I (r.t.) S (ref.) X | I (r.t.) I (ref.) | I (r.t.) I (ref.) | I (r.t.) I (ref.) | I (r.t.) I (ref.) | I (r.t.) S (ref.) | I (r.t.) S (ref.) X | I (r.t.) S (ref.) X | I (r.t.) S (ref.) X | I (r.t.) S (ref.) X | I (r.t.) S (ref.) X | I (r.t.) S (ref.) X | I (r.t.) S (ref.) X | PS (r.t.) S (ref.) X | I (r.t.) S (ref.) X |
| Maleic 1:1 (2.9, 5.7) | I (r.t.) S (ref.) X | I (r.t.) S (ref.) X | I (r.t.) S (ref.) X | PS (ref.) S (ref.) X | S-oil (ref.) | I (r.t.) I (ref.) | I (r.t.) I (ref.) | I (r.t.) I (ref.) | PS (ref.) S (ref.) X | X(+1°) S | PS (r.t.) S (ref.) X | I (r.t.) S (ref.) X | I (r.t.) S (ref.) X | I (r.t.) S (ref.) X | I (r.t.) S (ref.) X | I (r.t.) S (ref.) X | S (r.t.) | PS (r.t.) S (ref.) X |
| Maleic 1:1 (1.9, 6.07) | I (r.t.) S (ref.) X | I (r.t.) S (ref.) X | I (r.t.) S (ref.) X | I (r.t.) S (ref.) X | I (r.t.) I (ref.) | I (r.t.) I (ref.) | I (r.t.) I (ref.) | I (r.t.) I (ref.) | I (r.t.) S (ref.) X | I (r.t.) S (ref.) | I (r.t.) S (ref.) X | I (r.t.) S (ref.) X | I (r.t.) S (ref.) X | I (r.t.) S (ref.) X | I (r.t.) S (ref.) X | I (r.t.) S (ref.) X | I (r.t.) S (ref.) X | I (r.t.) S (ref.) X |
| L-Tartaric 1:1 (2.89, 4.4) | I (r.t.) I (ref.) | I (r.t.) I (ref.) | I (r.t.) I (ref.) | I (r.t.) I (ref.) | I (r.t.) I (ref.) | I (r.t.) I (ref.) | I (r.t.) I (ref.) | I (r.t.) I (ref.) | I (r.t.) I (ref.) | PS (r.t.) S (ref.) X | I (r.t.) S (ref.) X | I (r.t.) S (ref.) X | I (r.t.) S (ref.) X | PS (r.t.) S (ref.) X | PS (ref.) | S (ref.) X | I (r.t.) S (ref.) X | I (r.t.) S (ref.) X |
| Fumaric 1:1 (3.0, 4.4) | I (r.t.) I (ref.) | I (r.t.) I (ref.) | I (r.t.) I (ref.) | I (r.t.) I (ref.) | I (r.t.) I (ref.) | I (r.t.) I (ref.) | I (r.t.) I (ref.) | I (r.t.) I (ref.) | I (r.t.) I (ref.) | PS (r.t.) S (ref.) X | X (+1°) | PS (r.t.) S (ref.) X | I (r.t.) S (ref.) X | PS (r.t.) S (ref.) X | I (r.t.) S (ref.) X | S (r.t.) X | I (r.t.) I (ref.) | I (r.t.) I (ref.) X |
| DL-Mandelic 1:1 (3.4) | S (r.t.) X(+1°) X | I (r.t.) S (ref.) X | I (r.t.) S (ref.) X | I (r.t.) S (ref.) X | I (r.t.) I (ref.) | I (r.t.) I (ref.) | I (r.t.) I (ref.) | PS (ref.) X | I (r.t.) S (ref.) X | I (r.t.) S (ref.) X | I (r.t.) S (ref.) X | I (r.t.) S (ref.) X | I (r.t.) S (ref.) X | I (r.t.) S (ref.) X | I (r.t.) S (ref.) X | I (r.t.) S (ref.) X | S (r.t.) | I (r.t.) S (ref.) X |

(r.t.) = room temperature (ref) = reflux S = soluble PS = partially soluble I = insoluble X = solids observed

FIG. 2

| A | B | C | D | E | F | G | H |
|---|---|---|---|---|---|---|---|
| Salt | Free base (g) | Solvent | Yield (g) | Major Endotherm Peaks (°C) | Theoretical | Found | $^1$H NMR solvent |
| HCl (31a) | 1.0 | 1:20 EtOH/Et$_2$O (31 mL/g) | 1.0 | 213.47 | C: 48.58 H: 7.34 N: 30.21 | C: 48.38 H: 7.34 N: 30.12 | CD$_3$OD |
| Bis HCl (31b) | 14.0 | 1:13 EtOH/Et$_2$O (14 mL/g) | 16.4 | 213.23, 241.38) | C: 44.23 H: 6.93 N: 27.51 | C: 44.24 H: 6.81 N: 27.42 | CD$_3$OD |
| Hydrogen Malonate (31c) | 0.9 | 20:1 EtOAc/EtOH (35 mL/g) | 1.1 | 148.82, 159.16 | C: 49.31 H: 6.90 N: 25.55 | C: 49.26 H: 6.88 N: 25.65 | CD$_3$OD |
| Hydrogen Maleinate (31d-1) (form Mal-A) | 1.5 | 1:16 EtOH/Et$_2$O (28 mL/g) | 1.8 | 105.20 118.86 (exoth) 153.14 158.28 | C: 50.66 H: 6.71 N: 24.87 | C: 50.57 H: 6.66 N: 24.69 | CD$_3$OD |
| Hydrogen Maleinate (31d-2) (form Mal-B) | | From exposure of of Mal-A to humidity | | 159.04 | | | |
| Hydrogen Fumarate (31e) | 1.5 | EtOH (23 mL/g) | 1.8 | 232.36 | C: 50.66 H: 6.71 N: 24.87 | C: 50.56 H: 6.67 N: 24.95 | CD$_3$OD |
| Hydrogen L(+)-Tartrate (31f) | 1.5 | 1:16 EtOH/Et$_2$O (28 mL/g) | 1.8 | 215.71 | C: 49.05 H: 7.00 N: 26.12 | C: 48.95 H: 7.16 N: 26.12 | DMSO |
| D,L-Mandelate (31g) | 1.5 | 1:16 EtOH/Et$_2$O (28 mL/g) | 2.0 | 163.04 | C: 56.78 H: 7.04 N: 23.03 | C: 56.86 H: 7.04 N: 23.12 | CD$_3$OD |
| Tosylate (31h-1) (Tos-A) | 1.2 | MTBE (15 mL/g) | 1.6 | 110.34 | C: 52.16 H: 6.76 N: 22.12 S: 6.33 | C: 52.23 H: 6.82 N: 22.32 S: 6.34 | CD$_3$OD |
| Tosylate (31h-2) (Tos-B) | 1.2 | From exposure of of Tos-A to humidity | | 51.18 | | | |
| Mesylate (31i) | 1.5 | MeCN (15 mL/g) | 1.2 | 183.52 | C: 44.64 H: 7.02 N: 26.03 S: 7.45 | C: 44.67 H: 7.09 N: 26.13 S: 7.27 | CD$_3$OD |
| Saccharinate (31j) | 1.2 | 1:16 EtOH/Et$_2$O (30 mL/g) | 1.7 | 204.96 | C: 51.05 H: 6.04 N: 24.35 | C: 51.09 H: 6.06 N: 24.36 | DMSO |

XRPD of 31a, Hydrochloride Salt Form

FIG. 3B

Selected XRPD Peak List for 31a, Hydrochloride Salt Form

| Angle, 2θ | d spacing, °A | Relative intensity, % |
|---|---|---|
| 6.78 | 13.02681 | 12.2 |
| 7.19 | 12.28934 | 5.8 |
| 9.92 | 8.91107 | 10.9 |
| 10.24 | 8.63187 | 100 |
| 16.63 | 5.32583 | 10.9 |
| 19.59 | 4.52644 | 3.7 |
| 19.82 | 4.47601 | 3.2 |
| 20.32 | 4.36694 | 4.9 |
| 22.13 | 4.01431 | 3.7 |
| 22.71 | 3.91184 | 24.8 |
| 25.24 | 3.52565 | 4.2 |
| 25.72 | 3.46098 | 14.4 |
| 27.14 | 3.28345 | 3.9 |
| 30.99 | 2.88319 | 4.9 |

DSC of 31a, Hydrochloride Salt Form

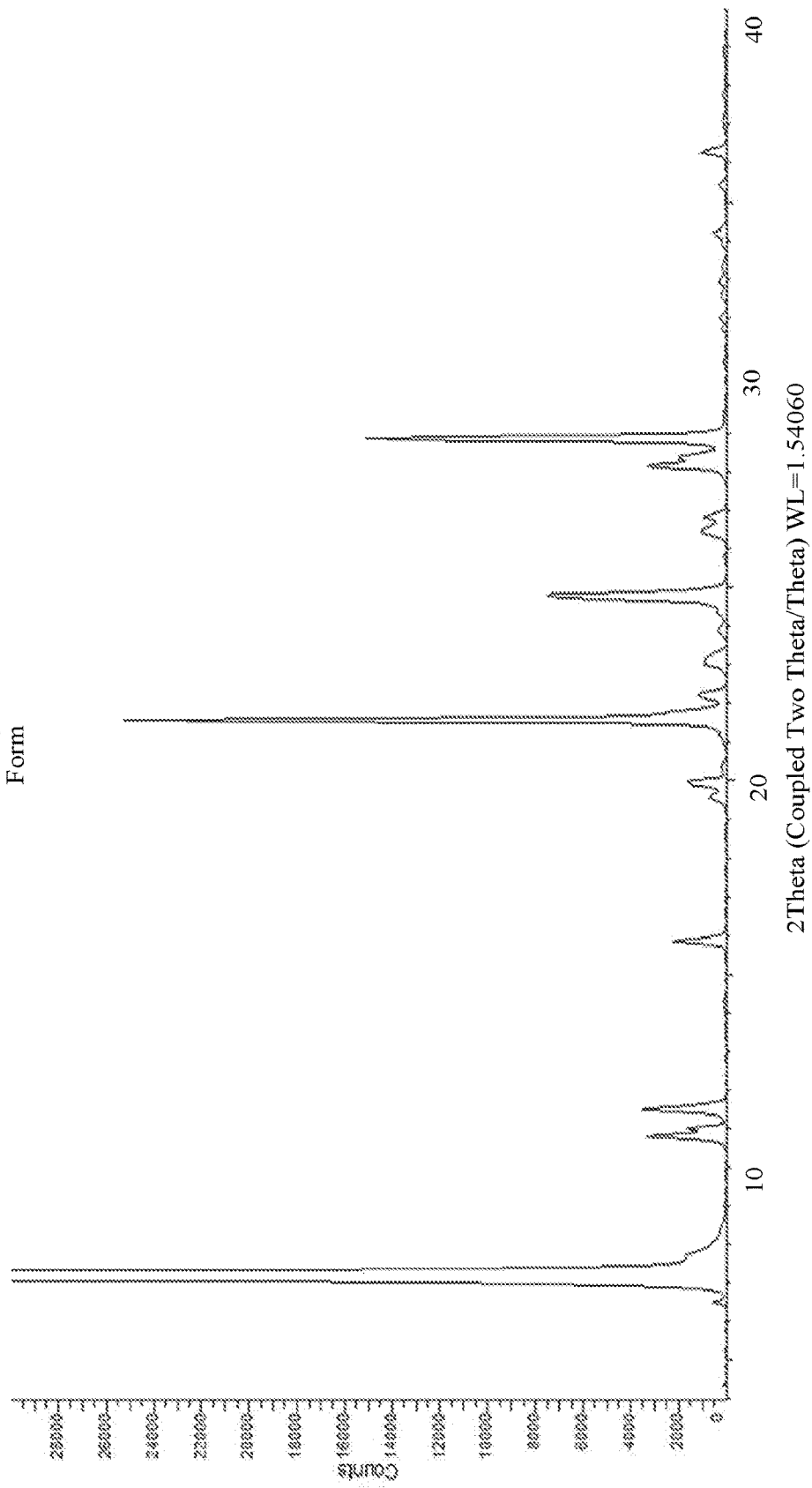

FIG. 4B

Selected XRPD Peak List for 31b, bis-Hydrochloride Salt Form

| Angle, 2θ | d spacing, °A | Relative intensity, % |
|---|---|---|
| 7.20 | 12.27252 | 100 |
| 10.80 | 8.18326 | 1 |
| 10.97 | 8.06214 | 0.4 |
| 11.50 | 7.68791 | 1 |
| 15.85 | 5.58721 | 0.6 |
| 19.94 | 4.44923 | 0.4 |
| 21.58 | 4.11506 | 7.5 |
| 24.78 | 3.59028 | 2.3 |
| 26.83 | 3.32073 | 0.3 |
| 28.18 | 3.16451 | 1 |
| 28.88 | 3.0895 | 4.5 |

DSC for 31b, bis-Hydrochloride Salt Form

XRPD of 31c, Hydrogen Malonate Salt Form

FIG. 5B

Selected XRPD Peak List for 31c, Hydrogen Malonate Salt Form

| Angle, 2 θ | d spacing, °A | Relative intensity, % |
|---|---|---|
| 7.59 | 11.63447 | 100 |
| 8.92 | 9.90534 | 2 |
| 10.40 | 8.49625 | 2.4 |
| 10.80 | 8.18579 | 1.8 |
| 17.98 | 4.92979 | 1.2 |
| 20.30 | 4.37071 | 1 |
| 20.74 | 4.27862 | 1.6 |
| 21.28 | 4.17159 | 2.2 |
| 22.73 | 3.90913 | 1.3 |
| 23.67 | 3.7552 | 1.3 |
| 24.73 | 3.59764 | 2.3 |
| 26.23 | 3.3949 | 1.6 |
| 27.67 | 3.22152 | 2.4 |
| 28.48 | 3.13163 | 1 |
| 29.12 | 3.06452 | 1.1 |

DSC of 31c, Hydrogen Malonate Salt Form

XRPD of 31d-1, Hydrogen Maleinate Salt, Form Mal-A

FIG. 6B

Selected XRPD Peak List for 31d-1 Hydrogen Maleinate Form Mal-A

| Angle, 2 θ | d spacing, °A | Relative intensity, % |
|---|---|---|
| 6.08 | 14.52263 | 100 |
| 6.74 | 13.10492 | 56.4 |
| 7.40 | 11.94069 | 8.9 |
| 8.94 | 9.87886 | 4.3 |
| 9.08 | 9.73529 | 5.5 |
| 9.89 | 8.9369 | 8.1 |
| 19.39 | 4.57431 | 4 |
| 20.93 | 4.24119 | 9.85 |
| 21.18 | 4.19183 | 7.3 |
| 26.31 | 3.38423 | 24.1 |
| 27.12 | 3.28575 | 7.1 |

DSC of 31d-1, Hydrogen Maleinate Salt, Form Mal-A

XRPD of 31d-2, Hydrogen Maleinate Salt, Form Mal-B

FIG. 7B

Selected XRPD Peak List for 31d-2, Hydrogen Maleinate Salt, Form Mal-B

| Angle, 2θ | d spacing, °A | Relative intensity, % |
|---|---|---|
| 5.45 | 16.21189 | 5 |
| 7.24 | 12.19919 | 100 |
| 9.43 | 9.37101 | 45 |
| 10.79 | 8.19325 | 6.7 |
| 16.20 | 5.46745 | 3.6 |
| 17.21 | 5.14751 | 16 |
| 18.84 | 4.70602 | 4.5 |
| 19.23 | 4.61256 | 9 |
| 19.80 | 4.48068 | 5 |
| 20.21 | 4.38948 | 7.5 |
| 22.48 | 3.95265 | 8.9 |
| 23.23 | 3.82667 | 5.2 |
| 25.67 | 3.4673 | 89.9 |
| 27.73 | 3.21485 | 14 |

DSC of 31d-2, Hydrogen Maleinate Salt, Form Mal-B

XRPD of 31e, Hydrogen Fumarate Salt Form

FIG. 8B

Selected XRPD Peak List for 31e, Hydrogen Fumarate Salt Form

| Angle, 2θ | d spacing, °A | Relative intensity, % |
|---|---|---|
| 7.18 | 12.31057 | 100 |
| 10.34 | 8.54465 | 1.1 |
| 13.19 | 6.74397 | 1.6 |
| 14.28 | 6.1978 | 1.1 |
| 16.84 | 5.26205 | 6.1 |
| 20.28 | 4.37553 | 3.4 |
| 20.81 | 4.26428 | 1.2 |
| 21.39 | 4.15 | 2 |
| 22.08 | 4.02316 | 1.8 |
| 23.94 | 3.71411 | 1.9 |
| 25.63 | 3.47318 | 2 |
| 26.97 | 3.30309 | 7.7 |
| 30.11 | 2.96552 | 4.7 |

DSC of 31e, Hydrogen Fumarate Salt Form

XRPD for 31f, Hydrogen-*L*(+)Tartrate Salt Form

FIG. 9B

Selected XRPD Peak List for 31f, Hydrogen-$L$(+)Tartrate Salt Form

| Angle, 2θ | d spacing, °A | Relative intensity, % |
|---|---|---|
| 7.80 | 11.32371 | 100 |
| 8.83 | 10.00916 | 1.28 |
| 9.09 | 9.7195 | 0.7 |
| 11.09 | 7.9704 | 0.9 |
| 15.67 | 5.6515 | 1.7 |
| 19.59 | 4.52881 | 1.9 |
| 20.11 | 4.41252 | 0.7 |
| 21.08 | 4.21114 | 0.9 |
| 22.34 | 3.97692 | 1.2 |
| 22.87 | 3.88501 | 1.4 |
| 25.11 | 3.54371 | 1.6 |
| 27.82 | 3.20476 | 1.5 |
| 30.82 | 2.89875 | 0.8 |

DSC for 31f, Hydrogen-*L*(+)Tartrate Salt Form

XRPD of 31g, D,L-Mandelate Salt Form

FIG. 10B

Selected XRPD Peak List for 31g, D,L-Mandelate Salt Form

| Angle, 2 θ | d spacing, °A | Relative intensity, % |
|---|---|---|
| 7.39 | 11.9574 | 100 |
| 9.50 | 9.30745 | 2.8 |
| 11.14 | 7.93382 | 2.7 |
| 17.23 | 5.14296 | 6 |
| 17.68 | 5.01169 | 2.6 |
| 17.95 | 4.93691 | 3.3 |
| 19.68 | 4.50847 | 4.6 |
| 20.63 | 4.30283 | 2.4 |
| 21.77 | 4.07913 | 6.3 |
| 23.25 | 3.82359 | 4.6 |
| 23.68 | 3.74551 | 3.7 |
| 24.68 | 3.60391 | 2.4 |
| 25.06 | 3.55048 | 7.2 |
| 29.93 | 2.98311 | 3.1 |

DSC of 31g, D,L-Mandelate Salt Form

XRPD for 31h-1, Tosylate Salt Form Tos-A

FIG. 11B

Selected XRPD Peak List for 31h-1, Tosylate Salt Form Tos-A

| Angle, 2θ | d spacing, °A | Relative intensity, % |
|---|---|---|
| 5.70 | 15.4874 | 100 |
| 11.35 | 7.78855 | 62.9 |
| 17.12 | 5.17511 | 4.5 |
| 17.38 | 5.09975 | 14.8 |
| 18.86 | 4.70049 | 4 |
| 20.72 | 4.28416 | 12.9 |
| 21.32 | 4.16358 | 8.3 |
| 21.97 | 4.04287 | 10.9 |

DSC for 31h-1, Tosylate Salt Form Tos-A

XRPD for 31h-2, Tosylate Salt Form Tos-B

FIG. 12B

Selected XRPD Peak List for 31h-2, Tosylate Salt Form Tos-B

| Angle, 2 θ | d spacing, °A | Relative intensity, % |
|---|---|---|
| 6.54 | 13.50497 | 100 |
| 8.97 | 9.85096 | 27.7 |
| 9.69 | 9.12314 | 38.6 |
| 11.99 | 7.3729 | 22.6 |
| 13.08 | 6.76363 | 24.6 |
| 13.34 | 6.63223 | 33.6 |
| 15.33 | 5.77497 | 23.9 |
| 15.66 | 5.65551 | 24 |
| 16.29 | 5.4381 | 16.6 |
| 20.04 | 4.42826 | 18.4 |
| 23.08 | 3.85138 | 33.5 |
| 26.15 | 3.40443 | 19.2 |
| 26.59 | 3.34967 | 28.2 |

DSC for 31h-2, Tosylate Salt Form Tos-B

XRPD of 31i, Mesylate Salt Form

FIG. 13B

Selected XRPD Peak List 31i, Mesylate Salt Form

| Angle, 2 θ | d spacing, °A | Relative intensity, % |
|---|---|---|
| 5.79 | 15.26275 | 25.7 |
| 8.15 | 10.84326 | 100 |
| 9.11 | 9.70536 | 12.5 |
| 12.90 | 6.8576 | 2.8 |
| 17.39 | 5.09461 | 3.5 |
| 18.27 | 4.85104 | 2.8 |
| 19.19 | 4.62145 | 6.5 |
| 20.48 | 4.33397 | 10.2 |
| 22.02 | 4.03292 | 11.4 |
| 23.65 | 3.75967 | 5.1 |
| 27.53 | 3.23687 | 3.2 |

DSC of 31i, Mesylate Salt Form

XRPD for 31j, Saccharinate Salt Form

FIG. 14B

Selected XRPD Peak List for 31j, Saccharinate Salt Form

| Angle, 2 θ | d spacing, °A | Relative intensity, % |
|---|---|---|
| 6.44 | 13.71068 | 14.2 |
| 7.15 | 12.3583 | 100 |
| 8.26 | 10.69115 | 3.6 |
| 10.34 | 8.54959 | 3 |
| 11.73 | 7.53643 | 2.9 |
| 12.10 | 7.30768 | 6.2 |
| 12.29 | 7.19734 | 3.6 |
| 13.54 | 6.53621 | 6 |
| 16.79 | 5.27542 | 4 |
| 18.22 | 4.86621 | 2.9 |
| 19.28 | 4.59954 | 2.8 |
| 20.71 | 4.2864 | 3.4 |
| 21.40 | 4.14888 | 3.1 |
| 23.14 | 3.84128 | 4.6 |
| 25.52 | 3.48725 | 7.4 |
| 26.37 | 3.37697 | 8.4 |

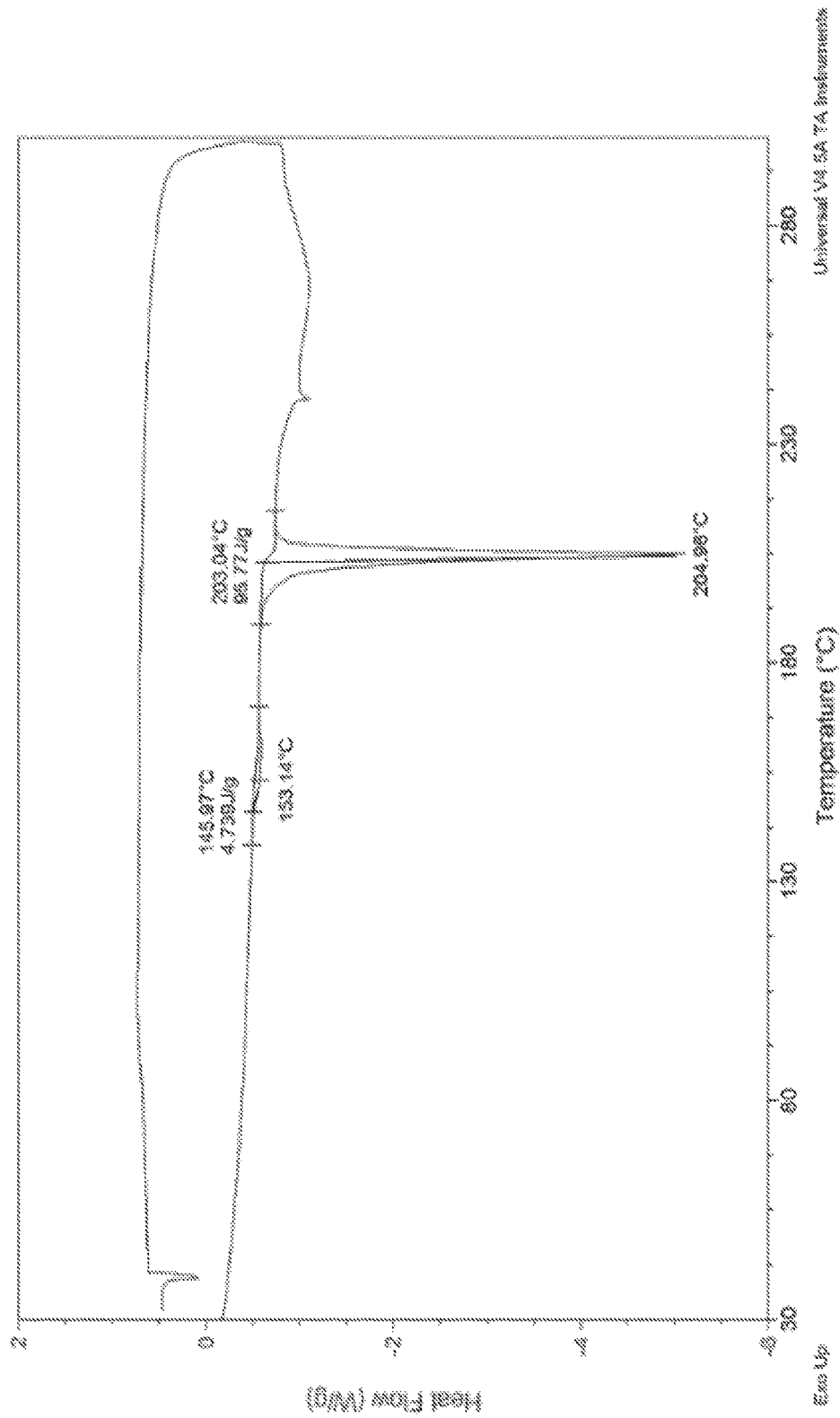

| Parameter | Baseline (mean ± SEM) | Vehicle (mean ± SEM) | Cmpd (31a) (mean ± SEM) |
|---|---|---|---|
| % Time Spent In NREM | 59 ± 2 | 50 ± 4 | 56 ± 4 |
| % Time Spent In REM | 11 ± 1 | 8 ± 2 | 10 ± 1 |
| % Time Spent In WAKE | 30 ± 1 | 42 ± 5† | 34 ± 3 |
| # NREM Bouts / Hr | 20 ± 1 | 20 ± 3 | 20 ± 2 |
| # REM Bouts / Hr | 8 ± 1 | 3 ± 1† | 6 ± 1 |
| # NREM Epochs / Hr | 24 ± 2 | 25 ± 3 | 24 ± 2 |
| # REM Epochs / Hr | 11 ± 1 | 5 ± 1† | 9 ± 1 |
| NREM Bout Length (s) | 133 ± 8 | 109 ± 18 | 130 ± 16 |
| REM Bout Length (s) | 67 ± 3 | 96 ± 6† | 75 ± 6* |
| # WAKE Bouts / Hr | 15 ± 1 | 24 ± 5 | 16 ± 3 |
| # Arousals / Hr | 7 ± 1 | 9 ± 2 | 8 ± 1 |
| Arousal Index | 22 ± 1 | 33 ± 6 | 24 ± 3 |

BREATHING CONTROL MODULATING COMPOUNDS, AND METHODS OF MAKING AND USING SAME

CROSS REFERENCE TO RELATED APPLICATION

This application is a 35 U.S.C. 371 National Phase Entry Application from PCT/US2016/039032, filed Jun. 23, 2016, which claims the benefit of U.S. Ser. No. 62/186,468 filed Jun. 30, 2015 and U.S. Ser. No. 62/328,277 filed Apr. 27, 2016, the disclosures of which are incorporated herein in their entirety by reference.

CROSS-REFERENCE TO RELATED APPLICATIONS

This application claims priority under 35 U.S.C. § 119(e) to U.S. Provisional Application No. 62/186,468, filed Jun. 30, 2015, and U.S. Provisional Application No. 62/328,277, filed Apr. 27, 2016, all of which are incorporated herein by reference in their entireties.

BACKGROUND OF THE INVENTION

Normal control of breathing is a complex process that involves, in part, the body's interpretation and response to chemical stimuli such as carbon dioxide, pH and oxygen levels in blood, tissues and the brain. Normal breathing control is also affected by other factors such as wakefulness (i.e., whether the patient is awake or sleeping), emotion, posture and vocalization. Within the brain medulla, there are respiratory control centers that interpret various feed-forward and feed-back signals that affect respiration by issuing commands to the muscles that perform the work of breathing. Key muscle groups are located in the abdomen, diaphragm, pharynx and thorax. Sensors located centrally and peripherally then provide input to the brain's central respiration control areas that enables response to changing metabolic requirements.

For example, ventilation sufficient to meet the body's metabolic needs is maintained primarily by the body's rapid response to changes in carbon dioxide ($CO_2$) levels. Increased $CO_2$ levels (hypercapnia) signal the body to increase breathing rate and depth, resulting in higher blood oxygen levels and subsequent lower blood $CO_2$ levels. Conversely, low $CO_2$ levels (hypocapnia) can result in periods of hypopnea (decreased breathing) or, in the extreme case, apnea (no breathing) since the stimulation to breathe is diminished.

There are many diseases in which loss of normal breathing control is a primary or secondary feature of the disease. Examples of diseases with a primary loss of breathing control are sleep apneas (central, mixed or obstructive; where the breathing repeatedly stops for 10 to 60 seconds) and congenital central hypoventilation syndrome. Secondary loss of breathing control may be due to chronic cardiopulmonary diseases (e.g., heart failure, chronic bronchitis, emphysema, and impending respiratory failure), excessive weight (e.g., obesity-hypoventilation syndrome), certain drugs (e.g., anesthetics, sedatives, sleeping aids, anxiolytics, hypnotics, alcohol, and narcotic analgesics and/or factors that affect the neurological system (e.g., stroke, tumor, trauma, radiation damage, and ALS). In chronic obstructive pulmonary diseases where the body is exposed to chronically high levels of carbon dioxide, the body adapts to the respiratory acidosis (lower pH) by a kidney mediated retention of bicarbonate, which has the effect of partially neutralizing the $CO_2$/pH respiratory stimulation. Thus, the patient is unable to mount a normal ventilatory response to changes in metabolic demand.

Sleep disordered breathing is an example of where abnormalities in the control of breathing lead to a serious and prevalent disease in humans. Sleep apnea is characterized by frequent periods of no or partial breathing. Key factors that contribute to these apneas include anatomical factors (e.g., obesity), decreased hypercapnic and hypoxic ventilatory responses (e.g., decreased response to high carbon dioxide and low oxygen levels, respectively) and loss of "wakefulness" (respiratory drive to pharyngeal dilator muscles during sleep). Apneic events result in intermittent hypoxia (and the associated oxidative stress) and eventually severe cardiovascular consequences (high blood pressure, stroke, heart attack).

Estimates for U.S. individuals afflicted with conditions wherein there is compromised respiratory control include sleep apneas (15-20 millions); obesity-hypoventilation syndrome (3-5 millions); chronic heart disease (5 millions); chronic obstructive pulmonary disease (COPD)/chronic bronchitis (10 millions); drug-induced hypoventilation (2-10 millions); and mechanical ventilation weaning (0.5 million).

There is a need in the art for novel compounds useful for restoring all or part of the body's normal breathing control system in response to changes in $CO_2$ and/or oxygen levels, with minimal side effects. Further, there is a need in the art for novel compounds that are useful for restoring all or part of the body's normal breathing control system and possess suitable pharmacokinetic properties, such as oral bioavailability. Further, there is a need in the art for novel compounds that are useful for restoring all or part of the body's normal breathing control system and may be administered orally and used in a chronic or acute manner. Further, there is a need in the art for novel compounds that are useful for restoring all or part of the body's normal breathing control system and may be administered parenterally (e.g., intravenously) and used in an acute manner. The present invention addresses and meets these needs.

BRIEF SUMMARY OF THE INVENTION

The invention provides a compound of formula (I), or a salt, solvate, enantiomer, diastereoisomer or tautomer thereof:

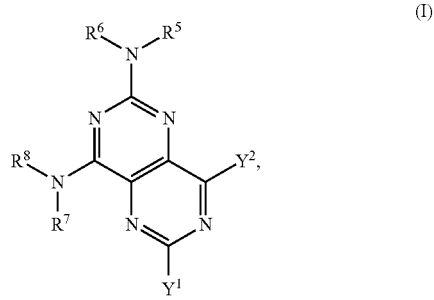

wherein in (I): one of the substituents selected from the group consisting of $Y^1$ and $Y^2$ is selected from the group consisting of —N($R^1$)-L-C($R^9$)($R^{10}$)OH,

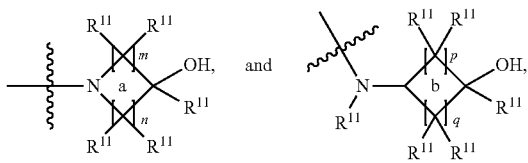

and the other substituent is —N(R$^1$)R$^2$; R$^1$, R$^5$ and R$^7$ are independently selected from the group consisting of hydrogen and optionally substituted C$_1$-C$_3$ alkyl; R$^2$ is selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; R$^6$ and R$^8$ are independently selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; R$^9$ and R$^{10}$ are independently selected from the group consisting of H and optionally substituted C$_1$-C$_3$-alkyl; or R$^9$ and R$^{10}$ combine with the carbon atom to which they are bound so as to form an optionally substituted C$_3$-C$_6$ cycloalkyl group; each instance of R$^{11}$ is independently selected from the group consisting of H and optionally substituted C$_1$-C$_3$-alkyl; wherein a —C(R$^{11}$)$_2$—C(R$^{11}$)$_2$— group within ring b is optionally replaced by an optionally substituted 1,2-phenylene group that is fused with ring b; each occurrence of independently optionally substituted C$_1$-C$_3$ alkylene; m and n are independently selected from the group consisting of 1, 2, 3 and 4, such that 2≤(m+n)≤4; p and q are independently elected from the group consisting of 0, 1, 2, 3 and 4, such that 2≤(p+q)≤4; with the proviso that the alkyl group is not substituted with a hydroxy group.

In certain embodiments, the compound of formula (I) is the compound of formula (IIa), or a salt, solvate, enantiomer, diastereoisomer or tautomer thereof:

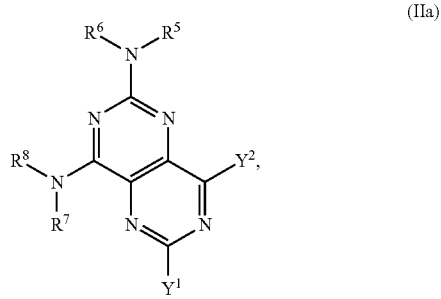

(IIa)

wherein in (IIa): one of the substituents selected from the group consisting of Y$^1$ and Y$^2$ is -L-C(R$^9$)(R$^{10}$)OH, and the other substituent is —N(R$^1$)R$^2$; R$^1$, R$^5$ and R$^7$ are independently selected from the group consisting of hydrogen and optionally substituted C$_1$-C$_3$ alkyl; R$^2$ is selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; R$^6$ and R$^8$ are independently selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; R$^9$ and R$^{10}$ are independently selected from the group consisting of hydrogen and optionally substituted C$_1$-C$_3$-alkyl; or R$^9$ and R$^{10}$ combine with the carbon atom to which they are bound so as to form an optionally substituted C$_3$-C$_6$ cycloalkyl group; L is optionally substituted C$_1$-C$_3$ alkylene; and with the proviso that the alkyl group is not substituted with a hydroxy group.

In certain embodiments, the compound of formula (I) is the compound of formula (IIb), or a salt, solvate, enantiomer, diastereoisomer or tautomer thereof:

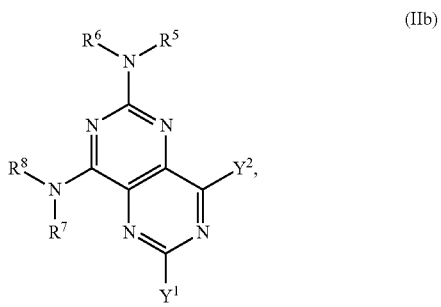

(IIb)

wherein in (IIb): one of the substituents selected from the group consisting of Y$^1$ and Y$^2$ is

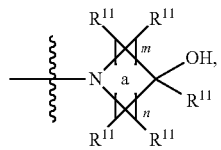

and the other substituent is —N(R$^1$)R$^2$; R$^1$, R$^5$ and R$^7$ are independently selected from the group consisting of H and optionally substituted C$_1$-C$_3$ alkyl; R$^2$ is selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; L is optionally substituted C$_1$-C$_3$ alkylene; and R$^6$ and R$^8$ are independently selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; each instance of R$^{11}$ is independently selected from the group consisting of hydrogen and optionally substituted C$_1$-C$_3$-alkyl; L is optionally substituted C$_1$-C$_3$ alkylene; m and n are independently selected from the group consisting of 1, 2, 3 and 4, such that 2≤m+n≤4; with the proviso that the alkyl group is not substituted with a hydroxy group.

In certain embodiments, the compound of formula (I) is a compound of formula (IIc), or a salt, solvate, enantiomer, diastereoisomer or tautomer thereof:

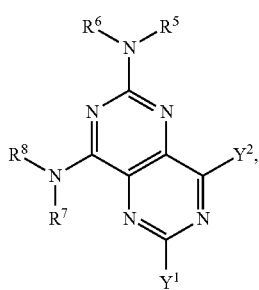

(IIc)

wherein in (IIc): one of the substituents selected from the group consisting of $Y^1$ and $Y^2$ is

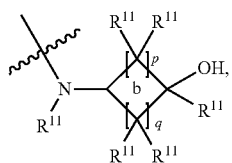

and the other substituent is —$(R^1)R^2$; $R^1$, $R^5$ and $R^7$ are independently selected from the group consisting of hydrogen and optionally substituted $C_1$-$C_3$ alkyl; $R^2$ is selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; $R^6$ and $R^8$ are independently selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; $R^9$ and $R^{10}$ are independently selected from the group consisting of H and optionally substituted $C_1$-$C_3$-alkyl; or $R^9$ and $R^{10}$ combine with the carbon atom to which they are bound so as to form an optionally substituted $C_3$-$C_6$ cycloalkyl group; each instance of $R^{11}$ is independently selected from the group consisting of H and optionally substituted $C_1$-$C_3$-alkyl; wherein a —$C(R^{11})_2$—$C(R^{11})_2$— group within ring b is optionally replaced by an optionally substituted 1,2-phenylene group that is fused with ring b; each occurrence of L is independently optionally substituted $C_1$-$C_3$ alkylene; p and q are s independently elected from the group consisting of 0, 1, 2, 3 and 4, such that $2 \leq p+q \leq 4$; with the proviso that the alkyl group is not substituted with a hydroxy group.

In certain embodiments of compounds of formulas (I), (IIa), (IIb) and (IIc), each occurrence of the alkyl group is optionally substituted with one or more substituents independently selected from the group consisting of $C_1$-$C_6$ alkyl, F, Cl, Br, I, and CN; each occurrence of the cycloalkyl, alkenyl or alkynyl group is optionally substituted with one or more substituents independently selected from the group consisting of $C_1$-$C_6$ alkyl, F, Cl, Br, I, and CN; each occurrence of the phenyl, phenylalkyl, aryl, arylalkyl, heteroarylalkyl or heteroaryl group is optionally substituted with one or more substituents independently selected from the group consisting of $C_1$-$C_6$ alkyl, $C_1$-$C_6$ alkoxy, hydroxy, F, Cl, Br, I, nitro, —$NH_2$, —$NH(C_1$-$C_6$ alkyl), —$N(C_1$-$C_6$ alkyl)($C_1$-$C_6$ alkyl), —$S(=O)_{0-2}(C_1$-$C_6$ alkyl), —$C(=O)OH$ and —$C(=O)OC_1$-$C_6$ alkyl.

In certain embodiments of compounds of formula (I), $R^1$, $R^5$ and $R^7$ are H. In certain embodiments of compounds of formula (I), $R^1$, $R^5$ and $R^7$ are independently optionally substituted $C_1$-$C_3$ alkyl. In certain embodiments of compounds of formula (I), $R^1$, $R^5$ and $R^7$ are H; and $R^9$ and $R^{10}$ are H. In certain embodiments of compounds of formula (I), $R^1$, $R^5$ and $R^7$ are H; $R^9$ is H; and $R^{10}$ are $CH_3$.

In certain embodiments, a compound of formula (I) is selected from the group consisting of: 2-(2,6-Bis-methylamino-8-propylamino-pyrimido[5,4-d]pyrimidin-4-ylamino)-ethanol (4); 2-[(2,6-Bis-methylamino-8-propylamino-pyrimido[5,4-d]pyrimidin-4-yl)-methyl-amino]-ethanol (6); 3-(2,6-Bis-methylamino-8-propylamino-pyrimido[5,4-d]pyrimidin-4-ylamino)-propan-1-ol (8); 1-(2,6-Bis-methylamino-8-propylamino-pyrimido[5,4-d]pyrimidin-4-ylamino)-propan-2-ol (10); (S)-1-(2,6-Bis-methylamino-8-propylamino-pyrimido[5,4-d]pyrimidin-4-ylamino)-propan-2-ol (12); (R)-1-(2,6-Bis-methylamino-8-propylamino-pyrimido[5,4-d]pyrimidin-4-ylamino)-propan-2-ol (14); 2-(2,6-Bis-methylamino-8-propylamino-pyrimido[5,4-d]-pyrimidin-4-ylamino)-2-methyl-propan-1-ol (16); (S)-2-(2,6-Bis-methylamino-8-propylamino-pyrimido[5,4-d]-pyrimidin-4-ylamino)-propan-1-ol (18); (R)-2-(2,6-Bis-methylamino-8-propylamino-pyrimido[5,4-d]-pyrimidin-4-ylamino)-propan-1-ol (20); 3-(2,6-Bis-methylamino-8-propylamino-pyrimido[5,4-d]pyrimidin-4-ylamino)-1,1,1-trifluoro-propan-2-ol (22); 1-(2,6-Bis-methylamino-8-propylamino-pyrimido[5,4-d]pyrimidin-4-ylamino)-butan-2-ol (24); 3-(2,6-Bis-methylamino-8-propylamino-pyrimido[5,4-d]pyrimidin-4-ylamino)-butan-2-ol (26); 2-(2,6-Bis-ethylamino-8-propylamino-pyrimido[5,4-d]pyrimidin-4-ylamino)-ethanol (27); 2-[8-Propylamino-2,6-bis-(2,2,2-trifluoro-ethylamino)-pyrimido[5,4-d]pyrimidin-4-ylamino]-ethanol (28); 1-(2,6-Bis-methylamino-8-propylamino-pyrimido[5,4-d]pyrimidin-4-ylamino)-2-methyl-propan-2-ol (31); 1-(2,6-Bis-ethylamino-8-propylamino-pyrimido[5,4-d]-pyrimidin-4-ylamino)-2-methyl-propan-2-ol (32); 1-[2,6-Bis-(2,2-difluoro-ethylamino)-8-propylamino-pyrimido[5,4-d]-pyrimidin-4-ylamino]-2-methyl-propan-2-ol (33); 2-Methyl-1-[8-propylamino-2,6-bis-(2,2,2-trifluoro-ethylamino)-pyrimido[5,4-d]pyrimidin-4-ylamino]-propan-2-ol (34); I-[8-(2,2-difluoro-ethylamino)-2,6-bis-methylamino-pyrimido[5,4-d]pyrimidin-4-ylamino]-2-methyl-propan-2-ol (36); 1-{2,6-bis-methylamino-8-[(pyrimidin-2-ylmethyl)-amino]-pyrimido[5,4-d]pyrimidin-4-ylamino}-2-methyl-propan-2-ol (38); 1-[8-((R)-sec-butylamino)-2,6-bis-methylamino-pyrimido[5,4-d]-pyrimidin-4-ylamino]-2-methyl-propan-2-ol (40); 1-[8-((S)-sec-butylamino)-2,6-bis-methylamino-pyrimido[5,4-d]-pyrimidin-4-ylamino]-2-methyl-propan-2-ol (42); 1-(8-benzylamino-2,6-bis-methylamino-pyrimido[5,4-d]pyrimidin-4-ylamino)-2-methyl-propan-2-ol (44); 1-[8-(cyclopropylmethyl-amino)-2,6-bis-methylamino-pyrimido[5,4-d]pyrimidin-4-ylamino]-2-methyl-propan-2-ol (46); 1-[8-(2,2-difluoro-ethylamino)-2,6-bis-ethylamino-pyrimido[5,4-d]pyrimidin-4-ylamino]-2-methyl-propan-2-ol (47); 2-methyl-1-(2,6,8-tris-methylamino-pyrimido[5,4-d]-pyrimidin-4-ylamino)-propan-2-ol (48); 2-methyl-1-(2,6,8-tris-ethylamino-pyrimido[5,4-d]-pyrimidin-4-ylamino)-propan-2-ol (49); 2-(2,6,8-tris-methylamino-pyrimido[5,4-d]pyrimidin-4-ylamino)-ethanol (52); 2-[8-(cyclopropylmethyl-amino)-2,6-bis-methylamino-pyrimido[5,4-d]pyrimidin-4-ylamino]-ethanol (54); 2-[8-(2-methoxy-ethylamino)-2,6-bis-methylamino-pyrimido[5,4-d]pyrimidin-4-ylamino]- ethanol (56); 2-(2,6-bis-methylamino-8-prop-2-ynylamino-pyrimido[5,4-d]pyrimidin-4-ylamino)-ethanol (58); 2-[8-(2,2-difluoro-ethylamino)-2,6-bis-methylamino-pyrimido[5,4-d]-pyrimidin-4-ylamino]-ethanol (60); 2-[2,6-bis-methylamino-8-(2,2,2-trifluoro-ethylamino)-pyrimido[5,4-d]pyrimidin-4-ylamino]-ethanol (62); 2-(8-benzylamino-2,6-bis-methylamino-pyrimido[5,4-d]-pyrimidin-4-ylamino)-ethanol (64); 3-(8-ethylamino-2,6-bis-methylamino-pyrimido[5,4-d]-pyrimidin-4-ylamino)-propan-1-ol (67); 1-(2,6-bis-methylamino-8-propylamino-pyrimido[5,4-d]pyrimidin-4-yl)-pyrrolidin-3-ol (71); 1-[(2,6-bis-methylamino-8-propylamino-pyrimido[5,4-d]pyrimidin-4-ylamino)-methyl]-cyclobutanol (72); 1-[(2,6-bis-methylamino-8-propylamino-pyrimido[5,4-d]-pyrimidin-4-yl)-methyl-amino]-propan-2-ol (73); 3-[(2,6-bis-methylamino-8-propylamino-pyrimido[5,4-d]pyrimidin-4-ylamino)-methyl]-pentan-3-ol (74); 1-[(2,6-bis-methylamino-8-propylamino-pyrimido[5,4-d]pyrimidin-4-yl)-methyl-amino]-2-methyl-propan-2-ol (76); (1R,2S)-1-(2,6-bis-methylamino-8-propylamino-pyrimido[5,4-d]-pyrimidin-4-ylamino)-indan-2-ol (77); (1S,2S)-1-(2,6-bis-methylamino-8-propylamino-pyrimido[5,4-d]-pyrimidin-4-ylamino)-indan-2-ol (78); (1S,2R)-1-(2,6-bis-methylamino-8-propylamino-pyrimido[5,4-d]-pyrimidin-4-ylamino)-indan-2-ol (79); (1R,2R)-1-(2,6-bis-methylamino-8-propylamino-pyrimido[5,4-d]-pyrimidin-4-ylamino)-indan-2-ol (80); (2-(2,6-bis-methylamino-8-propylamino-pyrimido[5,4-d]-pyrimidin-4-ylamino)-indan-1-ol (81); (1R,2S)-2-(2,6-bis-methylamino-8-propylamino-pyrimido[5,4-d]pyrimidin-4-ylamino)-cyclohexanol (82); (1S,2S)-2-(2,6-bis-methylamino-8-propylamino-pyrimido[5,4-d]pyrimidin-4-ylamino)-cyclohexanol (83); (1S,2R)-2-(2,6-bis-methylamino-8-propylamino-pyrimido[5,4-d]pyrimidin-4-ylamino)-cyclohexanol (84); (1R,2R)-2-(2,6-bis-methylamino-8-propylamino-pyrimido[5,4-d]pyrimidin-4-ylamino)-cyclohexanol (85); (1S,2S)-2-(2,6-bis-methylamino-8-propylamino-pyrimido[5,4-d]pyrimidin-4-ylamino)-cyclopentanol (86); (1R,2R)-2-(2,6-bis-methylamino-8-propylamino-pyrimido[5,4-d]pyrimidin-4-ylamino)-cyclopentanol (87); 2-[6-(cyclopropylmethyl-amino)-4,8-bis-methylamino-pyrimido[5,4-d]pyrimidin-2-ylamino]-ethanol (90); 2-(4,8-bis-methylamino-6-propyl-amino-pyrimido[5,4-d]pyrimidin-2-ylamino)-ethanol (91); 2-(6-dimethylamino-4,8-bis-methylamino-pyrimido[5,4-d]-pyrimidin-2-ylamino)-ethanol (92); 1-(4,8-bis-methyl-amino-6-propylamino-pyrimido[5,4-d]pyrimidin-2-ylamino)-2-methyl-propan-2-ol (94); 1-(4,8-bis-methylamino-6-propylamino-pyrimido[5,4-d]-pyrimidin-2-ylamino)-propan-2-ol (95); 1-[(4,8-bis-methylamino-6-propylamino-pyrimido[5,4-d]pyrimidin-2-yl)-methyl-amino]-2-methyl-propan-2-ol (96); 1-[(4,8-bis-methylamino-6-propylamino-pyrimido[5,4-d]pyrimidin-2-yl)-methyl-amino]-propan-2-ol (97); 1-[6-((R)-sec-butylamino)-4,8-bis-methylamino-pyrimido[5,4-d]-pyrimidin-2-ylamino]-2-methyl-propan-2-ol (99); (R)-1-[6-((R)-sec-butylamino)-4,8-bis-methylamino-pyrimido[5,4-d]pyrimidin-2-ylamino]-propan-2-ol (100); (S)-1-[6-((R)-sec-butylamino)-4,8-bis-methylamino-pyrimido[5,4-d]pyrimidin-2-ylamino]-propan-2-ol (101); 1-[6-((S)-sec-butylamino)-4,8-bis-methylamino-pyrimido[5,4-d]-pyrimidin-2-ylamino]-2-methyl-propan-2-ol (103); (R)-1-[6-((S)-sec-butylamino)-4,8-bis-methylamino-pyrimido[5,4-d]pyrimidin-2-ylamino]-propan-2-ol (104); (S)-1-[6-((S)-sec-butylamino)-4,8-bis-methylamino-pyrimido[5,4-d]pyrimidin-2-ylamino]-propan-2-ol (105); 1-[6-(2,2-difluoro-ethylamino)-4,8-bis-methylamino-pyrimido[5,4-d]pyrimidin-2-ylamino]-2-methyl-propan-2-ol (107); 1-{4,8-bis-methylamino-6-[(pyrimidin-2-ylmethyl)-amino]-pyrimido[5,4-d]pyrimidin-2-ylamino}-2-methyl-propan-2-ol (109); 3-(4,8-bis-methylamino-6-propylamino-pyrimido[5,4-d]pyrimidin-2-ylamino)-1,1,1-trifluoro-propan-2-ol (111); (S)-1-(4,8-bis-methylamino-6-propylamino-pyrimido[5,4-d]pyrimidin-2-ylamino)-propan-2-ol (113); (R)-1-(4,8-bis-methylamino-6-propylamino-pyrimido[5,4-d]pyrimidin-2-ylamino)-propan-2-ol (115); 1-(4,8-bis-methylamino-6-propylamino-pyrimido[5,4-d]pyrimidin-2-ylamino)-butan-2-ol (117); 3-(4,8-Bis-methylamino-6-propylamino-pyrimido[5,4-d]pyrimidin-2-ylamino)-butan-2-ol (119); (1R,2S)-1-(4,8-bis-methylamino-6-propylamino-pyrimido[5,4-d]-pyrimidin-2-ylamino)-indan-2-ol (123); (1S,2S)-1-(4,8-bis-methylamino-6-propylamino-pyrimido[5,4-d]-pyrimidin-2-ylamino)-indan-2-ol (125); (1S,2R)-1-(4,8-bis-methylamino-6-propylamino-pyrimido[5,4-d]-pyrimidin-2-ylamino)-indan-2-ol (127); (1R,2R)-1-(4,8-bis-methylamino-6-propylamino-pyrimido[5,4-d]-pyrimidin-2-ylamino)-indan-2-ol (129); (1R,2S)-2-(4,8-bis-methylamino-6-propylamino-pyrimido[5,4-d]pyrimidin-2-ylamino)-cyclohexanol (131); (1S,2S)-2-(4,8-bis-methylamino-6-propylamino-pyrimido[5,4-d]pyrimidin-2-ylamino)-cyclohexanol (133); (1S,2R)-2-(4,8-bis-methylamino-6-propylamino-pyrimido[5,4-d]pyrimidin-2-ylamino)-cyclohexanol (135); (1R,2R)-2-(4,8-bis-methylamino-6-propylamino-pyrimido[5,4-d]pyrimidin-2-ylamino)-cyclohexanol (137); (1S,2S)-2-(4,8-bis-methylamino-6-propylamino-pyrimido[5,4-d]pyrimidin-2-ylamino)-cyclopentanol (139); (1R,2R)-2-(4,8-bis-methylamino-6-propylamino-pyrimido[5,4-d]pyrimidin-2-ylamino)-cyclopentanol (141); (S)-1-[6-(cyclopropylmethyl-amino)-4,8-bis-methylamino-pyrimido[5,4-d]pyrimidin-2-ylamino]-propan-2-ol (142); (S)-1-(6-allylamino-4,8-bis-methylamino-pyrimido[5,4-d]pyrimidin-2-ylamino)-propan-2-ol (143); (R)-1-[6-(cyclopropylmethyl-amino)-4,8-bis-methylamino-pyrimido[5,4-d]pyrimidin-2-ylamino]-propan-2-ol (144); (R)-1-(6-allylamino-4,8-bis-methylamino-pyrimido[5,4-d]pyrimidin-2-ylamino)-propan-2-ol (145); 1-[6-(cyclopropylmethyl-amino)-4,8-bis-methylamino-pyrimido[5,4-d]pyrimidin-2-ylamino]-butan-2-ol (146); 1-(6-ethylamino-4,8-bis-methylamino-pyrimido[5,4-d]pyrimidin-2-ylamino)-butan-2-ol (147); 2-methyl-1-(4,6,8-tris-methylamino-pyrimido[5,4-d]pyrimidin-2-ylamino)-propan-2-ol (149); 2-(6-allylamino-4,8-bis-methylamino-pyrimido[5,4-d]pyrimidin-2-ylamino)-ethanol (154); (S)-1-[(6-allylamino-4,8-bis-methylamino-pyrimido[5,4-d]-pyrimidin-2-yl)-propyl-amino]-propan-2-ol (155); (S)-1-[(6-allylamino-4,8-bis-methylamino-pyrimido[5,4-d]pyrimidin-2-yl)-methyl-amino]-propan-2-ol (156); (R)-1-[6-(2-methyl-allylamino)-4,8-bis-methylamino-pyrimido[5,4-d]-pyrimidin-2-ylamino]-propan-2-ol (158); (S)-1-[6-(2-methyl-allylamino)-4,8-bis-methylamino-pyrimido[5,4-d]-pyrimidin-2-ylamino]-propan-2-ol (159); 2-(4,8-bis-ethylamino-6-propylamino-pyrimido[5,4-d]pyrimidin-2-ylamino)-ethanol (162); 1-(4,8-bis-ethylamino-6-propylamino-pyrimido[5,4-d]pyrimidin-2-ylamino)-2-methyl-propan-2-ol (163); (S)-1-(4,6,8-Tris-ethylamino-pyrimido[5,4-d]pyrimidin-2-ylamino)-propan-2-ol (165); (S)-1-(4,8-bis-ethylamino-6-propylamino-pyrimido[5,4-d]-pyrimidin-2-ylamino)-propan-2-ol (166); (R)-1-(4,6,8-tris-ethylamino-pyrimido[5,4-d]pyrimidin-2-ylamino)-propan-2-ol (168); (R)-1-(4,8-bis-ethylamino-6-propylamino-pyrimido[5,4-d]-pyrimidin-2-ylamino)-propan-2-ol (169); (R)-1-[4,8-bis-ethylamino-6-(2-methyl-allylamino)-pyrimido[5,4-d]-pyrimidin-2-ylamino]-propan-2-ol (174); (S)-1-[4,8-bis-ethylamino-6-(2-methyl-allylamino)-pyrimido[5, 4-d]-pyrimidin-2-ylamino]-propan-2-ol (175); a salt, solvate, enantiomer, diastereoisomer or tautomer thereof and any combinations thereof.

In certain embodiments of compounds of formula (I), the salt comprises an acid addition salt, and the acid is at least one selected from the group consisting of sulfuric, hydrochloric, hydrobromic, hydroiodic, nitric, carbonic, phosphoric, formic, acetic, propionic, succinic, glycolic, gluconic, lactic, malic, tartaric, citric, ascorbic, maleic, glucuronic, fumaric, pyruvic, aspartic, glutamic, benzoic, anthranilic, mandelic, pamoic, 4-hydroxybenzoic, phenylacetic, methanesulfonic, ethanesulfonic, alginic, benzenesulfonic, pantothenic, sulfanilic, stearic, trifluoromethanesulfonic, β-hydroxyethanesulfonic, p-toluenesulfonic, cyclohexylaminosulfonic, O-hydroxybutyric, salicylic, galactaric and galacturonic, and any combinations thereof.

The invention also provides at least one crystalline salt of 1-(2,6-Bis-methylamino-8-propylamino-pyrimido[5,4-d]pyrimidin-4-yl amino)-2-methyl-propan-2-ol (31) selected from the group consisting of:
(i) Crystalline hydrochloride salt (31a), with a XRPD spectrum as per FIG. 3A; XRPD peaks as per FIG. 3B; and/or DSC spectrum as per FIG. 3C;
(ii) Crystalline bis-hydrochloride salt (31b), with a XRPD spectrum as per FIG. 4A; XRPD peaks as per FIG. 4B; and/or DSC spectrum as per FIG. 4C;
(iii) Crystalline hydrogen malonate salt (31c), with a XRPD spectrum as per FIG. 5A; XRPD peaks as per FIG. 5B; and/or DSC spectrum as per FIG. 5C;
(iv) Crystalline hydrogen maleinate salt Form Male-A (31d-1), with a XRPD spectrum as per FIG. 6A; XRPD peaks as per FIG. 6B; and/or DSC spectrum as per FIG. 6C;
(v) Crystalline hydrogen maleinate salt Form Male-B (31d-2), with a XRPD spectrum as per FIG. 7A; XRPD peaks as per FIG. 7B; and/or DSC spectrum as per FIG. 7C;
(vi) Crystalline hydrogen fumarate salt (31e), with a XRPD spectrum as per FIG. 8A; XRPD peaks as per FIG. 8B; and/or DSC spectrum as per FIG. 8C;
(vii) Crystalline hydrogen L(+)tartrate salt (31f), with a XRPD spectrum as per FIG. 9A; XRPD peaks as per FIG. 9B; DSC spectrum as per FIG. 9C;
(viii) Crystalline D,L-mandelate salt (31g), with a XRPD spectrum as per FIG. 10A; XRPD peaks as per FIG. 10B; and/or DSC spectrum as per FIG. 10C;
(ix) Crystalline tosylate salt form Tos-A (31h-1), with a XRPD spectrum as per FIG. 11A; XRPD peaks as per FIG. 11B; and/or DSC spectrum as per FIG. 11C;
(x) Crystalline tosylate salt form Tos-B (31h-2), with a XRPD spectrum as per FIG. 12A; XRPD peaks as per FIG. 12B; and/or DSC spectrum as per FIG. 12C;
(xi) Crystalline mesylate salt (31i), with a XRPD spectrum as per FIG. 13A; XRPD peaks as per FIG. 13B; and/or DSC spectrum as per FIG. 13C;
(xii) Crystalline saccharinate salt (31j), with a XRPD spectrum as per FIG. 14A; XRPD peaks as per FIG. 14B; and/or DSC spectrum as per FIG. 14C;
and any mixtures thereof.

The invention further provides a pharmaceutical composition comprising at least one compound of formula (I) and at least one pharmaceutically acceptable carrier or excipient.

In certain embodiments, the pharmaceutical composition further comprises at least one additional agent selected from the group consisting of doxapram, enantiomers of doxapram, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, and armodafinil. In other embodiments, the compound and the additional agent are physically mixed or physically separated in the composition. In yet other embodiments the pharmaceutical composition comprises at least one additional agent that causes changes in breathing control. In yet other embodiments, the additional agent is at least one selected from the group consisting of opioid narcotics, benzodiazepines, sedatives, sleeping aids, hypnotics, propofol, and any combinations thereof.

In certain embodiments, the pharmaceutical composition allows for modified delivery of the compound following oral administration to a subject. In other embodiments, the composition minimizes delivery of the compound to the stomach of the subject and maximizes delivery of the compound to the intestine of the subject.

In certain embodiments, the composition includes an enteric coating. In other embodiments, the compound is contained in a pharmaceutically suitable capsule. In other embodiments, the capsule contains granules or powder of the compound, or an admixture of the compound with the carrier or excipient. In yet other embodiments, the excipient comprises a binder, disintegrant, diluent, buffer, lubricant, glidant, antioxidant, antimicrobial preservative, colorant, or flavorant. In yet other embodiments, the capsule is enterically coated but the granules or powders of the compound are not enterically coated. In yet other embodiments, the granules or powders of the compound are coated with an enteric coating before being placed into the capsule. In yet other embodiments, the granules or powders of the compound are coated with a plurality of enteric coatings, as to provide delivery of drug to different regions of the intestine of the subject. In yet other embodiments, at least a portion of the granules or powders of the compound are enterically coated. In yet other embodiments, the capsule is coated with an enteric coating that is different from the enteric coating that coats the granules or powders of the compound.

In certain embodiments, the compound is coated onto a base particles so as to form a core. In other embodiments the base particle is not enterically coated and the composition is contained in a pharmaceutically acceptable capsule that is enterically coated. In other embodiments, the core is coated with an enteric coating, thereby forming an enterically coated bead. In yet other embodiments, the enterically coated bead is contained in a pharmaceutically acceptable capsule. In yet other embodiments, the capsule contains beads coated with a plurality of enteric coatings, so that the capsule provides delivery of the compound to different regions of the intestine of the subject. In yet other embodiments, the contents of the capsule are dissolved or suspended in a pharmaceutically acceptable liquid as to provide a liquid-filled capsule. In yet other embodiments, the capsule is enterically coated but the liquid formulate on contained within does not comprise an enteric coating.

The invention also provides a method of preventing or treating a breathing control disorder or disease in a subject in need thereof, the method comprising administering to the subject an effective amount of at least one compound of the invention or a salt, solvate, enantiomer, diastereoisomer or tautomer thereof.

In certain embodiments, the breathing control disorder or disease is at least one selected from the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), congenital central hypoventilation syndrome, Alzheimer's disease, Parkinson's disease, stroke, Duchenne muscular dystrophy, and brain and spinal cord traumatic injury. In other embodiments, the respiratory depression is caused by an anesthetic, a sedative, a sleeping aid, an anxiolytic agent, a hypnotic agent, alcohol or a narcotic.

In certain embodiments, the subject is further administered at least one agent useful for treating the breathing disorder or disease. In other embodiments, the agent is at least one selected from the group consisting of doxapram, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, and armodafinil. In other embodiments, the compound and the agent are separately administered to the subject. In yet other embodiments, the compound and the agent are co-administered to the subject, further wherein the compound and the agent are physically mixed or physically separated when administered to the subject.

In certain embodiments, the subject is further administered at least one additional therapeutic agent that changes normal breathing control in the subject. In other embodiments, the at least one additional agent is selected from the group consisting of opioid narcotics, benzodiazepines, sedatives, sleeping aids, hypnotics, propofol, and any combinations thereof.

In certain embodiments, the compound is administered in conjunction with the use of a mechanical ventilation device or positive airway pressure device on the subject.

In certain embodiments, the subject is a mammal or bird. In other embodiments, the mammal is a human.

In certain embodiments, the compound is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes.

The invention also provides a method of preventing destabilization or stabilizing breathing rhythm in a subject in need thereof, the method comprising administering to the subject an effective amount of at least one pharmaceutically acceptable carrier and at least one compound of the invention or a salt, solvate, enantiomer, diastereoisomer or tautomer thereof.

In certain embodiments, the destabilization is associated with a breathing control disorder or disease selected from the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), congenital central hypoventilation syndrome, Alzheimer's disease, Parkinson's disease, stroke, Duchenne muscular dystrophy, and brain and spinal cord traumatic injury. In other embodiments, the respiratory depression is caused by an anesthetic, a sedative, a sleeping aid, an anxiolytic agent, a hypnotic agent, alcohol or a narcotic. In yet other embodiments, the subject is further administered at least one agent useful for treating the breathing disorder or disease. In yet other embodiments, the agent is selected from the group consisting of doxapram, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, and armodafinil. In other embodiments, the compound and the agent are separately administered to the subject. In yet other embodiments, the compound and the agent are co-administered to the subject, further wherein the compound and the agent are physically mixed or physically separated when administered to the subject.

In certain embodiments, the subject is further administered at least one additional therapeutic agent that changes normal breathing control in the subject. In other embodiments, the at least one additional agent is selected from the group consisting of opioid narcotics, benzodiazepines, sedatives, sleeping aids, hypnotics, propofol, and any combinations thereof.

In certain embodiments, the compound is administered in conjunction with the use of a mechanical ventilation device or positive airway pressure device on the subject.

In certain embodiments, the subject is a mammal or bird. In other embodiments, the mammal is a human.

In certain embodiments, the compound is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1B are a set of tables summarizing results of a salt form and solvent screen for 1-(2,6-bis-methylamino-8-propylamino-pyrimido[5,4-d]pyrimidin-4-ylamino)-2-methyl-propan-2-ol (31) (pKa 2.32, 5.79).

FIG. 2 illustrates non-limiting gram scale preparation conditions of selected salts of 1-(2,6-bis-methylamino-8-propylamino-pyrimido[5,4-d]pyrimidin-4-ylamino)-2-methyl-propan-2-ol (31), as well as differential scanning calorimetry and mass spectroscopy data.

FIG. 3B depicts an illustrative XRPD peak list for 31a (hydrochloride salt form).

FIG. 4A depicts an illustrative XRPD of 31b (bis-hydrochloride salt form). FIG. 4B depicts an illustrative XRPD peak list for 31b (bis-hydrochloride salt form).

FIG. 5B depicts an illustrative XRPD peak list for 31c (hydrogen malonate salt form).

FIG. 6B depicts an illustrative XRPD peak list of 31d-1 (hydrogen maleinate form Mal-A).

FIG. 7B depicts an illustrative XRPD peak list for 31d-2 (hydrogen maleinate salt form Mal-B).

FIG. 8B depicts an illustrative XRPD peak list for 31e (hydrogen fumarate salt form).

FIG. 9B depicts an illustrative XRPD peak list for 31f (hydrogen-L(+)-tartrate salt form).

FIG. 10B depicts an illustrative XRPD Peak List for 31g (D,L-mandelate salt form).

FIG. 11B depicts an illustrative XRPD peak list for 31h-1 (tosylate salt form Tos-A).

FIG. 12B depicts an illustrative XRPD peak list for 31h-2 (tosylate salt form Tos-B).

FIG. 13B depicts an illustrative XRPD peak list 31i (mesylate salt form).

FIG. 14B depicts an illustrative XRPD peak list for 31j (saccharinate salt form). FIG. 14C depicts an illustrative DSC spectrum of 31j (saccharinate salt form).

DETAILED DESCRIPTION OF THE INVENTION

Figure 3A:
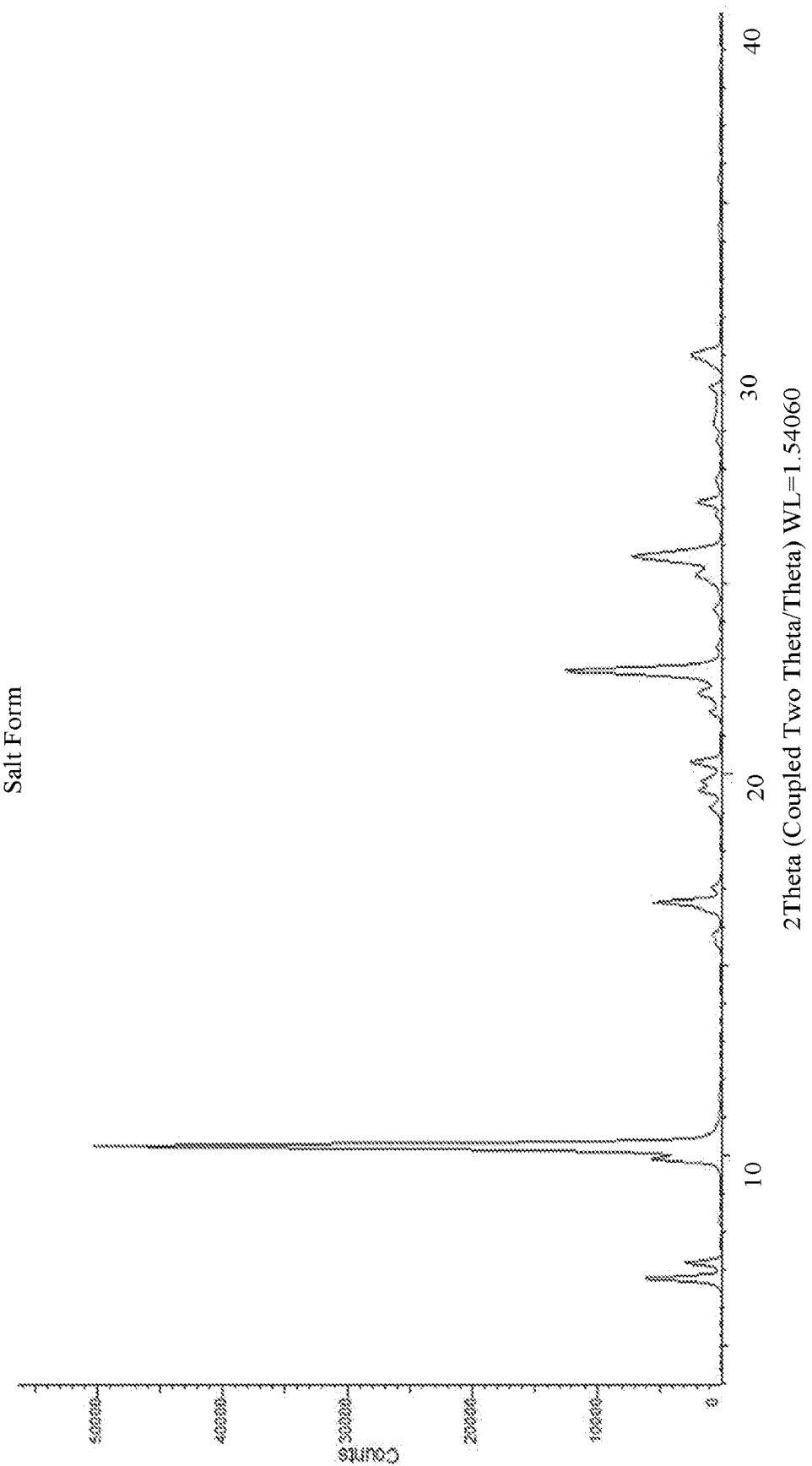
FIG. 3A depicts an illustrative XRPD spectrum of 31a (hydrochloride salt form).

The present invention relates to the discovery that the compounds of the invention are orally bioavailable breathing control modulators and useful in the prevention or treatment of breathing control disorders or diseases. Further, the compounds of the invention are breathing control modulators suitable in the prevention or treatment of breathing control disorders or diseases. In certain embodiments, the compounds are orally bioavailable.

In one aspect, the compounds of the invention prevent changes to the body's normal breathing control system, as a result of disorders and diseases and in response to changes in $CO_2$ and/or oxygen levels, with minimal side effects. In another aspect, the compounds of the invention decrease the incidence and severity of breathing control disturbances, such as apneas. In yet another aspect, the compounds of the invention decrease the incidence of apneic events and/or decrease the duration of apneic events. In yet another aspect, the compounds of the invention have good metabolic stability and oral bioavailability. In yet another aspect, the compounds of the invention do not interfere with the effectiveness of therapies that may cause changes to breathing control, such as opioid analgesia. Such breathing control-altering therapies benefit from administration of agents that support or restore normal breathing function.

In certain embodiments, the breathing control disorder or disease is selected from, but is not limited to, the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD) and sudden infant death syndrome (SIDS). In other embodiments, the respiratory depression is caused by an anesthetic, a sedative, a sleeping aid, an anxiolytic agent, a hypnotic agent, alcohol or a narcotic. In yet other embodiments, the respiratory depression is caused by genetic factors as manifested in, but not limited to, congenital central hypoventilation syndrome. In yet other embodiments, the respiratory depression is caused by neurological conditions such as, but not limited to, Alzheimer's disease, Parkinson's disease, stroke, Duchenne muscular dystrophy, and brain and spinal cord traumatic injury.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art.

In a non-limiting embodiment, the following terminology used to report blood gas measurements is well known to those skilled in the art and may be defined as such: minute ventilation (MV) is a measure of breathing volume per unit time and is given herein as mL/min; $pCO_2$ is partial pressure of carbon dioxide (gas) in (arterial) blood measured in mm Hg (millimeters of Hg); $pO_2$ is partial pressure of oxygen (gas) in (arterial) blood measured in mmHg (millimeters of Hg); $SaO_2$ is the percentage of oxyhemoglobin saturation (oxygen gas bound to hemoglobin) that correlates to the percentage of hemoglobin binding sites in the bloodstream occupied by oxygen; end-tidal $CO_2$ is the measurement of exhaled carbon dioxide gas as detected using calorimetry, capnometry, or capnography techniques.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

In one aspect, the terms "co-administered" and "co-administration" as relating to a subject refer to administering to the subject a compound of the invention or salt thereof along with a compound that may also treat breathing control disorders and/or with a compound that is useful in treating other medical conditions but which in themselves may alter breathing control. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "CYP450" as applied to enzymes refers to cytochrome P450 family of enzymes.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "$ED_{50}$" refers to the effective dose of a formulation that produces 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds," as used herein, is meant that a first molecule preferentially binds to a second molecule (e.g., a particular receptor or enzyme), but does not necessarily bind only to that second molecule.

As used herein, a "subject" may be a human or non-human mammal or a bird. Non-human mammals include, for example, livestock and pets, such as ovine, bovine, porcine, canine, feline and murine mammals. Preferably, the subject is human.

The term "treat," "treating" or "treatment," as used herein, means reducing the frequency or severity with which symptoms of a disease or condition are experienced by a subject by virtue of administering an agent or compound to the subject.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, alkoxy, tetrahydro-2-H-pyranyl, —$NH_2$, —N($CH_3$)$_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —N($CH_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl. In certain embodiments, the substituted alkyl is not substituted with a hydroxy group.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH=$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolinyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

The following abbreviations are used herein:
ABG: arterial blood gas; AcOH: acetic acid; ASV: adaptive servo ventilation; AUC: area under (the) curve; BOP: (benzotriazol-1-yloxy)tris(dimethylamino)phosphonium hexafluorophosphate; BiPAP: bi-level positive airway pressure; nBuOH: n-butanol; C: carbon atom or elemental carbon; $^{13}C$ NMR: carbon-13 nuclear magnetic resonance; $CHCl_3$: chloroform; $CDCl_3$: chloroform-d; $CH_2Cl_2$: dichloromethane or methylene dichloride; CPAP: continuous positive airway pressure; CSA: central sleep apnea; DBU: 1,8-diazabicyclo[5.4.0]undec-7-ene; DCM: dichloromethane or methylene dichloride; DIA: diaphragm (muscle); DIPEA: N,N-diisopropylethylamine; DMAc: N,N-dimethylacetamide; DMSO: dimethylsulfoxide; DMSO-$d_6$: dimethylsulfoxide-$d_6$; DSC: differential scanning calorimetry; EPAP: expiratory positive airway pressure; EtOAc: ethyl acetate; EtOH: ethanol; $Et_2O$: (di)ethyl ether; f: frequency (of respiration); F (%): bioavailability (percent); FID: flame ionization detector; GG: genioglussus; H: hydrogen atom or elemental hydrogen; $^1H$ NMR: proton or hydrogen-1 nuclear magnetic resonance; HCl: hydrochloric acid or a hydrochloride salt; HDPE: high-density polyethylene; hERG: human Ether-a-go-go Related Gene (Kv11.1 ion channel); $H_2SO_4$: sulfuric acid; HLM: human liver microsomes; HPLC: high pressure liquid chromatography; ICU: intensive care unit; IPA: isopropanol (or 2-propanol); IPAP: inspiratory positive airway pressure; kPa: kilopascal; LCMS: liquid chromatography-mass spectrometry; LOQ: limit of quantification; m: multiplet; MAP: mean arterial blood pressure; mbar: millibar (0.001 bar); MBP: mean blood pressure; MTBE: methyl tert-butyl ether; MeCN or $CH_3CN$: acetonitrile; MEK: methyl ethyl ketone; MeOH or $CH_3OH$: methanol; min: minute; mL (or ml): milliliter; MP: melting point; mpk: mg/kg; MV: inute volume (synonymous with $V_E$); ms: milli-second; MS: mass spectrometry; N: nitrogen atom or elemental nitrogen; NaCl: sodium chloride; $NaHCO_3$: sodium bicarbonate; NaOH: sodium hydroxide; $Na_2SO_4$: sodium sulfate; NAVA: neurally adjusted ventilatory assist; NIPPV: non-invasive positive pressure ventilation; NMR: nuclear magnetic resonance; O: oxygen atom or elemental oxygen; OA: obstructive apnea; PA: propargylamine (propargylic amine); PAV: proportional assist ventilation; PE or pet ether: petroleum ether; PEG: polyethylene glycol; PET: positron emission topography; ppm: part per million; q: quartet; RLM: rat liver microsomes; RR: respiratory rate; rt: room (ambient) temperature; s: singlet; $SpO_2$: arterial oxygen saturation; std: standard; t: triplet; THF: tetrahydrofuran; TV: tidal volume; UPLC: ultra performance liquid chromatography; $V_E$: minute (expired) volume (synonymous with MV); XRPD: x-ray powder diffraction (spectrum); δ (delta): delta (ppm); μL (μl): microliter.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

The invention includes a compound of formula (I), or a salt, solvate, enantiomer, diastereoisomer or tautomer thereof:

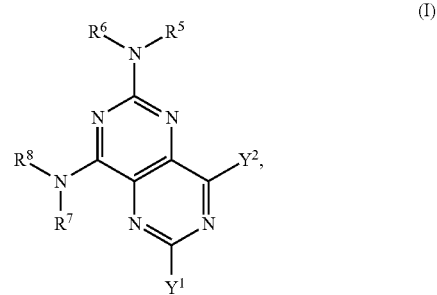

wherein in (I):
one of the substituents selected from the group consisting of $Y^1$ and $Y^2$ is selected from the group consisting of —N($R^1$)-L-C($R^9$)($R^{10}$)OH,

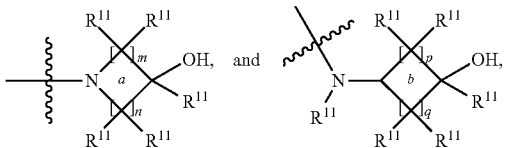

and the other substituent is —N($R^1$)$R^2$;
$R^1$, $R^5$ and $R^7$ are independently selected from the group consisting of hydrogen and optionally substituted $C_1$-$C_3$ alkyl;
$R^2$ is selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted;
$R^6$ and $R^8$ are independently selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted;
$R^9$ and $R^{10}$ are independently selected from the group consisting of H and optionally substituted $C_1$-$C_3$-alkyl; or $R^9$ and $R^{10}$ combine with the carbon atom to which they are bound so as to form an optionally substituted $C_3$-$C_6$ cycloalkyl group;
each instance of $R^{11}$ is independently selected from the group consisting of H and optionally substituted $C_1$-$C_3$-alkyl; wherein a —C($R^{11}$)$_2$—C($R^{11}$)$_2$— group within ring b is optionally replaced by an optionally substituted 1,2-phenylene group that is fused with ring b;

each occurrence of L is independently optionally substituted $C_1$-$C_3$ alkylene;

m and n are independently selected from the group consisting of 1, 2, 3 and 4, such that $2 \leq m+n \leq 4$;

p and q are independently selected from the group consisting of 0, 1, 2, 3 and 4, such that $2 \leq p+q \leq 4$;

with the proviso that the alkyl group is not substituted with a hydroxy group.

In certain embodiments, the compound of formula (I) is the compound of formula (IIa), or a salt, solvate, enantiomer, diastereoisomer or tautomer thereof:

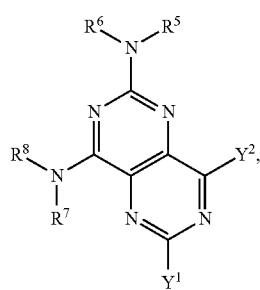
(IIa)

wherein in (IIa):

one of the substituents selected from the group consisting of $Y^1$ and $Y^2$ is -L-C($R^9$)($R^{10}$)OH, and the other substituent is —N($R^1$)$R^2$;

$R^1$, $R^5$ and $R^7$ are independently selected from the group consisting of hydrogen and optionally substituted $C_1$-$C_3$ alkyl;

$R^2$ is selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted;

$R^6$ and $R^8$ are independently selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted;

$R^9$ and $R^{10}$ are independently selected from the group consisting of hydrogen and optionally substituted $C_1$-$C_3$-alkyl; or $R^9$ and $R^{10}$ combine with the carbon atom to which they are bound so as to form an optionally substituted $C_3$-$C_6$ cycloalkyl group;

L is optionally substituted $C_1$-$C_3$ alkylene; and with the proviso that the alkyl group is not substituted with a hydroxy group.

In certain embodiments, the compound of formula (I) is the compound of formula (IIb), or a salt, solvate, enantiomer, diastereoisomer or tautomer thereof:

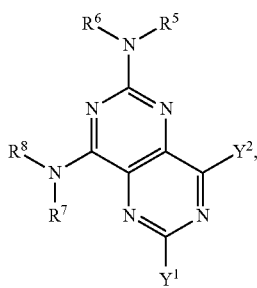
(IIb)

wherein in (IIb):

one of the substituents selected from the group consisting of $Y^1$ and $Y^2$ is

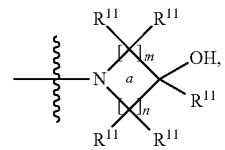

and the other substituent is —N($R^1$)$R^2$;

$R^1$, $R^5$ and $R^7$ are independently selected from the group consisting of H and optionally substituted $C_1$-$C_3$ alkyl;

$R^2$ is selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted; L is optionally substituted $C_1$-$C_3$ alkylene; and $R^6$ and $R^8$ are independently selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted;

each instance of $R^{11}$ is independently selected from the group consisting of hydrogen and optionally substituted $C_1$-$C_3$-alkyl;

L is optionally substituted $C_1$-$C_3$ alkylene;

m and n are independently selected from the group consisting of 1, 2, 3 and 4, such that $2 \leq m+n \leq 4$;

with the proviso that the alkyl group is not substituted with a hydroxy group.

In certain embodiments, the compound of formula (I) is the compound of formula (IIc), or a salt, solvate, enantiomer, diastereoisomer or tautomer thereof:

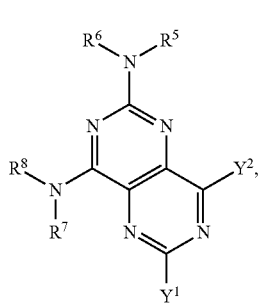
(IIc)

wherein in (IIc):
one of the substituents selected from the group consisting of $Y^1$ and $Y^2$ is

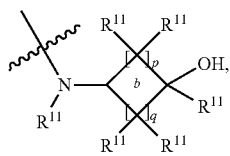

and the other substituent is —N(R$^1$)R$^2$;
$R^1$, $R^5$ and $R^7$ are independently selected from the group consisting of hydrogen and optionally substituted $C_1$-$C_3$ alkyl;
$R^2$ is selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted;
$R^6$ and $R^8$ are independently selected from the group consisting of alkyl, cycloalkyl, alkenyl, alkynyl, phenyl, phenylalkyl, aryl, arylalkyl, heteroarylalkyl and heteroaryl, wherein the alkyl, cycloalkyl, alkenyl, alkynyl, phenyl, phenylalkyl, aryl, arylalkyl, heteroarylalkyl or heteroaryl group is independently optionally substituted;
$R^9$ and $R^{10}$ are independently selected from the group consisting of H and optionally substituted $C_1$-$C_3$-alkyl; or $R^9$ and $R^{10}$ combine with the carbon atom to which they are bound so as to form an optionally substituted $C_3$-$C_6$ cycloalkyl group;
each instance of $R^{11}$ is independently selected from the group consisting of H and optionally substituted $C_1$-$C_3$-alkyl; wherein a —C(R$^{11}$)$_2$—C(R$^{11}$)$_2$— group within ring b is optionally replaced by an optionally substituted 1,2-phenylene group that is fused with ring b;
each occurrence of L is independently optionally substituted $C_1$-$C_3$ alkylene;
p and q are s independently elected from the group consisting of 0, 1, 2, 3 and 4, such that 2≤p+q≤4;
with the proviso that the alkyl group is not substituted with a hydroxy group.

In certain embodiments, each occurrence of the alkyl group is independently optionally substituted with one or more independently selected from the group consisting of $C_1$-$C_6$ alkyl, F, Cl, Br, I, and CN.

In certain embodiments, each occurrence of the cycloalkyl, alkenyl or alkynyl group is independently optionally substituted with one or more independently selected from the group consisting of $C_1$-$C_6$ alkyl, F, Cl, Br, I, and CN.

In certain embodiments, each occurrence of the phenyl, phenylalkyl, aryl, arylalkyl, heteroarylalkyl or heteroaryl group is independently optionally substituted with one or more independently selected from the group consisting of $C_1$-$C_6$ alkyl, $C_1$-$C_6$ alkoxy, hydroxy, F, Cl, Br, I, nitro, —NH$_2$, —NH($C_1$-$C_6$ alkyl), —N($C_1$-$C_6$ alkyl)($C_1$-$C_6$ alkyl), —S(=O)$_{0-2}$($C_1$-$C_6$ alkyl), —C(=O)OH and —C(=O)OC$_1$-$C_6$ alkyl.

In certain embodiments, $R^1$, $R^5$ and $R^7$ are H. In other embodiments, $R^1$, $R^5$ and $R^7$ are H; and $R^6$ and $R^8$ are independently optionally substituted $C_1$-$C_6$ alkyl. In yet other embodiments, $R^1$, $R^5$ and $R^7$ are H; and $R^6$ and $R^8$ are independently optionally substituted arylalkyl. In yet other embodiments, $R^1$, $R^5$ and $R^7$ are H; and $R^6$ and $R^8$ are independently optionally substituted alkenyl. In yet other embodiments, $R^1$, $R^5$ and $R^7$ are H; and $R^6$ and $R^8$ are independently optionally substituted alkynyl.

In certain embodiments, $R^1$, $R^5$ and $R^7$ are independently optionally substituted $C_1$-$C_3$-alkyl. In other embodiments, $R^1$, $R^5$ and $R^7$ are independently optionally substituted $C_1$-$C_3$-alkyl; and $R^6$ and $R^8$ are independently optionally substituted alkyl. In yet other embodiments, $R^1$, $R^5$ and $R^7$ are independently optionally substituted $C_1$-$C_3$-alkyl; and $R^6$ and $R^8$ are independently optionally substituted arylalkyl. In yet other embodiments, $R^1$, $R^5$ and $R^7$ are independently optionally substituted $C_1$-$C_3$-alkyl; and $R^6$ and $R^8$ are independently optionally substituted alkenyl. In yet other embodiments, $R^1$, $R^5$ and $R^7$ are independently optionally substituted $C_1$-$C_3$-alkyl; and $R^6$ and $R^8$ are independently optionally substituted alkynyl.

In certain embodiments, $R^1$, $R^5$ and $R^7$ are H; and $R^9$ and $R^{10}$ are H. In other embodiments, $R^1$, $R^5$ and $R^7$ are H; $R^9$ and $R^{10}$ are H; and $R^6$ and $R^8$ are independently optionally substituted alkyl. In yet other embodiments, $R^1$, $R^5$ and $R^7$ are H; $R^9$ and $R^{10}$ are H; and $R^6$ and $R^8$ are independently optionally substituted arylalkyl. In yet other embodiments, $R^1$, $R^5$ and $R^7$ are H; $R^9$ and $R^{10}$ are H; and $R^6$ and $R^8$ are independently optionally substituted alkenyl. In yet other embodiments, $R^1$, $R^5$ and $R^7$ are H; $R^9$ and $R^{10}$ are H; and $R^6$ and $R^8$ are independently optionally substituted alkynyl.

In certain embodiments, $R^1$, $R^5$ and $R^7$ are H; and $R^9$ and $R^{10}$ are CH$_3$. In other embodiments, $R^1$, $R^5$ and $R^7$ are H; $R^9$ and $R^{10}$ are CH$_3$; and $R^6$ and $R^8$ are independently optionally substituted alkyl. In yet other embodiments, $R^1$, $R^5$ and $R^7$ are H; $R^9$ and $R^{10}$ are CH$_3$; and $R^6$ and $R^8$ are independently optionally substituted arylalkyl. In yet other embodiments, $R^1$, $R^5$ and $R^7$ are H; $R^9$ and $R^{10}$ are CH$_3$; and $R^6$ and $R^8$ are independently optionally substituted alkenyl. In yet other embodiments, $R^1$, $R^5$ and $R^7$ are H; $R^9$ and $R^{10}$ are CH$_3$; and $R^6$ and $R^8$ are independently optionally substituted alkynyl.

In certain embodiments, $R^1$, $R^5$ and $R^7$ are H; $R^9$ is H; and $R^{10}$ is CH$_3$. In other embodiments, $R^1$, $R^5$ and $R^7$ are H; $R^9$ is H; $R^{10}$ is CH$_3$; and $R^6$ and $R^8$ are independently optionally substituted alkyl. In yet other embodiments, $R^1$, $R^5$ and $R^7$ are H; $R^9$ is H; $R^{10}$ is CH$_3$; and $R^6$ and $R^8$ are independently optionally substituted arylalkyl. In yet other embodiments, $R^1$, $R^5$ and $R^7$ are H; $R^9$ is H; $R^{10}$ is CH$_3$; and $R^6$ and $R^8$ are independently optionally substituted alkenyl. In yet other embodiments, $R^1$, $R^5$ and $R^7$ are H; $R^9$ is H; $R^{10}$ is CH$_3$; and $R^6$ and $R^8$ are independently optionally substituted alkynyl.

In certain embodiments, each occurrence of the alkyl group is independently optionally substituted with one or more independently selected from the group consisting of $C_1$-$C_6$ alkyl, F, Cl, Br, I, and CN.

In certain embodiments, each occurrence of the cycloalkyl, alkenyl or alkynyl group is independently optionally substituted with one or more independently selected from the group consisting of $C_1$-$C_6$ alkyl, F, Cl, Br, I, and CN.

In certain embodiments, each occurrence of the phenyl, phenylalkyl, aryl, arylalkyl, heteroarylalkyl or heteroaryl group is independently optionally substituted with one or more independently selected from the group consisting of $C_1$-$C_6$ alkyl, $C_1$-$C_6$ alkoxy, hydroxy, F, Cl, Br, I, nitro, —NH$_2$, —NH($C_1$-$C_6$ alkyl), —N($C_1$-$C_6$ alkyl)($C_1$-$C_6$ alkyl), —S(=O)$_{0-2}$($C_1$-$C_6$ alkyl), —C(=O)OH and —C(=O)OC$_1$-$C_6$ alkyl.

In certain embodiments, $R^1$ is selected from the group consisting of H, CH$_3$ and propyl.

In certain embodiments, $R^2$ is selected from the group consisting of CH$_3$, ethyl, CH$_2$CHF$_2$ and CH$_2$CF$_3$.

In certain embodiments, $R^5$ is selected from the group consisting of H and $CH_3$.

In certain embodiments, $R^6$ is selected from the group consisting of $CH_3$, ethyl, propyl, $CH_2CHF_2$, $CH_2CF_3$, $CH_2$(cyclopropyl), sec-Bu, $CH_2$(2-pyrimidine), $CH_2CH=CH_2$ and $CH_2C(CH_3)=CH_2$.

In certain embodiments, $R^7$ is selected from the group consisting of H and $CH_3$.

In certain embodiments, $R^8$ is selected from the group consisting of $CH_3$, ethyl, propyl, $CH_2CHF_2$, $CH_2CF_3$, $CH_2$(cyclopropyl), sec-Bu, $CH_2$(2-pyrimidine), benzyl, $CH_2CH_2OCH_3$ and $CH_2CCH$.

In certain embodiments, $R^9$ and $R^{10}$ are independently selected from the group consisting H, $CH_3$, ethyl and $CF_3$.

In certain embodiments, $R^{11}$ is selected from the group consisting of H and a fused phenylene ring.

In certain embodiments, L is selected from the group consisting of methylene, methyl substituted methylene, dimethyl substituted methylene and ethylene.

In certain embodiments, m and n are independently selected from the group consisting of 1 and 2.

In certain embodiments, p and q are independently selected from the group consisting of 0, 3 and 4.

In certain embodiments, $Y^1$ is selected from the group consisting of

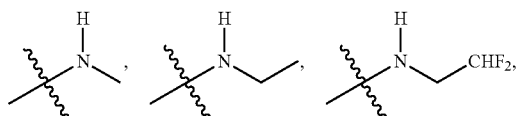

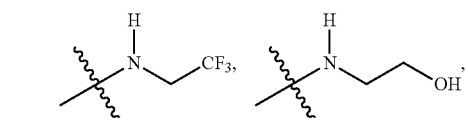

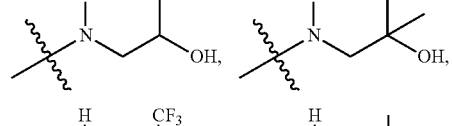

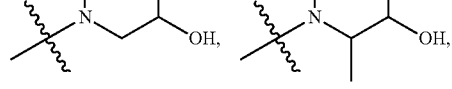

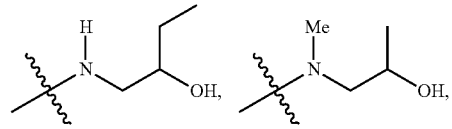

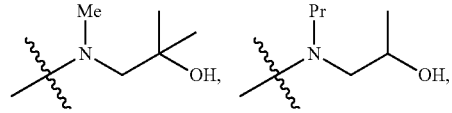

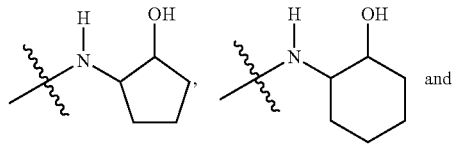
and

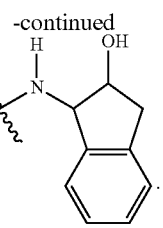
.

In certain embodiments, $Y^2$ is selected from the group consisting of

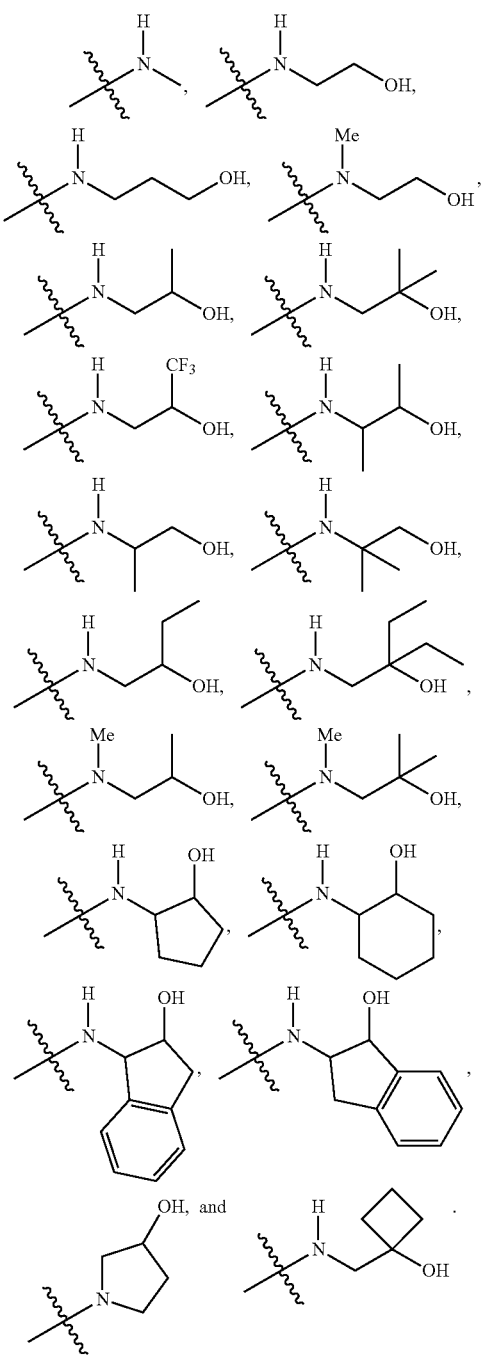

In certain embodiments, the compound of formula (I) is selected from the group consisting of:
2-(2,6-Bis-methylamino-8-propylamino-pyrimido[5,4-d]pyrimidin-4-ylamino)-ethanol (4); 2-[(2,6-Bis-methylamino-8-propylamino-pyrimido[5,4-d]pyrimidin-4-yl)-methyl-amino]-ethanol (6); 3-(2,6-Bis-methylamino-8-propylamino-pyrimido[5,4-d]pyrimidin-4-ylamino)-propan-1-ol (8); 1-(2,6-Bis-methylamino-8-propylamino-pyrimido[5,4-d]-pyrimidin-4-ylamino)-propan-2-ol (10); (S)-1-(2,6-Bis-methylamino-8-propylamino-pyrimido[5,4-d]pyrimidin-4-ylamino)-propan-2-ol (12); (R)-1-(2,6-Bis-methylamino-8-propylamino-pyrimido[5,4-d]pyrimidin-4-ylamino)-propan-2-ol (14); 2-(2,6-Bis-methylamino-8-propylamino-pyrimido[5,4-d]-pyrimidin-4-ylamino)-2-methyl-propan-1-ol (16); (S)-2-(2,6-Bis-methylamino-8-propylamino-pyrimido[5,4-d]-pyrimidin-4-ylamino)-propan-1-ol (18); (R)-2-(2,6-Bis-methylamino-8-propylamino-pyrimido[5,4-d]-pyrimidin-4-ylamino)-propan-1-ol (20); 3-(2,6-Bis-methylami-no-8-propylamino-pyrimido[5,4-d]pyrimidin-4-ylamino)-1,1,1-trifluoro-propan-2-ol (22); 1-(2,6-Bis-methylamino-8-propylamino-pyrimido[5,4-d]pyrimidin-4-ylamino)-butan-2-ol (24); 3-(2,6-Bis-methylamino-8-propylamino-pyrimido[5,4-d]pyrimidin-4-ylamino)-butan-2-ol (26); 2-(2,6-Bis-ethylamino-8-propylamino-pyrimido[5,4-d]pyrimidin-4-ylamino)-ethanol (27); 2-[8-Propylamino-2,6-bis-(2,2,2-trifluoro-ethylamino)-pyrimido[5,4-d]pyrimidin-4-ylamino]-ethanol (28); 1-(2,6-Bis-methylamino-8-propylamino-pyrimido[5,4-d]pyrimidin-4-ylamino)-2-methyl-propan-2-ol (31); 1-(2,6-Bis-ethylamino-8-propylamino-pyrimido[5,4-d]-pyrimidin-4-ylamino)-2-methyl-propan-2-ol (32); 1-[2,6-Bis-(2,2-difluoro-ethylamino)-8-propylamino-pyrimido[5,4-d]-pyrimidin-4-ylamino]-2-methyl-propan-2-ol (33); 2-Methyl-1-[8-propylamino-2,6-bis-(2,2,2-trifluoro-ethylamino)-pyrimido[5,4-d]pyrimidin-4-ylamino]-propan-2-ol (34); 1-[8-(2,2-difluoro-ethylamino)-2,6-bis-methylamino-pyrimido[5,4-d]pyrimidin-4-ylamino]-2-methyl-propan-2-ol (36); 1-{2,6-bis-methylamino-8-[(pyrimidin-2-ylmethyl)-amino]-pyrimido[5,4-d]pyrimidin-4-ylamino}-2-methyl-propan-2-ol (38); 1-[8-((R)-sec-butylamino)-2,6-bis-methylamino-pyrimido[5,4-d]-pyrimidin-4-ylamino]-2-methyl-propan-2-ol (40); 1-[8-((S)-sec-butylamino)-2,6-bis-methylamino-pyrimido[5,4-d]-pyrimidin-4-ylamino]-2-methyl-propan-2-ol (42); 1-(8-benzylamino-2,6-bis-methylamino-pyrimido[5,4-d]pyrimidin-4-ylamino)-2-methyl-propan-2-ol (44); 1-[8-(cyclopropylmethyl-amino)-2,6-bis-methylamino-pyrimido[5,4-d]pyrimidin-4-ylamino]-2-methyl-propan-2-ol (46); 1-[8-(2,2-difluoro-ethylamino)-2,6-bis-ethylamino-pyrimido[5,4-d]pyrimidin-4-ylamino]-2-methyl-propan-2-ol (47); 2-methyl-1-(2,6,8-tris-methylamino-pyrimido[5,4-d]-pyrimidin-4-ylamino)-propan-2-ol (48); 2-methyl-1-(2,6,8-tris-ethylamino-pyrimido[5,4-d]-pyrimidin-4-ylamino)-propan-2-ol (49); 2-(2,6,8-tris-methylamino-pyrimido[5,4-d]pyrimidin-4-ylamino)-ethanol (52); 2-[8-(cyclopropylmethyl-amino)-2,6-bis-methylamino-pyrimido[5,4-d]pyrimidin-4-ylamino]-ethanol (54); 2-[8-(2-methoxy-ethylamino)-2,6-bis-methylamino-pyrimido[5,4-d]pyrimidin-4-ylamino]-ethanol (56); 2-(2,6-bis-methylamino-8-prop-2-ynylamino-pyrimido[5,4-d]pyrimidin-4-ylamino)-ethanol (58); 2-[8-(2,2-difluoro-ethylamino)-2,6-bis-methylamino-pyrimido[5,4-d]-pyrimidin-4-ylamino]-ethanol (60); 2-[2,6-bis-methylamino-8-(2,2,2-trifluoro-ethylamino)-pyrimido[5,4-d]pyrimidin-4-ylamino]-ethanol (62); 2-(8-benzylamino-2,6-bis-methylamino-pyrimido[5,4-d]-pyrimidin-4-ylamino)-ethanol (64); 3-(8-ethylamino-2,6-bis-methylamino-pyrimido[5,4-d]-pyrimidin-4-ylamino)-propan-1-ol (67); 1-(2,6-bis-methylamino-8-propylamino-pyrimido[5,4-d]pyrimidin-4-yl)-pyrrolidin-3-ol (71); 1-[(2,6-bis-methylamino-8-propylamino-pyrimido[5,4-d]pyrimidin-4-ylamino)-methyl]-cyclobutanol (72); 1-[(2,6-bis-methylamino-8-propylamino-pyrimido[5,4-d]-pyrimidin-4-yl)-methyl-amino]-propan-2-ol (73); 3-[(2,6-bis-methylamino-8-propylamino-pyrimido[5,4-d]pyrimidin-4-ylamino)-methyl]-pentan-3-ol (74); 1-[(2,6-bis-methylamino-8-propylamino-pyrimido[5,4-d]pyrimidin-4-yl)-methyl-amino]-2-methyl-propan-2-ol (76); (1R,2S)-1-(2,6-bis-methylamino-8-propylamino-pyrimido[5,4-d]-pyrimidin-4-ylamino)-indan-2-ol (77); (1S,2S)-1-(2,6-bis-methylamino-8-propylamino-pyrimido[5,4-d]-pyrimidin-4-ylamino)-indan-2-ol (78); (1S,2R)-1-(2,6-bis-methylamino-8-propylamino-pyrimido[5,4-d]pyrimidin-4-ylamino)-indan-2-ol (79); (1R,2R)-1-(2,6-bis-methylamino-8-propylamino-pyrimido[5,4-d]-pyrimidin-4-ylamino)-indan-2-ol (80); (2-(2,6-bis-methylamino-8-propylamino-pyrimido[5,4-d]-pyrimidin-4-ylamino)-indan-1-ol (81); (1R,2S)-2-(2,6-bis-methylamino-8-propylamino-pyrimido[5,4-d]pyrimidin-4-ylamino)-cyclohexanol (82); (1S,2S)-2-(2,6-bis-methylamino-8-propylamino-pyrimido[5,4-d]pyrimidin-4-ylamino)-cyclohexanol (83); (1S,2R)-2-(2,6-bis-methylamino-8-propylamino-pyrimido[5,4-d]pyrimidin-4-ylamino)-cyclohexanol (84); (1R,2R)-2-(2,6-bis-methylamino-8-propylamino-pyrimido[5,4-d]pyrimidin-4-ylamino)-cyclohexanol (85); (1S,2S)-2-(2,6-bis-methylamino-8-propylamino-pyrimido[5,4-d]pyrimidin-4-ylamino)-cyclopentanol (86); (1R,2R)-2-(2,6-bis-methylamino-8-propylamino-pyrimido[5,4-d]pyrimidin-4-ylamino)-cyclopentanol (87); 2-[6-(cyclopropylmethyl-amino)-4,8-bis-methylamino-pyrimido[5,4-d]pyrimidin-2-ylamino]-ethanol (90); 2-(4,8-bis-methylamino-6-propylamino-pyrimido[5,4-d]pyrimidin-2-ylamino)-ethanol (91); 2-(6-dimethylamino-4,8-bis-methylamino-pyrimido[5,4-d]-pyrimidin-2-ylamino)-ethanol (92); 1-(4,8-bis-methylamino-6-propylamino-pyrimido[5,4-d]pyrimidin-2-ylamino)-2-methyl-propan-2-ol (94); 1-(4,8-bis-methylamino-6-propylamino-pyrimido[5,4-d]-pyrimidin-2-ylamino)-propan-2-ol (95); 1-[(4,8-bis-methylamino-6-propylamino-pyrimido[5,4-d]pyrimidin-2-yl)-methyl-amino]-2-methyl-propan-2-ol (96); 1-[(4,8-bis-methylamino-6-propylamino-pyrimido[5,4-d]pyrimidin-2-yl)-methyl-amino]-propan-2-ol (97); 1-[6-((R)-sec-butylamino)-4,8-bis-methylamino-pyrimido[5,4-d]-pyrimidin-2-ylamino]-2-methyl-propan-2-ol (99); (R)-1-[6-((R)-sec-butylamino)-4,8-bis-methylamino-pyrimido[5,4-d]pyrimidin-2-ylamino]-propan-2-ol (100); (S)-1-[6-((R)-sec-butylamino)-4,8-bis-methylamino-pyrimido[5,4-d]pyrimidin-2-ylamino]-propan-2-ol (101); 1-[6-((S)-sec-butylamino)-4,8-bis-methylamino-pyrimido[5,4-d]-pyrimidin-2-ylamino]-2-methyl-propan-2-ol (103); (R)-1-[6-((S)-sec-butylamino)-4,8-bis-methylamino-pyrimido[5,4-d]pyrimidin-2-ylamino]-propan-2-ol (104); (S)-1-[6-((S)-sec-butylamino)-4,8-bis-methylamino-pyrimido[5,4-d]pyrimidin-2-ylamino]-propan-2-ol (105); 1-[6-(2,2-difluoro-ethylamino)-4,8-bis-methylamino-pyrimido[5,4-d]pyrimidin-2-ylamino]-2-methyl-propan-2-ol (107); 1-{4,8-bis-methylamino-6-[(pyrimidin-2-ylmethyl)-amino]-pyrimido[5,4-d]pyrimidin-2-ylamino}-2-methyl-propan-2-ol (109); 3-(4,8-bis-methylamino-6-propylamino-pyrimido[5,4-d]pyrimidin-2-ylamino)-1,1,1-trifluoro-propan-2-ol (111); (S)-1-(4,8-bis-methylamino-6-propylamino-pyrimido[5,4-d]pyrimidin-2-ylamino)-propan-2-ol (113); (R)-1-(4,8-bis-methylamino-6-propylamino-pyrimido[5,4-d]pyrimidin-2-ylamino)-propan-2-ol (115); 1-(4,8-bis-methylamino- 6-propylamino-pyrimido[5,4-d]pyrimidin-2-ylamino)-butan-2-ol (117); 3-(4,8-Bis-methylamino-6-propylamino-pyrimido[5,4-d]pyrimidin-2-ylamino)-butan-2-ol (119); (1R,2S)-1-(4,8-bis-methylamino-6-propylamino-pyrimido[5,4-d]-pyrimidin-2-ylamino)-indan-2-ol (123); (1S,2S)-1-(4,8-bis-methylamino-6-propylamino-pyrimido[5,4-d]-pyrimidin-2-ylamino)-indan-2-ol (125); (1S,2R)-1-(4,8-bis-methylamino-6-propylamino-pyrimido[5,4-d]-pyrimidin-2-ylamino)-indan-2-ol (127); (1R,2R)-1-(4,8-bis-methylamino-6-propylamino-pyrimido[5,4-d]-pyrimidin-2-ylamino)-indan-2-ol (129); (1R,2S)-2-(4,8-bis-methylamino-6-propylamino-pyrimido[5,4-d]pyrimidin-2-ylamino)-cyclohexanol (131); (1S,2S)-2-(4,8-bis-methylamino-6-propylamino-pyrimido[5,4-d]pyrimidin-2-ylamino)-cyclohexanol (133); (1S,2R)-2-(4,8-bis-methylamino-6-propylamino-pyrimido[5,4-d]pyrimidin-2-ylamino)-cyclohexanol (135); (1R,2R)-2-(4,8-bis-methylamino-6-propylamino-pyrimido[5,4-d]pyrimidin-2-ylamino)-cyclohexanol (137); (1S,2S)-2-(4,8-bis-methylamino-6-propylamino-pyrimido[5,4-d]pyrimidin-2-ylamino)-cyclopentanol (139); (1R,2R)-2-(4,8-bis-methylamino-6-propylamino-pyrimido[5,4-d]pyrimidin-2-ylamino)-cyclopentanol (141); (S)-1-[6-(cyclopropylmethyl-amino)-4,8-bis-methylamino-pyrimido[5,4-d]pyrimidin-2-ylamino]-propan-2-ol (142); (S)-1-(6-allylamino-4,8-bis-methylamino-pyrimido[5,4-d]pyrimidin-2-ylamino)-propan-2-ol (143); (R)-1-[6-(cyclopropylmethyl-amino)-4,8-bis-methylamino-pyrimido[5,4-d]pyrimidin-2-ylamino]-propan-2-ol (144); (R)-1-(6-allylamino-4,8-bis-methylamino-pyrimido[5,4-d]pyrimidin-2-ylamino)-propan-2-ol (145); 1-[6-(cyclopropylmethyl-amino)-4,8-bis-methylamino-pyrimido[5,4-d]pyrimidin-2-ylamino]-butan-2-ol (146); 1-(6-ethylamino-4,8-bis-methylamino-pyrimido[5,4-d]pyrimidin-2-ylamino)-butan-2-ol (147); 2-methyl-1-(4,6,8-tris-methylamino-pyrimido[5,4-d]pyrimidin-2-ylamino)-propan-2-ol (149); 2-(6-allylamino-4,8-bis-methylamino-pyrimido[5,4-d]pyrimidin-2-ylamino)-ethanol (154); (S)-1-[(6-allylamino-4,8-bis-methylamino-pyrimido[5,4-d]-pyrimidin-2-yl)-propyl-amino]-propan-2-ol (155); (S)-1-[(6-allylamino-4,8-bis-methylamino-pyrimido[5,4-d]pyrimidin-2-yl)-methyl-amino]-propan-2-ol (156); (R)-1-[6-(2-methyl-allylamino)-4,8-bis-methylamino-pyrimido[5,4-d]-pyrimidin-2-ylamino]-propan-2-ol (158); (S)-1-[6-(2-methyl-allylamino)-4,8-bis-methylamino-pyrimido[5,4-d]-pyrimidin-2-ylamino]-propan-2-ol (159); 2-(4,8-bis-ethylamino-6-propylamino-pyrimido[5,4-d]pyrimidin-2-ylamino)-ethanol (162); 1-(4,8-bis-ethylamino-6-propylamino-pyrimido[5,4-d]pyrimidin-2-ylamino)-2-methyl-propan-2-ol (163); (S)-1-(4,6,8-Tris-ethylamino-pyrimido[5,4-d]pyrimidin-2-ylamino)-propan-2-ol (165); (S)-1-(4,8-bis-ethylamino-6-propylamino-pyrimido[5,4-d]-pyrimidin-2-ylamino)-propan-2-ol (166); (R)-1-(4,6,8-tris-ethylamino-pyrimido[5,4-d]pyrimidin-2-ylamino)-propan-2-ol (168); (R)-1-(4,8-bis-ethylamino-6-propylamino-pyrimido[5,4-d]-pyrimidin-2-ylamino)-propan-2-ol (169); (R)-1-[4,8-bis-ethylamino-6-(2-methyl-allylamino)-pyrimido[5,4-d]-pyrimidin-2-ylamino]-propan-2-ol (174); (S)-1-[4,8-bis-ethylamino-6-(2-methyl-allylamino)-pyrimido[5,4-d]-pyrimidin-2-ylamino]-propan-2-ol (175); a salt, solvate, enantiomer, diastereoisomer or tautomer thereof; and any combinations thereof.

In certain embodiments, the salt comprises an acid that is at least one selected from the group consisting of sulfuric, hydrochloric, hydrobromic, hydroiodic, nitric, carbonic, phosphoric, formic, acetic, propionic, succinic, glycolic, gluconic, lactic, malic, tartaric, citric, ascorbic, glucuronic, maleic, mandelic, fumaric, pyruvic, aspartic, glutamic, benzoic, anthranilic, 4-hydroxybenzoic, phenylacetic, mandelic, pamoic, methanesulfonic, ethanesulfonic, benzenesulfonic, pantothenic, sulfanilic, stearic, alginic, trifluoromethane sulfonic, 2-hydroxyethanesulfonic, p-toluenesulfonic, cyclohexylaminosulfonic, β-hydroxybutyric, salicylic, galactaric, galacturonic, and saccharin, and any combinations thereof.

In certain embodiments, the at least one compound of the invention is a component of a pharmaceutical composition further including at least one pharmaceutically acceptable carrier.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$ a N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Synthesis

The compounds described herein, and other related compounds having different substituents are synthesized using techniques and materials described herein and as described, for example, in Fieser & Fieser's Reagents for Organic Synthesis, Vol. 1-17 (John Wiley and Sons, 1991); Rodd's Chemistry of Carbon Compounds, Vol. 1-5 and Supplementals (Elsevier Science Publishers, 1989); Organic Reactions, Vol. 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry, 4$^{th}$ Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein. See, for example, Northen, et al., 2002, J. Chem. Soc., Perkin Trans. 1, 108-115; DOI: 10.1039/B102224P.

In non-limiting examples, compounds of formula (I) may be prepared by the additions of primary alkylamines to a chlorinated pyrimido-pyrimidine intermediate (A), in which one alkylamine contains a pendant alcohol moiety (Schemes 1-3). The aminoalkanol can be added at various stages; for example reacted directly with tetrachloro-pyrimido[5,4-d] pyrimidine (A; Scheme 2) or alternatively, added to a mono-alkylamino-trichloro-pyrimido[5,4-d]pyrimidine (B; Scheme 1) or alternatively, added to a bis-alkylamino-dichloro-pyrimido[5,4-d]pyrimidine (F; Scheme 3).

Analogs were also prepared following the general synthetic scheme in which first an amine is added to tetrachloro-pyrimido[5,4-d]pyrimidine (i); secondly an alcohol is added to the resultant alkylamino-trichloro-pyrimido[5,4-d]pyrimidine (ii); and lastly, an amine undergoes bis-addition upon reaction with alkyl-amino-dichloro-pyrimido[5,4-d] pyrimidinyl-alkanol (iii) (Scheme 4).

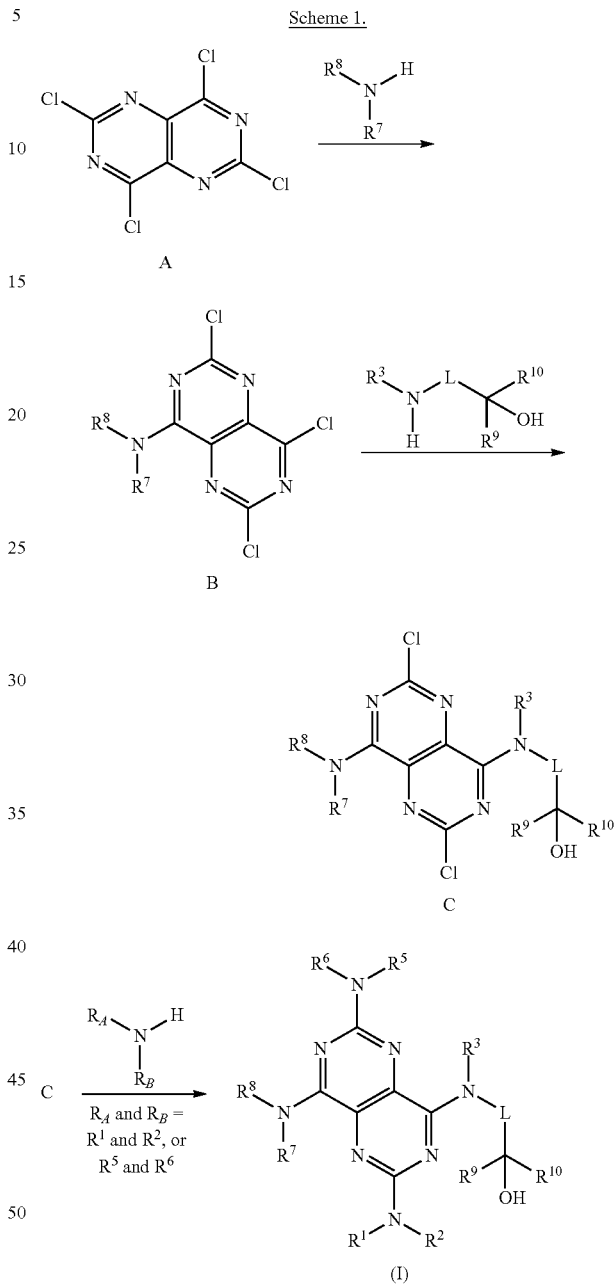

35
-continued
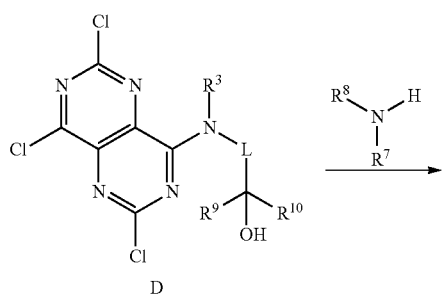
D
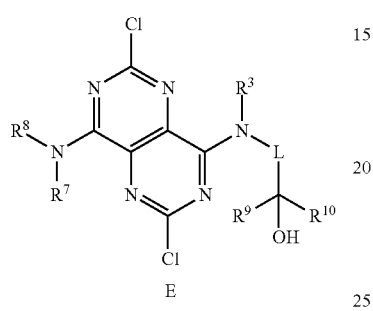
E
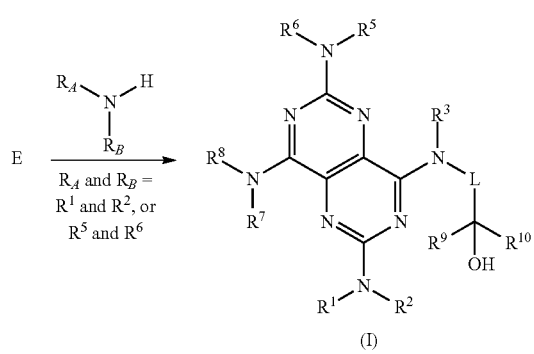
(I)
Scheme 3
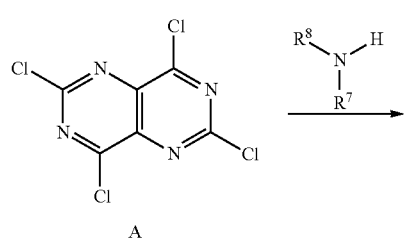
A
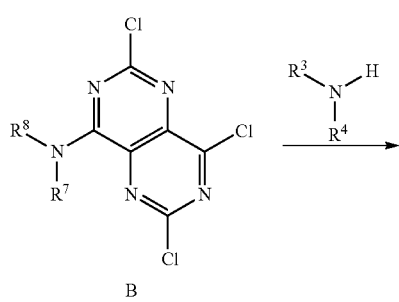
B
36
-continued
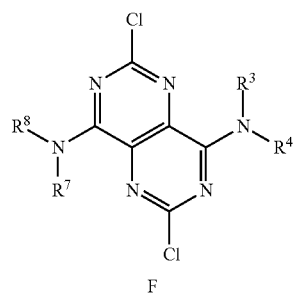
F
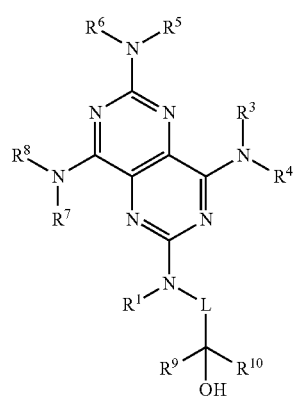
(I)
Scheme 4
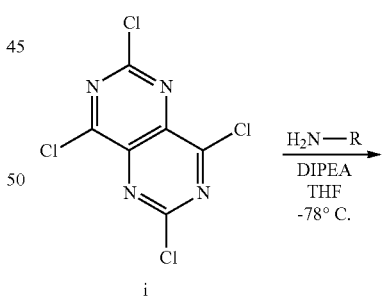
i
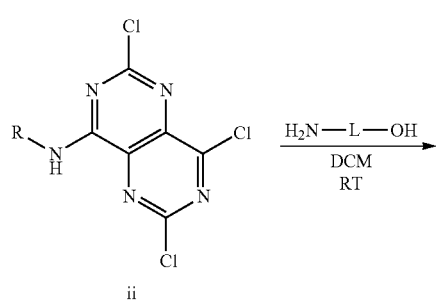
ii

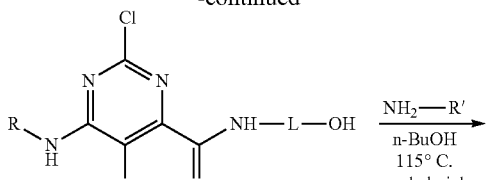

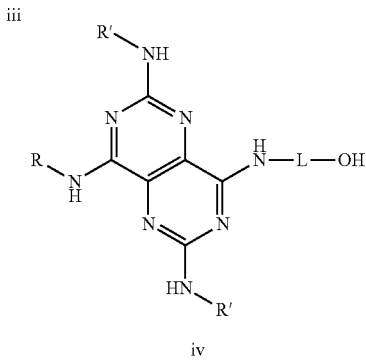

iii iv

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and tert-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as tert-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile tert-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

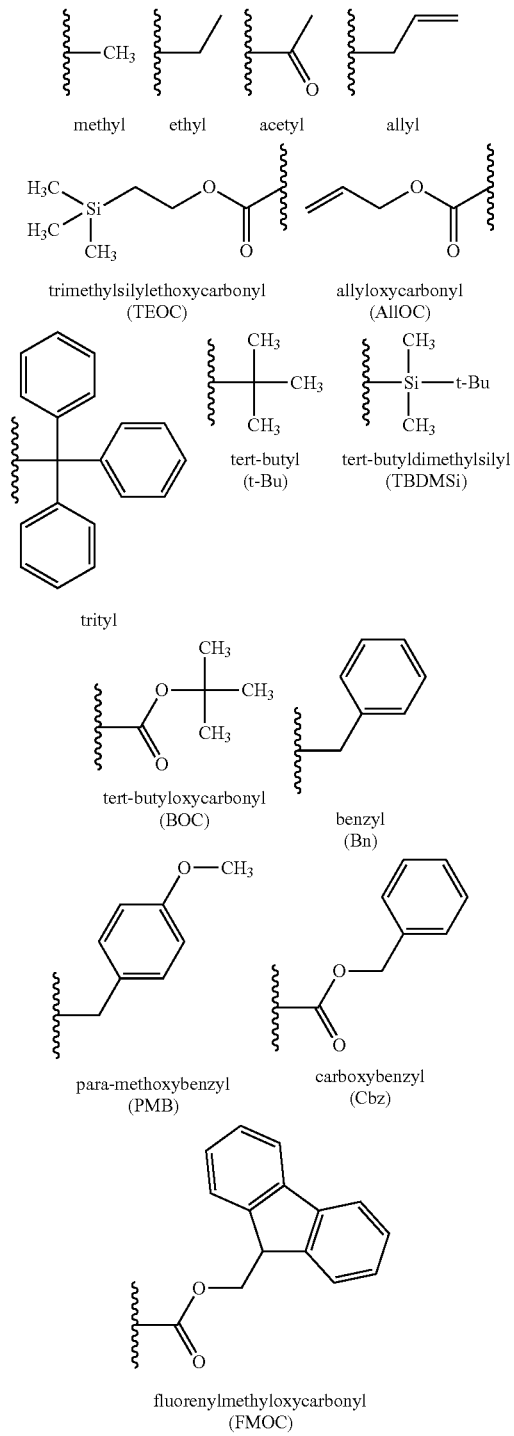

Other protecting groups, plus a detailed description of techniques applicable to the creation of protecting groups and their removal are described in Greene & Wuts, Protective Groups in Organic Synthesis, 3rd Ed., John Wiley &

Sons, New York, N.Y., 1999, and Kocienski, Protective Groups, Thieme Verlag, New York, N.Y., 1994, which are incorporated herein by reference for such disclosure.

The compounds of the invention may be prepared according to the general methodology illustrated in the synthetic schemes described above. The reagents and conditions described herein may be modified to allow the preparation of the compounds of the invention, and such modifications are known to those skilled in the art. The schemes included herein are intended to illustrate but not limit the chemistry and methodologies that one skilled in the art may use to make compounds of the invention.

Salts

The compounds described herein may form salts with acids and/or bases, and such salts are included in the present invention. In certain embodiments, the salts are pharmaceutically acceptable salts. The term "salts" embraces addition salts of free acids and/or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hemisulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Acid addition salts are generally formed by combining the target freebase with a salt former in a solvent, forming a solution, and collecting the salt as a solid. The molar ratio of salt former to free base may vary (e.g., 1:1, 2:1, 1:2, etc.). A ratio of 1:1 may be preferred. Solvents may include, but are not limited to methyl ethyl ketone, methyl isobutyl ketone, ethyl acetate, isopropyl acetate, water, heptane, methyl tert-butyl ether, cyclohexane, toluene, methanol, ethanol, n-propanol, isopropanol, n-butanol, 2-butanol, isoamyl alcohol, tetrahydrofuran and acetonitrile, and mixtures thereof. Mixtures of the freebase and salt former in a solvent may form a clear solution at temperatures ranging from about room temperature to the reflux temperature of the solvent or mixture of solvents being used to prepare the salt. Solid salts may be formed by concentrating the dissolved mixture of salt former and free base, or by allowing the mixture to stand or stir for a period of time, optionally including the cooling of the mixture to a temperature lower than that at which the solution of free base and salt former was initially prepared. Isolated, solid salts may be characterized for stoichiometry using titration, elemental analysis and/or 1H NMR, and for crystallinity using DSC and XRPD and other methodologies known within the art.

Figure 3C:
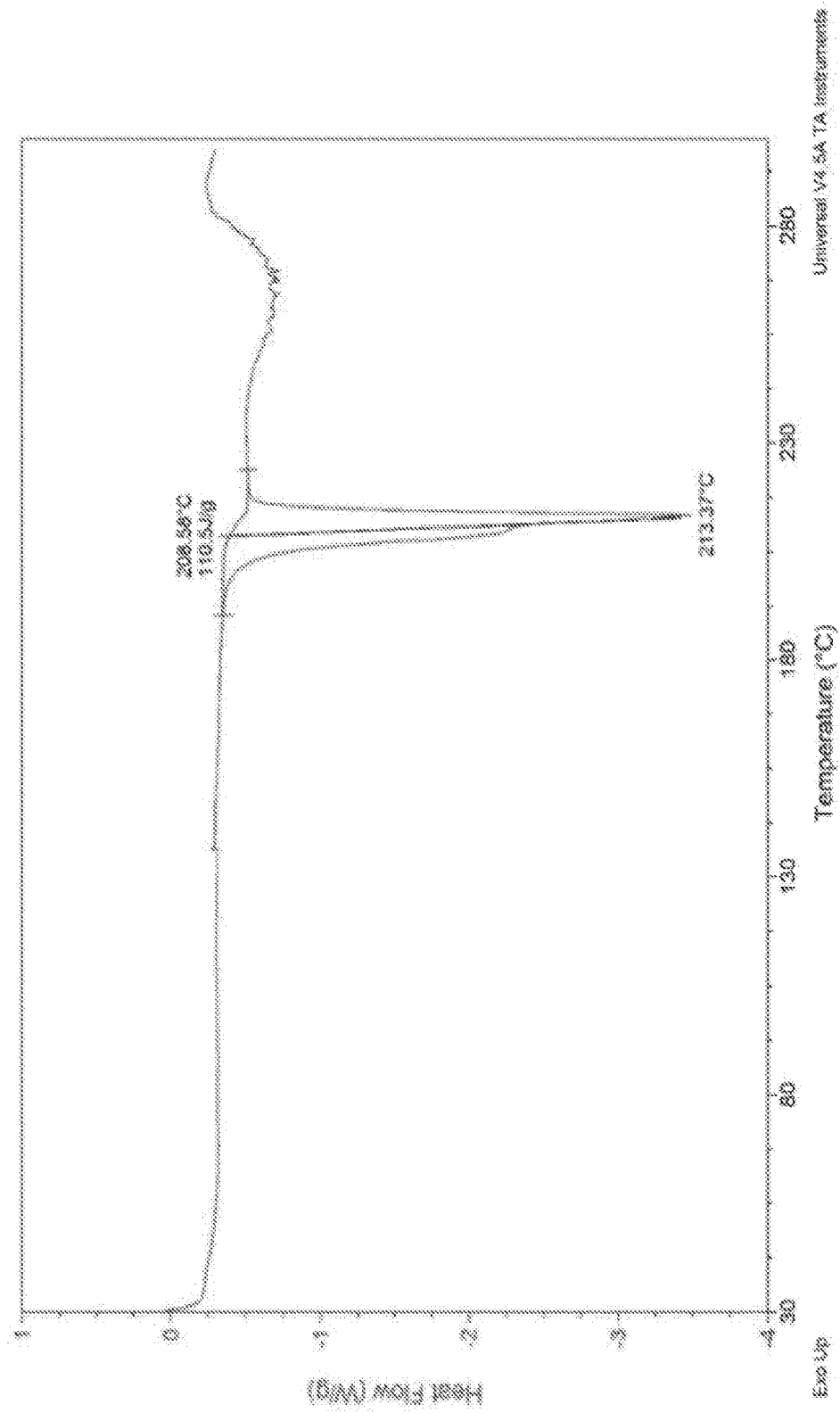
FIG. 3C depicts an illustrative DSC spectrum of 31a (hydrochloride salt form).
Figure 4C:
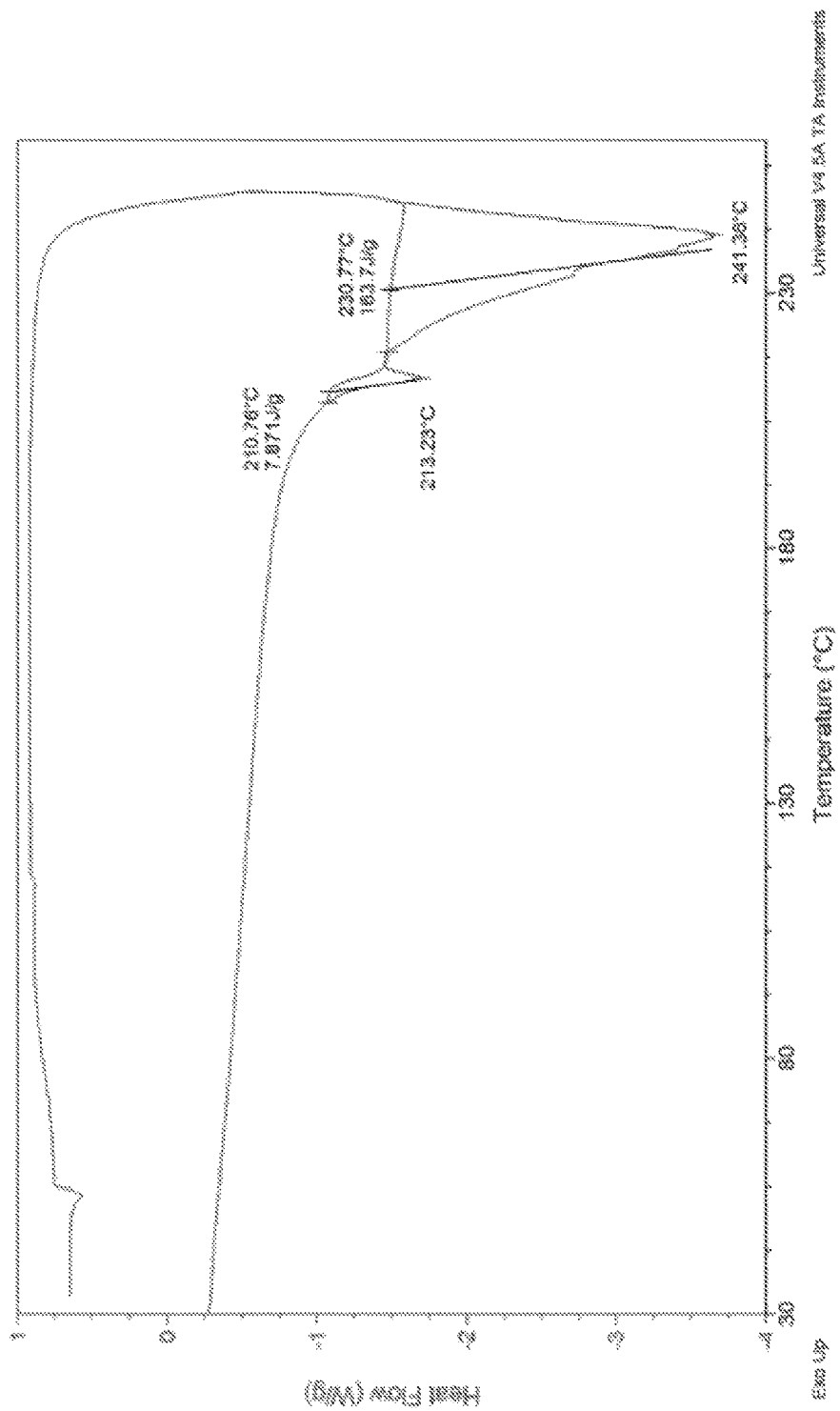
FIG. 4C depicts an illustrative DSC spectrum for 31b (bis-hydrochloride salt form).
Figure 5A:
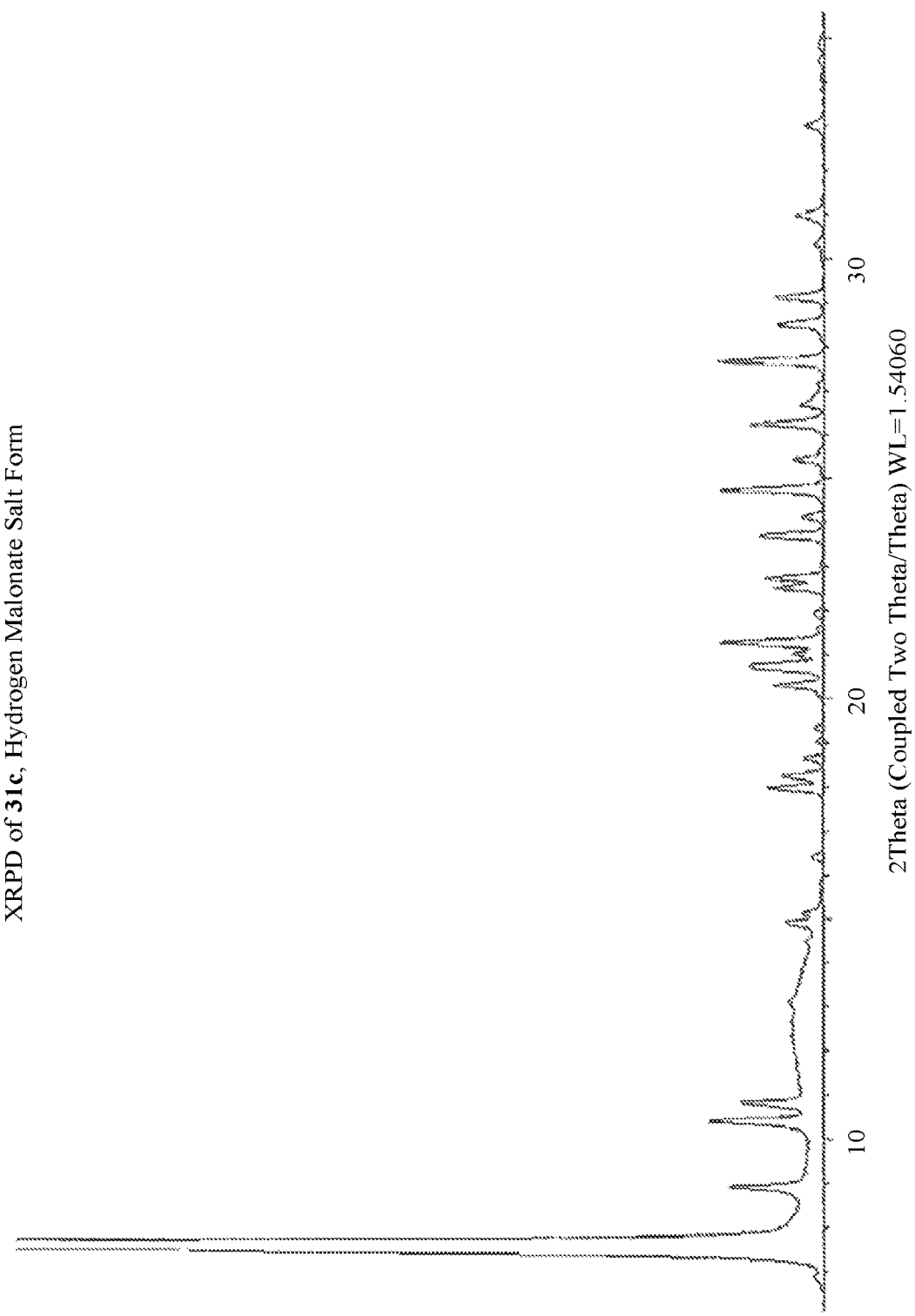
FIG. 5A depicts an illustrative XRPD spectrum for 31c (hydrogen malonate salt form).
Figure 5C:
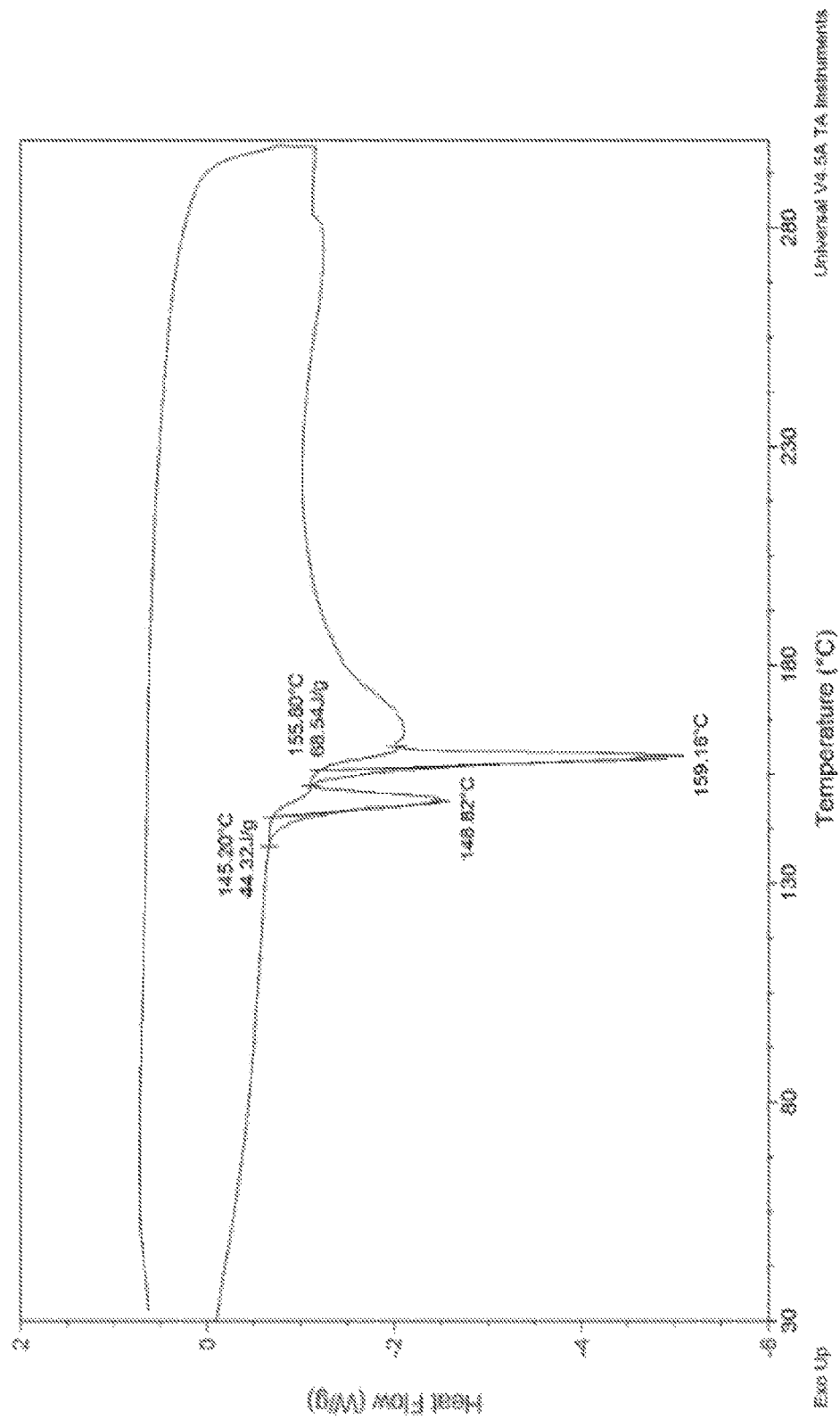
FIG. 5C depicts an illustrative DSC spectrum of 31c (hydrogen malonate salt form).
Figure 6A:
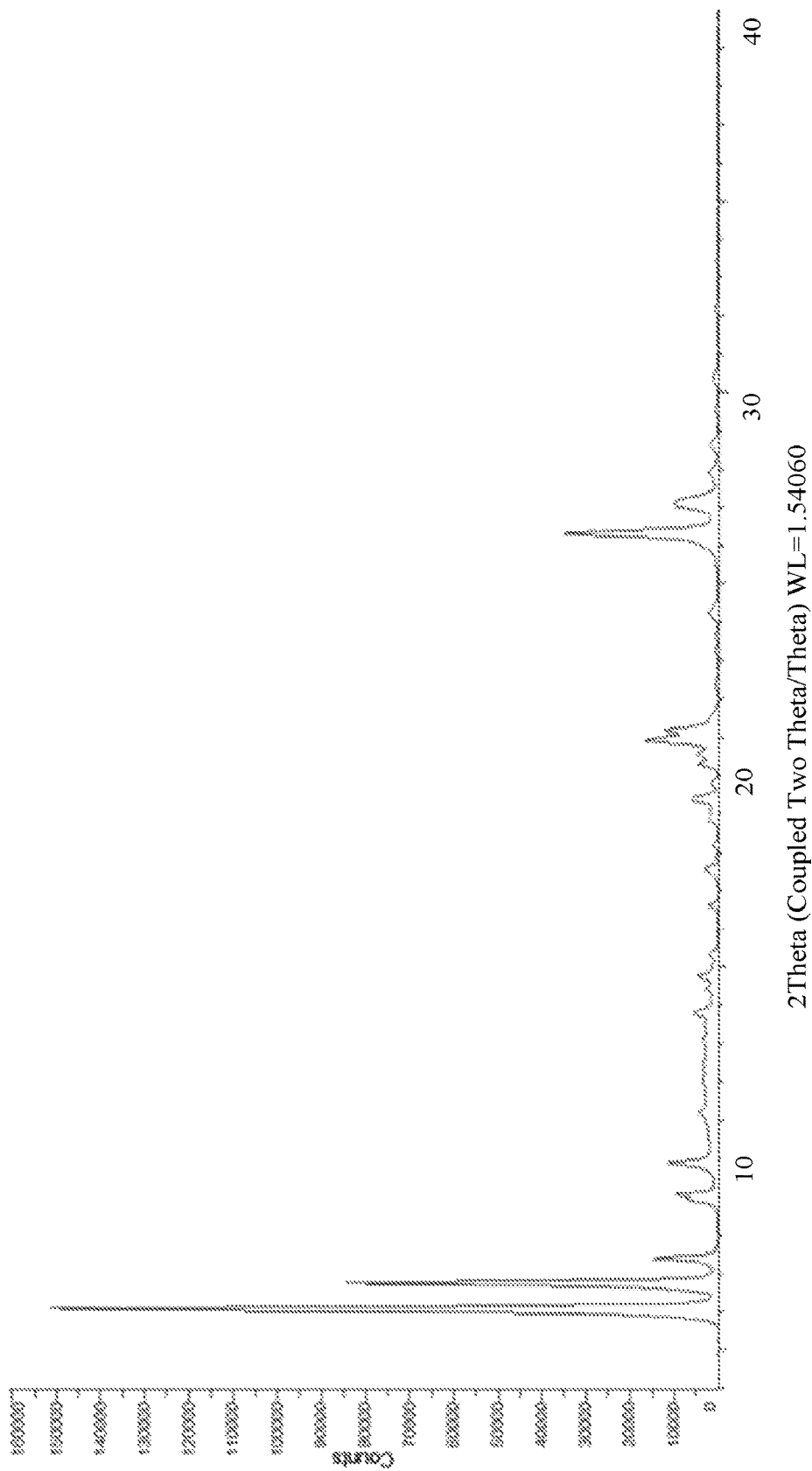
FIG. 6A depicts an illustrative XRPD spectrum of 31d-1 (hydrogen maleinate salt form Mal-A).
Figure 6C:
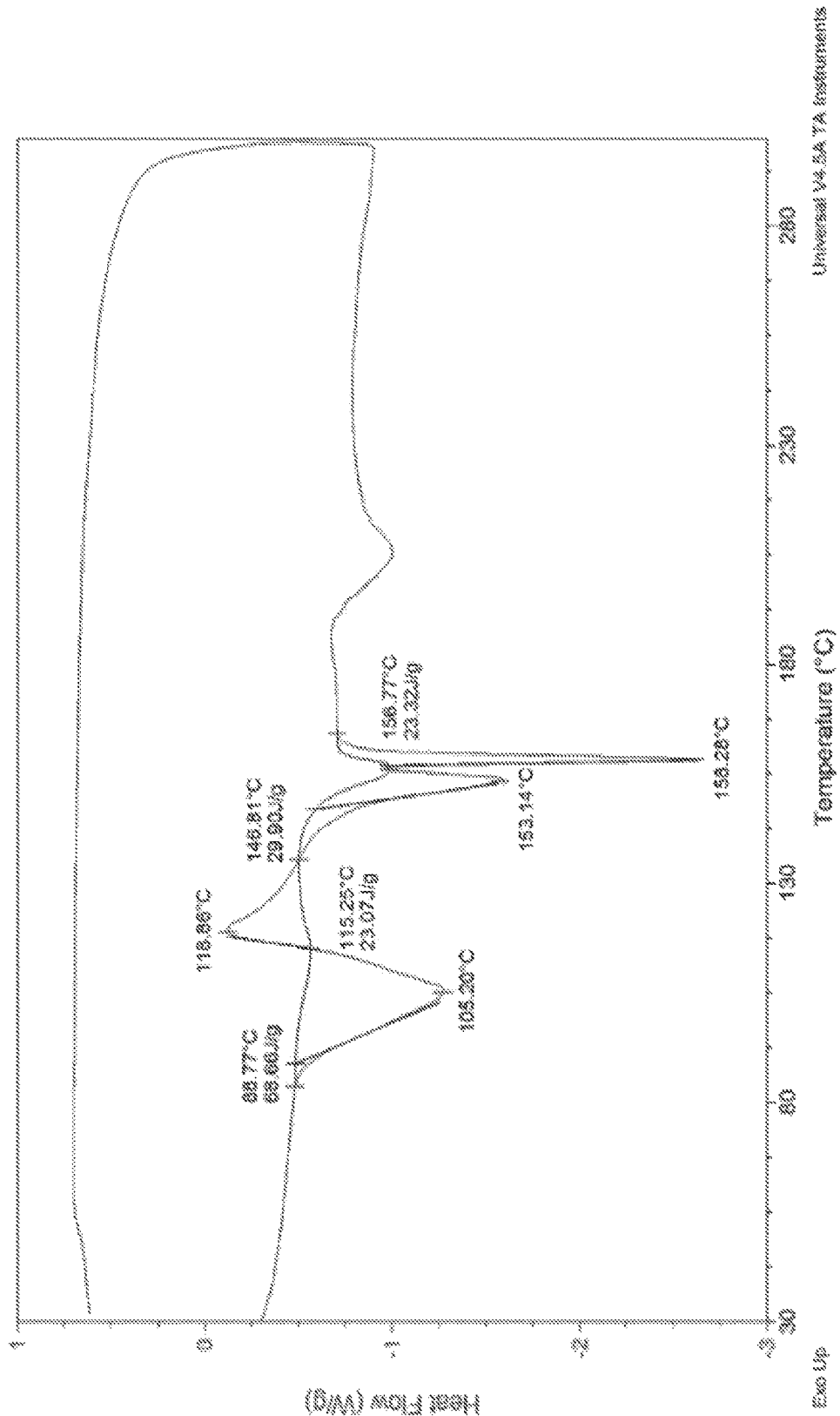
FIG. 6C depicts an illustrative DSC spectrum of 31d-1 (hydrogen maleinate salt form Mal-A).
Figure 7A:
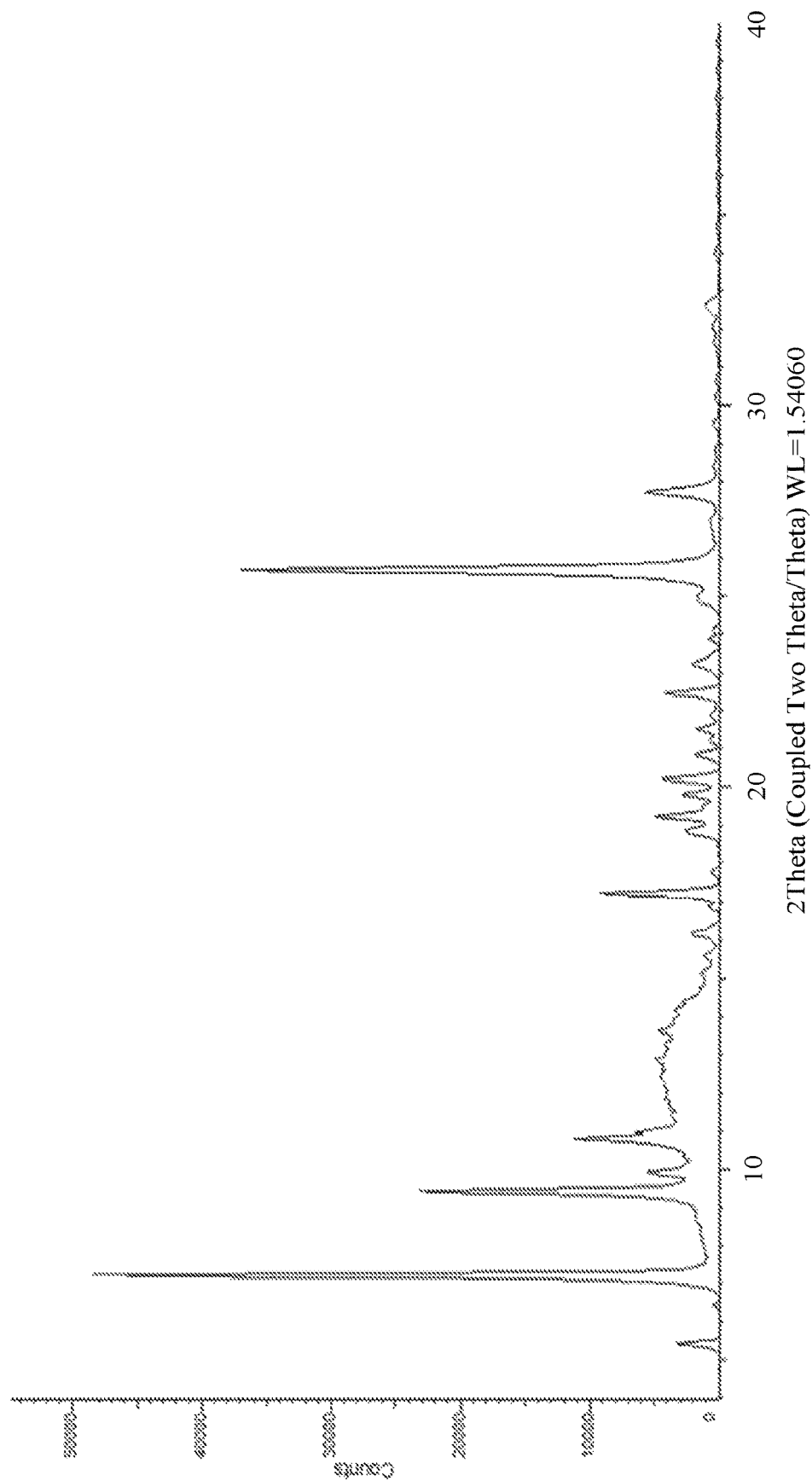
FIG. 7A depicts an illustrative XRPD spectrum of 31d-2 (hydrogen maleinate salt form Mal-B).
Figure 7C:
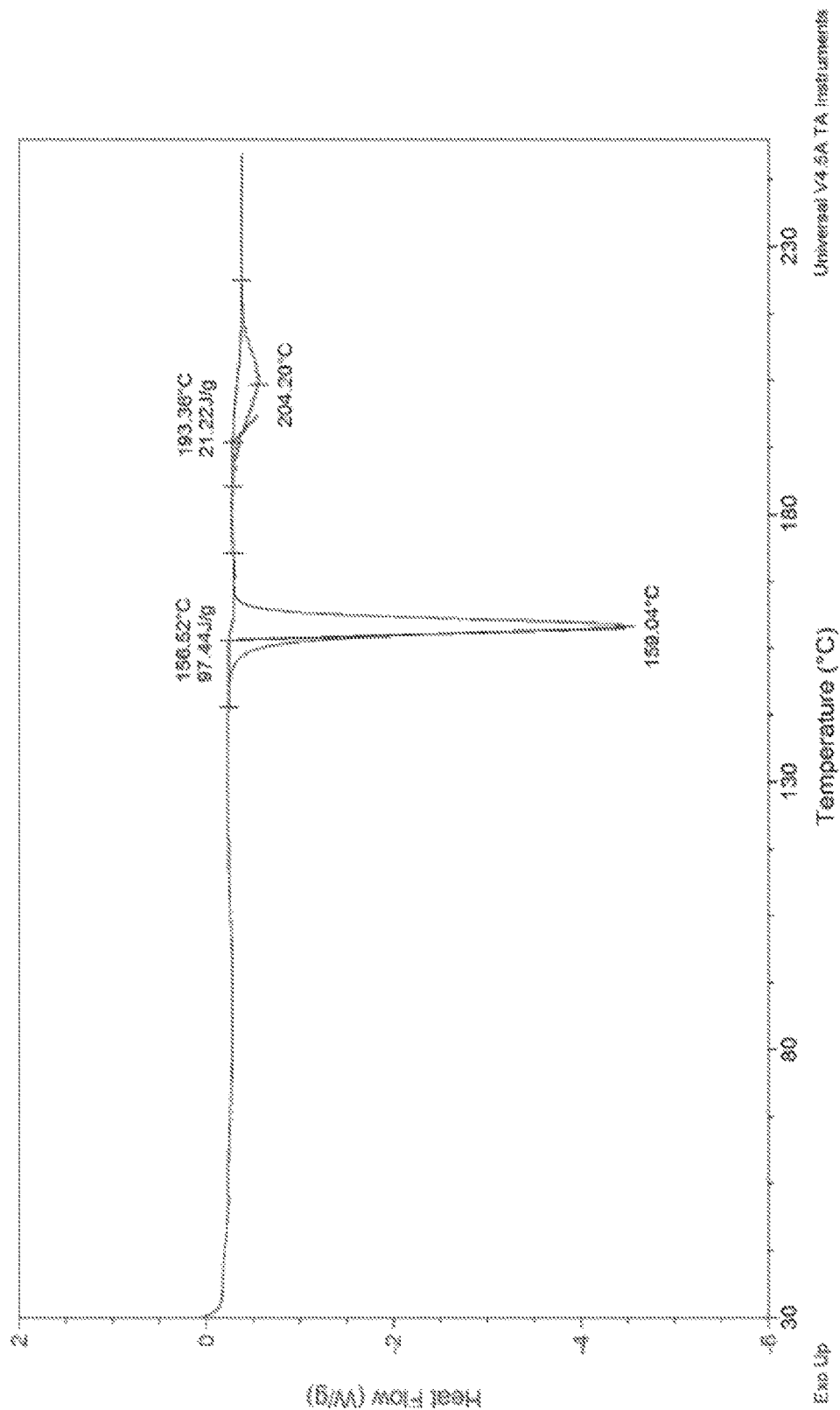
FIG. 7C depicts an illustrative DSC spectrum of 31d-2 (hydrogen maleinate salt form Mal-B).
Figure 8A:
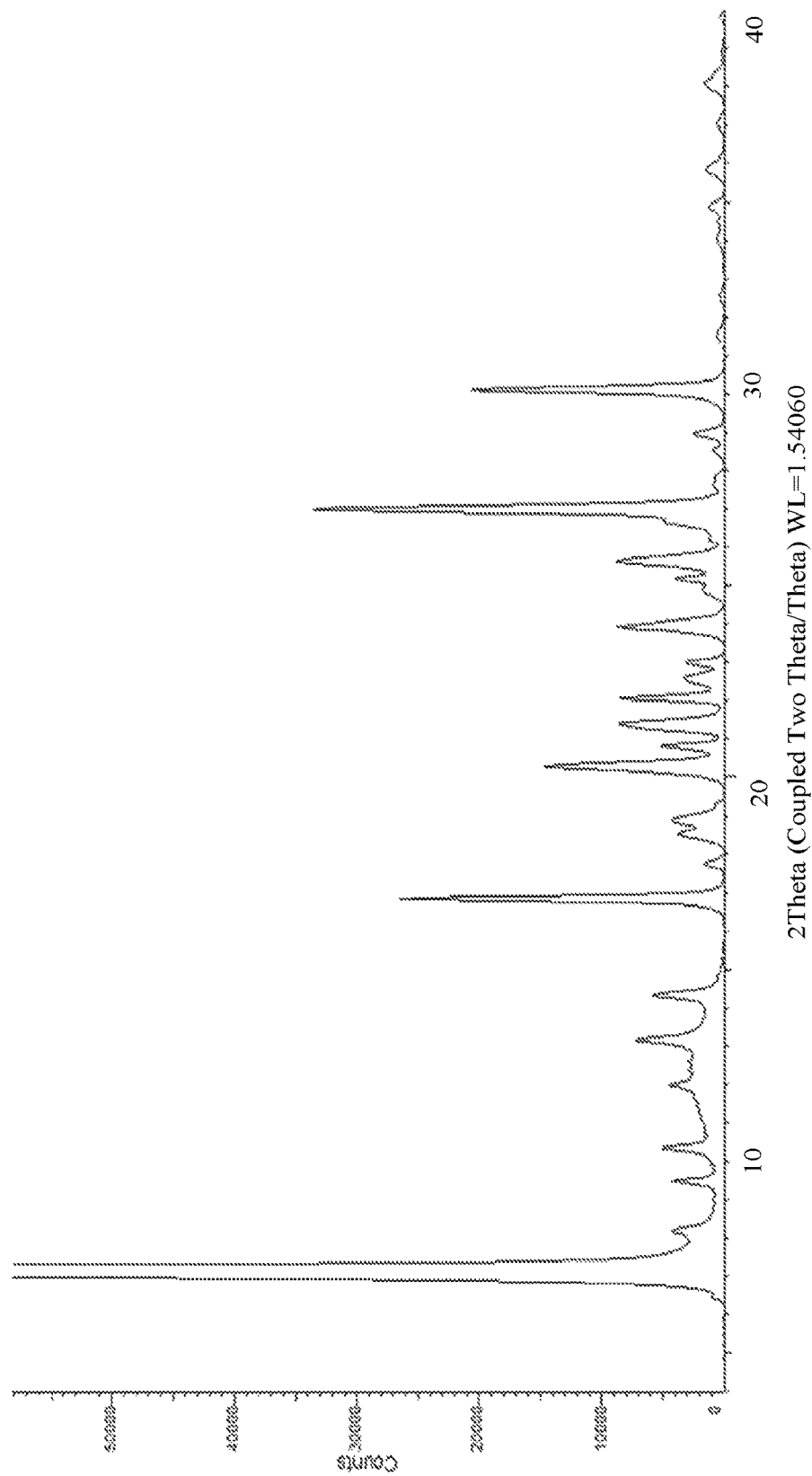
FIG. 8A depicts an illustrative XRPD spectrum of 31e (hydrogen fumarate salt form).
Figure 8C:
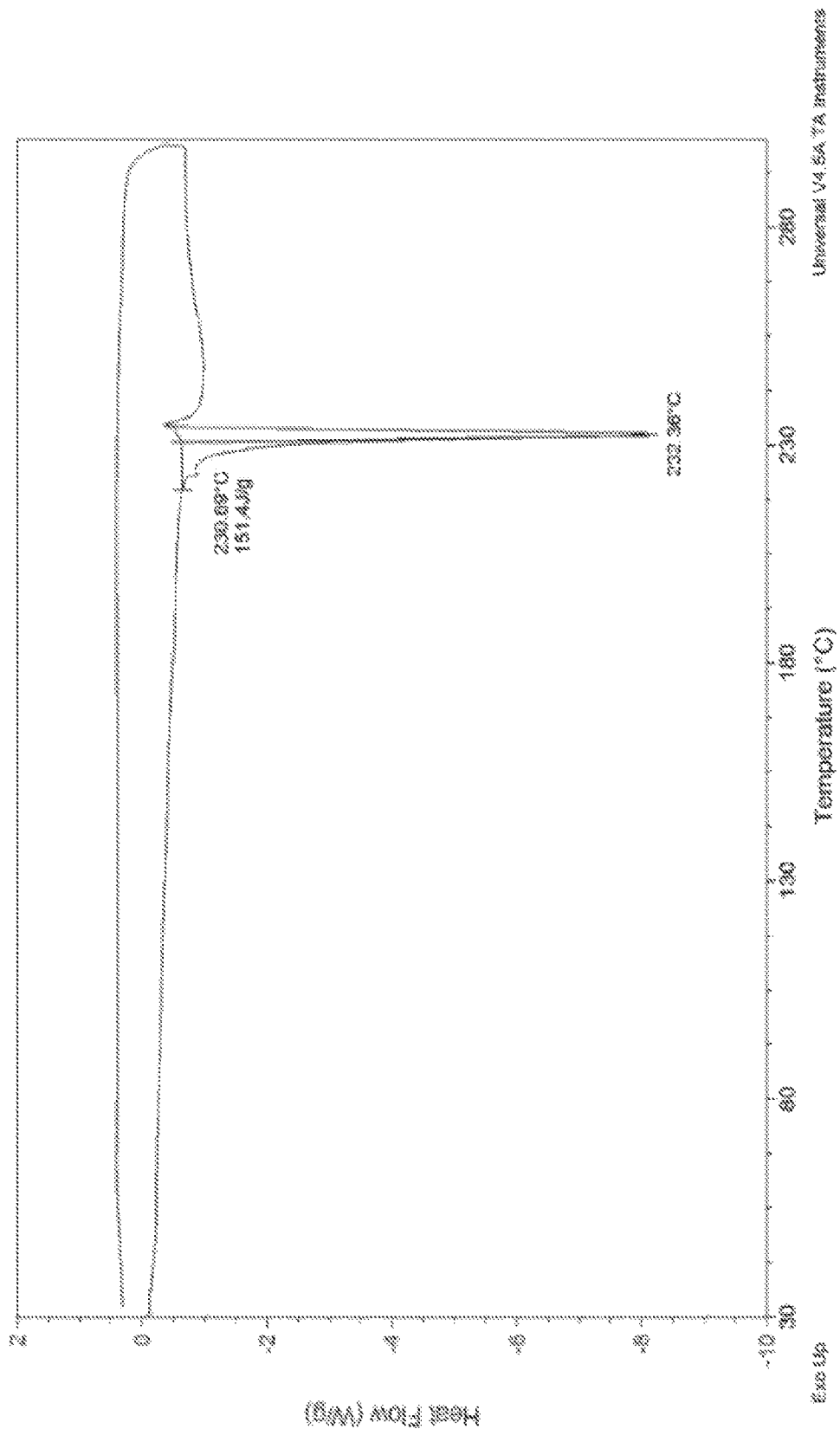
FIG. 8C depicts an illustrative DSC spectrum for 31e (hydrogen fumarate salt form).
Figure 9A:
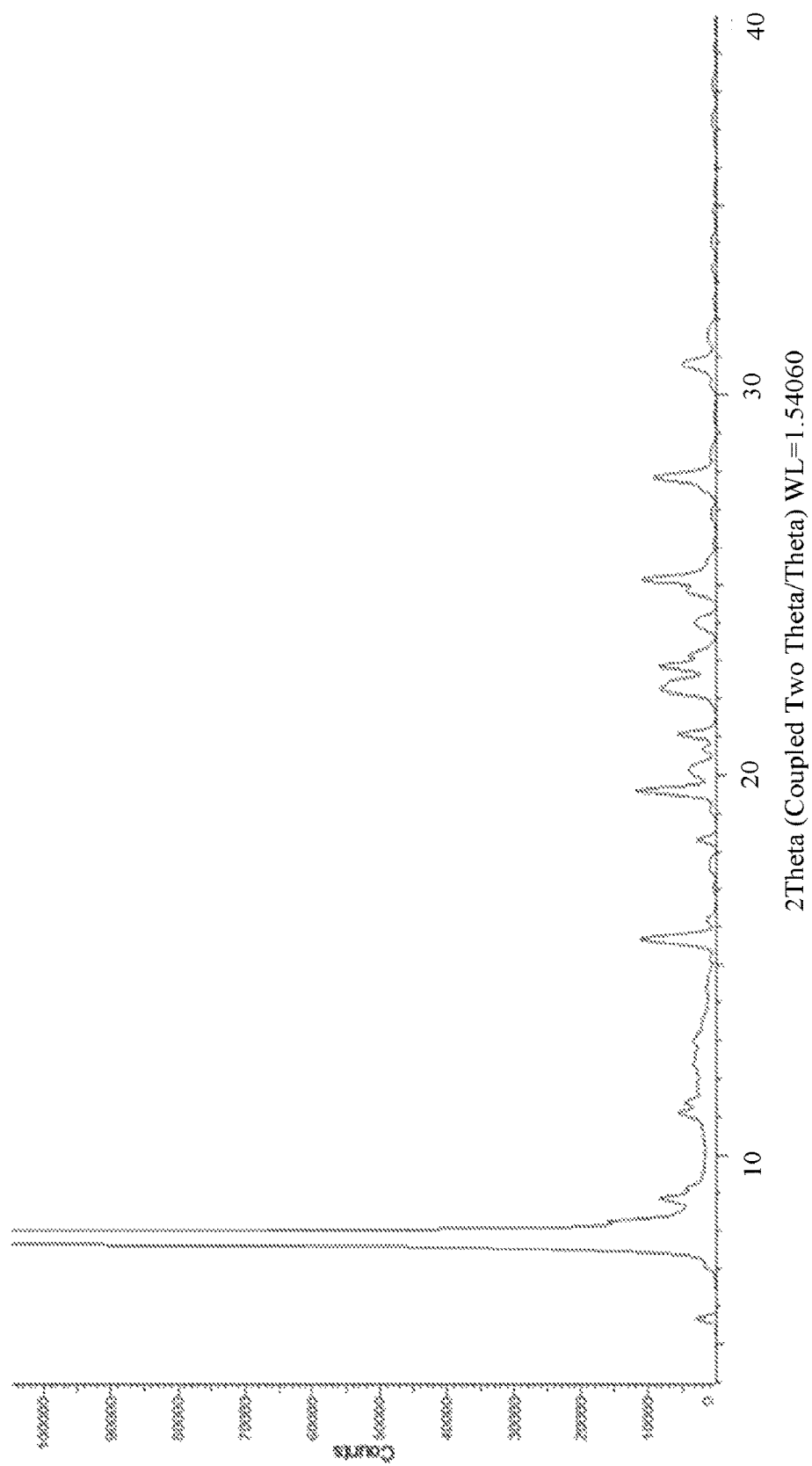
FIG. 9A depicts an illustrative XRPD spectrum for 31f (hydrogen-L(+)-tartrate salt form).
Figure 9C:
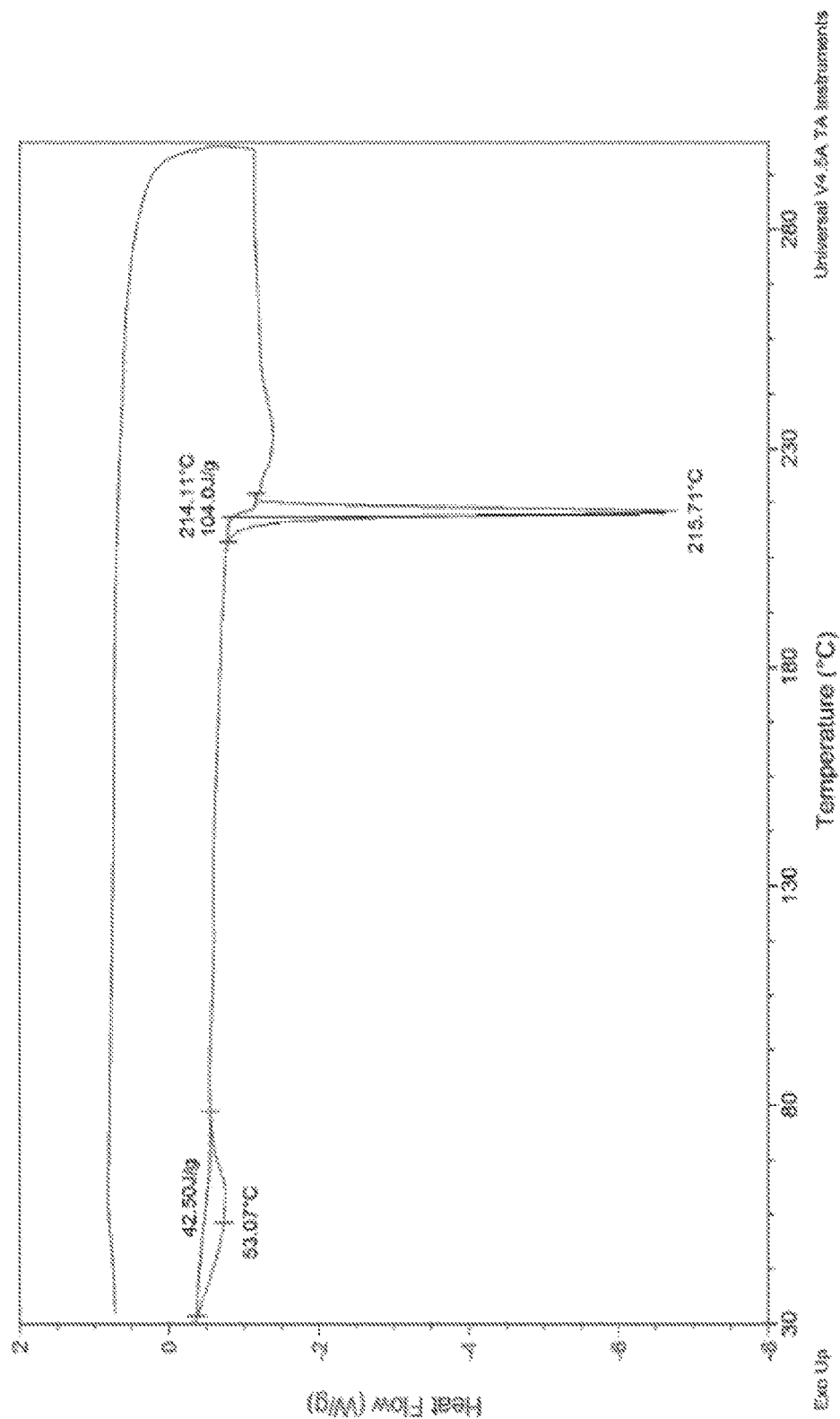
FIG. 9C depicts an illustrative DSC spectrum for 31f (hydrogen-L(+)-tartrate salt form).
Figure 10A:
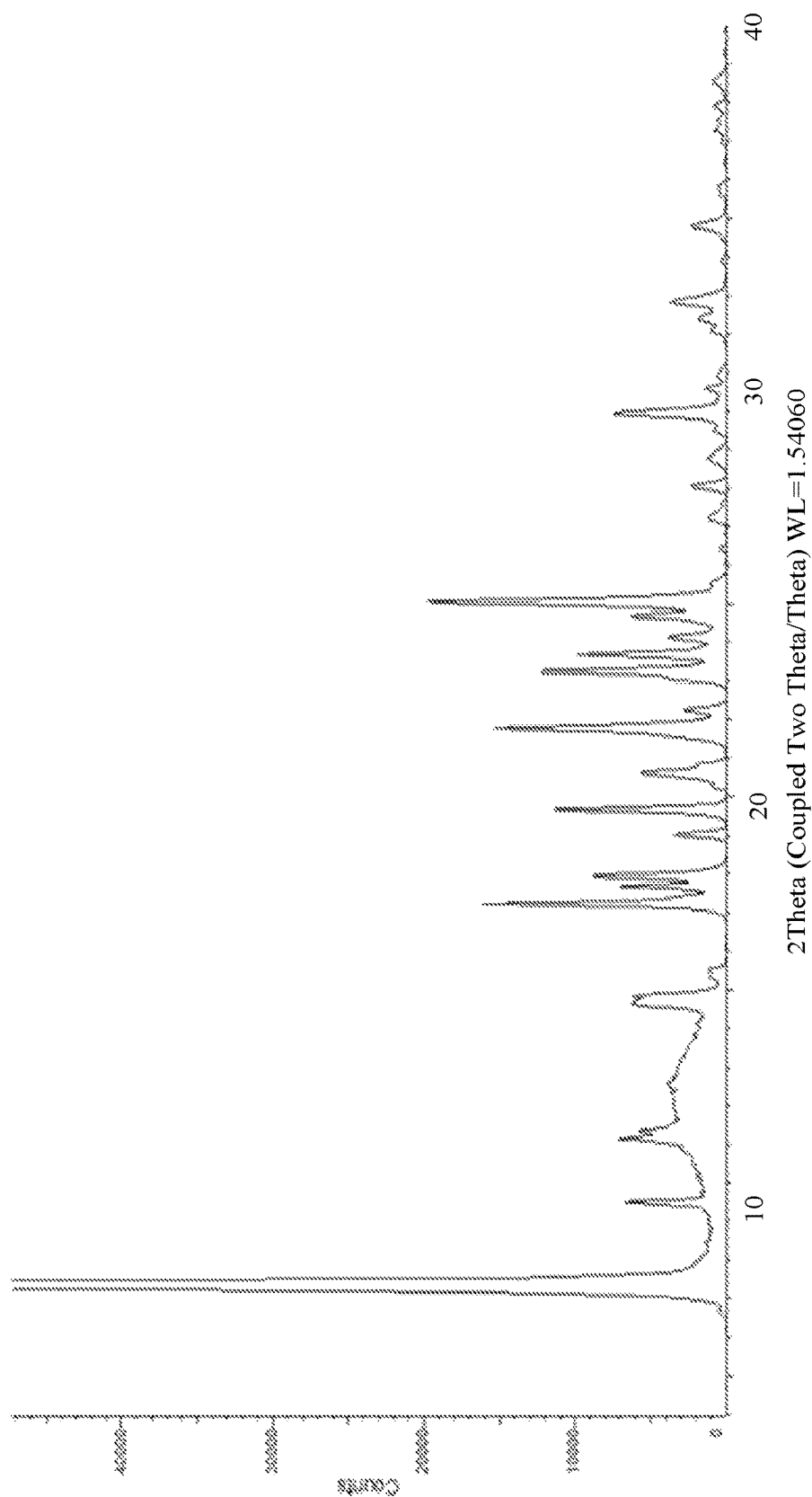
FIG. 10A depicts an illustrative XRPD spectrum of 31g (D,L-mandelate salt form).
Figure 10C:
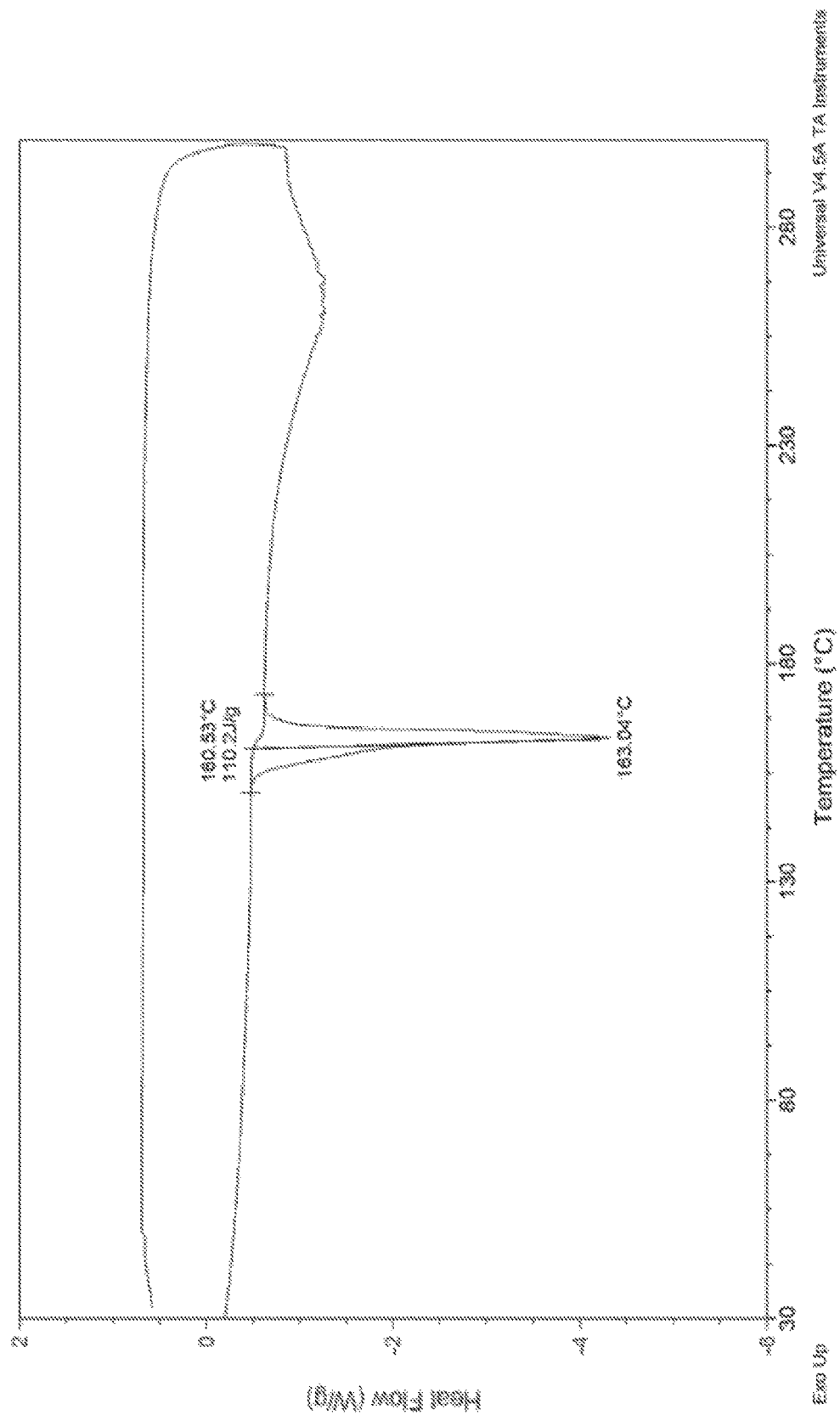
FIG. 10C depicts an illustrative DSC spectrum for 31g (D,L-mandelate salt form).
Figure 11A:
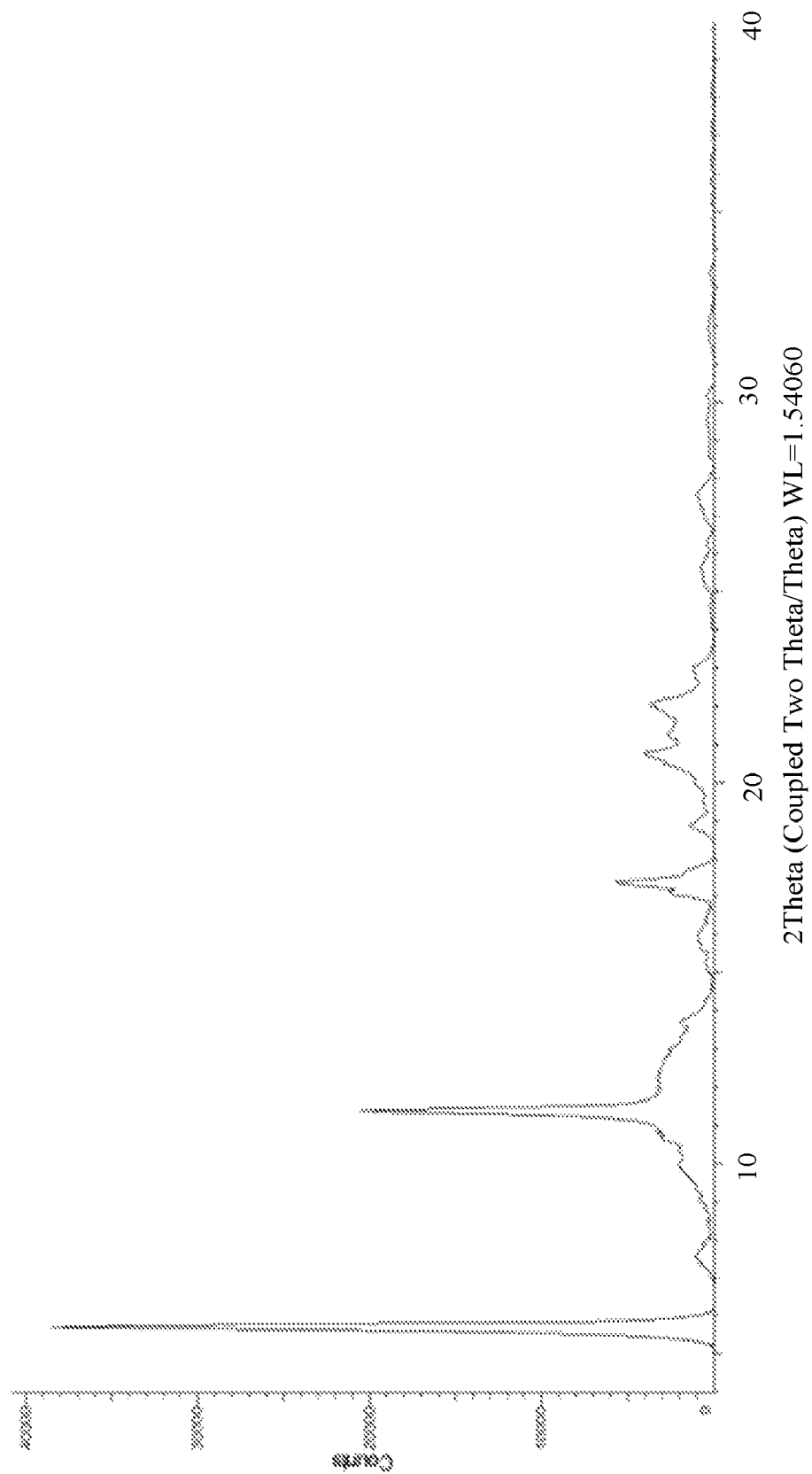
FIG. 11A depicts an illustrative XRPD spectrum for 31h-1 (tosylate salt form Tos-A).
Figure 11C:
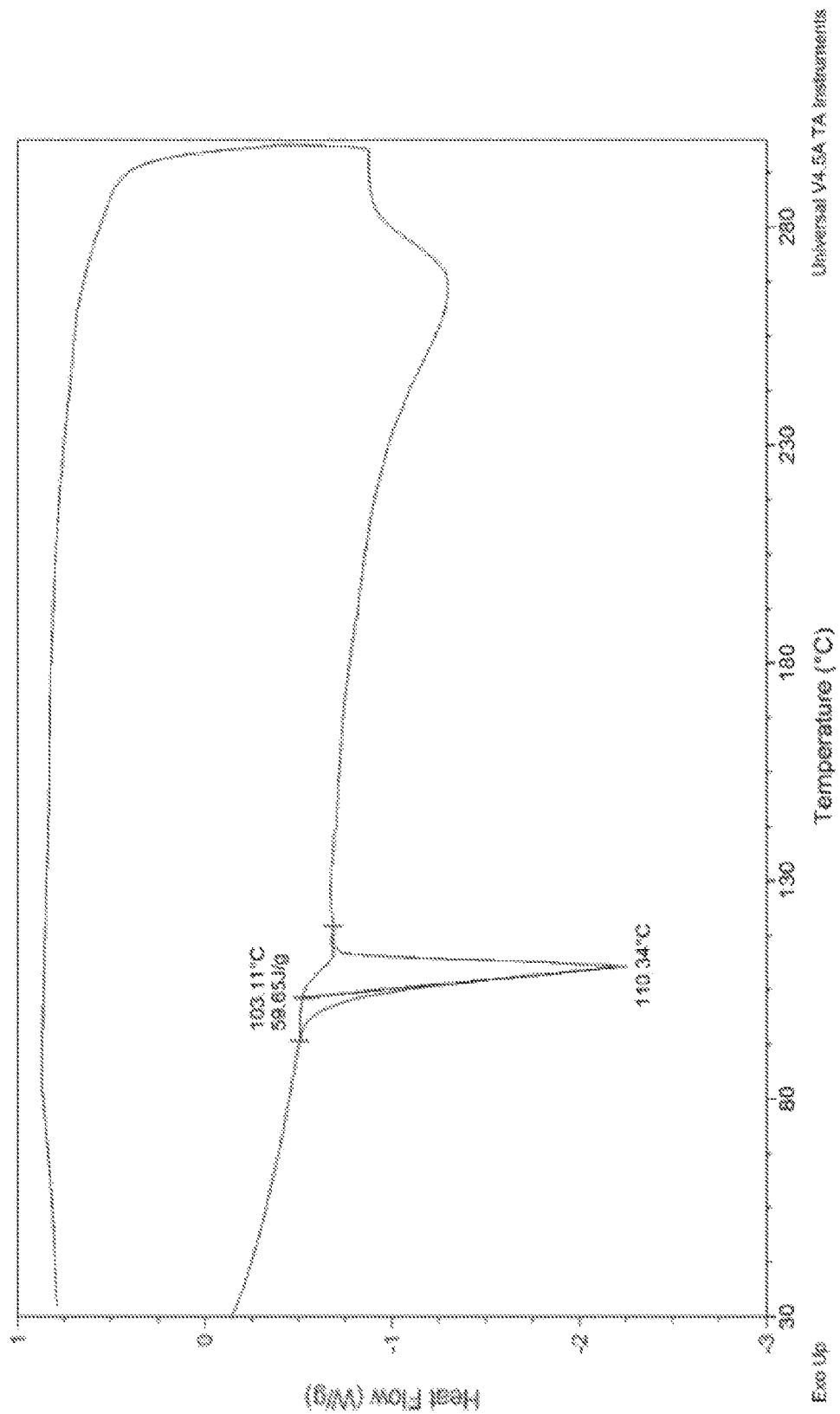
FIG. 11C depicts an illustrative DSC spectrum for 31h-1 (tosylate salt form Tos-A).
Figure 12A:
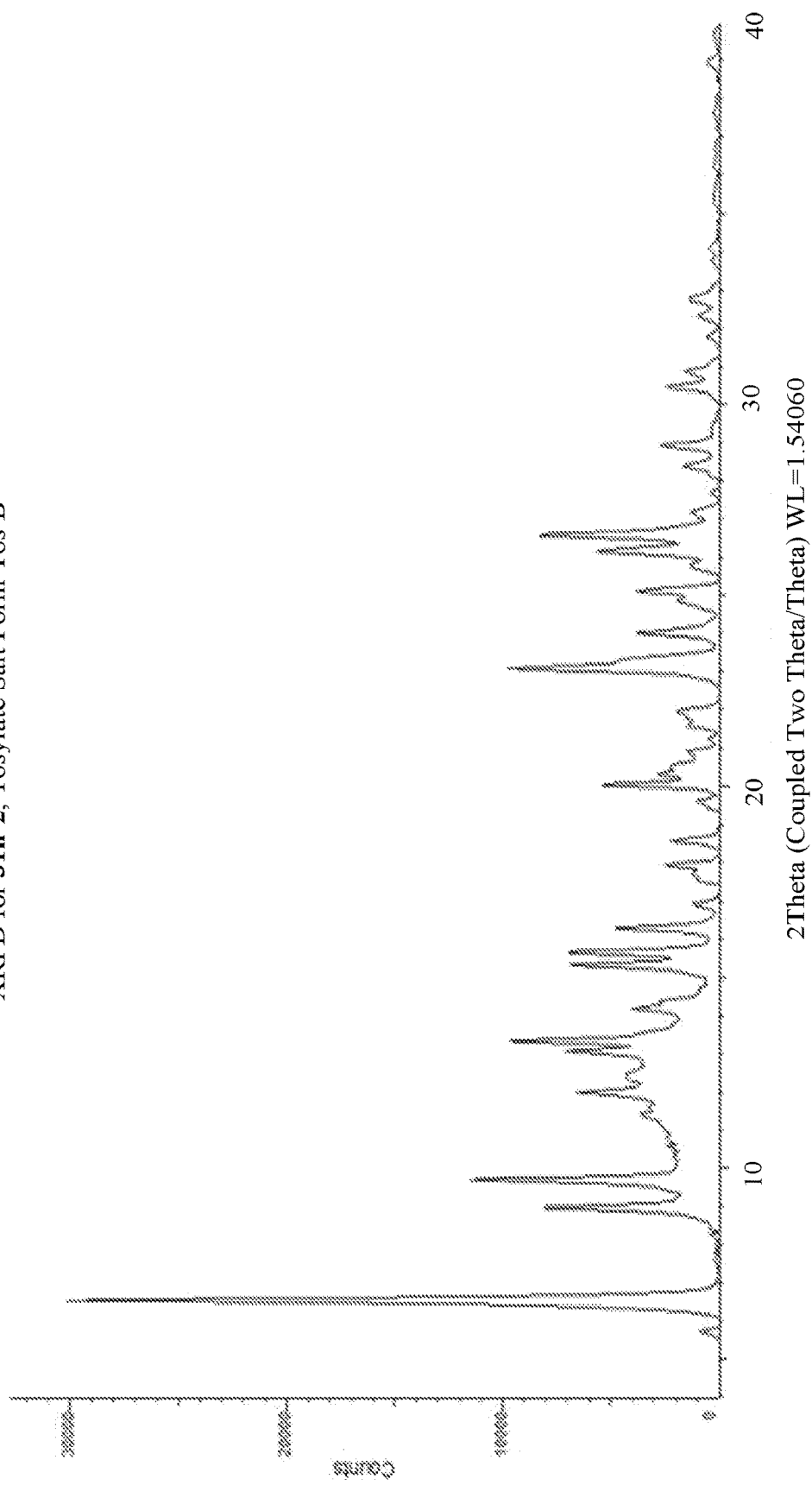
FIG. 12A depicts an illustrative XRPD spectrum for 31h-2 (tosylate salt form Tos-B).
Figure 12C:
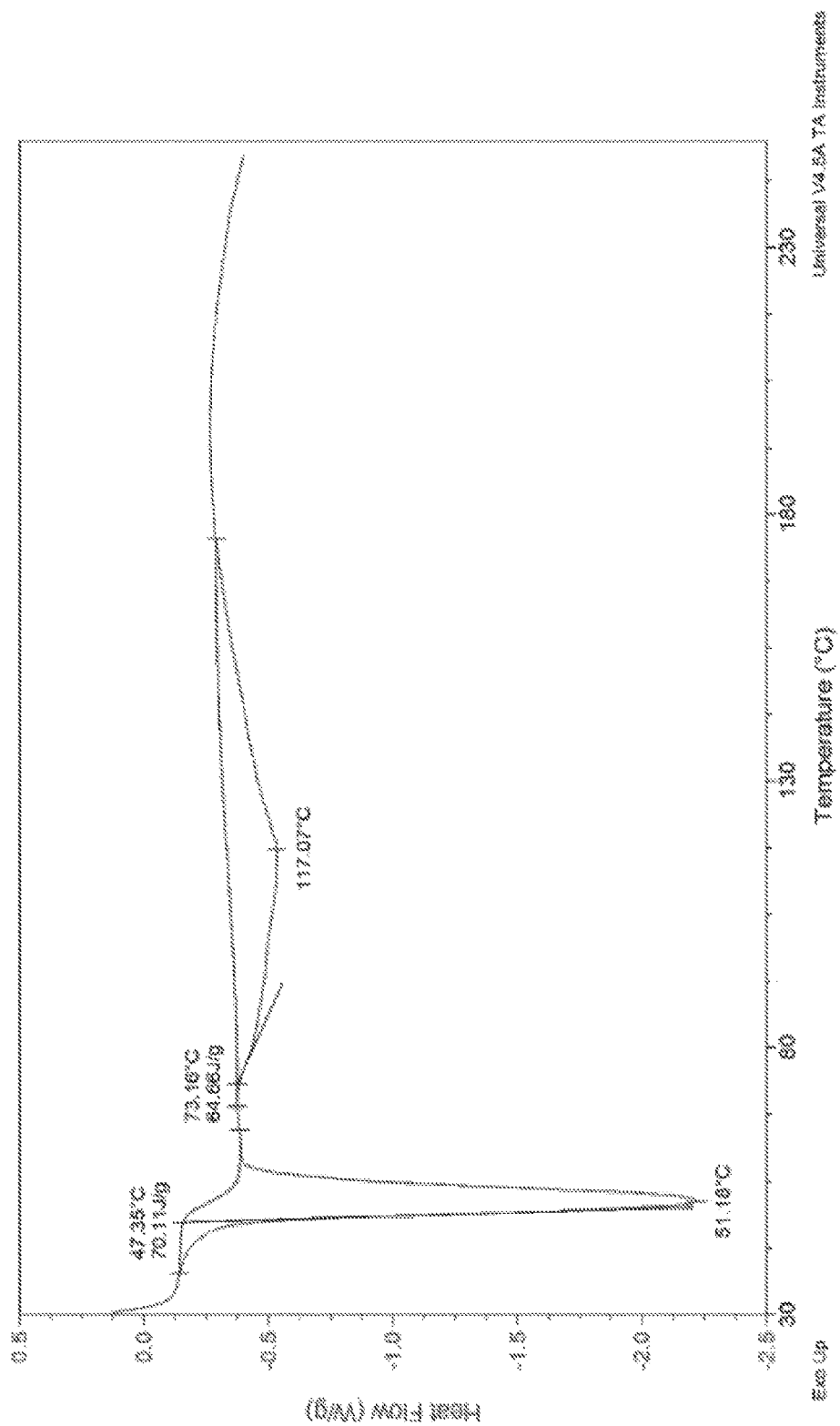
FIG. 12C depicts an illustrative DSC spectrum for 31h-2 (tosylate salt form Tos-B).
Figure 13A:
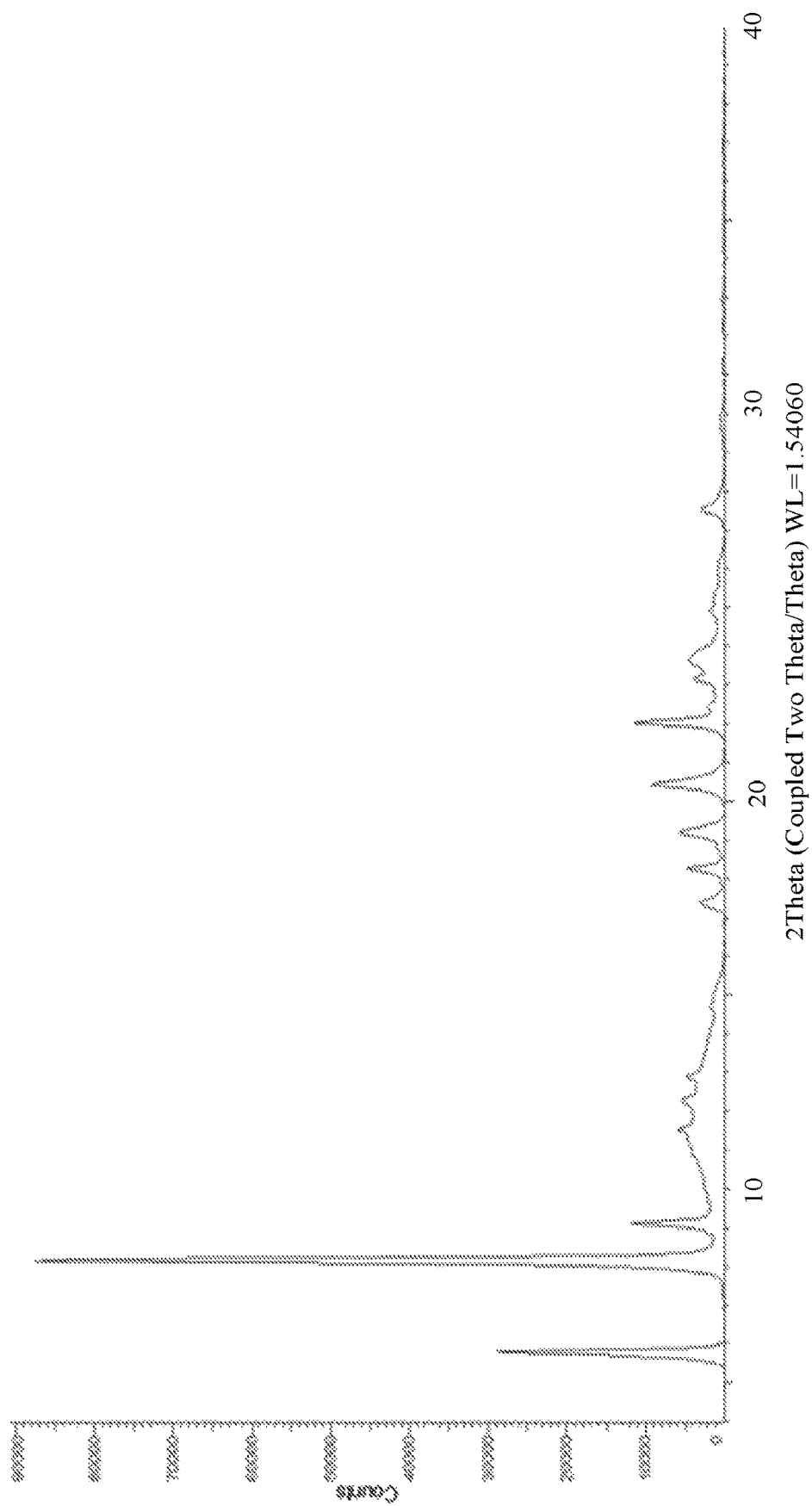
FIG. 13A depicts an illustrative XRPD spectrum of 31i (mesylate salt form).
Figure 13C:
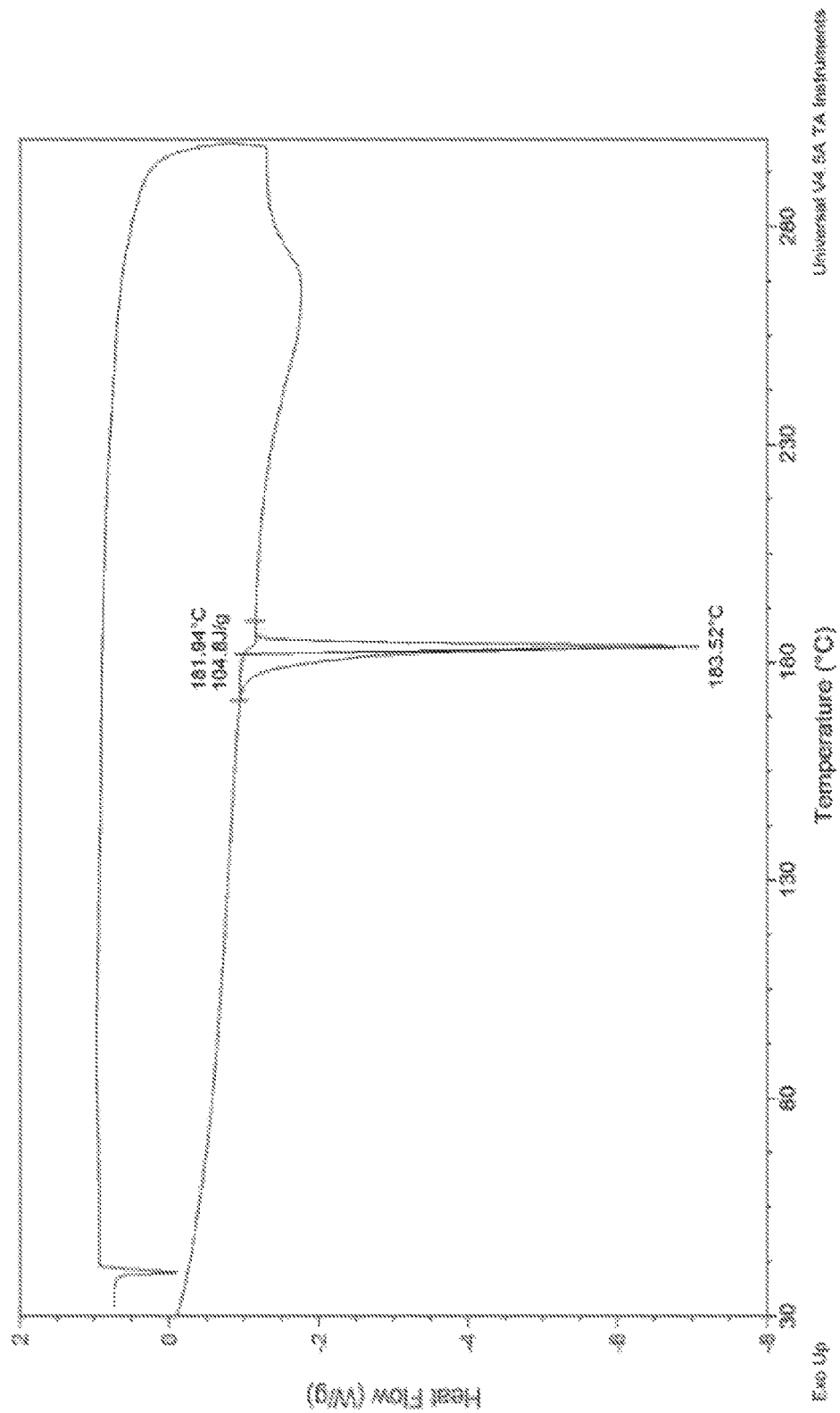
FIG. 13C depicts an illustrative DSC spectrum for 31i (mesylate salt form).
Figure 14A:
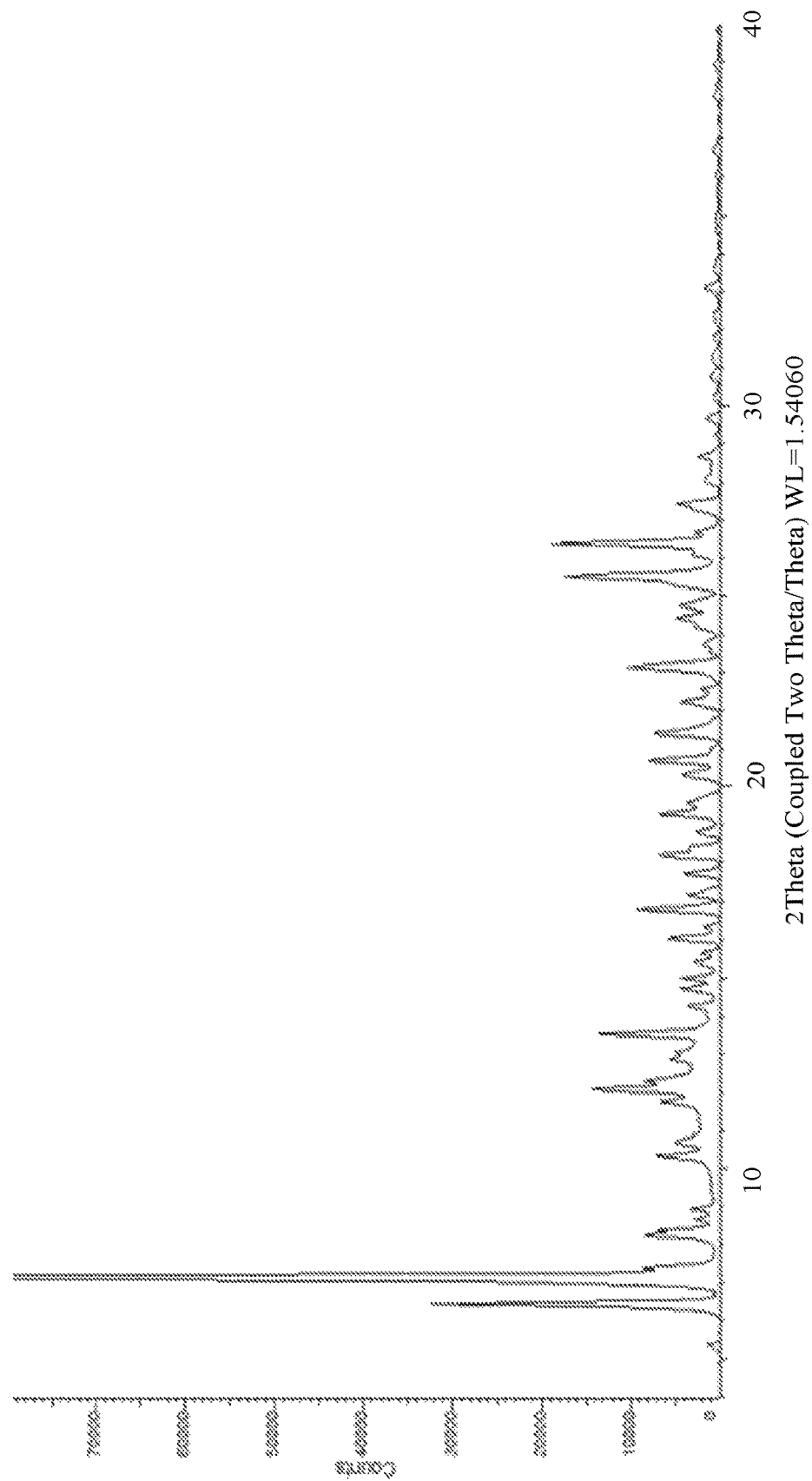
FIG. 14A depicts an illustrative XRPD spectrum for 31j (saccharinate salt form).
Figure 15:
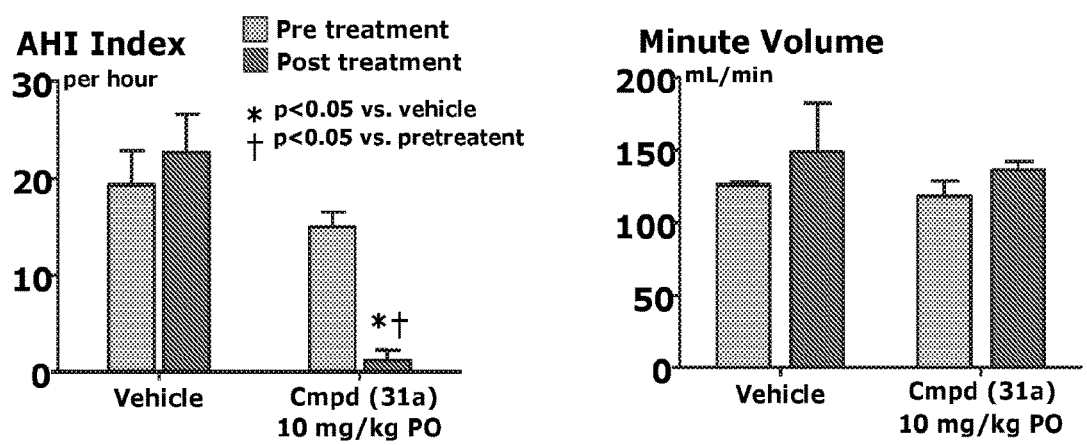
FIG. 15 depicts a set of graphs illustrating that 1-(2,6-bis-methylamino-8-propylamino-pyrimido[5,4-d]pyrimidin-4-yl amino)-2-methyl-propan-2-ol hydrochloride salt (31a) reduces apnea-hypopnea index in morphine-tolerant rats (CSA model) without significantly increasing minute volume.
Figure 16A:
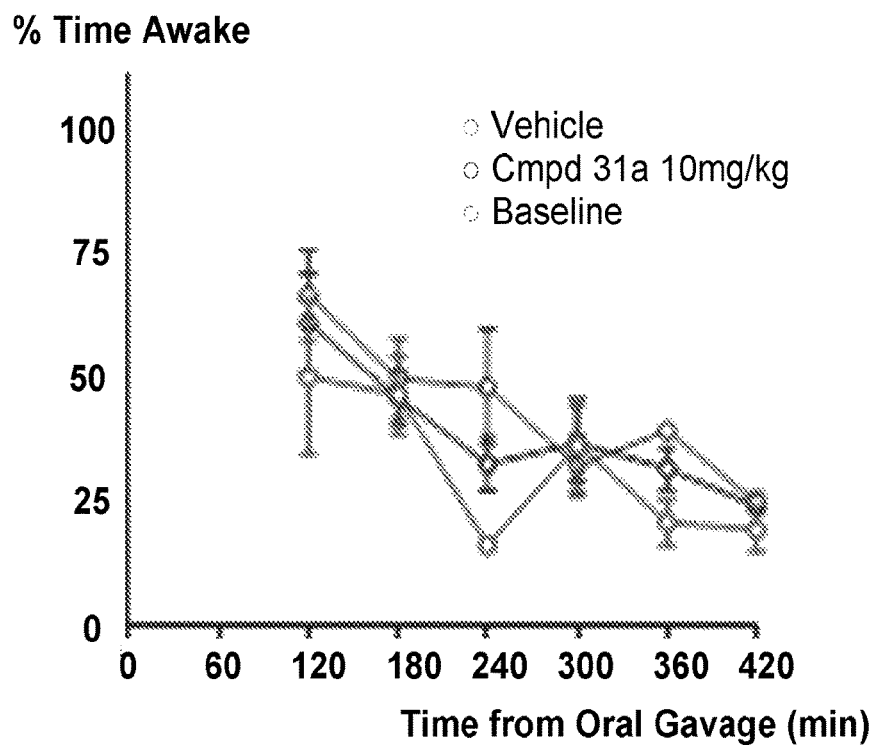
FIGS. 16A-16C illustrate graphs of the % time spent in each sleep-wake state (FIG. 16A: Awake, FIG. 16B: REM, FIG. 16C: NREM) during baseline (drug-naïve) and after oral gavage with vehicle and 1-(2,6-bis-methylamino-8-propylamino-pyrimido[5,4-d]pyrimidin-4-yl amino)-2-methyl-propan-2-ol hydrochloride salt (31a) (10 mg/kg). Values are means±SEM.
Figure 16B:
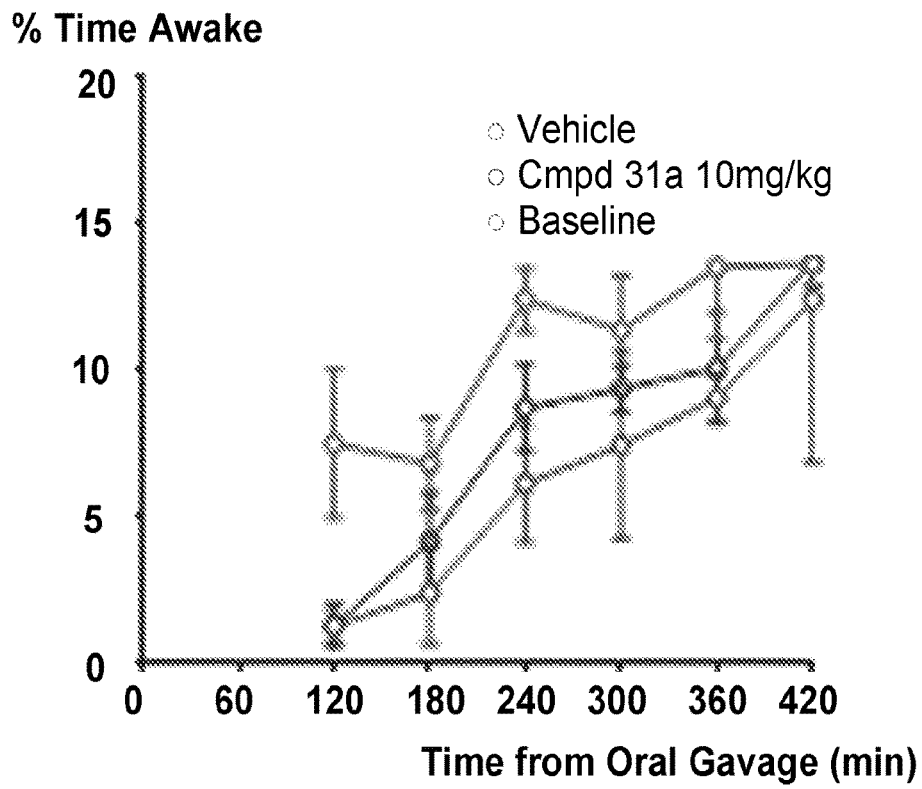
Figure 16C:
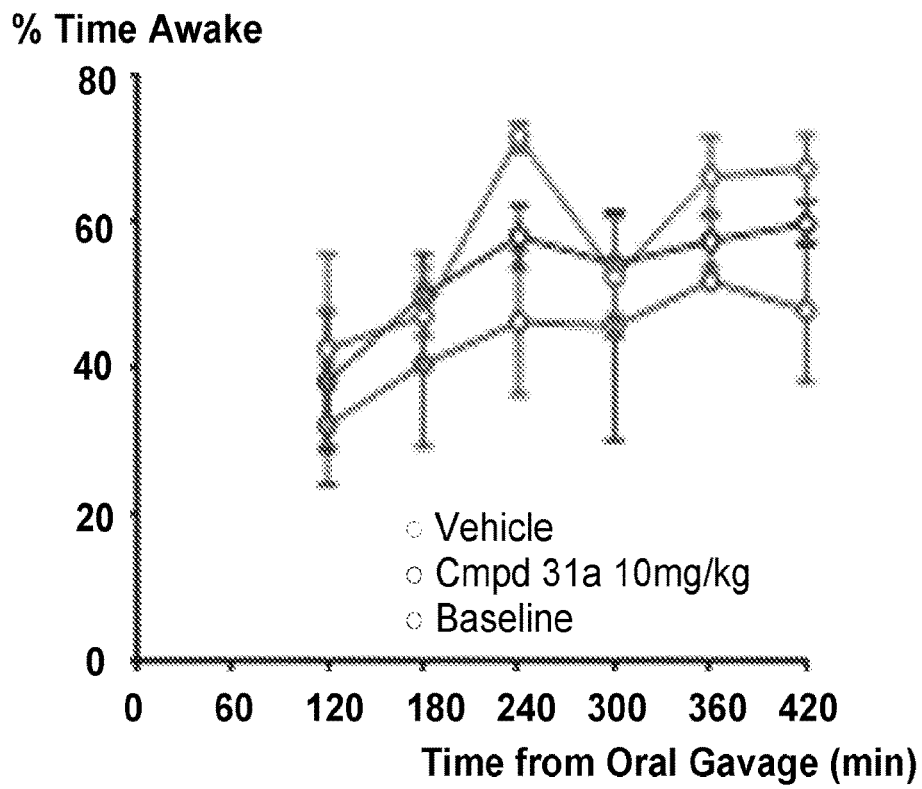
Figure 17A:
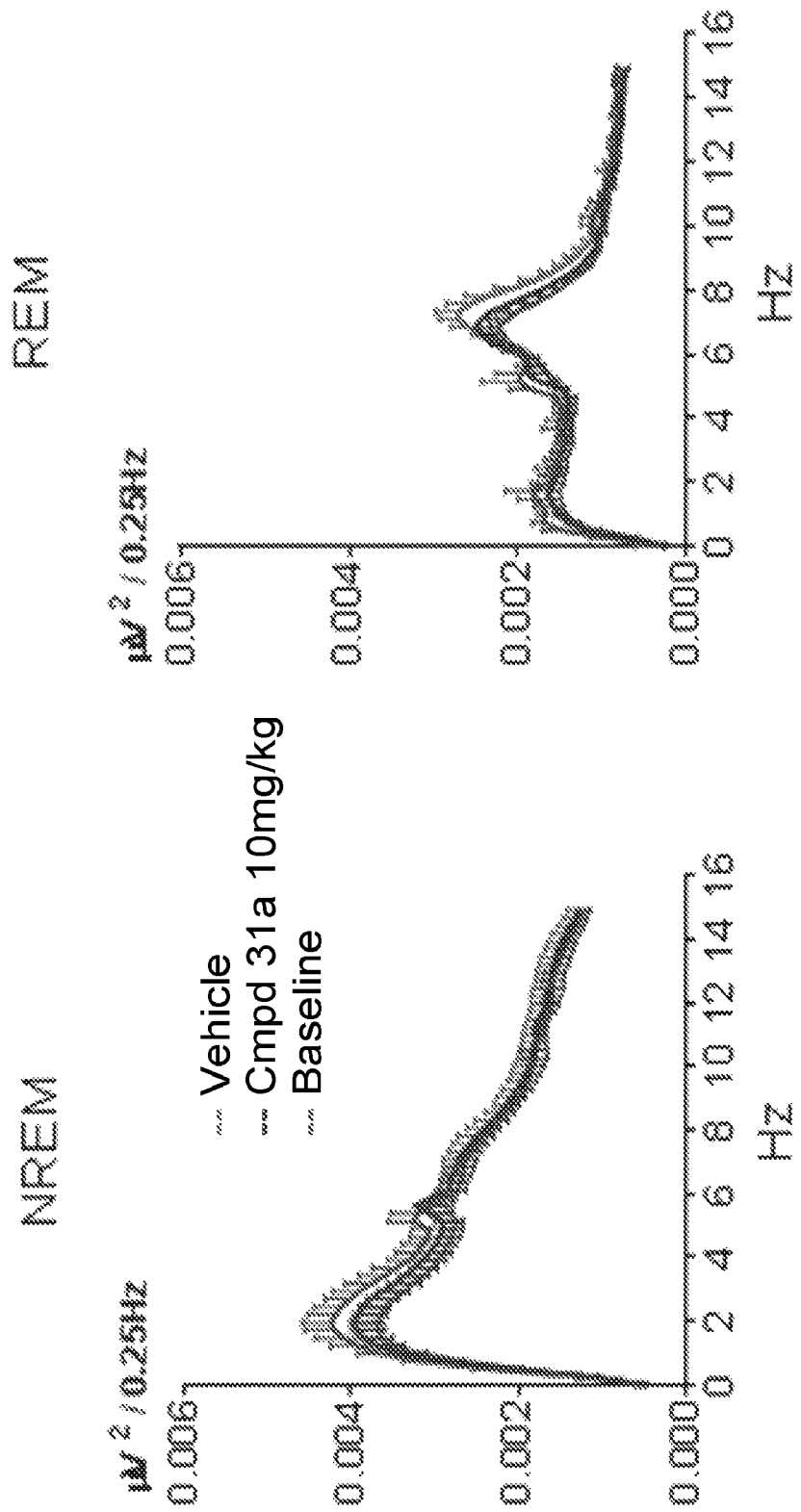
FIGS. 17A-17B illustrate a set of graphs illustrating NREM and REM sleep quality as assessed by measuring the absolute power density ($\mu V^2/0.25$ Hz) and relative power density (% total power between 0.5 Hz to 30 Hz) during baseline (drug nave), vehicle, and 1-(2,6-bis-methylamino-8-propylamino-pyrimido[5,4-d]pyrimidin-4-yl amino)-2-methyl-propan-2-ol hydrochloride salt (31a) (10 mg/kg PO) treatment. The first 2 hours after dosing were not included in the post-dose measurements because of the strong gavage effect on time spent asleep that was detected immediately after vehicle and administration of test article. Values are means±SEM.
Figure 17B:
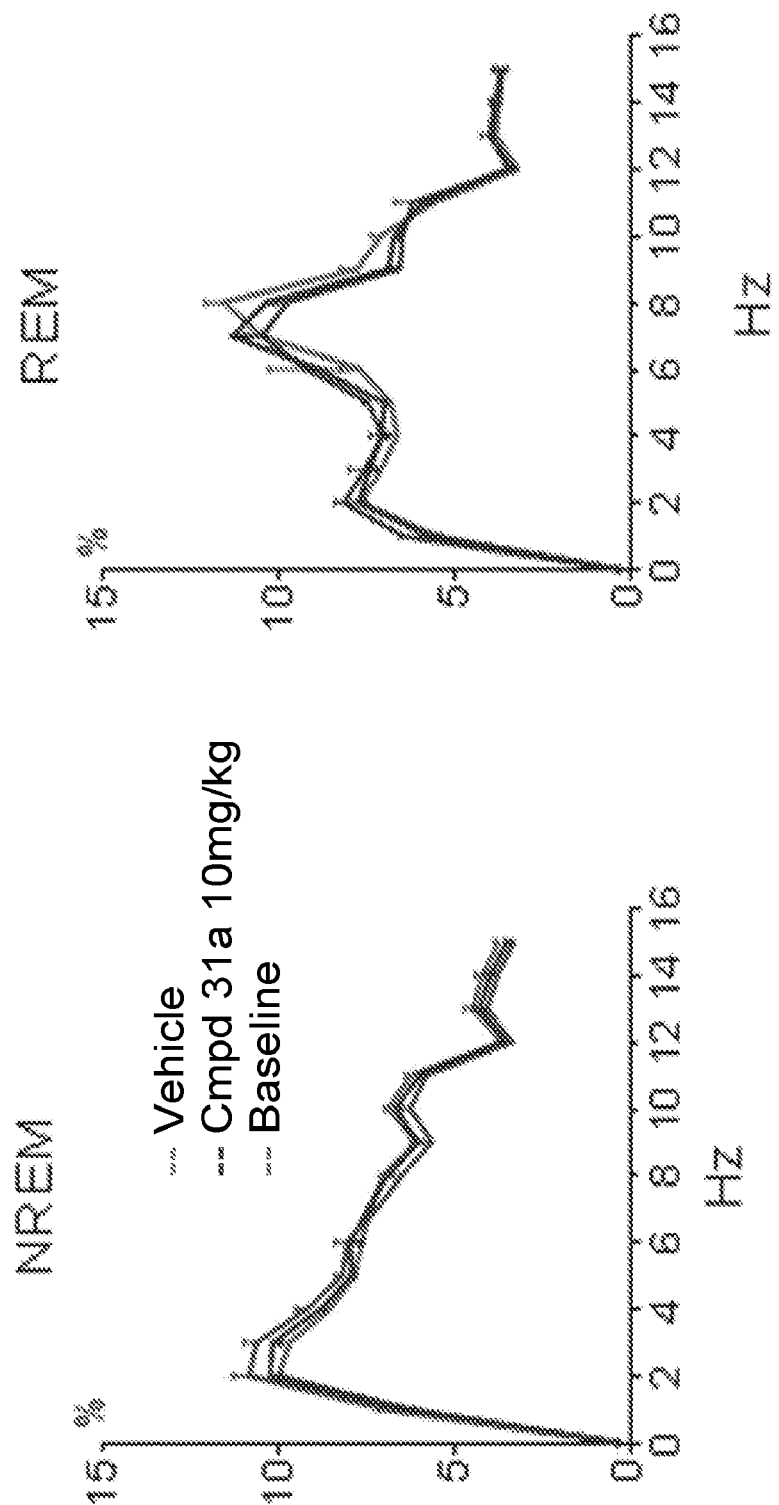
Figure 18:
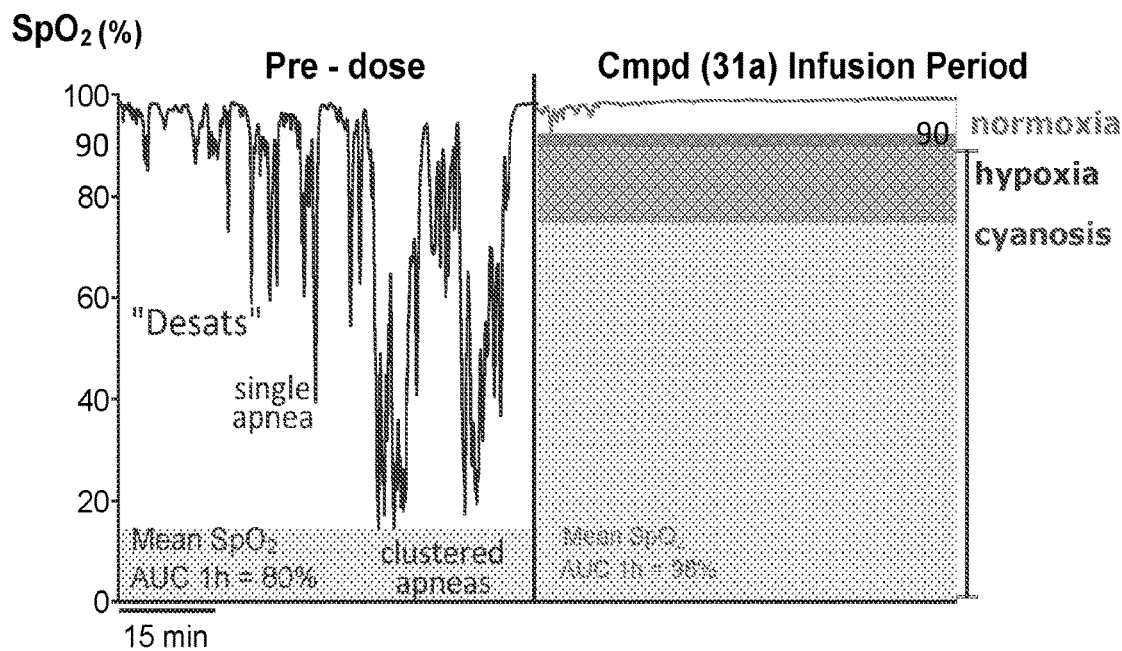
FIG. 18 depicts a graph illustrating the reduction of $SpO_2$ desaturations after the administration of 1-(2,6-bis-methylamino-8-propylamino-pyrimido[5,4-d]pyrimidin-4-yl amino)-2-methyl-propan-2-ol hydrochloride salt (31a).
Figure 19:
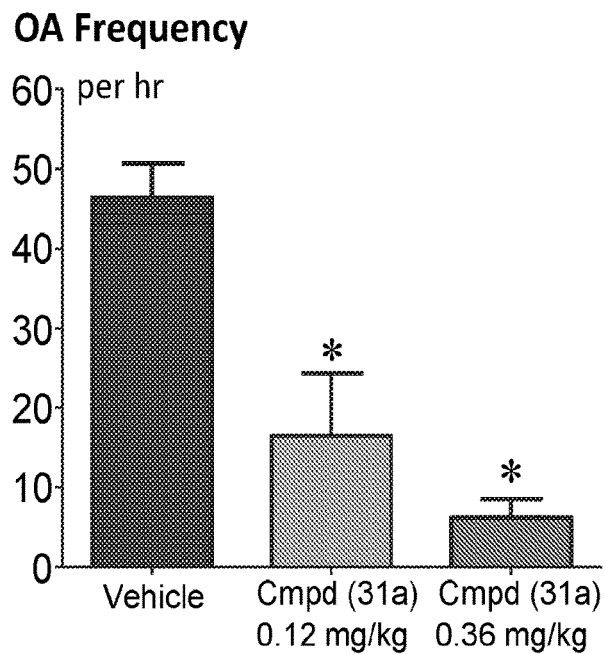
FIG. 19 depicts a graph illustrating the reduction of frequency of obstructive apneas (OA) after the administration of 1-(2,6-bis-methylamino-8-propylamino-pyrimido[5,4-d]pyrimidin-4-yl amino)-2-methyl-propan-2-ol hydrochloride salt (31a).
Figure 20:
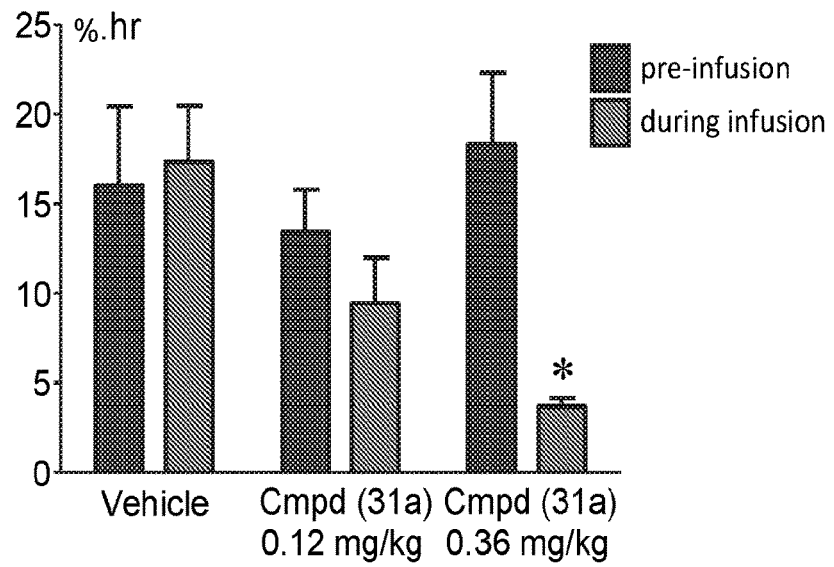
FIG. 20 depicts a graph illustrating the reduction of arterial oxygen content deficit after the administration of 1-(2,6-bis-methylamino-8-propylamino-pyrimido[5,4-d]pyrimidin-4-yl amino)-2-methyl-propan-2-ol hydrochloride salt (31a).
Figure 21A:
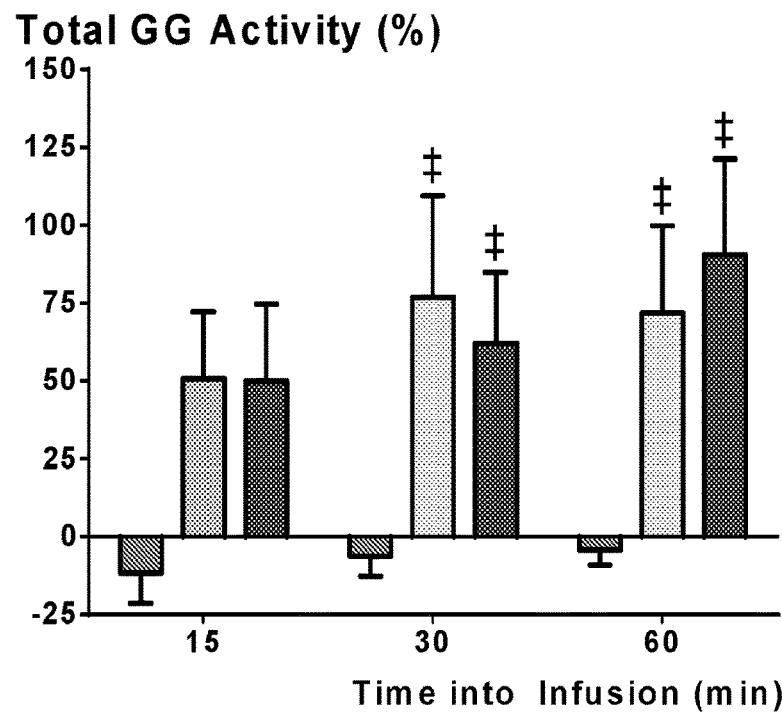
FIG. 21A depicts a graph illustrating increases of airway (genioglossus, or GG) responses in rats, to evoked obstructions after the administration of 1-(2,6-bis-methylamino-8-propylamino-pyrimido[5,4-d]pyrimidin-4-yl amino)-2-methyl-propan-2-ol hydrochloride salt (31a).
Figure 21B:
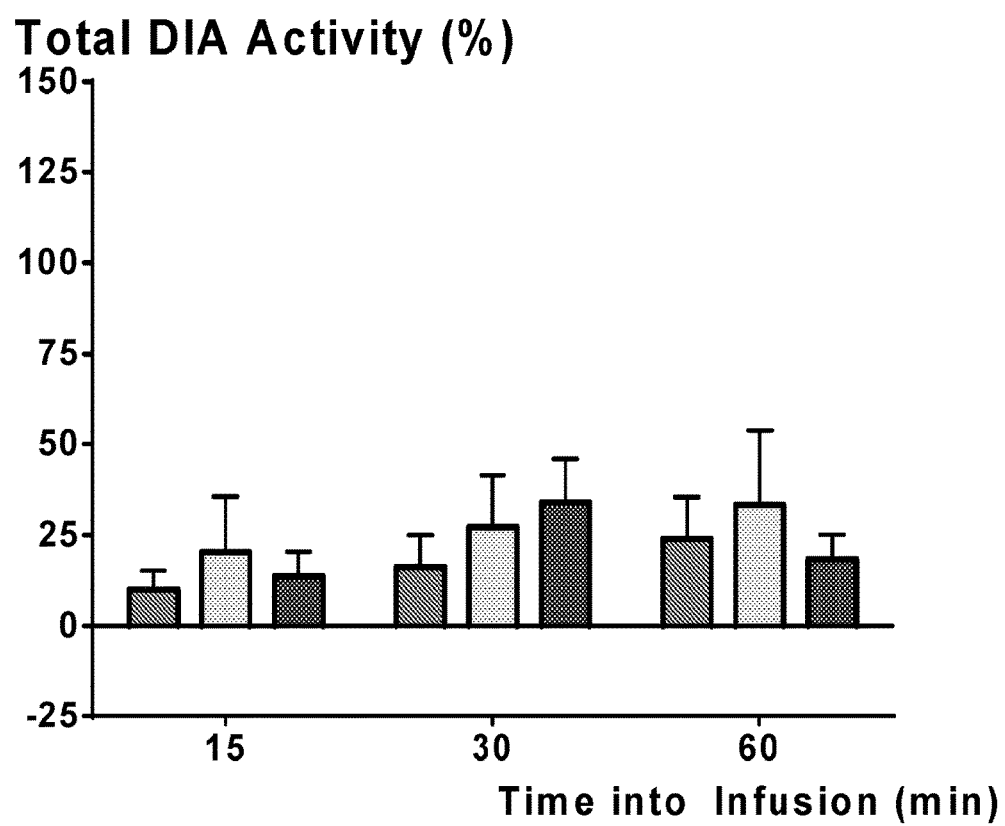
FIG. 21B depicts a graph illustrating insignificant increases of diaphragm (DIA) responses, in the same rats, to evoked obstructions after the administration of 1-(2,6-bis-methylamino-8-propylamino-pyrimido[5,4-d]pyrimidin-4-yl amino)-2-methyl-propan-2-ol hydrochloride salt (31a). Red bar—Vehicle; Light blue bar—Middle dose (MD) cmpd (31a) infusion involved administering 0.008 mg/kg/min for 15 minutes (loading phase) followed by 0.002 mg/kg/min for 45 minutes (maintenance phase); Dark blue bar—High dose (HD) cmpd (31a) infusion entailed administering 0.024 mg/kg/min for 15 minutes (loading phase) followed by 0.006 mg/kg/min for 45 minutes (maintenance phase).
Figure 22:
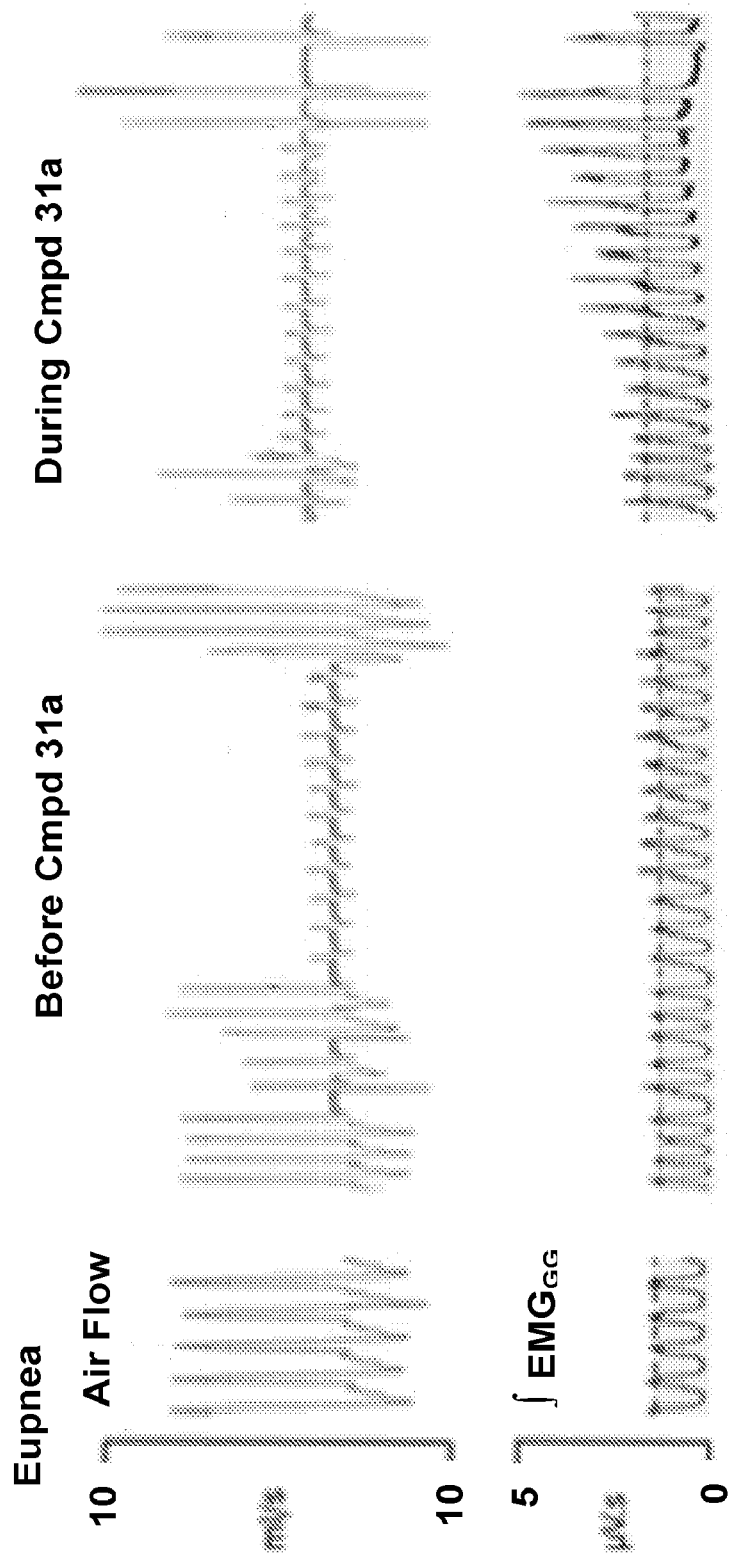
FIG. 22 depicts a graph illustrating the increase in the upper airway (total genioglossus EMG amplitude) response to spontaneous obstructive apneas in rats after the administration of 1-(2,6-bis-methylamino-8-propylamino-pyrimido[5,4-d]pyrimidin-4-yl amino)-2-methyl-propan-2-ol hydrochloride salt (31a).

In certain embodiments, the salts of the invention are crystalline. In other embodiments, the salts of the invention are non-crystalline or amorphous. In yet other embodiment, a crystalline salt of 1-(2,6-Bis-methylamino-8-propylamino-pyrimido[5,4-d]pyrimidin-4-yl amino)-2-methyl-propan-2-ol (31) is at least one selected from the group consisting of:

(i) Crystalline hydrochloride salt (31a), with a XRPD spectrum as per FIG. 3A, XRPD peaks as per FIG. 3B, and/or DSC (differential scanning calorimetry) spectrum per FIG. 3C;

(ii) Crystalline bis-hydrochloride salt (31b), with a XRPD spectrum as per FIG. 4A, XRPD peaks as per FIG. 4B, and/or DSC spectrum per FIG. 4C;

(iii) Crystalline hydrogen malonate salt (31c), with a XRPD spectrum as per FIG. 5A, XRPD peaks as per FIG. 5B, and/or DSC spectrum per FIG. 5C;

(iv) Crystalline hydrogen maleinate salt form Mal-A (31d-1), with a XRPD spectrum as per FIG. 6A, XRPD peaks as per FIG. 6B, and/or DSC spectrum per FIG. 6C;

(v) Crystalline hydrogen maleinate salt Form Mal-B (31d-2), with a XRPD spectrum as per FIG. 7A, XRPD peaks as per FIG. 7B, and/or DSC spectrum per FIG. 7C;

(vi) Crystalline hydrogen fumarate salt (31e), with a XRPD spectrum as per FIG. 8A, XRPD peaks as per FIG. 8B, and/or DSC spectrum per FIG. 8C;

(vii) Crystalline hydrogen L(+)-tartrate salt (31f), with a XRPD spectrum as per FIG. 9A, XRPD peaks as per FIG. 9B, and/or DSC spectrum per FIG. 9C;

(viii) Crystalline D,L-mandelate salt (31g), with a XRPD spectrum as per FIG. 10A, XRPD peaks as per FIG. 10B, and/or DSC spectrum per FIG. 10C;

(ix) Crystalline tosylate salt form Tos-A (31h-1), with a XRPD spectrum as per FIG. 11A, XRPD peaks as per FIG. 11B, and/or DSC spectrum per FIG. 11C;

(x) Crystalline tosylate salt form Tos-B (31h-2), with a XRPD spectrum as per FIG. 12A, XRPD peaks as per FIG. 12B, and/or DSC spectrum per FIG. 12C;

(xi) Crystalline mesylate salt (31i), with a XRPD spectrum as per FIG. 13A, XRPD peaks as per FIG. 13B, and/or DSC spectrum per FIG. 13C;

(xii) Crystalline saccharinate salt (31j), with a XRPD spectrum as per FIG. 14A, XRPD peaks as per FIG. 14B, and/or DSC spectrum per FIG. 14C;

and any mixtures thereof.

Combination and Concurrent Therapies

In certain embodiments, the compounds of the invention are useful in the methods of present invention when used concurrently with at least one additional compound useful for preventing and/or treating breathing control disorders. In certain embodiments, the compounds of the invention are useful in the methods of present invention in combination with at least one additional compound useful for preventing and/or treating breathing control disorders.

These additional compounds may comprise compounds of the present invention or other compounds, such as commercially available compounds, known to treat, prevent, or reduce the symptoms of breathing disorders. In certain embodiments, the combination of at least one compound of the invention, or a salt, solvate, enantiomer, diastereoisomer or tautomer thereof, and at least one additional compound useful for preventing and/or treating breathing disorders has additive, complementary or synergistic effects in the prevention and/or treatment of disordered breathing, and in the prevention and/or treatment of sleep-related breathing disorders.

In a non-limiting example, the compounds of the invention or a salt thereof may be used concurrently or in combination with one or more of the following drugs: doxapram, enantiomers of doxapram, acetazolamide, almitrine, theophylline, caffeine, methylprogesterone and related compounds, sedatives that increase arousal threshold in sleep disordered breathing patients (such as eszopiclone and zolpidem), benzodiazepine receptor agonists (e.g., zolpidem, zaleplon, estazolam, flurazepam, quazepam, temazepam, triazolam) orexin antagonists (e.g., suvorexant), tricyclic antidepressants (e.g., doxepin), serotonergic modulators, adenosine and adenosine receptor and nucleoside transporter modulators, cannabinoids (such as, but not limited to, dronabinol), orexins, melatonin agonists (such as ramelteon), compounds known as ampakines, sodium oxybate, modafinil, and armodafinil.

In a non-limiting example, the compounds of the invention or a salt thereof may be used concurrently or in combination with inhaled therapeutics such as oxygen and carbon dioxide as for the treatment of sleep disordered breathing.

Non-limiting examples of ampakines are the pyrrolidine derivative racetam drugs such as piracetam and aniracetam; the "CX-" series of drugs which encompass a range of benzoylpiperidine and benzoylpyrrolidine structures, such as CX-516 (6-(piperidin-1-yl-carbonyl)quinoxaline), CX-546 (2,3-dihydro-1,4-benzodioxin-7-yl-(1-piperidyl)-methanone), CX-614 (2H,3H,6aH-pyrrolidino(2,1-3',2')-1,3-oxazino-(6',5'-5,4)benzo(e)1,4-dioxan-10-one), CX-691 (2,1,3-benzoxadiazol-6-yl-piperidin-1-yl-methanone), CX-717, CX-701, CX-1739, CX-1763, and CX-1837; benzothiazide derivatives such as cyclothiazide and IDRA-21 (7-chloro-3-methyl-3,4-dihydro-2H-1,2,4-benzothiadiazine 1,1-dioxide); biarylpropylsulfonamides such as LY-392,098, LY-404,187 (N-[2-(4'-cyanobiphenyl-4-yl)propyl]propane-2-sulfonamide), LY-451,646 and LY-503,430 (4'-{(1S)-1-fluoro-2-[(isopropylsulfonyl)amino]-1-methylethyl}-N-methylbiphenyl-4-carboxamide).

In one embodiment, the invention includes a composition comprising a compound of the invention and at least one agent selected from the group consisting of doxapram, enantiomers of doxapram, enantiomers of doxapram, acetazolamide, almitrine, theophylline, caffeine, methylprogesterone and related compounds, sedatives that increase arousal threshold in sleep disordered breathing patients (such as eszopiclone or zolpidem), benzodiazepine receptor agonists (such as zolpidem, zaleplon, estazolam, flurazepam, quazepam, temazepam, or triazolam), orexin antagonists (e.g. suvorexant), tricyclic antidepressants (such as doxepin), serotonergic modulators, adenosine and adenosine receptor and nucleoside transporter modulators, cannabinoids (such as but not limited to dronabinol), orexins, melatonin agonists (such as ramelteon), compounds known as ampakines, sodium oxybate, modafinil, armodafinil, and inhaled therapeutics such as oxygen and carbon dioxide gases.

In another non-limiting example, the compounds of the invention, or a salt, solvate, enantiomer, diastereoisomer or tautomer thereof, may be used concurrently or in combination with one or more of the following drugs and drug classes known to cause changes in breathing control: opioid narcotics (such as morphine, fentanyl, codeine, hydromorphone, hydrocodone, oxymorphone, oxycodone, meperidine, butorphanol, carfentanil, buprenorphine, methadone, nalbuphine, propoxyphene, pentazocine, remifentanil, alfentanil, sufentanil and tapentadol); benzodiazepines (such as midazolam); and sedatives (such as zolipidem and eszopiclone); sodium oxybate and propofol. In certain embodiments, the invention includes a composition comprising a compound of the invention and at least one agent known to cause changes in breathing control. In certain embodiments, the at least one agent is selected from the group consisting of opioid narcotics, benzodiazepines, sedatives, sleeping aids and propofol.

In another non-limiting example, the compounds of the invention, or a salt, solvate, enantiomer, diastereoisomer or tautomer thereof, may be used concurrently or in combination with one or more of the following drugs and drug classes known to either aid the onset of sleep, maintain sleep and/or alter arousal threshold: zolipidem, zaleplon, eszopiclone, ramelteon, estazolam, temazepam, doxepin, sodium oxybate, phenobarbital and other barbiturates, diphenhydramine, doxylamine and related compounds, for example. The combination of a sleep promoting/stabilizing drug and the compounds of the invention may act additively or synergistically to improve indices of sleep disordered breathing. In certain embodiments, the compounds of the invention stabilize respiratory pattern (i.e., decrease variation in respiratory rate and tidal volume on a breath-by-breath basis) and respiratory drive (i.e., decrease fluctuations in the neural control of the respiratory muscles), thereby decreasing the incidence of central and obstructive apneas whilst the sleep promoting/stabilizing drug prevents patient arousal from sleep if residual apneas persist. Blood gas derangements associated with a residual apnea may elicit chemoreceptor stimulation, which in turn elicits generalized central nervous system arousal. Patients with a low arousal threshold from sleep wake early and often (i.e., experience sleep fragmentation) and these patients experience a ventilatory overshoot due to the sudden awakening in excess of the level of chemoreceptor stimulation. Sleep promoting/stabilizing drugs delay cortical arousal and permit a more appropriate ventilatory response to apnea-induced chemoreceptor stimulation. The patient benefits from delayed arousal from sleep because sleep fragmentation decreases and hyperventilation-driven central apneas decrease.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

In certain embodiments, the compound and the agent are physically mixed in the composition. In other embodiments, the compound and the agent are physically separated in the composition.

In certain embodiments, the compound of the invention is co-administered with a compound that is used to treat another disorders but incidentally causes loss or depression of breathing control. In this aspect, the compound of the invention blocks or otherwise reduces depressive effects on normal breathing control caused by the compound with which they are co-administered. Such compound that treats another disorder but depresses breathing control includes but is not limited to anesthetics, sedatives, sleeping aids, anxiolytics, hypnotics, alcohol, and narcotic analgesics. The co-administered compound may be administered individually, or a combined composition as a mixture of solids and/or liquids in a solid, gel or liquid formulation or as a solution, according to methods known to those familiar with the art.

In certain embodiments, a compound of the present invention is co-administered with at least one additional compound useful for treating breathing control disorders and with at least one compound that is used to treat other disorder but causes a loss of breathing control. In this aspect, the compound of the invention works in an additive, complementary or synergistic manner with the co-administered breathing control agent to block or otherwise reduce depressive effects on normal breathing control caused by other compounds with which they are combined. A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In certain embodiments, a compound of the present invention may be packaged with at least one additional compound useful for treating breathing control disorders. In other embodiments, a compound of the present invention may be packaged with a therapeutic agent known to cause changes in breathing control, such as, but not limited to, anesthetics, sedatives, anxiolytics, hypnotics, alcohol, and narcotic analgesics. A co-package may be based upon, but not limited to, dosage units.

Methods

In one aspect, the present invention includes a method of preventing or treating a breathing control disorder or disease in a subject in need thereof. The method includes administering to the subject an effective amount of at least one compound of the invention or a salt, solvate, enantiomer, diastereoisomer or tautomer thereof, which is optionally part of a pharmaceutical formulation further comprising at least a pharmaceutically acceptable carrier.

In another aspect, the present invention includes a method of preventing destabilization of or stabilizing breathing rhythm in a subject in need thereof. The method includes administering to the subject an effective amount of at least one compound of the invention or a salt, solvate, enantiomer, diastereoisomer or tautomer thereof, which is optionally part of a pharmaceutical formulation further comprising at least a pharmaceutically acceptable carrier.

In certain embodiments, administering the formulation of the invention stabilizes the breathing rhythm of the subject. In other embodiments, administering the formulation of the invention increases minute ventilation in the subject.

In certain embodiments, the destabilization is associated with a breathing control disorder or disease.

In certain embodiments, the breathing disorder or disease is selected from the group consisting of narcotic-induced respiratory depression, anesthetic-induced respiratory depression, sedative-induced respiratory depression, sleeping aid-induced respiratory depression, anxiolytic-induced respiratory depression, hypnotic-induced respiratory depression, alcohol-induced respiratory depression, analgesic-induced respiratory depression, sleep apnea (includes but not limited to mixed central, obstructive, anatomical), apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), Alzheimer's disease, Parkinson's disease, stroke, Duchenne muscular dystrophy, and brain and spinal cord traumatic injury. In other embodiments, the respiratory depression is caused by an anesthetic, a sedative, an anxiolytic agent, a hypnotic agent, alcohol or a narcotic. In yet other embodiments, the compounds of the invention or a salt, solvate, enantiomer, diastereoisomer or tautomer thereof may be used concurrently or in combination with one or more of the following drugs and drug classes known to either aid the onset of sleep, maintain sleep and/or alter arousal threshold: zolipidem, zaleplon, eszopiclone, ramelteon, estazolam, temazepam, sodium oxybate, doxepin, phenobarbital and other barbiturates, diphenhydramine, doxylamine and related compounds for example.

In certain embodiments, the subject is further administered at least one additional compound useful for preventing or treating the breathing disorder or disease. In other embodiments, the at least one additional compound is selected from the group consisting of doxapram, enantiomers of doxapram, acetazolamide, almitrine, theophylline, caffeine, methylprogesterone and related compounds, sedatives such as eszopiclone and zolpidem, sodium oxybate, benzodiazepine receptor agonists (e.g. zolpidem, zaleplon, eszopiclone, estazolam, flurazepam, quazepam, temazepam, triazolam), orexin antagonists (e.g. suvorexant), tricyclic antidepressants (e.f. doxepin), serotonergic modulators, adenosine and adenosine receptor and nucleoside transporter modulators, cannabinoids (such as but not limited to dronabinol), orexins, melatonin agonists (such as ramelteon) and compounds known as ampakines.

In yet other embodiments, the formulation is administered to the subject in conjunction with the use of a mechanical ventilation device or positive airway pressure device. In certain embodiments, the formulation is administered to the subject by an inhalational, topical, oral, nasal, buccal, rectal, pleural, peritoneal, vaginal, intramuscular, subcutaneous, transdermal, epidural, intrathecal or intravenous route. In other embodiments, the subject is a bird or a mammal including but not limited to mouse, rat, ferret, guinea pig, non-human primate (such as monkey), dog, cat, horse, cow, pig and other farm animals. In certain embodiments, the subject is a human.

Pharmaceutical Compositions and Formulations

The invention also encompasses the use of pharmaceutical compositions of at least one compound of the invention or a salt, solvate, enantiomer, diastereoisomer or tautomer thereof to practice the methods of the invention. Such a pharmaceutical composition may consist of at least one compound of the invention or a salt, solvate, enantiomer, diastereoisomer or tautomer thereof, in a form suitable for administration to a subject, or the pharmaceutical composition may comprise at least one compound of the invention or a salt, solvate, enantiomer, diastereoisomer or tautomer thereof, and one or more pharmaceutically acceptable carriers, one or more additional ingredients, or some combination of these. The at least one compound of the invention may be present in the pharmaceutical composition in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g. cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g. Recombumin®), solubilized gelatins (e.g. Gelofusine®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients"

include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non-ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a breathing disorder event. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a breathing control disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of breathing disorders in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 lag and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of breathing disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a breathing disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

In one embodiment, compounds of the invention may be formulated to prepare a pharmaceutical composition for oral administration. In further embodiments, the composition for oral administration may be designed to promote a modified release of the drug, such that the location, extent and rate of exposure of the compound when ingested are modulated. Factors that affect the target zone for exposure of a drug may be the drug's pH or enzymatic stability, reactivity with other drugs (e.g., certain antibiotics), solubility as a salt or free base, ionization behavior, and pharmacodynamic and pharmacokinetic behaviors in specific environments. Some drugs are better absorbed in the duodenum or other intestinal locations.

Delayed release is a particularly useful mode of modified release that delivers drug in its most concentrated form to the duodenum or other intestinal location. In a preferred embodiment, compounds of the present invention are formulated to promote delivery to the duodenum and, optionally, other intestinal locations. Delayed release may be achieved using compositions that include enteric coatings. Enteric coatings are insoluble in highly acidic environments, with the polyacidic coating remaining non-ionized and intact at gastric pH. However, under mildly acidic (>pH 5.5), neutral or mildly alkaline conditions (pH 6.5-7.6) of the duodenum or other intestinal regions, the coating ionizes, swells and breaks down, exposing the coated entity to the environment. Coating options exist to allow ionization at or near a specific pH (e.g. Eudragit L-110, ionization threshold pH 6.0; Eudragit S-100, ionization threshold pH 7.0).

In a further embodiment, compounds of the present invention may be formulated with an enteric coating which has been modified by adding plasticizers to the polymer before coating. The plasticizers may be added to adjust resistance to chipping or cracking of the coating, while also lowering the glass transition temperature of the coating to enable smooth and even spreadability of the coating during its application. Suitable plasticizers include polyethylene glycol 8000 (PEG 8000), triethyl citrate (TEC), and triacetin, which may be incorporated into the polymeric enteric coating agent.

Compounds of the present invention may be enterically formulated under a variety of dosage forms, including (but not limited to) capsules, granules of the active drug itself, beads, and tablets. In one embodiment, the composition may comprise a drug encapsulated in a capsule that is enterically coated to release the drug in the duodenum or other intestinal environment. In one aspect of the invention, pharmaceutically acceptable capsules include hard capsules, which may be composed of plant derived polysaccharides, starches, and cellulose, or gelatin. In another embodiment, pharmaceutically acceptable capsules include soft gelatin capsules. The gelatin capsule may be composed of animal derived collagen or from a hypromellose, a modified form of cellulose, and manufactured using optional mixtures of gelatin, water and plasticizers such as sorbitol or glycerol In one embodiment, molecules of the invention may be encapsulated in pure granular or powdered form, with no carriers, excipients or other pharmaceutically acceptable additives. In other embodiments, molecules of the invention may be encapsulated together with one or more pharmaceutically acceptable carriers, excipients, antioxidants (e.g., sodium metabisulfite, butylated hydroxy toluene [BHT]), antifungals, (e.g., benzoic and ascorbic acids and their salts, and phenolic compounds such as methyl, ethyl, propyl and butyl p-hydroxybenzoate (parabens)), antimicrobial preservatives (e.g., sodium benzoate, sorbic acid), colorants, and flavorants. The excipients may aid in capsule-filling behavior, stability, and in the distribution of the drug when the capsule disintegrates in the body. In another embodiment, granules and/or powders of compounds of the present invention may be enterically coated before being placed in a capsule. The enterically coated granules and/or powders placed in the capsule may feature one or several types of enteric coating to enable delivery of the drug to different regions of the intestine. The capsule may lack enteric coating or may be coated with an enteric coating matching or differing entirely from the coating applied to any of the enterically coated material inside the capsule.

In a further embodiment, molecules of the invention may be encapsulated in a liquid in the form of a solution or suspension in water or various pharmaceutically acceptable oils or other dispersion medium (e.g., mineral oil, sesame oil, safflower oil, coconut oils), optionally with such excipients as co-solvents (e.g., propylene glycol, glycerol), solubility enhancers (e.g., sorbitol, dextrose), wetting agents (e.g.; polysorbates [Tweens], sorbitan esters [Span], hydrophobic colloids [cellulose derivatives], thickening agents (e.g., methylcellulose, microcrystalline cellulose), buffers (e.g., disodium hydrogen phosphate), antioxidants (e.g., butylated hydroxy toluene [BHT], citric acid, potassium sorbate), antifungals (e.g., benzoic and ascorbic acids and their salts, and phenolic compounds such as methyl, ethyl, propyl and butyl p-hydroxybenzoate (parabens)) antimicrobial preservatives (e.g., sodium benzoate, sorbic acid), colorants and flavorants. In some embodiments, compounds of the present invention may be formulated for liquid filled capsules in the form of the pure drug as granules and/or powders in the liquid. In a related embodiment, the capsule contained the drug in liquid may be enterically coated. In another embodiment, granules and/or powders of compounds of the invention may be enterically coated before being placed in a liquid and the combination placed in a capsule. The enterically coated granules and/or powder may feature one or several types of enteric coating to enable deliver of the drug to different regions of the intestine. The capsule may lack enteric coating or may be coated with an enteric coating matching or differing entirely from the coating applied to any of the enterically coated material inside the capsule.

In another embodiment, molecules of the present invention may be encapsulated in a capsule comprised of material which affords post-gastric drug delivery without the need for the separate application of an enteric coating (e.g., Entericare enteric softgels). The molecules may be encapsulated in such capsules as granules or powders with or without excipients, and as solutions or suspensions as described above.

In some embodiments, the solid particles of the compounds of the present invention, as a variety of particle sizes and particle size distributions, may be admixed with excipients such as microcrystalline cellulose or lactose and formed as a bead which comprise the drug-containing core onto which the enteric coating is applied. In some embodiments, molecules of the current invention may be formed as a suspension or solution including, optionally, buffers (e.g., aq. 1 N HCl with tris-hydroxymethyl-aminomethane [TRIS]), and binders (e.g., Opadry Clear Coat Powder) and coated onto a base particle, for example sugar beads (e.g., Sugar Spheres, NF particles) to form a bead. In another embodiment, the beads may be enterically coated. In yet another embodiment, molecules of the invention may be formulated as enterically coated beads, as described above, and the beads further formulated by encapsulation. In a further embodiment, a combination of beads with different types of enteric coating may be encapsulated, such that once released from the capsule, compounds of the invention are made available in a controlled manner at different regions ranging from the duodenum to other parts of the intestine. The capsule may lack enteric coating or may be coated with an enteric coating matching or differing entirely from the coating applied to any of the enterically coated material inside the capsule.

In a further embodiment, compounds of the present invention may be formulated as tablets or caplets which alone or in combination with other formulation components deliver drug to the duodenum or other intestinal region. In one embodiment, compounds of the invention are formulated as tablets or caplets which are enterically coated and which constitute the dosage form administered. In another embodiment, tablets or caplets of suitable size and shape may be placed inside a capsule. In one such embodiment, the capsule may be enterically coated and contain non-enterically coated tablets or caplets which are released from the capsule in the duodenum or other intestinal region. In yet another such embodiment, the capsule may be designed to disintegrate in the stomach and release enterically coated tablets or caplets for subsequent delivery to duodenum or other intestinal regions. In yet another such embodiment, the capsule and tablets or caplets contained within may both be enterically coated to provide further control over the release of the tablets or caplets from the capsule, and the subsequent release of the drug from the tablet or caplet. In a further related embodiment, tablets or caplets featuring a variety of enteric coating may combined and place in a capsule which itself may optionally be enterically coated as well. Materials which are useful for enteric coatings for tablets and caplets include but are not limited to those described above for application to capsules.

Enteric coatings may permit premature drug release in acidic media. In a still further embodiment, compounds of the present invention may be formulated such that a subcoating is applied before the enteric coating is applied. The subcoating may comprise application to the enteric substrate of a soluble subcoating agent, examples of which are hydroxypropylmethylcellulose, povidone, hydroxypropyl cellulose, polyethylene glycol 3350, 4500, 8000, methyl cellulose, pseudo ethylcellulose and amylopectin. A thin subcoating layer on the enteric substrate impedes water penetration through the enteric coating on the capsule shell or into the core where the active ingredient is located, preventing premature drug release. The subcoating may also promote the release of the drug in a basic environment by moderating the acidic microenvironment at the interface between the core and the enteric coating. In some embodiments, compounds of the present invention are formulated with a subcoating containing organic acids intended to promote more rapid polymer dissolution of a capsule as the coating degrades in environments with pH 5-6, promoting a rapid release of the drug in basic media.

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). It is understood that similar type of film coating or polymeric products from other companies may be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propylpara-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes.

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S.

Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the composition is designed to promote controlled release of the drug, such that the location, extent and rate of exposure of the compound when administered are modulated. Factors that affect the target zone for exposure of an orally administered drug may be the drug's pH and enzymatic stability, reactivity with other drugs (e.g., certain antibiotics), solubility as a salt or free base, ionization behavior, and pharmacodynamic and pharmacokinetic behaviors in specific environments.

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets that are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include targeted delivery within the gastrointestinal tract upon oral administration, extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example water, pH, temperature, enzymes, bacteria, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations. The active drug substance can also be coated on an implantable medical device to be eluted or be released using a remotely activated system.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation (drug embedded in polymeric matrices).

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 24 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 24 hours, about 12 hours, about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 24 hours, about 12 hours, about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

A drug may be better absorbed in the duodenum or other intestinal locations. A particularly useful mode of controlled release is one which minimizes release of drug in the stomach, while delivering drug in its most concentrated form to the duodenum or other intestinal locations. In certain embodiments, the compounds of the present invention are formulated to promote delivery to the duodenum and, optionally, other intestinal locations. Controlled release that delivers drug to the duodenum or other intestinal regions may be achieved using compositions that include enteric coatings. Enteric coatings are insoluble in highly acidic environments, often comprising a polyacidic coating that remains non-ionized and intact at gastric pH. However, under mildly acidic (>pH 5.5) or neutral or mildly alkaline conditions (pH 6.5-7.6) of the duodenum or other intestinal regions, the coating ionizes, swells and breaks down, exposing the coated entity to the environment. Coating options exist to allow ionization at or near a specific pH (e.g. Eudragit L-110, ionization threshold pH 6.0; Eudragit S-100, ionization threshold pH 7.0). It is understood that similar type or grade of film coating or polymeric products from other companies may be used.

In certain embodiments, compounds of the present invention are formulated with an enteric coating, which has been modified by adding plasticizers to the polymer before coating. The plasticizers may be added to adjust resistance to chipping or cracking of the coating, while also lowering the glass transition temperature of the coating to enable smoothness and even spreadability of the coating during its application. Suitable plasticizers include polyethylene glycol 8000 (PEG 8000), triethyl citrate (TEC), and triacetin, which may be incorporated into the polymeric enteric coating agent.

Compounds of the present invention may be enterically formulated under a variety of dosage forms, including (but not limited to) capsules, granules of the active drug itself, beads, micro spheres, and tablets. In certain embodiments, the composition comprises a drug encapsulated in a capsule enterically coated to release the drug in the duodenum or other intestinal environment. In other embodiments, pharmaceutically acceptable capsules include hard capsules. In yet other embodiments, pharmaceutically acceptable capsules include soft gelatin capsules.

In certain embodiments, a compound of the invention is encapsulated in pure granular or powdered form, with no carriers, excipients or other pharmaceutically acceptable additives. In other embodiments, a compound of the invention is encapsulated together with one or more pharmaceutically acceptable carriers, excipients, antioxidants, antifungals, (e.g., benzoic and ascorbic acids and their salts, and phenolic compounds such as methyl, ethyl, propyl and butyl p-hydroxybenzoate (parabens)), antimicrobial preservatives, colorants, and flavorants. The excipients may aid in capsule-filling behaviour, stability, and in the distribution of the drug when the capsule disintegrates in the body. In other embodiments, granules and/or powders of a compound of the present invention are enterically coated before being placed in a capsule. The enterically coated granules and/or powders placed in the capsule may feature one or several types of enteric coating to enable delivery of the drug to different regions of the intestine. The capsule may lack enteric coating or may be coated with an enteric coating that is the same as or distinct from the coating applied to any of the enterically coated materials inside the capsule.

In certain embodiments, a compound of the invention is encapsulated in a liquid in the form of a solution or suspension in water or various pharmaceutically acceptable oils or other dispersion medium, optionally with such excipients as co-solvents (e.g., PEG 300, PEG 400, propylene glycol, glycerol, tween 80, ethanol), solubility enhancers (e.g., sorbitol, dextrose), wetting agents (e.g., thickening agents), buffers (e.g., disodium hydrogen phosphate), antioxidants, antifungals, preservatives, colorants and flavorants. In certain embodiments, a compound of the present invention is formulated for liquid filled capsules in the form of the pure drug as granules and/or powders in the liquid. In other embodiments, the capsule containing the compound in liquid is enterically coated. In yet other embodiments, granules and/or powders of a compound of the invention are enterically coated before being placed in a liquid and the combination placed in a capsule. The enterically coated granules and/or powder may feature one or several types of enteric coating to enable delivery of the drug to distinct regions of the intestine. The capsule may lack enteric coating or may be coated with an enteric coating that is the same as or distinct from the coating applied to any of the enterically coated materials inside the capsule.

In certain embodiments, a compound of the present invention is encapsulated in a capsule comprised of material that affords post-gastric drug delivery without the need for the separate application of an enteric coating (e.g., Entericare enteric softgels). The compound may be encapsulated in such capsules as granules or powders with or without excipients, and as solutions or suspensions as described above.

In certain embodiments, the solid particles of a compound of the present invention, as a variety of particle sizes and particle size distributions, are admixed with excipients such as microcrystalline cellulose or lactose and formed as a bead that comprises the drug-containing core onto which the enteric coating is applied. In other embodiments, a compound of the present invention is formed as a suspension or solution including, optionally, buffers (e.g., aq. 1 N HCl with tris(hydroxymethyl)aminomethane "TRIS"), and binders (e.g., Opadry Clear Coat Powder) and coated onto a base particle, for example sugar beads (e.g., Sugar Spheres, NF particles) to form a bead. In yet other embodiments, the beads are enterically coated. In yet other embodiments, a compound of the invention is formulated as enterically coated beads, as described above, and the beads further formulated by encapsulation. In yet other embodiments, a combination of beads with different types of enteric coating is encapsulated, such that once released from the capsule, the compound of the invention is made available in a controlled manner at different regions ranging from the duodenum to other parts of the intestine. The capsule may lack enteric coating or may be coated with an enteric coating that is the same as or distinct from the coating applied to any of the enterically coated materials inside the capsule.

In certain embodiments, a compound of the present invention is formulated as tablets or caplets which alone or in combination with other formulation components deliver drug to the duodenum or other intestinal region. In other embodiments, a compound of the invention is formulated as tablets or caplets that are enterically coated and that constitute the dosage form administered. In yet other embodiments, tablets or caplets of suitable size and shape are placed inside a capsule. In yet other embodiments, the capsule is enterically coated and contains non-enterically coated tablets or caplets, which are released from the capsule in the duodenum or other intestinal region. In yet other embodiments, the capsule is designed to disintegrate in the stomach and release enterically coated tablets or caplets for subsequent delivery to duodenum or other intestinal regions. In yet other embodiments, the capsule and tablets or caplets contained within are both enterically coated to provide further control over the release of the tablets or caplets from the capsule, and the subsequent release of the drug from the tablet or caplet. In yet other embodiments, tablets or caplets featuring a variety of enteric coating are combined and placed in a capsule which itself may optionally be enterically coated as well. Materials useful for enteric coatings for tablets and caplets include but are not limited to those described above for application to capsules.

Enteric coatings may permit premature drug release in acidic media. In certain embodiments, a compound of the present invention is formulated such that a subcoating is applied before the enteric coating is applied. The subcoating may comprise application to the enteric substrate of a soluble subcoating agent, examples of which are hydroxypropylmethylcellulose, povidone, hydroxypropyl cellulose, polyethylene glycol 3350, 4500, 8000, methyl cellulose, pseudo ethylcellulose and amylopectin. It is understood that similar type of synthetic and semisynthetic polymeric products from other companies may be used. A thin subcoating layer on the enteric substrate impedes water penetration through the enteric coating on the capsule shell or into the core where the active ingredient is located, preventing premature drug release. The subcoating may also promote the release of the drug in a basic environment by moderating the acidic microenvironment at the interface between the core and the enteric coating. In certain embodiments, a compound of the present invention is formulated with a subcoating containing organic acids intended to promote more rapid polymer dissolution of a capsule as the coating degrades in environments with pH 5-6, promoting a rapid release of the drug in basic media.

Mechanical Devices

In one aspect of the invention, a method of treating a patient without normal ventilation and normal breathing control comprises administering the composition useful within the invention as described herein, and additionally treating the patient using a device to support breathing. Such devices include, but are not limited to, ventilation devices, CPAP and BiPAP devices.

Mechanical ventilation is a method to mechanically assist or replace spontaneous breathing. Mechanical ventilation is typically used after an invasive intubation, a procedure wherein an endotracheal or tracheostomy tube is inserted into the airway. It is normally used in acute settings, such as in the ICU, for a short period of time during a serious illness. It may also be used at home or in a nursing or rehabilitation institution, if patients have chronic illnesses that require long-term ventilation assistance. The main form of mechanical ventilation is positive pressure ventilation, which works by increasing the pressure in the patient's airway and thus forcing air into the lungs. Less common today are negative pressure ventilators (for example, the "iron lung") that create a negative pressure environment around the patient's chest, thus sucking air into the lungs. Mechanical ventilation is often a life-saving intervention, but carries many potential complications including pneumothorax, airway injury, alveolar damage, and ventilator-associated pneumonia. For this reason the pressure and volume of gas used is strictly controlled, and discontinued as soon as possible. Types of mechanical ventilation are: conventional positive pressure ventilation, high frequency ventilation, non-invasive ventilation (non-invasive positive pressure ventilation or NIPPY), proportional assist ventilation (PAY), adaptive servo ventilation (ASV) and neurally adjusted ventilatory assist (NAVA).

Non-invasive ventilation refers to all modalities that assist ventilation without the use of an endotracheal tube. Non-invasive ventilation is primarily aimed at minimizing patient discomfort and the complications associated with invasive ventilation, and is often used in cardiac disease, exacerbations of chronic pulmonary disease, sleep apnea, and neuromuscular diseases. Non-invasive ventilation refers only to the patient interface and not the mode of ventilation used; modes may include spontaneous or control modes and may be either pressure or volume cycled modes. Some commonly used modes of NIPPV include:

(a) Continuous positive airway pressure (CPAP): This kind of machine has been used mainly by patients for the treatment of sleep apnea at home, but now is in widespread use across intensive care units as a form of ventilatory support. The CPAP machine stops upper airway obstruction by delivering a stream of compressed air via a hose to a nasal pillow, nose mask or full-face mask, splinting the airway open (keeping it open under air pressure) so that unobstructed breathing becomes possible, reducing and/or preventing apneas and hypopneas. When the machine is turned on, but prior to the mask being placed on the head, a flow of air comes through the mask. After the mask is placed on the head, it is sealed to the face and the air stops flowing. At this point, it is only the air pressure that accomplishes the desired result. This has the additional benefit of reducing or eliminating the extremely loud snoring that sometimes accompanies sleep apnea.

(b) Bi-level positive airway pressure (BIPAP): Pressures alternate between inspiratory positive airway pressure (IPAP) and a lower expiratory positive airway pressure (EPAP), triggered by patient effort. On many such devices, backup rates may be set, which deliver IPAP pressures even if patients fail to initiate a breath.

(c) Intermittent positive pressure ventilation (IPPV), via mouthpiece or mask.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.
Materials:

Unless otherwise noted, all remaining starting materials were obtained from commercial suppliers and used without purification. Final products are typically isolated as salts unless noted otherwise.

Example 1: 2-(2,6-Bis-methylamino-8-propylamino-pyrimido[5,4-d]pyrimidin-4-ylamino)-ethanol (4) and Corresponding Hydrochloride Salt (4a)

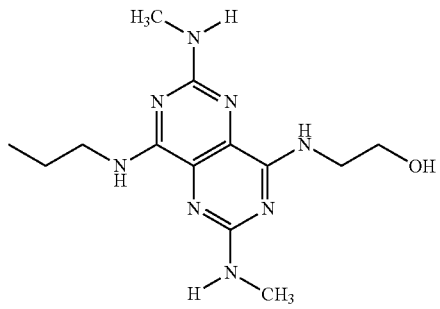

(a) Propyl-(2,6,8-trichloro-pyrimido[5,4-d]pyrimidin-4-yl)-amine (2)

To a suspension of 2,4,6,8-tetrachloro-pyrimido[5,4-d]pyrimidine (1) (3.00 g, 11.15 mmol) in THF (40 mL) at −78° C., propylamine (880 µL, 10.71 mmol) in THF (7 mL) was added via syringe pump (during 20 min) followed by DIPEA (2.12 mL, 12.27 mmol) in THF (7 mL). The reaction mixture was stirred at −78° C. for additional 30 min, and then allowed to reach the room temperature. Water (200 mL) was added and the resulting suspension was extracted with EtOAc (3×200 mL). The combined organic extracts were washed with brine (250 mL) and dried over solid anhydrous MgSO$_4$. After filtration, the solvent was removed and the residue was purified by flash column chromatography using gradient elution from PE/EtOAc (99:1) to PE/EtOAc (5:1) to give propyl-(2,6,8-trichloro-pyrimido[5,4-d]pyrimidin-4-yl)-amine (2) (2.91 g, 93% yield). 300 MHz $^1$H NMR (CDCl$_3$, ppm): 7.22 (1H, br s) 3.69-3.60 (2H, m) 1.78 (2H, sextet, J=7.4 Hz) 1.05 (3H, t, J=7.4 Hz). ESI-MS (m/z): 292, 294, 296, 298 [M+1-1]$^+$.

(b) 2-(2,6-Dichloro-8-propylamino-pyrimido[5,4-d]pyrimidin-4-ylamino)-ethanol (3)

2-Amino-ethanol (2.90 mL, 47.85 mmol) (in 10 mL of dichloromethane) was added in portions to a solution of propyl-(2,6,8-trichloro-pyrimido[5,4-d]pyrimidin-4-yl)-amine (2) (5.60 g, 19.14 mmol) in dichloromethane (180 mL) at 0° C. The reaction mixture was stirred at room temperature for 1 h. Saturated NaHCO$_3$ (100 mL) was added and the resulting suspension was extracted with chloroform (3×100 mL). After filtration, the combined organic extracts were washed with water and dried over solid anhydrous MgSO$_4$. After filtration, the solvent was removed and the residue was purified by flash column chromatography using gradient elution from PE/EtOAc (5:1) to PE/EtOAc (1:2) to give 2-(2,6-dichloro-8-propylamino-pyrimido[5,4-d]pyrimidin-4-ylamino)-ethanol (3) (5.53 g, 91% yield). 300 MHz $^1$H NMR (CDCl$_3$, ppm): 7.30 (1H, t, J=5.7 Hz) 6.91 (1H, t, J=5.7 Hz) 3.96-3.88 (2H, m) 3.83-3.74 (2H, m) 3.61-3.51 (2H, m) 2.62 (1H, T, J=4.9 Hz) 1.80-1.66 (2H, m) 1.02 (3H, t, J=7.4 Hz). ESI-MS (m/z): 317, 319, 321 [M+H]$^+$.

(c) 2-(2,6-Bis-methylamino-8-propylamino-pyrimido[5,4-d]pyrimidin-4-ylamino)-ethanol (4)

A mixture of 2-(2,6-dichloro-8-propylamino-pyrimido[5,4-d]pyrimidin-4-yl amino)-ethanol (3) (5.53 g, 17.43 mmol) and methylamine (40% water solution) (15.00 mL) in n-butanol (50 mL) was heated at 115° C. for 72 h in a closed vial. After cooling, a saturated NaHCO$_3$ solution (100 mL) was added and the resulting suspension was extracted with EtOAc (3×150 mL). The combined organic extracts were washed with water (300 mL), then with brine (300 mL) and dried over solid anhydrous MgSO$_4$. After filtration, the solvent was removed and the residue was purified by flash column chromatography using gradient elution from PE/EtOAc (5:1) to PE/EtOAc (1:3) to give 2-(2,6-bis-methylamino-8-propylamino-pyrimido[5,4-d]pyrimidin-4-ylamino)-ethanol (4) (3.39 g, 63% yield). 300 MHz $^1$H NMR (CDCl$_3$, ppm): 7.03-6.83 (1H, m) 6.61-6.41 (1H, m) 4.84-4.48 (3H, m) 3.89-3.83 (2H, m) 3.72-3.64 (2H, m) 3.51-3.41 (2H, m) 2.96 (3H, d, J=4.9 Hz) 2.95 (3H, d, J=4.9 Hz) 1.69 (2H, sextet, J=7.4 Hz) 1.00 (3H, t, J=7.4 Hz). ESI-MS (m/z): 307 [M+H]$^+$.

(d) 2-(2,6-Bis-methylamino-8-propylamino-pyrimido[5,4-d]pyrimidin-4-ylamino)-ethanol hydrochloride (4a)

A 2M HCl/diethyl ether solution (4.64 mL, 9.27 mmol) was added to a solution of 2-(2,6-bis-methylamino-8-propylamino-pyrimido[5,4-d]pyrimidin-4-ylamino)-ethanol (4) (2.84 g, 9.27 mmol) in diethyl ether (50 mL) and methanol (25 mL). The mixture was stirred for 1 h at room temperature and the resultant precipitate was filtered, washed with diethyl ether (20 mL), and dried to give 2-(2,6-bis-methylamino-8-propylamino-pyrimido[5,4-d]pyrimidin-4-ylamino)-ethanol hydrochloride (4a) (3.13 g, 98% yield). 300 MHz $^1$H NMR (D$_2$O, ppm): 3.85 (2H, t, J=5.4 Hz) 3.68 (2H, t, J=5.4 Hz) 3.44 (2H, t, J=7.3 Hz) 2.95 (3H, s) 2.94 (3H, s) 1.68 (2H, sextet, J=7.4 Hz) 0.97 (3H, t, J=7.4 Hz). ESI-MS (m/z): 307 [M+H]$^+$; MP: 201-203° C.

Scheme 5

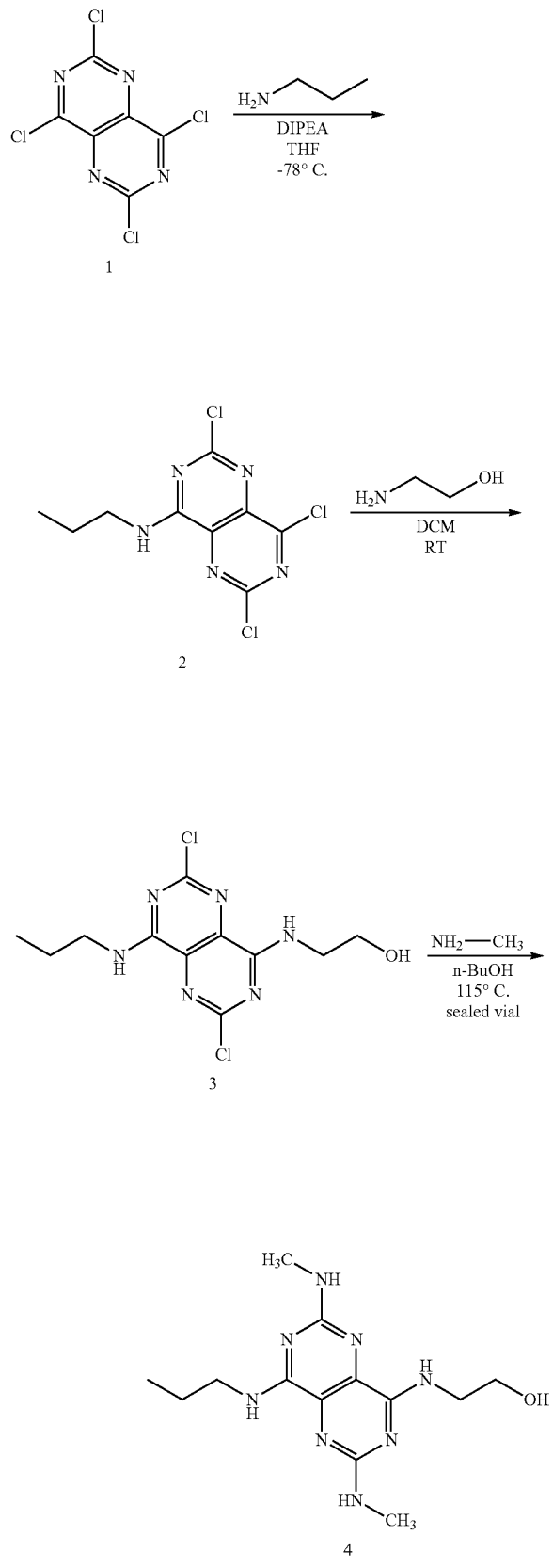

Example 2: 2-[(2,6-Bis-methylamino-8-propylamino-pyrimido[5,4-d]pyrimidin-4-yl)-methyl-amino]-ethanol (6) and Corresponding Hydrochloride Salt (6a)

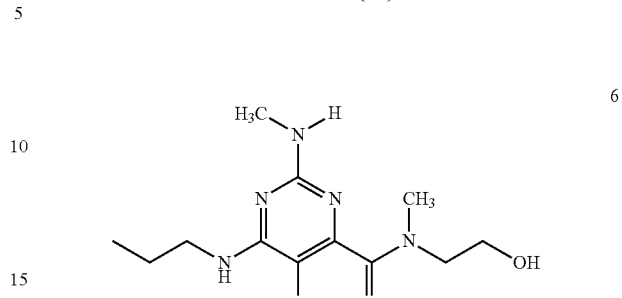

(a) 2-[(2,6-Dichloro-8-propylamino-pyrimido[5,4-d]pyrimidin-4-yl)-methyl-amino]-ethanol (5)

2-Methylamino-ethanol (740 µL, 3.00 mmol) was added to a solution of propyl-(2,6,8-trichloro-pyrimido[5,4-d]pyrimidin-4-yl)-amine (2) (350 mg, 1.20 mmol) in dichloromethane (15 mL) at 0° C. The reaction mixture was stirred at room temperature for 2h. After this time, a saturated NaHCO$_3$ (30 mL) was added, and the resulting suspension was extracted with dichloromethane (3×10 mL). The combined organic extracts were washed with water (30 mL) and dried over solid anhydrous MgSO$_4$. After filtration, the solvent was removed and the residue was purified by flash column chromatography using gradient elution from PE/EtOAc (9:1) to PE/EtOAc (1:1) to give 2-[(2,6-dichloro-8-propylamino-pyrimido[5,4-d]pyrimidin-4-yl)-methyl-amino]-ethanol (5) (230 mg, 58% yield). 300 MHz $^1$H NMR (CDCl$_3$, ppm): 7.08 (1H, br s) 4.39-4.13 (2H, m) 4.05-3.98 (2H, m) 3.85 (1H, br s) 3.59-3.50 (2H, m) 3.38 (3H, s) 1.72 (2H, sextet, J=7.4 Hz) 1.02 (3H, t, J=7.4 Hz). ESI-MS (m/z): 331, 333, 335 [M+1-1]$^+$.

(b) 2-[(2,6-Bis-methylamino-8-propylamino-pyrimido[5,4-d]pyrimidin-4-yl)-methyl-amino]-ethanol (6)

A mixture of 2-[(2,6-dichloro-8-propylamino-pyrimido[5,4-d]pyrimidin-4-yl)-methyl-amino]-ethanol (5) (210 g mg, 0.63 mmol) and methylamine (40% water solution) (330 µL, 4.25 mmol) in n-butanol (3 mL) was heated at 100° C. for 40 h in a closed vial. After cooling, a saturated NaHCO$_3$ solution (20 mL) was added and the resulting suspension was extracted with EtOAc (3×25 mL). The combined organic extracts were washed with water (30 mL), then with brine (30 mL) and dried over solid anhydrous MgSO$_4$. After filtration, the solvent was removed and the residue was purified by flash column chromatography using gradient elution from PE/EtOAc (9:1) to PE/EtOAc (1:4) to give 2-[(2,6-bis-methylamino-8-propylamino-pyrimido[5,4-d]pyrimidin-4-yl)-methyl-amino]-ethanol (6) (80 mg, 40% yield). 400 MHz $^1$H NMR (CDCl$_3$, ppm): 6.86-6.73 (1H, m) 6.5-6.2 (1H, m) 4.72-4.51 (2H, m) 4.18 (2H, t, J=4.9 Hz) 3.95 (2H, t, J=4.9 Hz) 3.49-3.41 (2H, m) 3.27 (3H, m) 2.96 (3H, d, J=5.1 Hz) 2.96 (3H, d, J=5.1 Hz) 1.74-1.64 (2H, m) 1.00 (3H, t, J=7.4 Hz). ESI-MS (m/z): 321 [M+H]$^+$.

(c) 2-[(2,6-Bis-methylamino-8-propylamino-pyrimido[5,4-d]pyrimidin-4-yl)-methyl-amino]-ethanol hydrochloride (6a)

A 2M HCl/diethyl ether solution (115 μL, 0.23 mmol) was added to the solution of 2-[(2,6-bis-methylamino-8-propylamino-pyrimido[5,4-d]pyrimidin-4-yl)-methyl-amino]-ethanol (6) (74 mg, 0.23 mmol) in diethyl ether (5 mL). The mixture was stirred for 30 min at room temperature and then the precipitate were filtered, washed with diethyl ether (3 mL), and dried to give 2-[(2,6-bis-methylamino-8-propylamino-pyrimido[5,4-d]pyrimidin-4-yl)-methyl-amino]-ethanol hydrochloride (6a) (81 mg, 99% yield). 400 MHz $^1$H NMR (CDCl$_3$, ppm): 14.2-13.7 (1H, m) 8.4-7.7 (2H, m) 6.7-6.3 (1H, m) 4.28-3.77 (4H, m) 3.64-3.49 (2H, m) 3.28 (3H, s) 3.03-2.97 (6H, m) 1.83-1.72 (2H, m) 1.02 (3H, t, J=7.4 Hz). ESI-MS (m/z): 321 [M+H]$^+$; MP: 165-167° C.

Example 3: 3-(2,6-Bis-methylamino-8-propylamino-pyrimido[5,4-d]pyrimidin-4-ylamino)-propan-1-ol (8) and Corresponding Hydrochloride Salt (8a)

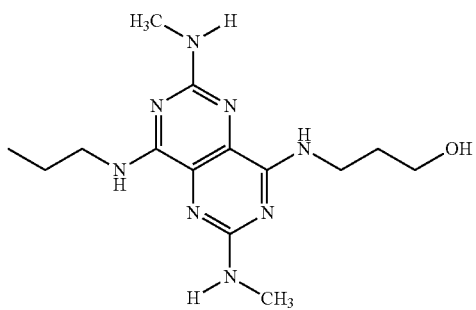

8

(a) 3-(2,6-Dichloro-8-propylamino-pyrimido[5,4-d]pyrimidin-4-ylamino)-propan-1-ol (7)

3-(2,6-Dichloro-8-propylamino-pyrimido[5,4-d]pyrimidin-4-ylamino)-propan-1-ol (7) was prepared from propyl-(2,6,8-trichloro-pyrimido[5,4-d]pyrimidin-4-yl)-amine (2) (300 mg, 1.03 mmol) and 3-amino-propan-1-ol in dichloromethane using procedure described for compound (5) to give 3-(2,6-dichloro-8-propylamino-pyrimido[5,4-d]pyrimidin-4-ylamino)-propan-1-ol (7) (260 mg, 77% yield). 400 MHz $^1$H NMR (CDCl$_3$, ppm): 7.17 (1H, t, J=6.3 Hz) 6.90 (1H, t, J=5.8 Hz) 3.79-3.73 (2H, m) 3.69 (2H, t, J=5.6 Hz) 3.59-3.53 (2H, m) 3.02 (1H, br s) 1.92-1.84 (2H, m) 1.72 (2H, sextet, J=7.4 Hz) 1.02 (3H, t, J=7.4 Hz). ESI-MS (m/z): 331, 333, 335 [M+1-1]$^+$.

(b) 3-(2,6-Bis-methylamino-8-propylamino-pyrimido[5,4-d]pyrimidin-4-ylamino)-propan-1-ol (8)

3-(2,6-Dichloro-8-propylamino-pyrimido[5,4-d]pyrimidin-4-yl amino)-propan-1-ol (7) (250 mg, 0.75 mmol) and methylamine (40% water solution) in n-butanol were reacted using the procedure described for compound (6). The crude product was purified by flash column chromatography using gradient elution from CH$_2$Cl$_2$ to CH$_2$Cl$_2$/MeOH (95:5) to give 3-(2,6-bis-methylamino-8-propylamino-pyrimido[5,4-d]pyrimidin-4-ylamino)-propan-1-ol (8) (200 mg, 83% yield). 400 MHz $^1$H NMR (CDCl$_3$, ppm): 6.73 (1H, s) 6.52 (1H, s) 4.88 (1H, s) 4.63 (1H, s) 4.57 (1H, s) 3.73-3.65 (2H, m) 3.59 (2H, t, J=5.5) 3.50-3.43 (2H, m) 2.97 (3H, d, J=5.2 Hz) 2.95 (3H, d, J=5.2 Hz) 1.83-1.75 (2H, m) 1.75-1.64 (2H, m) 1.00 (3H, t, J=7.4 Hz). ESI-MS (m/z): 321 [M+H]$^+$.

(c) 3-(2,6-Bis-methylamino-8-propylamino-pyrimido[5,4-d]pyrimidin-4-ylamino)-propan-1-ol hydrochloride (8a)

3-(2,6-Bis-methylamino-8-propylamino-pyrimido[5,4-d]pyrimidin-4-ylamino)-propan-1-ol (8) (190 mg, 0.59 mmol) and 2M HCl/diethyl ether in diethyl ether were reacted using procedure described for compound (6a) to afford the desired product (208 mg, 98% yield). 400 MHz $^1$H NMR (CD$_3$OD, ppm): 3.74-3.66 (4H, m) 3.56 (2H, t, J=7.2 Hz) 3.00 (6H, d, J=5.2 Hz) 1.97-1.88 (2H, m) 1.79-1.68 (2H, m) 1.02 (3H, t, J=7.4 Hz). ESI-MS (m/z): 321 [M+H]$^+$; MP: 178-180° C.

Example 4: 1-(2,6-Bis-methylamino-8-propylamino-pyrimido[5,4-d]-pyrimidin-4-ylamino)-propan-2-ol (10) and Corresponding Hydrochloride Salt (10a)

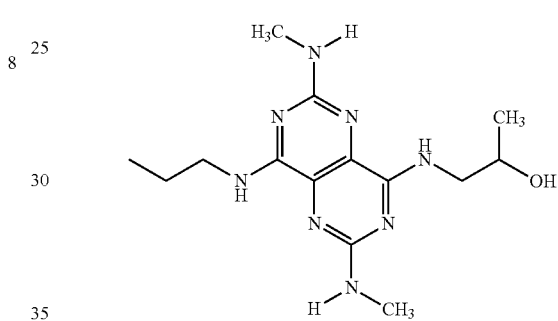

10

(a) 1-(2,6-Dichloro-8-propylamino-pyrimido[5,4-d]pyrimidin-4-ylamino)-propan-2-ol (9)

A mixture of propyl-(2,6,8-trichloro-pyrimido[5,4-d]pyrimidin-4-yl)-amine (2) (350 mg, 1.20 mmol), 1-amino-propan-2-ol (100 μL, 1.25 mmol) and N,N-diisopropylethyl amine (230 μL, 1.31 mmol) in dichloromethane (7 mL) was stirred at room temperature for 2h. A saturated NaHCO$_3$ solution (30 mL) was then added and the resulting suspension was extracted with dichloromethane (3×10 mL). The combined organic extracts were washed with water (30 mL) and dried over solid anhydrous MgSO$_4$. After filtration, the volatiles were removed, and the residue was dissolved in dichloromethane (5 mL) and filtered through a pad of silica gel. The solvent was evaporated to give 1-(2,6-dichloro-8-propylamino-pyrimido[5,4-d]pyrimidin-4-ylamino)-propan-2-ol (9) (380 mg, 96% yield). 300 MHz $^1$H NMR (CDCl$_3$, ppm): 7.31 (1H, t, J=5.7 Hz) 6.90 (1H, t, J=5.5 Hz) 4.19-4.08 (1H, m) 3.78 (1H, ddd, J=14.0, 6.6, 3.1 Hz) 3.60-3.51 (2H, m) 3.48 (1H, ddd, J=14.0, 7.8, 5.5 Hz) 2.67 (1H, s) 1.72 (2H, sextet, J=7.4 Hz) 1.30 (3H, d, J=6.3 Hz) 1.02 (3H, t, J=7.4 Hz). ESI-MS (m/z): 331, 333, 335 [M+H]$^+$.

(b) 1-(2,6-Bis-methylamino-8-propylamino-pyrimido[5,4-d]-pyrimidin-4-ylamino)-propan-2-ol (10)

1-(2,6-Dichloro-8-propylamino-pyrimido[5,4-d]pyrimidin-4-ylamino)-propan-2-ol (9) (370 mg, 1.12 mmol) and methylamine (40% water solution) were reacted in n-butanol using procedure described for compound 4 to give 1-(2,6-bis-methylamino-8-propylamino-pyrimido[5,4-d]-pyrimidin-4-ylamino)-propan-2-ol (10) (230 mg, 64% yield). 400 MHz $^1$H NMR (CDCl$_3$, ppm): 6.96-6.81 (1H, m) 6.59-6.42 (1H, m) 4.90 (1H, s) 4.69-4.51 (2H, m) 4.11-4.01 (1H, m) 3.64-3.56 (1H, m) 3.50 (1H, dd, J=7.1, 6.0 Hz) 3.47-3.42 (2H, m) 2.96 (3H, d, J=5.1 Hz) 2.95 (3H, d, J=5.1 Hz) 1.74-1.63 (2H, m) 1.23 (3H, d, J=6.4 Hz) 1.00 (3H, t, J=7.4 Hz). ESI-MS (m/z): 321 [M+1-1]$^+$.

(c) 1-(2,6-Bis-methylamino-8-propylamino-pyrimido[5,4-d]-pyrimidin-4-ylamino)-propan-2-ol hydrochloride (10a)

1-(2,6-Bis-methylamino-8-propylamino-pyrimido[5,4-d]-pyrimidin-4-ylamino)-propan-2-ol (10) (190 mg, 0.59 mmol) and 2M HCl/diethyl ether in diethyl ether were reacted using procedure described for compound 6a to afford 1-(2,6-bis-methylamino-8-propylamino-pyrimido[5,4-d]-pyrimidin-4-ylamino)-propan-2-ol hydrochloride (10a) (200 mg, 75% yield). 400 MHz $^1$H NMR (D$_2$O, ppm): 4.18-4.08 (1H, m) 3.63 (1H, dd, J=13.9, 4.1 Hz) 3.52 (1H, dd, J=13.9, 7.6 Hz) 3.47 (2H, t, J=7.2 Hz) 2.97 (3H, s) 2.95 (3H, s) 1.74-1.63 (2H, m) 1.25 (3H, d, J=6.4 Hz) 0.97 (3H, t, J=7.4 Hz). ESI-MS (m/z): 321 [M+H]$^+$; MP: 216-219° C.

Example 5: (S)-1-(2,6-Bis-methylamino-8-propylamino-pyrimido[5,4-d]pyrimidin-4-ylamino)-propan-2-ol (12) and Corresponding Hydrochloride Salt (12a)

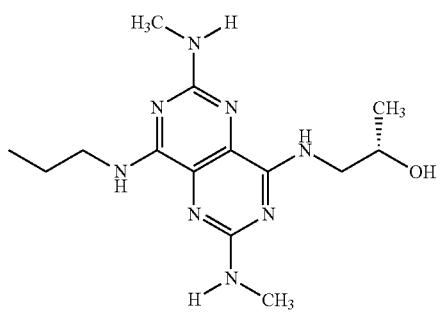

12

(a) (S)-1-(2,6-Dichloro-8-propylamino-pyrimido[5,4-d]pyrimidin-4-ylamino)-propan-2-ol (11)

Propyl-(2,6,8-trichloro-pyrimido[5,4-d]pyrimidin-4-yl)-amine (2) (300 mg, 1.03 mmol) and (S)-1-amino-propan-2-ol were reacted in dichloromethane (7 ml) using procedure described for compound 9 to give (S)-1-(2,6-dichloro-8-propylamino-pyrimido[5,4-d]pyrimidin-4-ylamino)-propan-2-ol (11) (333 mg, 98% yield). 300 MHz $^1$H NMR (CDCl$_3$, ppm): 7.32 (1H, t, J=5.8 Hz) 6.90 (1H, t, J=5.5 Hz) 4.19-4.08 (1H, m) 3.78 (1H, ddd, J=14.0, 6.6, 3.1 Hz) 3.60-3.42 (3H, m) 2.74 (1H, s) 1.72 (2H, sextet, J=7.4 Hz) 1.30 (3H, d, J=6.3 Hz) 1.01 (3H, t, J=7.4 Hz). ESI-MS (m/z): 331, 333, 335 [M+1-1]$^+$.

(b) (S)-1-(2,6-Bis-methylamino-8-propylamino-pyrimido[5,4-d]pyrimidin-4-ylamino)-propan-2-ol (12)

(S)-1-(2,6-Dichloro-8-propylamino-pyrimido[5,4-d]pyrimidin-4-ylamino)-propan-2-ol (11) (340 mg, 1.03 mmol) and methylamine (40% water solution) were reacted in n-butanol using procedure described for compound 4. The crude product was purified by flash column chromatography using gradient elution from CHCl$_3$ to CHCl$_3$/MeOH (9:1) to give (S)-1-(2,6-bis-methylamino-8-propylamino-pyrimido[5,4-d]pyrimidin-4-ylamino)-propan-2-ol (12) (160 mg, 48% yield). 300 MHz $^1$H NMR (CDCl$_3$, ppm): 6.97-6.84 (1H, m) 6.58-6.44 (1H, m) 4.92 (1H, s) 4.74-4.53 (2H, m) 4.13-3.99 (1H, m) 3.60 (1H, ddd, J=14.3, 6.4, 2.4 Hz) 3.53-3.39 (3H, m) 2.96 (3H, d, J=5.1 Hz) 2.94 (3H, d, J=5.1 Hz) 1.68 (2H, sextet, J=7.4 Hz) 1.22 (3H, d, J=6.4 Hz) 0.99 (3H, t, J=7.4 Hz). ESI-MS (m/z): 321 [M+1-1]$^+$.

(c) (S)-1-(2,6-Bis-methylamino-8-propylamino-pyrimido[5,4-d]pyrimidin-4-ylamino)-propan-2-ol hydrochloride (12a)

A 2M HCl/diethyl ether (220 μL, 0.44 mmol) was added to the solution of (S)-1-(2,6-bis-methylamino-8-propylamino-pyrimido[5,4-d]pyrimidin-4-ylamino)-propan-2-ol (12) (140 mg, 0.44 mmol) in diethyl ether (5 mL) and dichloromethane (6 mL). The mixture was stirred for 30 min at room temperature and then the volatiles were removed in vacuum. The residue was treated with diethyl ether (5 mL) and the resultant precipitate were filtered, washed with diethyl ether (3 mL), and dried to give (S)-1-(2,6-bis-methylamino-8-propylamino-pyrimido[5,4-d]pyrimidin-4-ylamino)-propan-2-ol hydrochloride (12a) (150 mg, 96% yield). 300 MHz $^1$H NMR (CD$_3$OD, ppm): 4.14-3.99 (1H, m) 3.69 (1H, dd, J=13.6, 4.0 Hz) 3.57 (2H, t, J=7.2 Hz) 3.48 (1H, dd, J=13.6, 7.6 Hz) 3.00 (3H, s) 2.99 (3H, s) 1.74 (2H, sextet, J=7.4 Hz) 1.24 (3H, d, J=6.3 Hz) 1.01 (3H, t, J=7.4 Hz). ESI-MS (m/z): 321 [M+H]$^+$; MP: 206-208° C.

Example 6: (R)-1-(2,6-Bis-methylamino-8-propylamino-pyrimido[5,4-d]pyrimidin-4-ylamino)-propan-2-ol (14) and Corresponding Hydrochloride Salt (14a)

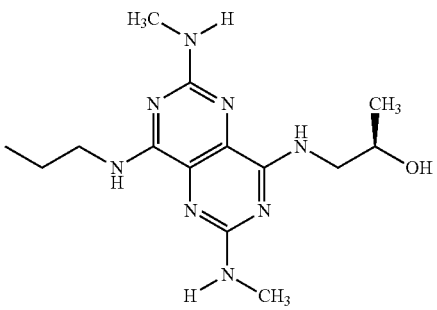

14

(a) (R)-1-(2,6-Dichloro-8-propylamino-pyrimido[5,4-d]pyrimidin-4-ylamino)-propan-2-ol (13)

Propyl-(2,6,8-trichloro-pyrimido[5,4-d]pyrimidin-4-yl)-amine (2) (300 mg, 1.03 mmol) and (R)-1-amino-propan-2-ol were reacted in dichloromethane using procedure described for compound 9 to give (R)-1-(2,6-dichloro-8-propylamino-pyrimido[5,4-d]pyrimidin-4-yl amino)-propan-2-ol (13) (333 mg, 98% yield). 300 MHz $^1$H NMR (CDCl$_3$, ppm): 7.32 (1H, t, J=5.8 Hz) 6.90 (1H, t, J=5.5 Hz) 4.19-4.08 (1H, m) 3.78 (1H, ddd, J=14.0, 6.6, 3.1 Hz)

3.60-3.42 (3H, m) 2.74 (1H, s) 1.72 (2H, sextet, J=7.4 Hz) 1.30 (3H, d, J=6.3 Hz) 1.01 (3H, t, J=7.4 Hz). ESI-MS (m/z): 331, 333, 335 [M+1-1]$^+$.

(b) (R)-1-(2,6-Bis-methylamino-8-propylamino-pyrimido[5,4-d]pyrimidin-4-ylamino)-propan-2-ol (14)

(R)-1-(2,6-Dichloro-8-propylamino-pyrimido[5,4-d]pyrimidin-4-ylamino)-propan-2-ol (13) (311 mg, 0.94 mmol) and methylamine (40% water solution) were reacted in n-butanol using procedure described for compound 4 to produce (R)-1-(2,6-bis-methylamino-8-propylamino-pyrimido[5,4-d]pyrimidin-4-ylamino)-propan-2-ol (14) (190 mg, 63% yield). 300 MHz $^1$H NMR (CDCl$_3$, ppm): 6.95-6.82 (1H, m) 6.57-6.41 (1H, m) 4.92 (1H, br s) 4.70-4.53 (2H, m) 4.13-4.01 (1H, m) 3.61 (1H, ddd, J=14.3, 6.3, 2.3) 3.54-3.41 (3H, m) 2.96 (3H, d, J=5.0 Hz) 2.95 (3H, d, J=5.0 Hz) 1.69 (2H, sextet, J=7.4 Hz) 1.23 (3H, d, J=6.4 Hz) 1.0 (3H, t, J=7.4 Hz). ESI-MS (m/z): 321 [M+1-1]$^+$.

(c) (R)-1-(2,6-Bis-methylamino-8-propylamino-pyrimido[5,4-d]pyrimidin-4-ylamino)-propan-2-ol Hydrochloride (14a)

(R)-1-(2,6-Bis-methylamino-8-propylamino-pyrimido[5,4-d]pyrimidin-4-ylamino)-propan-2-ol (14) (180 mg, 0.56 mmol) and 2M HCl/diethyl ether were reacted in dichloromethane using procedure described for compound (12a) to produce (R)-1-(2,6-bis-methylamino-8-propylamino-pyrimido[5,4-d]pyrimidin-4-ylamino)-propan-2-ol hydrochloride (14a) (170 mg, 85% yield). 300 MHz $^1$H NMR (CDCl$_3$, ppm): 14.25-13.60 (1H, m) 8.11-7.88 (1H, m) 7.67-7.46 (1H, m) 6.63-6.24 (1H, m) 4.88 (1H, br s) 4.23-4.10 (1H, m) 3.79-3.34 (4H, m) 3.09-2.86 (6H, m) 1.76 (2H, sextet, J=7.4 Hz) 1.28 (3H, d, J=5.6 Hz) 1.03 (3H, t, J=7.4 Hz). ESI-MS (m/z): 321 [M+H]$^+$; MP: 218-220° C.

Example 7: 2-(2,6-Bis-methylamino-8-propylamino-pyrimido[5,4-d]-pyrimidin-4-ylamino)-2-methyl-propan-1-ol (16) and Corresponding Hydrochloride Salt (16a)

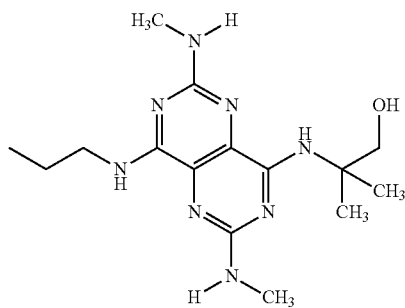

16

(a) 2-(2,6-Dichloro-8-propylamino-pyrimido[5,4-d]pyrimidin-4-ylamino)-2-methyl-propan-1-ol (15)

Propyl-(2,6,8-trichloro-pyrimido[5,4-d]pyrimidin-4-yl)-amine (2) (350 mg, 1.20 mmol) and 2-amino-2-methyl-propan-1-ol were reacted in dichloromethane using procedure described for compound 5 to give 2-(2,6-dichloro-8-propylamino-pyrimido[5,4-d]pyrimidin-4-ylamino)-2-methyl-propan-1-ol (15) (250 mg, 60% yield). 300 MHz $^1$H NMR (CDCl$_3$, ppm): 6.97 (1H, s) 6.89 (1H, t, J=5.5 Hz) 4.59 (1H, t, J=6.5 Hz) 3.77 (2H, d, J=6.5 Hz) 3.60-3.50 (2H, m) 1.72 (2H, sextet, J=7.4 Hz) 1.48 (6H, s) 1.02 (3H, t, J=7.4 Hz). ESI-MS (m/z): 345, 347, 349 [M+H]$^+$.

(b) 2-(2,6-Bis-methylamino-8-propylamino-pyrimido[5,4-d]-pyrimidin-4-ylamino)-2-methyl-propan-1-ol (16)

2-(2,6-Dichloro-8-propylamino-pyrimido[5,4-d]pyrimidin-4-ylamino)-2-methyl-propan-1-ol (15) (250 mg, 0.72 mmol) and methylamine (40% water solution) were reacted in n-butanol using procedure described for compound 4 to afford 2-(2,6-bis-methylamino-8-propylamino-pyrimido[5,4-d]-pyrimidin-4-ylamino)-2-methyl-propan-1-ol (16) (120 mg, 50% yield). 300 MHz $^1$H NMR (CDCl$_3$, ppm): 6.96 (1H, s) 6.72 (1H, s) 6.48 (1H, t, J=5.7 Hz) 4.62 (1H, q, J=5.0 Hz) 4.54 (1H, q, J=5.0 Hz) 3.70 (2H, s) 3.51-3.40 (2H, m) 2.96 (3H, d, J=5.0 Hz) 2.95 (3H, d, J=5.0 Hz) 1.76-1.62 (2H, m) 1.44 (6H, s) 1.00 (3H, t, J=7.4 Hz). ESI-MS (m/z): 335 [M+H]$^+$.

(c) 2-(2,6-Bis-methylamino-8-propylamino-pyrimido[5,4-d]-pyrimidin-4-ylamino)-2-methyl-propan-1-ol hydrochloride (16a)

2-(2,6-Bis-methylamino-8-propylamino-pyrimido[5,4-d]-pyrimidin-4-ylamino)-2-methyl-propan-1-ol (16) (115 mg, 0.34 mmol) was treated with 2M HCl/diethyl ether in dichloromethane using procedure described for compound (12a) to produce 2-(2,6-bis-methylamino-8-propylamino-pyrimido[5,4-d]-pyrimidin-4-ylamino)-2-methyl-propan-1-ol hydrochloride (16a) (125 mg, 99% yield). 400 MHz $^1$H NMR (CD$_3$OD, ppm): 3.82 (2H, s) 3.56 (2H, t, J=7.1 Hz) 3.00 (3H, s) 2.98 (3H, s) 1.79-1.68 (2H, m) 1.53 (6H, s) 1.01 (3H, t, J=7.4 Hz). ESI-MS (m/z): 335 [M+H]$^+$.

Example 8: (S)-2-(2,6-Bis-methylamino-8-propylamino-pyrimido[5,4-d]-pyrimidin-4-ylamino)-propan-1-ol (18) and Corresponding Hydrochloride Salt (18a)

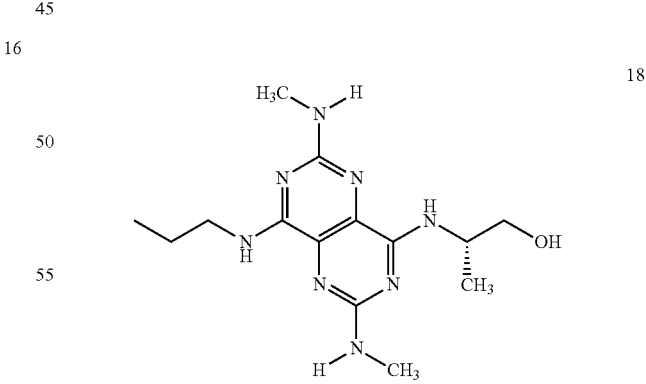

18

(a) (S)-2-(2,6-Dichloro-8-propylamino-pyrimido[5,4-d]pyrimidin-4-ylamino)-propan-1-ol (17)

(S)-2-(2,6-Dichloro-8-propylamino-pyrimido[5,4-d]pyrimidin-4-ylamino)-propan-1-ol (17) was prepared from propyl-(2,6,8-trichloro-pyrimido[5,4-d]pyrimidin-4-yl)- amine (2) (350 mg, 1.20 mmol) and (S)-2-aminopropan-1-ol in dichloromethane using procedure described for compound 5 to obtain the desired product (280 mg, 70% yield). 300 MHz $^1$H NMR (CDCl$_3$, ppm): 7.00 (1H, d, J=7.5 Hz) 6.90 (1H, t, J=5.4 Hz) 4.52-4.38 (1H, m) 3.90-3.79 (1H, m) 3.77-3.67 (1H, m) 3.60-3.51 (2H, m) 2.48 (1H, s) 1.79-1.66 (2H, m) 1.35 (3H, d, J=6.8 Hz) 1.02 (3H, t, J=7.4 Hz). ESI-MS (m/z): 331, 333, 335 [M+H]$^+$.

(b) (S)-2-(2,6-Bis-methylamino-8-propylamino-pyrimido[5,4-d]-pyrimidin-4-ylamino)-propan-1-ol (18)

(S)-2-(2,6-Bis-methylamino-8-propylamino-pyrimido[5,4-d]-pyrimidin-4-ylamino)-propan-1-ol (18) was prepared from (S)-2-(2,6-dichloro-8-propylamino-pyrimido [5,4-d] pyrimidin-4-ylamino)-propan-1-ol (17) (280 mg, 0.85 mmol) and methylamine (40% water solution) in n-butanol using procedure described for compound 4 to obtain the desired product (160 mg, 59% yield). 300 MHz $^1$H NMR (CDCl$_3$, ppm): 6.61-6.39 (2H, m) 4.86 (1H, br s) 4.69-4.49 (2H, m) 4.30-4.15 (1H, m) 3.79 (1H, dd, J=11.0, 2.8 Hz) 3.67 (1H, dd, J=11.0, 7.4 Hz) 3.51-3.41 (2H, m) 2.97 (3H, d, J=5.2 Hz) 2.94 (3H, d, J=5.2 Hz) 1.76-1.61 (2H, m) 1.33 (3H, d, J=6.9 Hz) 1.00 (3H, t, J=7.4 Hz). ESI-MS (m/z): 321 [M+1-1]$^+$.

(c) (S)-2-(2,6-Bis-methylamino-8-propylamino-pyrimido[5,4-d]-pyrimidin-4-ylamino)-propan-1-ol Hydrochloride (18a)

(S)-2-(2,6-Bis-methylamino-8-propylamino-pyrimido[5,4-d]-pyrimidin-4-ylamino)-propan-1-ol hydrochloride (18a) was prepared from (S)-2-(2,6-bis-methylamino-8-propylamino-pyrimido[5,4-d]-pyrimidin-4-ylamino)-propan-1-ol (18) (150 mg, 0.47 mmol) and 2M HCl/diethyl ether in diethyl ether using procedure described for compound 6a to obtain the desired product (135 mg, 80% yield). 400 MHz $^1$H NMR (CD$_3$OD, ppm): 4.51-4.40 (1H, m) 3.72 (1H, dd, J=11.1, 4.8 Hz) 3.67 (1H, dd, J=11.1, 5.5 Hz) 3.60 (2H, t, J=7.3 Hz) 3.03 (3H, s) 3.00 (3H, s) 1.81-1.70 (2H, m) 1.33 (3H, d, J=6.8 Hz) 1.02 (3H, t, J=7.4 Hz). ESI-MS (m/z): 321 [M+H]$^+$.

Example 9: (R)-2-(2,6-Bis-methylamino-8-propylamino-pyrimido[5,4-d]-pyrimidin-4-ylamino)-propan-1-ol (20) and Corresponding Hydrochloride Salt (20a)

(a) (R)-2-(2,6-Dichloro-8-propylamino-pyrimido[5,4-d]pyrimidin-4-ylamino)-propan-1-ol (19)

Propyl-(2,6,8-trichloro-pyrimido[5,4-d]pyrimidin-4-yl)-amine (2) (270 mg, 0.93 mmol) and (R)-2-aminopropan-1-ol were reacted in dichloromethane using procedure described for compound 9 to give (R)-2-(2,6-dichloro-8-propylamino-pyrimido[5,4-d]pyrimidin-4-yl amino)-propan-1-ol (19) (275 mg, 90% yield). 300 MHz $^1$H NMR (CDCl$_3$, ppm): 6.98 (1H, d, J=7.7 Hz) 6.89 (1H, t, J=5.3 Hz) 4.52-4.38 (1H, m) 3.84 (1H, dd, J=11.2, 3.9 Hz) 3.72 (1H, dd, J=11.2, 5.9 Hz) 3.60-3.51 (2H, m) 2.39 (1H, s) 1.79-1.66 (2H, m) 1.36 (3H, d, J=6.8 Hz) 1.02 (3H, t, J=7.4 Hz). ESI-MS (m/z): 331, 333, 335 [M+H]$^+$.

(b) (R)-2-(2,6-Bis-methylamino-8-propylamino-pyrimido[5,4-d]-pyrimidin-4-ylamino)-propan-1-ol (20)

(R)-2-(2,6-dichloro-8-propylamino-pyrimido[5,4-d]pyrimidin-4-ylamino)-propan-1-ol (19) (269 mg, 0.81 mmol) and methylamine (40% water solution) were reacted in n-butanol using procedure described for compound 4 to afford (R)-2-(2,6-bis-methylamino-8-propylamino-pyrimido[5,4-d]-pyrimidin-4-ylamino)-propan-1-ol (20) (180 mg, 69% yield). 300 MHz $^1$H NMR (CDCl$_3$, ppm): 6.67-6.43 (2H, m) 5.0-4.5 (3H, m) 4.30-4.13 (1H, m) 3.79 (1H, dd, J=11.0, 2.8 Hz) 3.68 (1H, dd, J=11.0, 7.4 Hz) 3.51-3.41 (2H, m) 2.97 (3H, d, J=5.1 Hz) 2.95 (3H, d, J=5.1 Hz) 1.77-1.62 (2H, m) 1.34 (3H, d, J=6.9 Hz) 1.00 (3H, t, J=7.4 Hz). ESI-MS (m/z): 321 [M+H]$^+$.

(c) (R)-2-(2,6-Bis-methylamino-8-propylamino-pyrimido[5,4-d]-pyrimidin-4-ylamino)-propan-1-ol Hydrochloride (20a)

(R)-2-(2,6-Bis-methylamino-8-propylamino-pyrimido[5,4-d]-pyrimidin-4-ylamino)-propan-1-ol (20) (143 mg, 0.45 mmol) was treated with 2M HCl/diethyl ether in diethyl ether using procedure described for compound 6a to produce (R)-2-(2,6-bis-methyl amino-8-propylamino-pyrimido[5,4-d]-pyrimidin-4-ylamino)-propan-1-ol hydrochloride (20a) (150 mg, 93% yield). 300 MHz $^1$H NMR (CD$_3$OD, ppm): 4.50-4.38 (1H, m) 3.72 (1H, dd, J=11.1, 4.9 Hz) 3.67 (1H, dd, J=11.1, 5.4 Hz) 3.58 (2H, t, J=7.2 Hz) 3.02 (3H, s) 2.99 (3H, s) 1.81-1.70 (2H, m) 1.33 (3H, d, J=6.8 Hz) 1.01 (3H, t, J=7.4 Hz). ESI-MS (m/z): 321 [M+H]$^+$; MP: 197-199° C.

Example 10: 3-(2,6-Bis-methylamino-8-propylamino-pyrimido[5,4-d]pyrimidin-4-ylamino)-1,1,1-trifluoro-propan-2-ol (22) and Corresponding Hydrochloride Salt (22a)

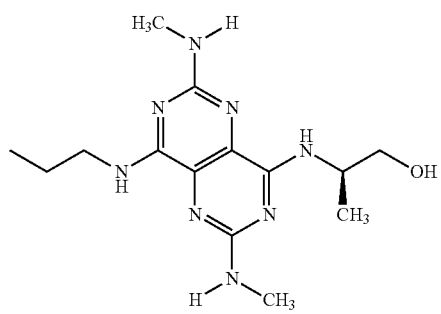

20

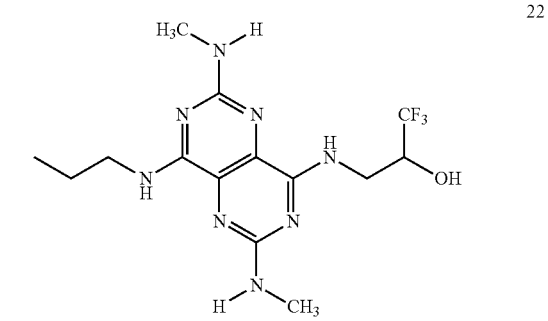 [SMILES: CCCNc1nc(NC)nc2c(NCC(C)O)nc(NC)nc12]

22

(a) 3-(2,6-Dichloro-8-propylamino-pyrimido[5,4-d]pyrimidin-4-ylamino)-1,1,1-trifluoro-propan-2-ol (21)

A mixture of propyl-(2,6,8-trichloro-pyrimido[5,4-d]pyrimidin-4-yl)-amine (2) (250 mg, 0.85 mmol) and 3-amino-1,1,1-trifluoro-propan-2-ol (221 mg, 1.71 mmol) in THF (7 mL) was stirred at room temperature for 18h. A saturated NaHCO$_3$ solution (30 mL) was added, the resulting suspension was extracted with dichloromethane (3×10 mL). The combined organic extracts were washed with brine (30 mL) and dried over solid anhydrous Na$_2$SO$_4$. After filtering, the solvent was removed and the residue was purified by flash column chromatography using gradient elution from PE/EtOAc (3:1) to PE/EtOAc (1:9) to give 3-(2,6-dichloro-8-propylamino-pyrimido[5,4-d]pyrimidin-4-ylamino)-1,1,1-trifluoro-propan-2-ol (21) (277 mg, 84% yield). ESI-MS (m/z): 385, 387, 389 [M+H]$^+$.

(b) 3-(2,6-Bis-methylamino-8-propylamino-pyrimido[5,4-d]pyrimidin-4-ylamino)-1,1,1-trifluoro-propan-2-ol (22)

3-(2,6-Dichloro-8-propylamino-pyrimido[5,4-d]pyrimidin-4-ylamino)-1,1,1-trifluoro-propan-2-ol (21) (277 mg, 0.72 mmol) and methylamine (40% water solution) were reacted in n-butanol at 125° C. using procedure described for compound 4 to give 3-(2,6-bis-methylamino-8-propylamino-pyrimido[5,4-d]pyrimidin-4-ylamino)-1,1,1-trifluoro-propan-2-ol (22) (250 mg, 93% yield). 300 MHz $^1$H NMR (CDCl$_3$, ppm): 6.69-6.87 (2H, m) 6.55-6.46 (1H, m) 4.73-4.58 (2H, m) 4.26-4.14 (1H, m) 3.90-3.74 (2H, m) 3.51-3.40 (2H, m) 2.96 (3H, d, J=5.0 Hz) 2.95 (3H, d, J=5.0 Hz) 1.69 (2H, sextet, J=7.4 Hz) 1.0 (3H, t, J=7.4 Hz). ESI-MS (m/z): 375 [M+H]$^+$.

(c) 3-(2,6-Bis-methylamino-8-propylamino-pyrimido[5,4-d]pyrimidin-4-ylamino)-1,1,1-trifluoro-propan-2-ol Hydrochloride (22a)

3-(2,6-Bis-methylamino-8-propylamino-pyrimido[5,4-d]pyrimidin-4-ylamino)-1,1,1-trifluoro-propan-2-ol (22) (220 mg, 0.59 mmol) was treated with 2M HCl/diethyl ether in dichloromethane using procedure described for compound 12a to produce 3-(2,6-bis-methylamino-8-propylamino-pyrimido[5,4-d]pyrimidin-4-ylamino)-1,1,1-trifluoro-propan-2-ol hydrochloride (22a) (185 mg, 76% yield). 300 MHz $^1$H NMR (CDCl$_3$, ppm): 13.89-13.57 (1H, m) 8.29-8.09 (1H, m) 7.60-7.45 (1H, m) 6.35-6.15 (1H, m) 5.35-5.18 (1H, m) 4.99-4.86 (1H, m) 4.42-4.27 (1H, m) 3.91-3.69 (2H, m) 3.68-3.57 (2H, m) 3.10-3.02 (3H, m) 2.96 (3H, d, J=4.8 Hz) 1.76 (2H, sextet, J=7.4 Hz) 1.04 (3H, t, J=7.4 Hz). ESI-MS (m/z): 375 [M+H]$^+$; MP: 230-232° C.

Example 11: 1-(2,6-Bis-methylamino-8-propylamino-pyrimido[5,4-d]pyrimidin-4-ylamino)-butan-2-ol (24) and Corresponding Hydrochloride Salt (24a)

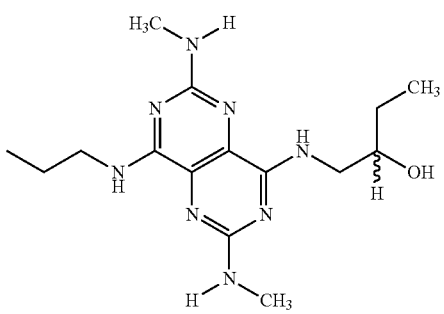

24

(a) 1-(2,6-Dichloro-8-propylamino-pyrimido[5,4-d]pyrimidin-4-ylamino)-butan-2-ol (23)

Propyl-(2,6,8-trichloro-pyrimido[5,4-d]pyrimidin-4-yl)-amine (2) (350 mg, 1.20 mmol) and 1-amino-butan-2-ol were reacted in butanol using procedure described for compound 9 The product was purified by flash column chromatography using gradient elution from CH$_2$Cl$_2$ to CH$_2$Cl$_2$/EtOAc (4:1) as eluent to give to give 1-(2,6-dichloro-8-propylamino-pyrimido[5,4-d]pyrimidin-4-ylamino)-butan-2-ol (23) (350 mg, 84% yield). 300 MHz $^1$H NMR (CDCl$_3$, ppm): 7.29 (1H, t, J=5.7 Hz) 6.90 (1H, t, J=5.7 Hz) 3.89-3.74 (2H, m) 3.60-3.45 (3H, m) 2.63 (1H, d, J=3.8 Hz) 1.72 (2H, sextet, J=7.4 Hz) 1.67-1.51 (2H, m) 1.03 (3H, t, J=7.4 Hz) 1.02 (3H, t, J=7.4 Hz). ESI-MS (m/z): 345, 347, 349 [M+H]$^+$.

(b) 1-(2,6-Bis-methylamino-8-propylamino-pyrimido[5,4-d]pyrimidin-4-ylamino)-butan-2-ol (24)

1-(2,6-Dichloro-8-propylamino-pyrimido[5,4-d]pyrimidin-4-ylamino)-butan-2-ol (23) (350 mg, 1.01 mmol) and methylamine (40% water solution) were reacted in n-butanol using procedure described for compound 4. The crude product was purified by flash column chromatography using gradient elution from CH$_2$Cl$_2$/EtOAc (9:1) to CH$_2$Cl$_2$/EtOAc (1:4) as eluent to give 1-(2,6-bis-methylamino-8-propylamino-pyrimido[5,4-d]pyrimidin-4-ylamino)-butan-2-ol (24) (275 mg, 81% yield). 300 MHz $^1$H NMR (CDCl$_3$, ppm): 6.96-6.80 (1H, m) 6.57-6.43 (1H, m) 4.92 (1H, s) 4.72-4.50 (2H, m) 3.84-3.69 (1H, m) 3.63 (1H, ddd, J=14.3, 6.3, 2.1 Hz) 3.56-3.38 (3H, m) 2.96 (3H, d, J=5.2 Hz) 2.94 (3H, d, J=5.2 Hz) 1.68 (2H, sextet, J=7.4 Hz) 1.60-1.45 (2H, m) 0.99 (6H, t, J=7.4 Hz). ESI-MS (m/z): 335 [M+H]$^+$.

(c) 1-(2,6-Bis-methylamino-8-propylamino-pyrimido[5,4-d]pyrimidin-4-ylamino)-butan-2-ol Hydrochloride (24a)

1-(2,6-Bis-methylamino-8-propylamino-pyrimido[5,4-d]pyrimidin-4-ylamino)-butan-2-ol (24) (270 mg, 0.81 mmol) and 2M HCl/diethyl ether in diethyl ether were reacted using procedure described for compound 6a to produce 1-(2,6-bis-methylamino-8-propylamino-pyrimido[5,4-d]pyrimidin-4-ylamino)-butan-2-ol hydrochloride (24a) (240 mg, 80% yield). 300 MHz $^1$H NMR (CD$_3$OD, ppm) 3.85-3.72 (2H, m) 3.58 (2H, t, J=7.1 Hz) 3.49 (1H, dd, J=14.3, 8.3 Hz) 3.00 (6H, s) 1.75 (2H, sextet, J=7.4 Hz) 1.66-1.42 (2H, m) 1.02 (6H, t, J=7.4 Hz). ESI-MS (m/z): 335 [M+H]$^+$.

Example 12: 3-(2,6-Bis-methylamino-8-propylamino-pyrimido[5,4-d]pyrimidin-4-yl amino)-butan-2-ol (26) and Corresponding Hydrochloride Salt (26a)

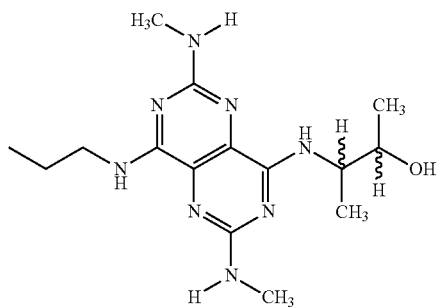

(a) 3-(2,6-Dichloro-8-propylamino-pyrimido[5,4-d]pyrimidin-4-ylamino)-butan-2-ol (25)

Propyl-(2,6,8-trichloro-pyrimido[5,4-d]pyrimidin-4-yl)-amine (2) (360 mg, 1.23 mmol) and 3-amino-butan-2-ol were reacted in n-butanol using procedure described for compound 21. The product was purified by flash column chromatography using gradient elution from PE/EtOAc (95:5) to PE/EtOAc (5:95) to give 3-(2,6-dichloro-8-propylamino-pyrimido[5,4-d]pyrimidin-4-ylamino)-butan-2-ol (25) (330 mg, 78% yield). 300 MHz $^1$H NMR (CDCl$_3$, ppm): 7.14 (1H, d, J=8.6 Hz) 6.91 (1H, t, J=5.6 Hz) 4.38-4.24 (1H, m) 4.01-3.89 (1H, m) 3.61-3.49 (2H, m) 2.53 (1H, d, J=3.5 Hz) 1.79-1.65 (2H, m) 1.34 (3H, d, J=6.7 Hz) 1.26 (3H, d, J=6.3 Hz) 1.01 (3H, t, J=7.4 Hz). ESI-MS (m/z): 345, 347, 349 [M+H]$^+$.

(b) 3-(2,6-Bis-methylamino-8-propylamino-pyrimido[5,4-d]pyrimidin-4-ylamino)-butan-2-ol (26)

3-(2,6-Dichloro-8-propylamino-pyrimido[5,4-d]pyrimidin-4-ylamino)-butan-2-ol (25) (330 mg, 0.95 mmol) and methylamine (40% water solution) were reacted in n-butanol at 120° C. using procedure described for compound 4 to afford 3-(2,6-bis-methylamino-8-propyl amino-pyrimido[5,4-d]pyrimidin-4-ylamino)-butan-2-ol (26) (208 mg, 66% yield). 400 MHz $^1$H NMR (CDCl$_3$, ppm): 6.60 (1H, d, J=6.3 Hz) 6.54-6.48 (1H, m) 4.68-4.54 (2H, m) 4.35 (1H, br s) 4.0 (1H, sextet, J=6.8 Hz) 3.82 (1H, pentet, J=6.2 Hz) 3.49-3.43 (2H, m) 2.96 (3H, d, J=5.2 Hz) 2.94 (3H, d, J=5.2 Hz) 1.69 (2H, sextet, J=7.4 Hz) 1.32 (3H, d, J=6.8 Hz) 1.23 (3H, d, J=6.2 Hz) 0.99 (3H, t, J=7.4 Hz). ESI-MS (m/z): 335 [M+H]$^+$.

(c) 3-(2,6-Bis-methylamino-8-propylamino-pyrimido[5,4-d]pyrimidin-4-ylamino)-butan-2-ol Hydrochloride (26a)

3-(2,6-Bis-methylamino-8-propylamino-pyrimido[5,4-d]pyrimidin-4-ylamino)-butan-2-ol (26) (208 mg, 0.62 mmol) was treated with 2M HCl/diethyl ether in diethyl ether using procedure described for compound 6a to afford 3-(2,6-bis-methylamino-8-propylamino-pyrimido[5,4-d]pyrimidin-4-ylamino)-butan-2-ol hydrochloride (26a) (170 mg, 74% yield). 400 MHz $^1$H NMR (CD$_3$OD, ppm): 4.43-4.35 (1H, m) 3.96-3.89 (1H, m) 3.59 (2H, t, J=7.2 Hz) 3.02 (3H, s) 3.01 (3H, s) 1.76 (2H, sextet, J=7.4 Hz) 1.32 (3H, d, J=6.7 Hz) 1.21 (3H, d, J=6.4 Hz) 1.02 (3H, t, J=7.4 Hz). ESI-MS (m/z): 335 [M+H]$^+$.

Example 13: 2-(2,6-Bis-ethylamino-8-propylamino-pyrimido[5,4-d]pyrimidin-4-ylamino)-ethanol (27) and Corresponding Hydrochloride Salt (27a)

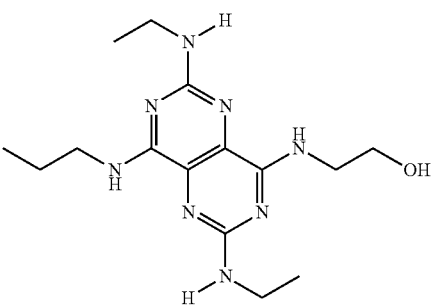

(a) 2-(2,6-Bis-ethylamino-8-propylamino-pyrimido[5,4-d]pyrimidin-4-ylamino)-ethanol (27)

A mixture of 2-(2,6-dichloro-8-propylamino-pyrimido[5,4-d]pyrimidin-4-yl amino)-ethanol (3) (250 mg, 0.79 mmol) and ethylamine (70% water solution) (1.20 mL) in n-butanol (2 mL) was heated at 120° C. for 48 h in a closed vial. After cooling, a saturated NaCl solution (20 mL) was added and the resulting suspension was extracted with EtOAc (3×30 mL). The combined organic extracts were washed with brine (30 mL) and dried over solid anhydrous Na$_2$SO$_4$. The solvent was removed and the residue was purified by flash column chromatography using gradient elution from CH$_2$Cl$_2$/EtOAc (99:1) to CH$_2$Cl$_2$/EtOAc (9:1) to give 2-(2,6-bis-ethylamino-8-propylamino-pyrimido[5,4-d]pyrimidin-4-ylamino)-ethanol (27) (220 mg, 83% yield). 400 MHz $^1$H NMR (CDCl$_3$, ppm): 6.90 (1H, s) 6.49 (1H, s) 4.62 (2H, br s) 4.52 (1H, s) 3.88-3.84 (2H, m) 3.71-3.64 (2H, m) 3.50-3.34 (6H, m) 1.69 (2H, sextet, J=7.4 Hz) 1.23 (3H, t, J=7.2 Hz) 1.22 (3H, t, J=7.2 Hz) 1.00 (3H, t, J=7.4 Hz). ESI-MS (m/z): 335 [M+H]$^+$.

(b) 2-(2,6-Bis-ethylamino-8-propylamino-pyrimido[5,4-d]pyrimidin-4-ylamino)-ethanol Hydrochloride (27a)

2-(2,6-Bis-ethylamino-8-propylamino-pyrimido[5,4-d]pyrimidin-4-ylamino)-ethanol (27) (190 mg, 0.62 mmol) was treated with 2M HCl/diethyl ether in diethyl ether/ethanol (2/1) using procedure described for compound 12a to produce 2-(2,6-bis-ethylamino-8-propylamino-pyrimido[5,4-d]pyrimidin-4-ylamino)-ethanol hydrochloride (27a) (185 mg, 88% yield). 400 MHz $^1$H NMR (CD$_3$OD, ppm): 3.82-3.77 (2H, m) 3.76-3.65 (2H, m) 3.56 (2H, t, J=7.0 Hz) 3.53-3.41 (4H, m) 1.79-1.68 (2H, m) 1.30-1.19 (6H, m) 1.01 (3H, t, J=7.4 Hz). ESI-MS (m/z): 335 [M+H]$^+$; MP: 192-194° C.

Example 14: 2-[8-Propylamino-2,6-bis-(2,2,2-trifluoro-ethylamino)-pyrimido[5,4-d]pyrimidin-4-ylamino]-ethanol (28) and Corresponding Hydrochloride Salt (28a)

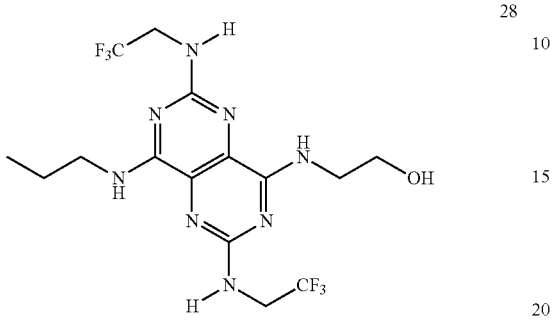

(a) 2-[8-Propylamino-2,6-bis-(2,2,2-trifluoro-ethyl-amino)-pyrimido[5,4-d]pyrimidin-4-yl amino]-ethanol (28)

A mixture of 2-(2,6-dichloro-8-propylamino-pyrimido[5,4-d]pyrimidin-4-yl amino)-ethanol (3) (240 mg, 0.76 mmol) and 2,2,2-trifluoro-ethylamine (726 μL, 9.12 mmol) in n-butanol (2 mL) was heated at 120° C. for 72 h in a closed vial. The reaction mixture was cooled and the precipitate were filtered, washed with ethanol (2×5 mL) and dried to give 2-[8-propyl amino-2,6-bis-(2,2,2-trifluoro-ethylamino)-pyrimido[5,4-d]pyrimidin-4-ylamino]-ethanol (28) (310 mg, 92% yield). 400 MHz $^1$H NMR (DMSO-$d_6$, ppm): 8.3-7.6 (1H, br s) 7.41 (1H, br s) 4.36-4.18 (4H, m) 3.72-3.37 (6H, m, overlapped with water) 1.63 (2H, sextet, J=7.3 Hz) 0.92 (3H, t, J=7.3 Hz). ESI-MS (m/z): 443 [M+H]$^+$.

(b) 2-[8-Propylamino-2,6-bis-(2,2,2-trifluoro-ethyl-amino)-pyrimido[5,4-d]pyrimidin-4-yl amino]-ethanol Hydrochloride (28a)

2-[8-Propylamino-2,6-bis-(2,2,2-trifluoro-ethylamino)-pyrimido[5,4-d]pyrimidin-4-ylamino]-ethanol (28) (250 mg, 0.57 mmol) was treated with 2M HCl/diethyl ether in CH$_2$Cl$_2$ using procedure described for compound 6a to produce 2-[8-propylamino-2,6-bis-(2,2,2-trifluoroethylamino)-pyrimido[5,4-d]pyrimidin-4-ylamino]ethanol hydrochloride (28a) (250 mg, 92% yield). 400 MHz $^1$H NMR (CD$_3$OD, ppm): 4.28 (2H, q, J=9.1 Hz) 4.27 (2H, q, J=9.1 Hz) 3.83-3.78 (2H, m) 3.77-3.72 (2H, m) 3.60 (2H, t, J=7.1 Hz) 1.80-1.70 (2H, m) 1.02 (3H, t, J=7.4 Hz). ESI-MS (m/z): 443 [M+H]$^+$; MP: 254-255° C.

Example 15: 1-(2,6-Bis-methylamino-8-propylamino-pyrimido[5,4-d]pyrimidin-4-yl amino)-2-methyl-propan-2-ol (31) and Corresponding Hydrochloride Salt (31a)

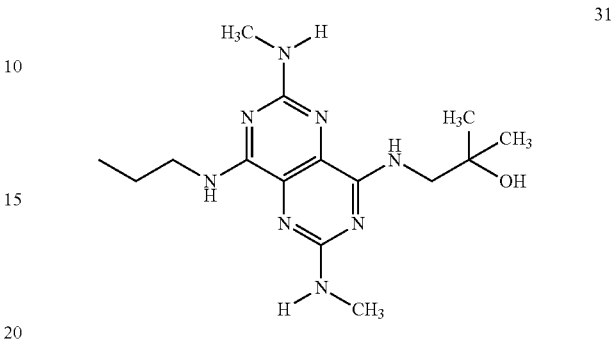

(a) 2-Methyl-1-(2,6,8-trichloro-pyrimido[5,4-d]pyrimidin-4-ylamino)-propan-2-ol (29)

To a suspension of 2,4,6,8-tetrachloro-pyrimido[5,4-d]pyrimidine (1) (3.50 g, 13.01 mmol) in THF (200 mL) at −78° C., 1-amino-2-methyl-propan-2-ol (1.17 mL, 12.36 mmol) in THF (20 mL) was added via syringe pump (during about 30 min) followed by DIPEA (2.93 mL, 16.91 mmol) in THF (20 mL). The reaction mixture was stirred at −78° C. for additional 30 min, and then allowed to reach the room temperature. Water (250 mL) was added and the resulting suspension was extracted with EtOAc (3×100 mL). The combined organic extracts were washed with water (150 mL), then with brine (150 mL) and dried over solid anhydrous MgSO$_4$. After filtration, the solvent was removed and the residue was purified by flash column chromatography using gradient elution from PE/EtOAc (10:4) to PE/EtOAc (1:1) to give 2-methyl-1-(2,6,8-trichloro-pyrimido[5,4-d]pyrimidin-4-ylamino)-propan-2-ol (29)(3.67 g, 92% yield). 300 MHz $^1$H NMR (CDCl$_3$, ppm): 7.70-7.58 (1H, m) 3.70 (2H, d, J=6.1 Hz) 1.80 (1H, s) 1.36 (6H, s). ESI-MS (m/z): 322, 324, 326, 328 [M+H]$^+$.

(b) 1-(2,6-Dichloro-8-propylamino-pyrimido[5,4-d]pyrimidin-4-ylamino)-2-methyl-propan-2-ol (30)

Propylamine (1.03 mL, 12.50 mmol) and DIPEA (2.56 mL, 14.79 mmol) were added to a solution of 2-methyl-1-(2,6,8-trichloro-pyrimido[5,4-d]pyrimidin-4-ylamino)-propan-2-ol (29) (3.67 g, 11.38 mmol) in dichloromethane (50 mL) at 0° C. The reaction mixture was stirred at room temperature for 2h. After this time, a saturated NaHCO$_3$ (100 mL) was added and the resulting suspension was extracted with dichloromethane (3×50 mL). The combined organic extracts were washed with water (100 mL) and dried over solid anhydrous MgSO$_4$. After filtration, the solvent was removed and the residue was purified by flash column chromatography using gradient elution from PE/EtOAc (5:1) to PE/EtOAc (2:1) to give 1-(2,6-dichloro-8-propylamino-pyrimido[5,4-d]pyrimidin-4-ylamino)-2-methyl-propan-2-ol (30) (3.10 g, 79% yield). 300 MHz $^1$H NMR (CDCl$_3$, ppm): 7.28 (1H, t, J=6.2 Hz) 6.94-6.84 (1H, m) 3.62 (2H, d, J=6.2 Hz) 3.60-3.51 (2H, m) 2.36 (1H, s) 1.72 (2H, sextet, J=7.4 Hz) 1.32 (6H, s) 1.01 (3H, t, J=7.4 Hz). ESI-MS (m/z): 345, 347, 349 [M+H]$^+$.

(c) 1-(2,6-Bis-methylamino-8-propylamino-pyrimido[5,4-d]pyrimidin-4-ylamino)-2-methyl-propan-2-ol (31)

1-(2,6-Dichloro-8-propylamino-pyrimido[5,4-d]pyrimidin-4-ylamino)-2-methyl-propan-2-ol (30) (3.10 g, 8.98 mmol) and methylamine (40% water solution) (7.7 mL) were reacted in n-butanol (20 mL) heated at 115° C. for 72 h. After cooling, a saturated NaHCO$_3$ solution (100 mL) was added and the resulting suspension was extracted with EtOAc (3×75 mL). The combined organic extracts were washed with water (100 mL), then with a brine solution (100 mL) and lastly, dried over solid anhydrous MgSO$_4$. After filtration, the solvent was removed and the residue was purified by flash column chromatography using gradient elution from CH$_2$Cl$_2$/MeOH (99:1) to CH$_2$Cl$_2$/MeOH (95:5) to give 1-(2,6-bis-methylamino-8-propylamino-pyrimido[5,4-d]pyrimidin-4-ylamino)-2-methyl-propan-2-ol (31) (2.30 g, 77% yield). 300 MHz $^1$H NMR (CDCl$_3$, ppm): 6.98-6.83 (1H, m) 6.55-6.45 (1H, m) 5.24-5.06 (1H, m) 4.70-4.53 (2H, m) 3.52 (2H, d, J=6.3 Hz) 3.50-3.41 (2H, m) 2.97 (3H, d, J=5.1 Hz) 2.94 (3H, d, J=5.1 Hz) 1.76-1.61 (2H, m) 1.27 (6H, s) 1.00 (3H, t, J=7.4 Hz). ESI-MS (m/z): 335 [M+1-1]$^+$.

(d) 1-(2,6-Bis-methylamino-8-propylamino-pyrimido[5,4-d]pyrimidin-4-ylamino)-2-methyl-propan-2-ol Hydrochloride (31a)

A 2M HCl/diethyl ether solution (3.42 mL, 6.84 mmol) was added to the solution of 1-(2,6-bis-methylamino-8-propylamino-pyrimido[5,4-d]pyrimidin-4-ylamino)-2-methyl-propan-2-ol (31) (2.30 g, 6.88 mmol) in diethyl ether (60 mL) and ethanol (3 mL). The mixture was stirred for 0.5 h at room temperature and the resultant precipitate were filtered and washed with diethyl ether (60 mL) to give 1-(2,6-bis-methylamino-8-propylamino-pyrimido[5,4-d]pyrimidin-4-ylamino)-2-methyl-propan-2-ol hydrochloride (31a) (2.36 g, 92% yield). 300 MHz $^1$H NMR (CD$_3$OD, ppm): 3.64 (2H, s) 3.57 (2H, t, J=7.2H) 3.00 (6H, s) 1.82-1.67 (2H, m) 1.27 (6H, s) 1.02 (3H, t, J=7.4 Hz). ESI-MS (m/z): 335 [M+H]$^+$; MP: 205-208° C. Anal. Calcd for C$_{15}$H$_{27}$ClN$_8$O: C, 48.58; H, 7.34; N, 30.21. Found: C, 48.33; H, 7.34; N, 30.00.

Example 16: 1-(2,6-Bis-ethylamino-8-propylamino-pyrimido[5,4-d]-pyrimidin-4-ylamino)-2-methyl-propan-2-ol (32) and Corresponding Hydrochloride Salt (32a)

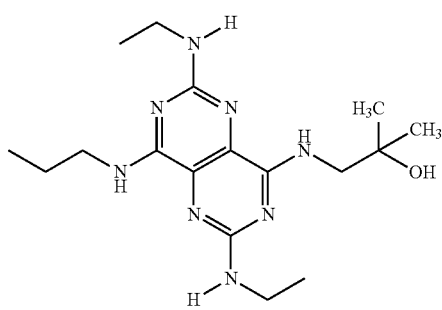

32

(a) 1-(2,6-Bis-ethylamino-8-propylamino-pyrimido[5,4-d]-pyrimidin-4-ylamino)-2-methyl-propan-2-ol (32)

1-(2,6-Dichloro-8-propylamino-pyrimido[5,4-d]pyrimidin-4-ylamino)-2-methyl-propan-2-ol (30) (300 mg, 0.87 mmol) was reacted with ethylamine (70% water solution) in n-butanol using procedure described for compound (27) to afford 1-(2,6-bis-ethylamino-8-propylamino-pyrimido[5,4-d]-pyrimidin-4-ylamino)-2-methyl-propan-2-ol (32) (220 mg, 70% yield). 300 MHz $^1$H NMR (CDCl$_3$, ppm): 6.86 (1H, t, J=6.3 Hz) 6.46 (1H, t, J=5.8 Hz) 5.21 (1H, s) 4.58 (1H, t, J=5.5 Hz) 4.51 (1H, t, J=5.5 Hz) 3.51 (2H, d, J=6.3 Hz) 3.49-3.33 (6H, m) 1.75-1.61 (2H, m) 1.27 (6H, s) 1.23 (3H, t, J=7.2 Hz) 1.21 (3H, t, J=7.2 Hz) 1.00 (3H, t, J=7.4 Hz). ESI-MS (m/z): 363 [M+H]$^+$.

(b) 1-(2,6-Bis-ethylamino-8-propylamino-pyrimido[5,4-d]-pyrimidin-4-ylamino)-2-methyl-propan-2-ol hydrochloride (32a)

1-(2,6-Bis-ethylamino-8-propylamino-pyrimido[5,4-d]-pyrimidin-4-ylamino)-2-methyl-propan-2-ol (32) (175 mg, 0.48 mmol) was treated with 2M HCl/diethyl ether in diethyl ether/methanol (1/1) using procedure described for compound 12a to obtain 1-(2,6-bis-ethylamino-8-propylamino-pyrimido[5,4-d]-pyrimidin-4-ylamino)-2-methyl-propan-2-ol hydrochloride (32a) (170 mg, 88% yield). 300 MHz $^1$H NMR (CD$_3$OD, ppm): 3.64 (2H, s) 3.56 (2H, t, J=7.1 Hz) 3.48 (4H, q, J=7.1 Hz) 1.83-1.65 (2H, m) 1.36-1.14 (12H, m) 1.01 (3H, t, J=7.4 Hz). ESI-MS (m/z): 363 [M+H]$^+$; MP: 199-201° C.

Example 17: 1-[2,6-Bis-(2,2-difluoro-ethylamino)-8-propylamino-pyrimido[5,4-d]-pyrimidin-4-ylamino]-2-methyl-propan-2-ol (33) and Corresponding Hydrochloride Salt (33a)

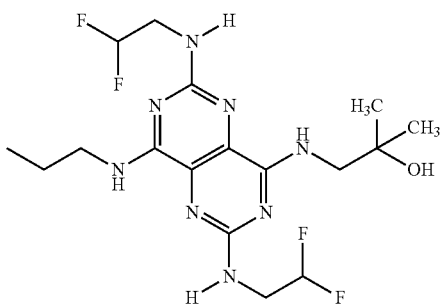

33

(a) 1-[2,6-Bis-(2,2-difluoro-ethylamino)-8-propylamino-pyrimido[5,4-d]-pyrimidin-4-ylamino]-2-methyl-propan-2-ol (33)

1-(2,6-Dichloro-8-propylamino-pyrimido[5,4-d]pyrimidin-4-ylamino)-2-methyl-propan-2-ol (30) (300 mg, 0.87 mmol) and 2,2-difluoro-ethylamine were reacted in n-butanol using procedures described elsewhere herein. The product was purified by flash column chromatography using gradient elution from PE/EtOAc (5:1) to PE/EtOAc (1:1) to give 1-[2,6-bis-(2,2-difluoro-ethylamino)-8-propylamino-pyrimido[5,4-d]-pyrimidin-4-ylamino]-2-methyl-propan-2-ol (33) (200 mg, 53% yield). 300 MHz $^1$H NMR (CDCl$_3$, ppm): 6.85 (1H, t, J=6.0 Hz) 6.47 (1H, t, J=6.0 Hz) 5.97 (1H, tt, J=56.5, 4.3 Hz) 5.94 (1H, tt, J=56.5, 4.3 Hz) 4.94-4.80 (2H, m) 3.88-3.68 (5H, m) 3.53 (2H, d, J=6.4 Hz) 3.51-3.42 (2H, m) 1.76-1.62 (2H, m) 1.29 (6H, s) 1.00 (3H, t, J=7.4 Hz). ESI-MS (m/z): 435 [M+H]$^+$.

(b) 1-[2,6-Bis-(2,2-difluoro-ethylamino)-8-propylamino-pyrimido[5,4-d]-pyrimidin-4-ylamino]-2-methyl-propan-2-ol Hydrochloride (33a)

1-[2,6-Bis-(2,2-difluoro-ethylamino)-8-propylamino-pyrimido[5,4-d]-pyrimidin-4-yl amino]-2-methyl-propan-2-ol (33) (170 mg, 0.39 mmol) was treated with 2M HCl/diethyl ether in diethyl ether using procedure described for compound 6a to give 1-[2,6-bis-(2,2-difluoro-ethylamino)-8-propylamino-pyrimido[5,4-d]-pyrimidin-4-ylamino]-2-methyl-propan-2-ol hydrochloride (33a) (170 mg, 92% yield). 400 MHz $^1$H NMR (CD$_3$OD, ppm): 6.04 (2H, t, J=56.5 Hz) 3.98-3.73 (4H, m) 3.64 (2H, s) 3.62-3.51 (2H, m) 1.81-1.66 (2H, m) 1.28 (6H, s) 1.02 (3H, t, J=7.4 Hz). ESI-MS (m/z): 435 [M+H]$^+$; MP: 245-247° C.

Example 18: 2-Methyl-1-[8-propylamino-2,6-bis-(2,2,2-trifluoro-ethylamino)-pyrimido[5,4-d]pyrimidin-4-ylamino]-propan-2-ol (34) and Corresponding Hydrochloride Salt (34a)

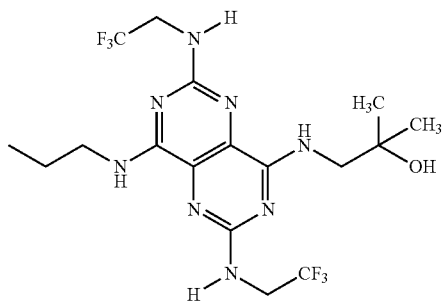

34

(a) 2-Methyl-1-[8-propylamino-2,6-bis-(2,2,2-trifluoro-ethylamino)-pyrimido[5,4-d]pyrimidin-4-ylamino]-propan-2-ol (34)

1-(2,6-Dichloro-8-propylamino-pyrimido[5,4-d]pyrimidin-4-ylamino)-2-methyl-propan-2-ol (30) (300 mg, 0.87 mmol) and 2,2,2-trifluoro-ethylamine were reacted in n-butanol using procedures previously to afford 2-methyl-1-[8-propylamino-2,6-bis-(2,2,2-trifluoro-ethylamino)-pyrimido[5,4-d]pyrimidin-4-ylamino]-propan-2-ol (34) (390 mg, 95% yield). 300 MHz $^1$H NMR (CD$_3$OD, ppm): 4.34-4.14 (4H, m) 3.66 (2H, s) 3.60 (2H, t, J=6.8 Hz) 1.82-1.66 (2H, m) 1.28 (6H, s) 1.02 (3H, t, J=7.4 Hz). ESI-MS (m/z): 471 [M+H]$^+$.

(b) 2-Methyl-1-[8-propylamino-2,6-bis-(2,2,2-trifluoro-ethylamino)-pyrimido[5,4-d]pyrimidin-4-ylamino]-propan-2-ol Hydrochloride (34a)

2-Methyl-1-[8-propylamino-2,6-bis-(2,2,2-trifluoro-ethylamino)-pyrimido[5,4-d]pyrimidin-4-ylamino]-propan-2-ol (34) (344 mg, 0.73 mmol) was treated with 2M HCl/diethyl ether in methanol using procedure described for compound 12a to produce 2-methyl-1-[8-propylamino-2,6-bis-(2,2,2-trifluoro-ethylamino)-pyrimido[5,4-d]pyrimidin-4-ylamino]-propan-2-ol hydrochloride (34a) (255 mg, 69% y). 300 MHz $^1$H NMR (DMSO-d$_6$, ppm): 9.6-7.8 (3H, m) 7.68 (1H, s) 7.53 (1H, s) 4.4-3.9 (4H, m, overlapped with water) 3.58-3.38 (4H, m) 1.72-1.55 (2H, m) 1.17 (6H, s) 0.93 (3H, t, J=7.4 Hz). ESI-MS (m/z): 471 [M+H]$^+$; MP: 257-259° C.

Example 19: 1-[8-(2,2-Difluoro-ethylamino)-2,6-bis-methylamino-pyrimido[5,4-d]pyrimidin-4-ylamino]-2-methyl-propan-2-ol (36) and Corresponding Hydrochloride Salt (36a)

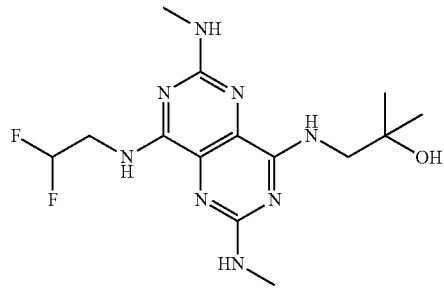

36

(a) 1-[2,6-Dichloro-8-(2,2-difluoro-ethylamino)-pyrimido[5,4-d]pyrimidin-4-ylamino]-2-methyl-propan-2-ol (35)

2-Methyl-1-(2,6,8-trichloro-pyrimido[5,4-d]pyrimidin-4-ylamino)-propan-2-ol (29) (550 mg, 1.71 mmol) and 2,2-difluoro-ethylamine in THF were reacted using procedures described elsewhere herein to obtain 1-[2,6-dichloro-8-(2,2-difluoro-ethylamino)-pyrimido[5,4-d]pyrimidin-4-ylamino]-2-methyl-propan-2-ol (35) (609 mg, 97% yield). ESI-MS (m/z): 367, 369, 371 [M+H]$^+$.

(b) 1-[8-(2,2-Difluoro-ethylamino)-2,6-bis-methylamino-pyrimido[5,4-d]pyrimidin-4-ylamino]-2-methyl-propan-2-ol (36)

1-[2,6-Dichloro-8-(2,2-difluoro-ethylamino)-pyrimido[5,4-d]pyrimidin-4-ylamino]-2-methyl-propan-2-ol (35) (300 mg, 0.82 mmol) and methylamine (40% water solution) were reacted in n-butanol at 125° C. using procedure described for compound (4) to produce 1-[8-(2,2-difluoro-ethylamino)-2,6-bis-methylamino-pyrimido[5,4-d]pyrimidin-4-ylamino]-2-methyl-propan-2-ol (36) (172 mg, 59% yield). 400 MHz $^1$H NMR (CDCl$_3$, ppm): 6.89 (1H, t, J=5.0 Hz) 6.63 (1H, t, J=5.0 Hz) 6.0 (1H, tt, J=56.4, 4.4 Hz) 4.84 (1H, s) 4.69-4.56 (2H, m) 3.96-3.84 (2H, m) 3.54 (2H, d, J=6.4 Hz) 2.97 (3H, d, J=5.2 Hz) 2.94 (3H, d, J=5.2 Hz) 1.28 (6H, s). ESI-MS (m/z): 357 [M+H]$^+$.

(c) 1-[8-(2,2-Difluoro-ethylamino)-2,6-bis-methylamino-pyrimido[5,4-d]pyrimidin-4-ylamino]-2-methyl-propan-2-ol Hydrochloride (36a)

1-[8-(2,2-Difluoro-ethylamino)-2,6-bis-methylamino-pyrimido[5,4-d]pyrimidin-4-ylamino]-2-methyl-propan-2-ol (36) (150 mg, 0.42 mmol) and 2M HCl/diethyl ether were reacted in CH$_2$Cl$_2$ (7 ml) using procedure described for compound (12a) to give 1-[8-(2,2-difluoro-ethylamino)-2,6- bis-methylamino-pyrimido[5,4-d]pyrimidin-4-ylamino]-2-methyl-propan-2-ol hydrochloride (36a) (335 mg, 82% yield). 400 MHz $^1$H NMR (CDCl$_3$, ppm): 8.18-7.85 (2H, m) 7.66 (1H, br s) 6.67-6.38 (1H, m) 6.05 (1H, tt, J=56.0, 4.2 Hz) 4.94 (1H, br s) 4.15-3.85 (2H, m) 3.70-3.52 (2H, m) 3.10-2.89 (6H, m) 1.34 (6H, s). ESI-MS (m/z): 357 [M+H]$^+$; MP: 223-225° C.

Example 20: 1-{2,6-Bis-methylamino-8-[(pyrimidin-2-ylmethyl)-amino]-pyrimido[5,4-d]pyrimidin-4-ylamino}-2-methyl-propan-2-ol (38) and Corresponding Hydrochloride Salt (38a)

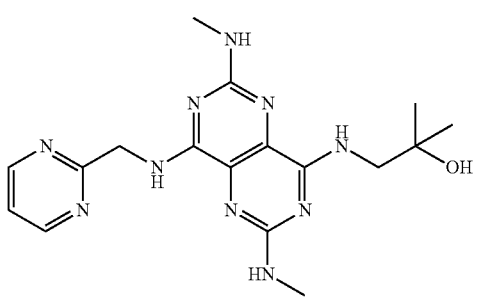

38

(a) 1-{2,6-Dichloro-8-[(pyrimidin-2-ylmethyl)-amino]-pyrimido[5,4-d]pyrimidin-4-ylamino}-2-methyl-propan-2-ol (37)

A mixture of 2-methyl-1-(2,6,8-trichloro-pyrimido[5,4-d]pyrimidin-4-ylamino)-propan-2-ol (29) (250 mg, 0.78 mmol), pyrimidin-2-ylmethanamine (114 mg, 0.78 mmol) and N,N-diisopropylethylamine (272 µL, 1.56 mmol) in n-butanol (4 mL) was heated at 70° C. for 2h. The reaction mixture was cooled to room temperature, the precipitate were filtered, washed with n-butanol (3 mL), then ethanol (3 mL) and dried to give 1-{2,6-dichloro-8-[(pyrimidin-2-ylmethyl)-amino]-pyrimido[5,4-d]pyrimidin-4-ylamino}-2-methyl-propan-2-ol (37) (300 mg, 97% yield). 300 MHz $^1$H NMR (CDCl$_3$, ppm): 8.78 (2H, d, J=4.9 Hz) 8.09 (1H, t, J=5.0 Hz) 7.33-7.23 (1H, m) 7.27 (1H, t. J=4.9 Hz) 5.02 (2H, d, J=5.0 Hz) 3.64 (2H, d, J=6.3 Hz) 2.28 (1H, s) 1.33 (6H, s). ESI-MS (m/z): 395, 397, 399 [M+H]$^+$.

(b) 1-{2,6-Bis-methylamino-8-[(pyrimidin-2-ylmethyl)-amino]-pyrimido[5,4-d]pyrimidin-4-ylamino}-2-methyl-propan-2-ol (38)

1-{2,6-Dichloro-8-[(pyrimidin-2-ylmethyl)-amino]-pyrimido[5,4-d]pyrimidin-4-ylamino}-2-methyl-propan-2-ol (37) (300 mg, 0.76 mmol) and methylamine (1 mL, 40% water solution) were heated in DMSO (2 mL) at 115° C. for 72 h in a closed vial. After cooling, a saturated NaHCO$_3$ solution (100 mL) was added and the resulting suspension was extracted with EtOAc (3×25 mL). The combined organic extracts were washed with water (10 mL), then with a brine solution (10 mL) and dried over solid anhydrous MgSO$_4$. After filtration, the product was purified by flash column chromatography using gradient elution from CH$_2$Cl$_2$ to CH$_2$Cl$_2$/EtOH (4:1) to give pure 1-{2,6-bis-methylamino-8-[(pyrimidin-2-ylmethyl)-amino]-pyrimido[5,4-d]pyrimidin-4-ylamino}-2-methyl-propan-2-ol (38) (120 mg, 41% yield). 300 MHz $^1$H NMR (CDCl$_3$, ppm): 8.76 (2H, d, J=4.9 Hz) 7.67-7.57 (1H, m) 7.22 (1H, t, J=4.9 Hz) 6.96-6.84 (1H, m) 5.27 (1H, br s) 4.95 (2H, d, J=5.1 Hz) 4.71-4.57 (2H, m) 3.54 (2H, d, J=6.3 Hz) 2.99 (3H, d, J=5.1 Hz) 2.96 (3H, d, J=5.1 Hz) 1.28 (6H, s). ESI-MS (m/z): 385 [M+H]$^+$.

(c) 1-{2,6-Bis-methylamino-8-[(pyrimidin-2-ylmethyl)-amino]-pyrimido[5,4-d]pyrimidin-4-ylamino}-2-methyl-propan-2-ol Hydrochloride (38a)

1-{2,6-Bis-methylamino-8-[(pyrimidin-2-ylmethyl)-amino]-pyrimido[5,4-d]pyrimidin-4-ylamino}-2-methyl-propan-2-ol (38) (110 mg, 0.29 mmol) and 2M HCl/diethyl ether were reacted in diethyl ether/EtOH (5/1) using procedure described for compound (6a) to produce 1-[2,6-bis-methylamino-8-[(pyrimidin-2-ylmethyl)-amino]-pyrimido[5,4-d]pyrimidin-4-ylamino]-2-methyl-propan-2-ol hydrochloride (38a) (110 mg, 90% yield). 300 MHz $^1$H NMR (CD$_3$OD, ppm): 8.78 (2H, d, J=5.0 Hz) 7.42 (1H, t, J=5.0 Hz) 4.99 (2H, s) 3.66 (2H, s) 3.03 (3H, s) 2.86 (3H, s) 1.28 (6H, s). ESI-MS (m/z): 385 [M+H]$^+$; MP: 169-170° C.

Example 21: 1-[8-((R)-sec-Butylamino)-2,6-bis-methylamino-pyrimido[5,4-d]-pyrimidin-4-ylamino]-2-methyl-propan-2-ol (40) and Corresponding Hydrochloride (40a)

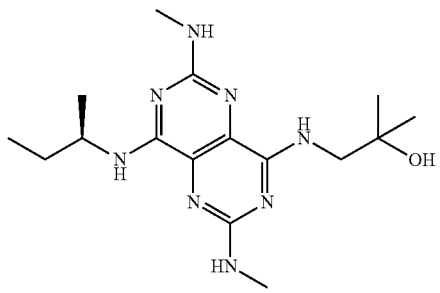

40

(a) (R)-1-(8-sec-Butylamino-2,6-dichloro-pyrimido[5,4-d]pyrimidin-4-ylamino)-2-methyl-propan-2-ol (39)

A mixture of 2-methyl-1-(2,6,8-trichloro-pyrimido[5,4-d]pyrimidin-4-ylamino)-propan-2-ol (29) (250 mg, 0.78 mmol) and (R)-butan-2-amine (93 µL, 0.93 mmol) and N,N-diisopropylethylamine (202 µL, 1.17 mmol) in CH$_2$Cl$_2$ (5 mL) was stirred at room temperature for 16 h. Water (10 mL) was added and the resulting suspension was extracted with methylene chloride (3×20 mL). The combined organic extracts were washed with water (30 mL) and dried over solid anhydrous MgSO$_4$. After filtration, the solvent was removed and the product was filtered through a silica gel pad using PE/EtOAc as eluent to give, after rotary evaporation, (R)-1-(8-sec-butylamino-2,6-dichloro-pyrimido[5,4-d]pyrimidin-4-ylamino)-2-methyl-propan-2-ol (39) (255 mg, 91% yield). 300 MHz $^1$H NMR (CDCl$_3$, ppm): 7.29 (1H, t, J=6.2 Hz) 6.69 (1H, d, J=8.7 Hz) 4.36-4.20 (1H, m) 3.62 (2H, d, J=6.2 Hz) 2.36 (1H, s) 1.71-1.58 (2H, m) 1.32 (6H, s) 1.28 (3H, d, J=6.6 Hz) 0.97 (3H, t, J=7.4 Hz). ESI-MS (m/z): 359, 361, 363 [M+H]$^+$.

(b) 1-[8-((R)-sec-Butylamino)-2,6-bis-methylamino-pyrimido[5,4-d]-pyrimidin-4-ylamino]-2-methyl-propan-2-ol (40)

(R)-1-(8-sec-Butylamino-2,6-dichloro-pyrimido[5,4-d] pyrimidin-4-ylamino)-2-methyl-propan-2-ol (39) (250 mg, 0.70 mmol) and methylamine (40% water solution, 700 µL)) were reacted in n-butanol (3 mL) at 125° C. for 96 h. A saturated sodium bicarbonate solution (10 mL) was added and the resulting suspension was extracted with EtOAc (3×15 mL). The combined organic extracts were washed with a brine solution (30 mL) and dried over solid anhydrous MgSO$_4$. After filtration, the solvent was removed and the product was purified by flash column chromatography using gradient elution from PE/acetone (10:1) to PE/acetone (4:1) to give 1-[8-((R)-sec-butylamino)-2,6-bis-methylamino-pyrimido[5,4-d]-pyrimidin-4-ylamino]-2-methyl-propan-2-ol (40) (176 mg, 73% yield). 300 MHz $^1$H NMR (CDCl$_3$, ppm): 6.95-6.82 (1H, m) 6.29 (1H, d, J=8.3 Hz) 5.28 (1H, br s) 4.70-4.49 (2H, m) 4.22-4.02 (1H, m) 3.52 (2H, d, J=6.3 Hz) 2.98-2.91 (6H, m) 1.72-1.50 (2H, m) 1.27 (6H, s) 1.26 (3H, t, J=6.7 Hz) 0.96 (3H, t, J=7.4 Hz). ESI-MS (m/z): 349 [M+H]$^+$.

(c) 1-[8-((R)-sec-Butylamino)-2,6-bis-methylamino-pyrimido[5,4-d]-pyrimidin-4-ylamino]-2-methyl-propan-2-ol Hydrochloride (40a)

1-[8-((R)-sec-Butylamino)-2,6-bis-methylamino-pyrimido[5,4-d]-pyrimidin-4-ylamino]-2-methyl-propan-2-ol (40) (176 mg, 0.51 mmol) and 2M HCl/diethyl ether were reacted in diethyl ether/EtOH (5/1) using procedure described for compound (6a) to produce 1-[8-((R)-sec-butylamino)-2,6-bis-methylamino-pyrimido[5,4-d]-pyrimidin-4-ylamino]-2-methyl-propan-2-ol hydrochloride (40a) (170 mg, 87% yield). 300 MHz $^1$H NMR (CD$_3$OD, ppm): 4.40-4.20 (1H, m) 3.65 (2H, s) 3.11-2.86 (6H, m) 1.80-1.58 (2H, m) 1.35-1.22 (3H, m) 1.27 (6H, s) 0.99 (3H, t, J=7.4 Hz). ESI-MS (m/z): 349 [M+H]$^+$; MP: 173-175° C.

Example 22: 1-[8-((S)-sec-Butylamino)-2,6-bis-methylamino-pyrimido[5,4-d]-pyrimidin-4-ylamino]-2-methyl-propan-2-ol (42) and Corresponding Hydrochloride Salt (42a)

(a) (S)-1-(8-sec-Butylamino-2,6-dichloro-pyrimido[5,4-d]pyrimidin-4-ylamino)-2-methyl-propan-2-ol (41)

2-Methyl-1-(2,6,8-trichloro-pyrimido[5,4-d]pyrimidin-4-ylamino)-propan-2-ol (29) (250 mg, 0.78 mmol) and (S)-butan-2-amine in CH$_2$Cl$_2$ were reacted using procedure described for compound (39) to give (S)-1-(8-sec-butylamino-2,6-dichloro-pyrimido[5,4-d]pyrimidin-4-ylamino)-2-methyl-propan-2-ol (41) (253 mg, 90% yield). 300 MHz $^1$H NMR (CDCl$_3$, ppm): 7.31-7.24 (1H, m) 6.68 (1H, d, J=8.7 Hz) 4.36-4.20 (1H, m) 3.62 (2H, d, J=6.2 Hz) 2.36 (1H, s) 1.71-1.58 (2H, m) 1.32 (6H, s) 1.28 (3H, d, J=6.6 Hz) 0.97 (3H, t, J=7.4 Hz). ESI-MS (m/z): 359, 361, 363 [M+H]$^+$.

(b) 1-[8-((S)-sec-Butylamino)-2,6-bis-methylamino-pyrimido[5,4-d]-pyrimidin-4-ylamino]-2-methyl-propan-2-ol (42)

(S)-1-(8-sec-Butylamino-2,6-dichloro-pyrimido[5,4-d] pyrimidin-4-ylamino)-2-methyl-propan-2-ol (41) (250 mg, 0.70 mmol) and methylamine (40% water solution) were reacted in n-butanol at 125° C. using procedure described for compound (4) to give 1-[8-((S)-sec-butylamino)-2,6-bis-methylamino-pyrimido[5,4-d]-pyrimidin-4-ylamino]-2-methyl-propan-2-ol (42) (180 mg, 74% yield). 300 MHz $^1$H NMR (CDCl$_3$, ppm): 6.95-6.82 (1H, m) 6.29 (1H, d, J=8.3 Hz) 5.19 (1H, br s) 4.66-4.51 (2H, m) 4.22-4.02 (1H, m) 3.53 (2H, d, J=6.3 Hz) 2.98-2.91 (6H, m) 1.72-1.50 (2H, m) 1.27 (6H, s) 1.26 (3H, t, J=6.7 Hz) 0.96 (3H, t, J=7.4 Hz). ESI-MS (m/z): 349 [M+H]$^+$.

(c) 1-[8-((S)-sec-Butylamino)-2,6-bis-methylamino-pyrimido[5,4-d]-pyrimidin-4-ylamino]-2-methyl-propan-2-ol Hydrochloride (42a)

1-[8-((S)-sec-Butylamino)-2,6-bis-methylamino-pyrimido[5,4-d]-pyrimidin-4-ylamino]-2-methyl-propan-2-ol (42) (150 mg, 0.43 mmol) and 2M HCl/diethyl ether were reacted in diethyl ether/EtOH (5/1) using procedure described for compound (6a) to produce 1-[8-((S)-sec-butylamino)-2,6-bis-methylamino-pyrimido[5,4-d]-pyrimidin-4-ylamino]-2-methyl-propan-2-ol hydrochloride (42a) (155 mg, 94% yield). 300 MHz $^1$H NMR (CD$_3$OD, ppm): 4.40-4.20 (1H, m) 3.65 (2H, s) 3.00 (3H, s) 2.98 (3H, s) 1.80-1.58 (2H, m) 1.35-1.22 (3H, m) 1.27 (6H, s) 0.99 (3H, t, J=7.4 Hz). ESI-MS (m/z): 349 [M+H]$^+$; MP: 170-172° C.

Example 23: 1-(8-Benzylamino-2,6-bis-methyl-amino-pyrimido[5,4-d]pyrimidin-4-ylamino)-2-methyl-propan-2-ol (44) and Corresponding Hydrochloride Salt (44a)

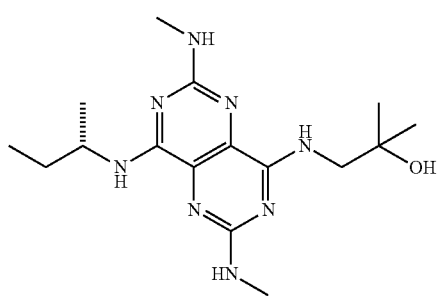

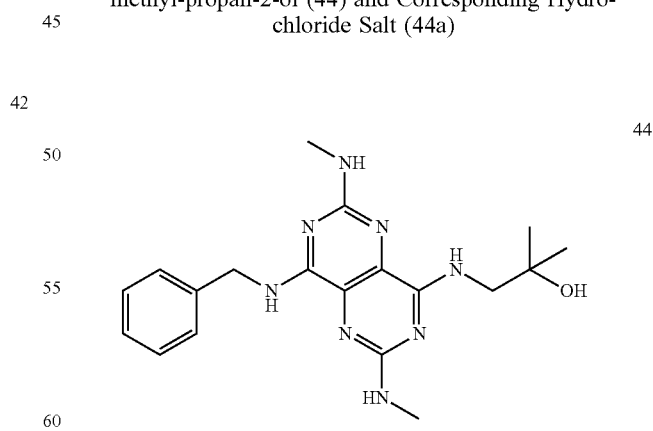

(a) 1-(8-Benzylamino-2,6-dichloro-pyrimido[5,4-d] pyrimidin-4-ylamino)-2-methyl-propan-2-ol (43)

2-Methyl-1-(2,6,8-trichloro-pyrimido[5,4-d]pyrimidin-4-ylamino)-propan-2-ol (29) (250 mg, 0.78 mmol), benzylamine (102 µL, 0.93 mmol) and N,N-diisopropylethylamine (202 µL, 1.17 mmol) in n-butanol (5 mL) were stirred at room temperature for 3 h. Water (10 mL) was added and the resulting suspension was extracted with EtOAc (3×20 mL). The combined organic extracts were washed with a brine solution (30 mL) and dried over solid anhydrous Na$_2$SO$_4$. After filtration, the solvent was removed and the product was purified by flash column chromatography using gradient elution from CH$_2$Cl$_2$ to CH$_2$Cl$_2$/EtOAc (9:1) to give 1-(8-benzylamino-2,6-dichloro-pyrimido[5,4-d]pyrimidin-4-ylamino)-2-methyl-propan-2-ol (43) (290 mg, 95% yield). 300 MHz $^1$H NMR (CDCl$_3$, ppm): 7.40-7.28 (6H, m) 7.14 (1H, t, J=5.9 Hz) 4.78 (2H, d, J=5.9 Hz) 3.63 (2H, d, J=6.3 Hz) 2.19 (1H, br s) 1.32 (6H, s). ESI-MS (m/z): 393, 395, 397 [M+H]$^+$.

(b) 1-(8-Benzylamino-2,6-bis-methylamino-pyrimido[5,4-d]pyrimidin-4-ylamino)-2-methyl-propan-2-ol (44)

1-(8-Benzylamino-2,6-dichloro-pyrimido[5,4-d]pyrimidin-4-ylamino)-2-methyl-propan-2-ol (43) (280 mg, 0.71 mmol) and methylamine (40% water solution, 1.1 mL) were reacted in n-butanol (6 mL) at 120° C. for 72 h. After cooling, a saturated NaHCO$_3$ solution (10 mL) was added, the resulting suspension was extracted with EtOAc (3×20 mL). The combined organic extracts were washed with a brine solution (30 mL) and dried over solid anhydrous Na$_2$SO$_4$. After filtration, the solvent was removed and the product was purified by flash column chromatography using gradient elution from CH$_2$Cl$_2$/EtOAc (9:1) to CH$_2$Cl$_2$/EtOAc (1:4) as eluent to give pure 1-(8-benzylamino-2,6-bis-methylamino-pyrimido[5,4-d]pyrimidin-4-ylamino)-2-methyl-propan-2-ol (44) (212 mg, 78% yield). 400 MHz $^1$H NMR (CDCl$_3$, ppm): 7.38-7.24 (5H, m) 6.98-6.89 (1H, m) 6.87-6.79 (1H, m) 5.10 (1H, s) 4.73 (2H, d, J=6.1 Hz) 4.68 (1H, br s) 4.63-4.55 (1H, m) 3.52 (2H, d, J=6.3 Hz) 2.97 (3H, d, J=5.1 Hz) 2.90 (3H, d, J=5.1 Hz) 1.27 (6H, s). ESI-MS (m/z): 383 [M+H]$^+$.

(c) 1-(8-Benzylamino-2,6-bis-methylamino-pyrimido[5,4-d]pyrimidin-4-ylamino)-2-methyl-propan-2-ol Hydrochloride (44a)

1-(8-Benzylamino-2,6-bis-methylamino-pyrimido[5,4-d]pyrimidin-4-ylamino)-2-methyl-propan-2-ol (44) (175 mg, 0.46 mmol) and 2M HCl/diethyl ether were reacted in diethyl ether/MeOH (5/1) using procedure described for compound (6a) to produce 1-(8-benzylamino-2,6-bis-methylamino-pyrimido[5,4-d]pyrimidin-4-ylamino)-2-methyl-propan-2-ol hydrochloride (44a) (155 mg, 80% yield). 400 MHz $^1$H NMR (CD$_3$OD, ppm): 7.44-7.40 (2H, m) 7.38-7.32 (2H, m) 7.31-7.26 (1H, m) 4.79 (2H, s) 3.65 (2H, s) 3.00 (3H, s) 2.98 (3H, s) 1.28 (6H, s). ESI-MS (m/z): 383 [M+H]$^+$; MP: 227-228° C.

Example 24: 1-[8-(Cyclopropylmethyl-amino)-2,6-bis-methylamino-pyrimido[5,4-d]pyrimidin-4-ylamino]-2-methyl-propan-2-ol (46) and Corresponding Hydrochloride Salt (46a)

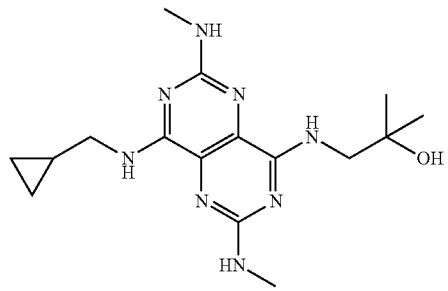

46

(a) 1-[2,6-Dichloro-8-(cyclopropylmethyl-amino)-pyrimido[5,4-d]pyrimidin-4-ylamino]-2-methyl-propan-2-ol (45)

2-Methyl-1-(2,6,8-trichloro-pyrimido[5,4-d]pyrimidin-4-ylamino)-propan-2-ol (29) (250 mg, 0.78 mmol) and cyclopropylmethanamine (80 µL, 0.93 mmol) and N,N-diisopropylethylamine (202 µL, 1.17 mmol) were stirred in n-butanol (5 mL) at ambient temperature for 3 h. Water (10 mL) was added, the resulting suspension was extracted with EtOAc (3×20 mL). The combined organic extracts were washed with a brine solution (30 mL) and dried over solid anhydrous Na$_2$SO$_4$. After filtration, the solvent was removed and the product was purified by flash column chromatography using gradient elution from CH$_2$Cl$_2$/EtOAc (99:1) to CH$_2$Cl$_2$/EtOAc (9:1) as eluent to give 1-[2,6-dichloro-8-(cyclopropylmethyl-amino)-pyrimido[5,4-d]pyrimidin-4-ylamino]-2-methyl-propan-2-ol (45) (200 mg, 72% yield). ESI-MS (m/z): 357, 359, 361 [M+H]$^+$.

(b) 1-[8-(Cyclopropylmethyl-amino)-2,6-bis-methylamino-pyrimido[5,4-d]pyrimidin-4-ylamino]-2-methyl-propan-2-ol (46)

1-[2,6-Dichloro-8-(cyclopropylmethyl-amino)-pyrimido[5,4-d]pyrimidin-4-ylamino]-2-methyl-propan-2-ol (45) (200 mg, 0.56 mmol) and methylamine (40% water solution, 870 µL) were heated n-butanol (6 mL) at 120° C. for 72 h. After cooling, a saturated NaHCO$_3$ solution (10 mL) was added and the resulting suspension was extracted with EtOAc (3×20 mL). The combined organic extracts were washed with a brine solution (30 mL) and dried over solid anhydrous Na$_2$SO$_4$. After filtration and removal of solvents, the product was purified by flash column chromatography using gradient elution from CH$_2$Cl$_2$/EtOAc (9:1) to CH$_2$Cl$_2$/EtOAc (1:4) as eluent to give 1-[8-(cyclopropylmethyl-amino)-2,6-bis-methylamino-pyrimido[5,4-d]pyrimidin-4-ylamino]-2-methyl-propan-2-ol (46) (180 mg, 93% yield). 400 MHz $^1$H NMR (CDCl$_3$, ppm): 6.91 (1H, br s) 6.58 (1H, br s) 5.13 (1H, br s) 4.60 (2H, s) 3.53 (2H, d, J=6.3 Hz) 3.40-3.32 (2H, m) 2.99-2.93 (6H, m) 1.28 (6H, s) 1.18-1.07 (1H, m) 0.59-0.52 (2H, m) 0.33-0.28 (2H, m). ESI-MS (m/z): 347 [M+H]$^+$.

(c) 1-[8-(Cyclopropylmethyl-amino)-2,6-bis-methylamino-pyrimido[5,4-d]pyrimidin-4-ylamino]-2-methyl-propan-2-ol Hydrochloride (46a)

1-[8-(Cyclopropylmethyl-amino)-2,6-bis-methylamino-pyrimido[5,4-d]pyrimidin-4-ylamino]-2-methyl-propan-2- ol (46) (180 mg, 0.52 mmol) and 2M HCl/diethyl ether were reacted in diethyl ether using procedures previously to produce 1-[8-(cyclopropylmethyl-amino)-2,6-bis-methyl-amino-pyrimido[5,4-d]pyrimidin-4-ylamino]-2-methyl-propan-2-ol hydrochloride (46a) (145 mg, 73% yield). 400 MHz $^1$H NMR (CD$_3$OD, ppm): 3.66 (2H, s) 3.47 (2H, d, J=7.2 Hz) 3.02 (3H, s) 3.00 (3H, s) 1.28 (s, 6H), 1.26-1.14 (1H, m) 0.63-0.56 (2H, m) 0.39-0.33 (2H, m). ESI-MS (m/z): 347 [M+H]$^+$; MP: 215-216° C.

Example 25: 1-[8-(2,2-Difluoro-ethylamino)-2,6-bis-ethylamino-pyrimido[5,4-d]pyrimidin-4-ylamino]-2-methyl-propan-2-ol (47) and Corresponding Hydrochloride Salt (47a)

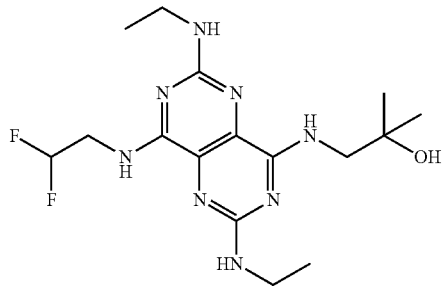

(a) 1-[8-(2,2-Difluoro-ethylamino)-2,6-bis-ethyl-amino-pyrimido[5,4-d]pyrimidin-4-ylamino]-2-methyl-propan-2-ol (47)

1-[2,6-Dichloro-8-(2,2-difluoro-ethylamino)-pyrimido[5,4-d]pyrimidin-4-yl amino]-2-methyl-propan-2-ol (35) (300 mg, 0.82 mmol) and ethylamine (70% water solution) were reacted in n-butanol using procedure described for compound (32) to give 1-[8-(2,2-difluoro-ethylamino)-2,6-bis-ethylamino-pyrimido[5,4-d]pyrimidin-4-ylamino]-2-methyl-propan-2-ol (47) (262 mg, 83% yield). 400 MHz $^1$H NMR (CDCl$_3$, ppm): 6.92-6.81 (1H, m) 6.66-6.53 (1H, m) 6.0 (1H, tt, J=56.4, 4.4 Hz) 4.89 (1H, s) 4.63 (1H, t, J=5.0 Hz) 4.59-4.52 (1H, m) 3.95-3.83 (2H, m) 3.52 (2H, d, J=6.3 Hz) 3.46-3.35 (4H, m) 1.28 (6H, s) 1.23 (3H, t, J=7.4 Hz) 1.21 (3H, t, J=7.4 Hz). ESI-MS (m/z): 385 [M+H]$^+$.

(b) 1-[8-(2,2-Difluoro-ethylamino)-2,6-bis-ethyl-amino-pyrimido[5,4-d]pyrimidin-4-yl amino]-2-methyl-propan-2-ol Hydrochloride (47a)

1-[8-(2,2-Difluoro-ethylamino)-2,6-bis-ethylamino-pyrimido[5,4-d]pyrimidin-4-ylamino]-2-methyl-propan-2-ol (47) (200 mg, 0.52 mmol) and 2M HCl/diethyl ether were reacted in CH$_2$Cl$_2$ using procedures described elsewhere herein to produce 1-[8-(2,2-difluoro-ethylamino)-2,6-bis-ethylamino-pyrimido[5,4-d]pyrimidin-4-ylamino]-2-methyl-propan-2-ol hydrochloride (47a) (170 mg, 78% yield). 400 MHz $^1$H NMR (CDCl$_3$, ppm): 8.24-7.97 (1H, m) 7.89 (1H, br s) 7.61 (1H, br s) 6.71-6.45 (1H, m) 6.20-5.88 (1H, m) 4.95-4.85 (1H, m) 4.12-3.85 (2H, m) 3.69-3.35 (6H, m) 1.34 (6H, s) 1.30-1.20 (6H, m). ESI-MS (m/z): 385 [M+H]$^+$; MP: 233-235° C.

Example 26: 2-Methyl-1-(2,6,8-tris-methylamino-pyrimido[5,4-d]-pyrimidin-4-ylamino)-propan-2-ol (48) and Corresponding Hydrochloride Salt (48a)

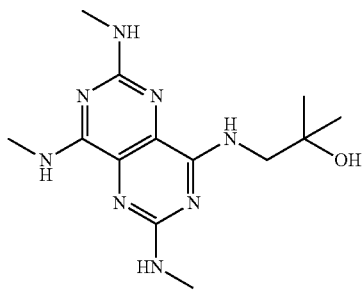

(a) 2-Methyl-1-(2,6,8-tris-methylamino-pyrimido[5,4-d]-pyrimidin-4-ylamino)-propan-2-ol (48)

A mixture of 2-methyl-1-(2,6,8-trichloro-pyrimido[5,4-d]pyrimidin-4-ylamino)-propan-2-ol (29) (400 mg, 1.24 mmol) and methylamine (40% water solution) (1.00 mL, 12.87 mmol) in n-butanol (5 mL) was stirred at room temperature for 2h and then heated at 120° C. for 96 h in the closed vial. After this time, a saturated NaHCO$_3$ solution (20 mL) was added and the resulting suspension was extracted with EtOAc (3×25 mL). The combined organic extracts were washed with water (30 mL), then with a brine solution (30 mL) and lastly dried over solid anhydrous Na$_2$SO$_4$. After filtration, the solvent was removed and the residue was purified by flash column chromatography using gradient elution from PE/acetone (5:1) to PE/acetone (1:1) to give 2-methyl-1-(2,6,8-tris-methylamino-pyrimido[5,4-d]-pyrimidin-4-ylamino)-propan-2-ol (48) (345 mg, 91% yield). 400 MHz $^1$H NMR (CDCl$_3$, ppm): 7.21 (1H, s) 6.28 (1H, s) 6.36-5.94 (1H, br s) 4.87 (1H, s) 3.52 (2H, d, J=6.0 Hz) 3.10 (3H, d, J=5.1 Hz) 2.99 (3H, d, J=5.0 Hz) 2.93 (3H, d, J=5.0 Hz) 1.28 (6H, s). ESI-MS (m/z): 307 [M+H]$^+$.

(b) 2-Methyl-1-(2,6,8-tris-methylamino-pyrimido[5,4-d]-pyrimidin-4-ylamino)-propan-2-ol Hydrochloride (48a)

2-Methyl-1-(2,6,8-tris-methylamino-pyrimido[5,4-d]-pyrimidin-4-ylamino)-propan-2-ol (62) (310 mg, 1.01 mmol) and 2M HCl/diethyl ether were reacted in diethyl ether/MeOH (1/1) using procedures described elsewhere herein to produce 2-methyl-1-(2,6,8-tris-methylamino-pyrimido[5,4-d]-pyrimidin-4-ylamino)-propan-2-ol hydrochloride (48a) (290 mg, 84% yield). 400 MHz $^1$H NMR (CD$_3$OD, ppm): 3.65 (2H, s) 3.13 (3H, s) 3.09 (3H, s) 2.99 (3H, s) 1.28 (6H, s). ESI-MS (m/z): 307 [M+H]$^+$; MP: 213-215° C.

Example 27: 2-Methyl-1-(2,6,8-tris-ethylamino-pyrimido[5,4-d]-pyrimidin-4-ylamino)-propan-2-ol (49) and Corresponding Hydrochloride Salt (49a)

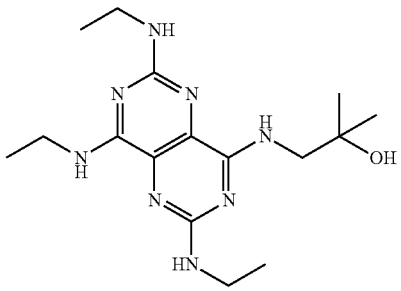

(a) 2-Methyl-1-(2,6,8-tris-ethylamino-pyrimido[5,4-d]-pyrimidin-4-ylamino)-propan-2-ol (49)

2-Methyl-1-(2,6,8-trichloro-pyrimido[5,4-d]pyrimidin-4-ylamino)-propan-2-ol (29) (300 mg, 0.93 mmol) and ethylamine (70% water solution) were reacted in n-butanol (5 mL) using procedures described elsewhere herein. The crude product was purified by flash column chromatography using gradient elution from PE/EtOAc (5:1) to PE/EtOAc (1:2) to give 2-methyl-1-(2,6,8-tris-ethylamino-pyrimido[5,4-d]-pyrimidin-4-ylamino)-propan-2-ol (49) (210 mg, 65% yield). 300 MHz $^1$H NMR (CDCl$_3$, ppm): 6.92-6.80 (1H, m) 6.45-6.34 (1H, m) 5.24-5.14 (1H, m) 4.64-4.55 (1H, m) 4.55-4.46 (1H, m) 3.58-3.48 (4H, m) 3.48-3.33 (4H, m) 1.32-1.17 (9H, m) 1.27 (6H, s). ESI-MS (m/z): 349 [M+H]$^+$.

(b) 2-Methyl-1-(2,6,8-tris-ethylamino-pyrimido[5,4-d]-pyrimidin-4-ylamino)-propan-2-ol Hydrochloride (49a)

2-Methyl-1-(2,6,8-tris-ethylamino-pyrimido[5,4-d]-pyrimidin-4-ylamino)-propan-2-ol (49) (190 mg, 0.55 mmol) and 2M HCl/diethyl ether were reacted in diethyl ether/EtOH (1/1) using procedures previously to produce 2-methyl-1-(2,6,8-tris-ethylamino-pyrimido[5,4-d]-pyrimidin-4-ylamino)-propan-2-ol hydrochloride (49a) (205 mg, 97% yield). 300 MHz $^1$H NMR (CD$_3$OD, ppm): 3.69-3.55 (4H, m) 3.55-3.38 (4H, m) 1.27 (6H, s) 1.34-1.19 (9H, m). ESI-MS (m/z): 349 [M+H]$^+$; MP: 192-194° C.

Example 28: 2-(2,6,8-Tris-methylamino-pyrimido[5,4-d]pyrimidin-4-ylamino)-ethanol (52) and Corresponding Hydrochloride Salt (52a)

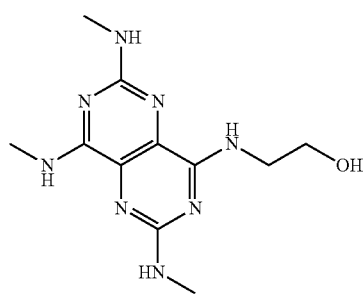

(a) 2-(2,6,8-Trichloro-pyrimido[5,4-d]pyrimidin-4-ylamino)-ethanol (50)

To a suspension of 2,4,6,8-tetrachloro-pyrimido[5,4-d]pyrimidine (1) (1.00 g, 3.70 mmol) in THF (50 mL), 2-amino-ethanol (200 μL, 3.32 mmol) and N,N-diisopropylethylamine (900 μL, 5.18 mmol) in THF (5 mL) was added dropwise at −78° C. The reaction mixture was stirred at −78° C. for 2h, and then allowed to reach the room temperature. Water (50 mL) was added and the resulting suspension was extracted with EtOAc (3×30 mL). The combined organic extracts were washed with water (50 mL), then with a brine solution (50 mL) and dried over solid anhydrous MgSO$_4$. After filtration, the solvent was removed; the residue was purified by flash column chromatography using PE/EtOAc (1:1) as eluent to give 2-(2,6,8-trichloro-pyrimido[5,4-d]pyrimidin-4-ylamino)-ethanol (50) (860 mg, 88% yield). 300 MHz $^1$H NMR (CDCl$_3$, ppm): 7.61 (1H, s) 3.99-3.93 (2H, m) 3.91-3.83 (2H, m) 1.99 (1H, s). ESI-MS (m/z): 294, 296, 298, 300 [M+H]$^+$.

(b) 2-(2,6-Dichloro-8-methylamino-pyrimido[5,4-d]pyrimidin-4-ylamino)-ethanol (51)

Methylamine (2M in THF, 2.04 mL, 2.04 mmol) was added to a solution of 2-(2,6,8-trichloro-pyrimido[5,4-d]pyrimidin-4-ylamino)-ethanol (50) (300 mg, 1.02 mmol) in THF (5 mL) at 0° C. The reaction mixture was stirred at room temperature for 2h. After this time a saturated NaHCO$_3$ solution (20 mL) was added and the resulting suspension was extracted with EtOAc (3×25 mL). The combined organic extracts were washed with water (50 mL) and dried over solid anhydrous Na$_2$SO$_4$. After filtration, the solvent was removed and the residue was purified by flash column chromatography using gradient elution from PE/EtOAc (5:1) to PE/EtOAc (1:1) to give 2-(2,6-dichloro-8-methylamino-pyrimido[5,4-d]pyrimidin-4-ylamino)-ethanol (51) (180 mg, 61% yield). 400 MHz $^1$H NMR (DMSO-d$_6$, ppm): 8.68 (1H, q, J=4.2 Hz) 8.44 (1H, s) 4.84 (1H, t, J=5.5 Hz) 3.61-3.55 (2H, m) 3.54-3.48 (2H, m) 2.93 (3H, d, J=4.2 Hz). ESI-MS (m/z): 289, 291, 293 [M+H]$^+$.

(c) 2-(2,6,8-Tris-methylamino-pyrimido[5,4-d]pyrimidin-4-ylamino)-ethanol (52)

2-(2,6-Dichloro-8-methylamino-pyrimido[5,4-d]pyrimidin-4-ylamino)-ethanol (51) (171 mg, 0.59 mmol) and methylamine (40% water solution) were reacted in n-butanol at 125° C. using procedure described for compound (4) to give 2-(2,6,8-tris-methylamino-pyrimido[5,4-d]pyrimidin-4-ylamino)-ethanol (52) (112 mg, 68% yield). 300 MHz $^1$H NMR (CDCl$_3$, ppm): 6.99-6.87 (1H, m) 6.54-6.41 (1H, m) 4.73-4.65 (1H, m) 4.63-4.54 (1H, m) 3.89-3.84 (2H, m) 3.72-3.65 (2H, m) 3.07 (3H, d, J=5.1 Hz) 2.97 (3H, d, J=5.1 Hz) 2.96 (3H, d, J=5.1 Hz). ESI-MS (m/z): 279 [M+H]$^+$.

(d) 2-(2,6,8-Tris-methylamino-pyrimido[5,4-d]pyrimidin-4-ylamino)-ethanol Hydrochloride (52a)

2-(2,6,8-Tris-methylamino-pyrimido[5,4-d]pyrimidin-4-ylamino)-ethanol (52) (112 mg, 0.40 mmol) and 2M HCl/diethyl ether in CH$_2$Cl$_2$ were using procedures described elsewhere herein to produce 2-(2,6,8-tris-methylamino-pyrimido[5,4-d]pyrimidin-4-ylamino)-ethanol hydrochloride (52a) (110 mg, 87% yield). 300 MHz $^1$H NMR (D$_2$O, ppm):

3.83 (2H, t, J=5.4 Hz) 3.66 (2H, t, J=5.4 Hz) 3.03 (3H, s) 2.95 (3H, s) 2.90 (3H, s). ESI-MS (m/z): 279 [M+H]⁺; MP: 252-254° C.

Example 29: 2-[8-(Cyclopropylmethyl-amino)-2,6-bis-methylamino-pyrimido[5,4-d]pyrimidin-4-ylamino]-ethanol (54) and Corresponding Hydrochloride Salt (54a)

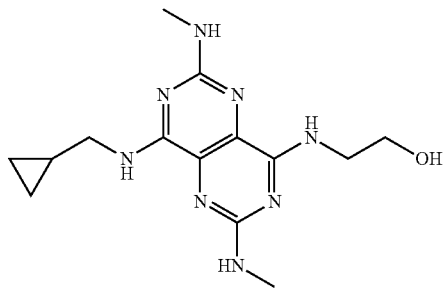

(a) 2-[2,6-Dichloro-8-(cyclopropylmethyl-amino)-pyrimido[5,4-d]pyrimidin-4-ylamino]-ethanol (53)

2-(2,6,8-Trichloro-pyrimido[5,4-d]pyrimidin-4-ylamino)-ethanol (50) (300 mg, 1.02 mmol) and cyclopropyl-methanamine were reacted in THF using procedures described elsewhere herein to give 2-[2,6-dichloro-8-(cyclopropylmethyl-amino)-pyrimido[5,4-d]pyrimidin-4-ylamino]-ethanol (53) (244 mg, 73% yield). 400 MHz ¹H NMR (DMSO-d₆, ppm): 8.77 (1H, t, J=6.0 Hz) 8.45 (1H, t, J=5.7 Hz) 4.84 (1H, t, J=5.5 Hz) 3.61-3.55 (2H, m) 3.55-3.48 (2H, m) 3.32-3.27 (2H, m) 1.20-1.09 (1H, m) 0.48-0.40 (2H, m) 0.33-0.26 (2H, m). ESI-MS (m/z): 329, 331, 333 [M+H]⁺.

(b) 2-[8-(Cyclopropylmethyl-amino)-2,6-bis-methyl-amino-pyrimido[5,4-d]pyrimidin-4-ylamino]-ethanol (54)

2-[2,6-Dichloro-8-(cyclopropylmethyl-amino)-pyrimido[5,4-d]pyrimidin-4-ylamino]-ethanol (53) (244 mg, 0.74 mmol) and methylamine (40% water solution) were reacted in 1,4-dioxane at 125° C. using procedure described for compound (4). The product was purified by flash column chromatography using gradient elution from EtOAc to EtOAc/EtOH (9:1) as eluent to give 2-[8-(cyclopropylmethyl-amino)-2,6-bis-methylamino-pyrimido[5,4-d]pyrimidin-4-ylamino]-ethanol (54) (80 mg, 34% yield). 300 MHz ¹H NMR (CDCl₃, ppm): 6.98-6.87 (1H, m) 6.62-6.52 (1H, m) 4.76-4.54 (3H, m) 3.89-3.84 (2H, m) 3.73-3.66 (2H, m) 3.35 (2H, dd, J=7.7, 5.6 Hz) 2.97 (3H, d, J=5.1 Hz) 2.96 (3H, d, J=5.1 Hz) 1.18-1.07 (1H, m) 0.60-0.52 (2H, m) 0.33-0.27 (2H, m). ESI-MS (m/z): 319 [M+H]⁺.

(c) 2-[8-(Cyclopropylmethyl-amino)-2,6-bis-methyl-amino-pyrimido[5,4-d]pyrimidin-4-ylamino]-ethanol Hydrochloride (54a)

2-[8-(Cyclopropylmethyl-amino)-2,6-bis-methylamino-pyrimido[5,4-d]pyrimidin-4-ylamino]-ethanol (54) (80 mg, 0.25 mmol) and 2M HCl/diethyl ether were reacted in CH₂Cl₂ using procedures described elsewhere herein to produce 2-[8-(cyclopropylmethyl-amino)-2,6-bis-methylamino-pyrimido[5,4-d]pyrimidin-4-ylamino]-ethanol hydrochloride (54a) (75 mg, 84% yield). 300 MHz ¹H NMR (D₂O, ppm): 3.83 (2H, t, J=5.4 Hz) 3.67 (2H, t, J=5.4) 3.31 (2H, d, J=7.1 Hz) 2.93 (3H, s) 2.91 (3H, s) 1.20-1.06 (1H, m) 0.62-0.53 (2H, m) 0.34-0.27 (2H, m). ESI-MS (m/z): 319 [M+H]⁺; MP: 206-208° C.

Example 30: 2-[8-(2-Methoxy-ethylamino)-2,6-bis-methylamino-pyrimido[5,4-d]pyrimidin-4-ylamino]-ethanol (56) and Corresponding Hydrochloride Salt (56a)

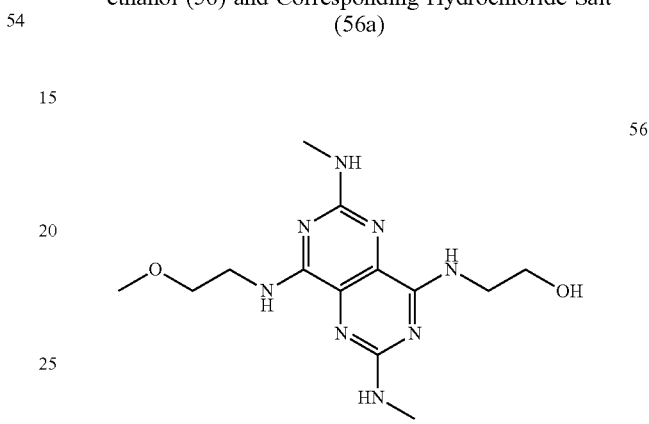

(a) 2-[2,6-Dichloro-8-(2-methoxy-ethylamino)-pyrimido[5,4-d]pyrimidin-4-ylamino]-ethanol (55)

2-(2,6,8-Trichloro-pyrimido[5,4-d]pyrimidin-4-ylamino)-ethanol (50) (300 mg, 1.02 mmol) and 2-methoxy-ethylamine were reacted in THF using procedures described elsewhere herein to give 2-[2,6-dichloro-8-(2-methoxy-ethylamino)-pyrimido[5,4-d]pyrimidin-4-ylamino]-ethanol (55) (246 mg, 72% yield). 400 MHz ¹H NMR (DMSO-d₆, ppm): 8.54 (1H, t, J=5.9 Hz) 8.47 (1H, t, J=5.7 Hz) 4.84 (1H, t, J=5.5 Hz) 3.64-3.56 (4H, m) 3.56-3.48 (4H, m) 3.27 (3H, s). ESI-MS (m/z): 333, 335, 337 [M+H]⁺.

(b) 2-[8-(2-Methoxy-ethylamino)-2,6-bis-methyl-amino-pyrimido[5,4-d]pyrimidin-4-yl amino]-ethanol (56)

2-[2,6-Dichloro-8-(2-methoxy-ethylamino)-pyrimido[5,4-d]pyrimidin-4-ylamino]-ethanol (55) (240 mg, 0.72 mmol) and methylamine (40% water solution) were reacted in n-butanol at 125° C. using procedure described for compound (4). The crude product was purified by flash column chromatography using gradient elution from EtOAc to EtOAc/EtOH (9:1) as eluent to give pure 2-[8-(2-methoxy-ethylamino)-2,6-bis-methylamino-pyrimido[5,4-d]pyrimidin-4-ylamino]-ethanol (56) (111 mg, 48% yield). 300 MHz ¹H NMR (CDCl₃, ppm): 6.95-6.87 (1H, m) 6.79-6.71 (1H, m) 4.70-4.53 (3H, m) 3.89-3.84 (2H, m) 3.74-3.65 (4H, m) 3.64-3.58 (2H, m) 3.40 (3H, s) 2.98-2.93 (6H, m). ESI-MS (m/z): 323 [M+1-1]⁺.

(c) 2-[8-(2-Methoxy-ethylamino)-2,6-bis-methyl-amino-pyrimido[5,4-d]pyrimidin-4-ylamino]-ethanol Hydrochloride (56a)

2-[8-(2-Methoxy-ethylamino)-2,6-bis-methylamino-pyrimido[5,4-d]pyrimidin-4-ylamino]-ethanol (56) (111 mg, 0.34 mmol) and 2M HCl/diethyl ether were reacted in CH₂Cl₂ using procedures described elsewhere herein to produce 2-[8-(2-methoxy-ethylamino)-2,6-bis-methyl-amino-pyrimido[5,4-d]pyrimidin-4-ylamino]-ethanol hydrochloride (56a) (115 mg, 93% yield). 300 MHz ¹H NMR (D₂O, ppm): 3.82 (2H, t, J=5.3 Hz) 3.75-3.60 (6H, m) 3.41 (3H, s) 2.93-2.85 (6H, m). ESI-MS (m/z): 323 [M+H]⁺; MP: 160-162° C.

Example 31: 2-(2,6-Bis-methylamino-8-prop-2-ynylamino-pyrimido[5,4-d]pyrimidin-4-ylamino)-ethanol (58) and Corresponding Hydrochloride Salt (58a)

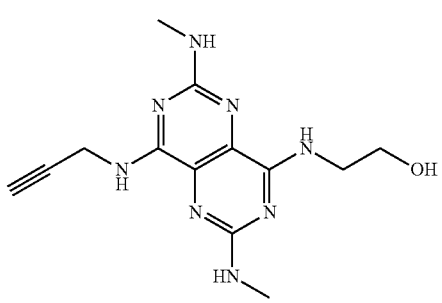

(a) 2-(2,6-Dichloro-8-prop-2-ynylamino-pyrimido[5,4-d]pyrimidin-4-ylamino)-ethanol (57)

2-(2,6,8-Trichloro-pyrimido[5,4-d]pyrimidin-4-ylamino)-ethanol (50) (300 mg, 1.02 mmol) and prop-2-yn-1-amine were reacted in THF using procedures described elsewhere herein to give 2-(2,6-dichloro-8-prop-2-ynylamino-pyrimido[5,4-d]pyrimidin-4-ylamino)-ethanol (57) (100 mg, 31% yield). 400 MHz ¹H NMR (DMSO-d₆, ppm): 9.05 (1H, s) 8.55 1H, t, J=5.7 Hz) 4.84 (1H, t, J=5.5 Hz) 4.18 (2H, s) 3.62-3.55 (2H, m) 3.55-3.49 (2H, m) 3.13 (1H, t, J=2.4 Hz). ESI-MS (m/z): 313, 315, 317 [M+H]⁺.

(b) 2-(2,6-Bis-methylamino-8-prop-2-ynylamino-pyrimido[5,4-d]pyrimidin-4-ylamino)-ethanol (58)

A mixture of 2-(2,6-dichloro-8-prop-2-ynylamino-pyrimido[5,4-d]pyrimidin-4-ylamino)-ethanol (57) (100 mg, 0.32 mmol) and methylamine (40% water solution) (330 µL, 4.25 mmol) in n-butanol (3 mL) was heated at 105° C. for 18h in a closed vial. After cooling, a saturated NaHCO₃ solution (20 mL) was added and the resulting suspension was extracted with EtOAc (3×25 mL). The combined organic extracts were washed with water (30 mL), then with a brine solution (30 mL) and dried over solid anhydrous MgSO₄. After filtration, the solvent was removed and the residue was purified by flash column chromatography using gradient elution from EtOAc to EtOAc/EtOH (9:1) to give 2-(2,6-bis-methylamino-8-prop-2-ynylamino-pyrimido[5,4-d]pyrimidin-4-ylamino)-ethanol (58) (37 mg, 38% yield). 400 MHz ¹H NMR (CDCl₃, ppm): 6.91 (1H, br s) 6.56 (1H, br s) 4.70 (1H, br s) 4.61 (1H, br s) 4.34-4.29 (2H, m) 3.90-3.84 (2H, m) 3.72-3.66 (2H, m) 2.99-2.94 (6H, m) 2.27-2.24 (1H, m). ESI-MS (m/z): 303 [M+H]⁺.

(c) 2-(2,6-Bis-methylamino-8-prop-2-ynylamino-pyrimido[5,4-d]pyrimidin-4-ylamino)-ethanol Hydrochloride (58a)

2-(2,6-Bis-methylamino-8-prop-2-ynylamino-pyrimido[5,4-d]pyrimidin-4-ylamino)-ethanol (58) (37 mg, 0.12 mmol) and 2M HCl/diethyl ether were reacted in CH₂Cl₂ using procedures described elsewhere herein to produce 2-(2,6-bis-methylamino-8-prop-2-ynylamino-pyrimido[5,4-d]pyrimidin-4-ylamino)-ethanol hydrochloride (58a) (40 mg, 96% yield). 300 MHz ¹H NMR (D₂O, ppm): 4.35-4.27 (2H, m) 3.90-3.82 (2H, m) 3.78-3.71 (2H, m) 2.98 (3H,$) 2.97 (3H, s) 2.76-2.72 (1H, m). ESI-MS (m/z): 303 [M+H]⁺; MP: 240-242° C.

Example 32: 2-[8-(2,2-Difluoro-ethylamino)-2,6-bis-methylamino-pyrimido[5,4-d]-pyrimidin-4-ylamino]-ethanol (60) and Corresponding Hydrochloride Salt (60a)

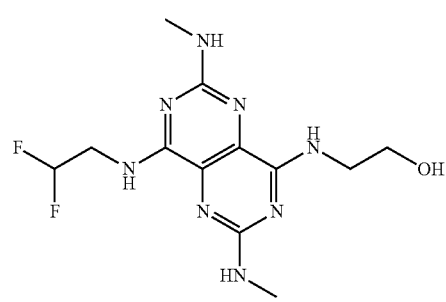

(a) 2-[2,6-Dichloro-8-(2,2-difluoro-ethylamino)-pyrimido[5,4-d]pyrimidin-4-ylamino]-ethanol (59)

2-(2,6,8-Trichloro-pyrimido[5,4-d]pyrimidin-4-ylamino)-ethanol (50) (240 mg, 0.81 mmol) and 2,2-difluoro-ethylamine were reacted in THF using procedures described elsewhere herein to give 2-[2,6-dichloro-8-(2,2-difluoro-ethylamino)-pyrimido[5,4-d]pyrimidin-4-ylamino]-ethanol (59) (190 mg, 69% yield). 300 MHz ¹H NMR (CDCl₃, ppm): 7.31 (1H, s) 7.05 (1H, t, J=6.3 Hz) 6.04 (1H, tt, J=55.5, 4.1 Hz) 4.01 (2H, tdd, J=14.4, 6.5, 4.1 Hz) 3.97-3.89 (2H, m) 3.84-3.76 (2H, m) 2.30 (1H, J=5.1 Hz). ESI-MS (m/z): 339, 341, 343 [M+H]⁺.

(b) 2-[8-(2,2-Difluoro-ethylamino)-2,6-bis-methylamino-pyrimido[5,4-d]-pyrimidin-4-ylamino]-ethanol (60)

2-[2,6-Dichloro-8-(2,2-difluoro-ethylamino)-pyrimido[5,4-d]pyrimidin-4-yl amino]-ethanol (59) (240 mg, 0.61 mmol) and methylamine (40% water solution) were reacted in n-butanol using procedure described for compound (4). The product was purified by flash column chromatography using gradient elution from CH₂Cl₂ to CH₂Cl₂/MeOH (95:5) to give 2-[8-(2,2-difluoro-ethylamino)-2,6-bis-methylamino-pyrimido[5,4-d]-pyrimidin-4-ylamino]-ethanol (60) (125 mg, 68% yield). 300 MHz ¹H NMR (DMSO-d₆, ppm): 7.32 (1H, t, J=6.1 Hz) 7.05 (1H, t, J=5.6 Hz) 6.28 (1H, q, J=4.6 Hz) 6.24 (1H, tt, J=56.5, 4.3 Hz) 6.16 (1H, q, J=4.6 Hz) 4.84 (1H, t, J=5.1 Hz) 3.93-3.73 (2H, m) 3.63-3.54 (2H, m) 3.53-3.44 (2H, m) 2.81 (3H, d, J=4.6 Hz) 2.79 (3H, d, J=4.6 Hz). ESI-MS (m/z): 329 [M+H]⁺.

(c) 2-[8-(2,2-Difluoro-ethylamino)-2,6-bis-methylamino-pyrimido[5,4-d]-pyrimidin-4-ylamino]-ethanol Hydrochloride (60a)

2-[8-(2,2-Difluoro-ethylamino)-2,6-bis-methylamino-pyrimido[5,4-d]-pyrimidin-4-ylamino]-ethanol (60) (125 mg, 0.38 mmol) and 2M HCl/diethyl ether were reacted in diethyl ether using procedure described for compound (6a) to produce 2-[8-(2,2-difluoro-ethylamino)-2,6-bis-methylamino-pyrimido[5,4-d]-pyrimidin-4-ylamino]-ethanol hydrochloride (60a) (125 mg, 90% yield). 400 MHz $^1$H NMR (CD$_3$OD, ppm): 6.14 (1H, tt, J=56.2, 4.0 Hz) 3.98 (2H, td, J=14.9, 4.0 Hz) 3.84-3.69 (4H, m) 3.03 (3H, s) 2.98 (3H, s). ESI-MS (m/z): 329 [M+H]$^+$; MP: 213-215° C.

Example 33: 2-[2,6-Bis-methylamino-8-(2,2,2-trifluoro-ethylamino)-pyrimido[5,4-d]pyrimidin-4-ylamino]-ethanol (62) and Corresponding Hydrochloride Salt (62a)

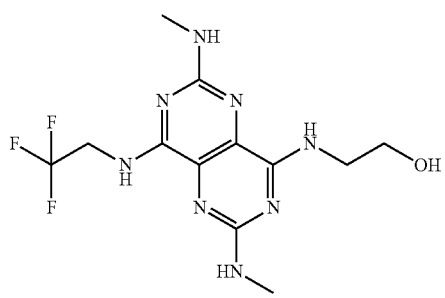

62

(a) 2-[2,6-Dichloro-8-(2,2,2-trifluoro-ethylamino)-pyrimido[5,4-d]pyrimidin-4-ylamino]-ethanol (61)

A mixture of 2-(2,6,8-Trichloro-pyrimido[5,4-d]pyrimidin-4-ylamino)-ethanol (50) (295 mg, 1.00 mmol) and 2,2,2-trifluoro-ethylamine (159 μL, 2.00 mmol) in n-butanol (2 mL) was stirred at room temperature for 3 h. A saturated NaHCO$_3$ solution (10 mL) was added and the resulting suspension was extracted with EtOAc (3×20 mL). The combined organic extracts were washed with a brine solution (30 mL) and dried over solid anhydrous Na$_2$SO$_4$. After filtration, the solvent was removed and the product was purified by flash column chromatography using gradient elution from CH$_2$Cl$_2$ to CH$_2$Cl$_2$/MeOH (95:5) to give pure 2-[2,6-dichloro-8-(2,2,2-trifluoro-ethylamino)-pyrimido[5,4-d]pyrimidin-4-ylamino]-ethanol (61) (300 mg, 84% yield). 300 MHz $^1$H NMR (CDCl$_3$, ppm): 7.38-7.30 (1H, m) 7.05 (1H, t, J=6.4 Hz) 4.31 (2H, qd, J=8.8, 6.8 Hz) 3.96-3.89 (2H, m) 3.85-3.77 (2H, m) 2.26 (1H, t, J=5.2 Hz). ESI-MS (m/z): 357, 359, 361 [M+1-1]$^+$.

(b) 2-[2,6-Bis-methylamino-8-(2,2,2-trifluoro-ethylamino)-pyrimido[5,4-d]pyrimidin-4-ylamino]-ethanol (62)

2-[2,6-Dichloro-8-(2,2,2-trifluoro-ethylamino)-pyrimido[5,4-d]pyrimidin-4-ylamino]-ethanol (61) (290 mg, 0.81 mmol) and methylamine (40% water solution) were reacted in n-butanol using procedures described elsewhere herein. The product was purified by flash column chromatography using gradient elution from CH$_2$Cl$_2$ to CH$_2$Cl$_2$/MeOH (98:25) to give 2-[2,6-bis-methylamino-8-(2,2,2-trifluoro-ethylamino)-pyrimido[5,4-d]pyrimidin-4-ylamino]-ethanol (62) (242 mg, 86% yield). 300 MHz $^1$H NMR (CDCl$_3$, ppm): 6.99-6.86 (1H, m) 6.65 (1H, t, J=5.8 Hz) 4.75-4.58 (2H, m) 4.37 (1H, s) 4.22 (2H, qd, J=9.1, 6.8 Hz) 3.89-3.84 (2H, m) 3.73-3.67 (2H, m) 2.97 (3H, d, J=5.1 Hz) 2.96 (3H, d, J=5.1 Hz). ESI-MS (m/z): 347 [M+H]$^+$.

(c) 2-[2,6-Bis-methylamino-8-(2,2,2-trifluoro-ethylamino)-pyrimido[5,4-d]pyrimidin-4-ylamino]-ethanol Hydrochloride (62a)

2-[2,6-Bis-methylamino-8-(2,2,2-trifluoro-ethylamino)-pyrimido[5,4-d]pyrimidin-4-ylamino]-ethanol (62) (125 mg, 0.38 mmol) and 2M HCl/diethyl ether were reacted in diethyl ether/MeOH (1/2) using procedures described elsewhere herein to produce 2-[2,6-bis-methylamino-8-(2,2,2-trifluoro-ethylamino)-pyrimido[5,4-d]pyrimidin-4-ylamino]-ethanol hydrochloride (62a) (210 mg, 95% yield). 300 MHz $^1$H NMR (CD$_3$OD, ppm): 4.38 (2H, q, J=9.3 Hz) 3.85-3.69 (4H, m) 3.04 (3H, s) 2.97 (3H, s). ESI-MS (m/z): 347 [M+H]$^+$; MP: 253-254° C.

Example 34: 2-(8-Benzylamino-2,6-bis-methylamino-pyrimido[5,4-d]-pyrimidin-4-ylamino)-ethanol (64) and Corresponding Hydrochloride Salt (64a)

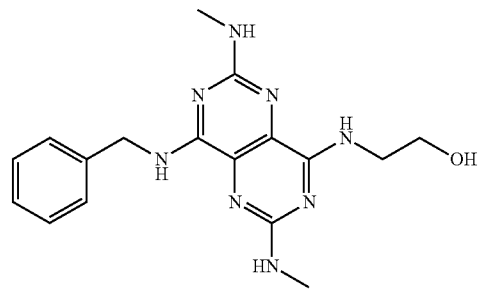

64

(a) 2-(8-Benzylamino-2,6-dichloro-pyrimido[5,4-d]pyrimidin-4-ylamino)-ethanol (63)

2-(2,6,8-Trichloro-pyrimido[5,4-d]pyrimidin-4-ylamino)-ethanol (50) (400 mg, 1.36 mmol) and benzylamine were reacted in dichloromethane using procedures described elsewhere herein to give 2-(8-benzylamino-2,6-dichloro-pyrimido[5,4-d]pyrimidin-4-ylamino)-ethanol (63) (380 mg, 77% yield). 300 MHz $^1$H NMR (CDCl$_3$, ppm): 7.41-7.27 (6H, m) 7.15 (1H, t, J=5.7 Hz) 4.77 (2H, d, J=5.9 Hz) 3.95-3.88 (2H, m) 3.82-3.74 (2H, m) 2.49 (1H, s). ESI-MS (m/z): 365, 367, 369 [M+H]$^+$.

(b) 2-(8-Benzylamino-2,6-bis-methylamino-pyrimido[5,4-d]-pyrimidin-4-ylamino)-ethanol (64)

2-(8-Benzylamino-2,6-dichloro-pyrimido[5,4-d]pyrimidin-4-ylamino)-ethanol (63) (370 mg, 1.01 mmol) and methylamine (40% water solution) were reacted in n-butanol using procedure described for compound (4) to give 2-(8-benzylamino-2,6-bis-methylamino-pyrimido[5,4-d]-pyrimidin-4-ylamino)-ethanol (64) (235 mg, 66% yield). 300 MHz $^1$H NMR (CDCl$_3$, ppm): 7.42-7.27 (5H, m) 6.95 (1H, t, J=6.1 Hz) 6.80 (1H, t, J=6.1 Hz) 4.73 (2H, d, J=6.1 Hz) 4.68 (1H, q, J=5.1 Hz) 4.58 (1H, q, J=5.1 Hz) 3.90-3.83 (2H, m) 3.73-3.65 (2H, m) 2.97 (3H, d, J=5.1 Hz) 2.92 (3H, d, J=5.1 Hz). ESI-MS (m/z): 355 [M+1-1]$^+$.

(c) 2-(8-Benzylamino-2,6-bis-methylamino-pyrimido[5,4-d]-pyrimidin-4-ylamino)-ethanol Hydrochloride (64a)

2-(8-Benzylamino-2,6-bis-methylamino-pyrimido[5,4-d]-pyrimidin-4-ylamino)-ethanol (64) (180 mg, 0.51 mmol) and 2M HCl/diethyl ether were reacted in diethyl ether/MeOH (5/1) using the procedure described for compound (6a) to produce 2-(8-benzylamino-2,6-bis-methylamino-pyrimido[5,4-d]-pyrimidin-4-ylamino)-ethanol hydrochloride (64a) (198 mg, 99% yield). 300 MHz $^1$H NMR (CD$_3$OD, ppm): 7.44-7.38 (2H, m) 7.38-7.23 (3H, m) 4.77 (2H, s) 3.83-3.76 (2H, m) 3.77-3.66 (2H, m) 2.98 (6H, s). ESI-MS (m/z): 355 [M+H]$^+$; MP: 181-183° C.

Example 35: 3-(8-Ethylamino-2,6-bis-methylamino-pyrimido[5,4-d]-pyrimidin-4-ylamino)-propan-1-ol (67) and Corresponding Hydrochloride Salt (67a)

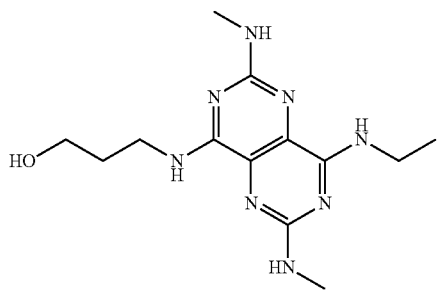

67

(a) 3-(2,6,8-Trichloro-pyrimido[5,4-d]pyrimidin-4-ylamino)-propan-1-ol (65)

To a suspension of 2,4,6,8-tetrachloro-pyrimido[5,4-d]pyrimidine (1) (600 mg, 2.23 mmol) in THF (10 mL) at −78° C., 3-amino-propan-1-ol (158 mg, 2.11 mmol) and N,N-diisopropylethylamine (500 μL, 2.90 mmol) in THF (5 mL) was added via syringe pump (over about 20 min). The mixture was stirred at −78° C. for additional 30 min, and then allowed to reach the room temperature. Water (40 mL) was added and the resulting suspension was extracted with EtOAc (3×30 mL). The combined organic extracts were washed with a brine solution (50 mL) and dried over solid anhydrous MgSO$_4$. After filtration, the solvent was removed and the residue was purified by flash column chromatography using PE/EtOAc (1:1) as eluent to give 3-(2,6,8-trichloro-pyrimido[5,4-d]pyrimidin-4-ylamino)-propan-1-ol (65) (630 mg, 97% yield). 300 MHz $^1$H NMR (CDCl$_3$, ppm): 7.77 (1H, s) 3.89-3.78 (4H, m) 2.35 (1H, s) 2.02-1.91 (2H, m). ESI-MS (m/z): 308, 310, 312, 314 [M+1-1]$^+$.

(b) 3-(2,6-Dichloro-8-ethylamino-pyrimido[5,4-d]pyrimidin-4-ylamino)-propan-1-ol (66)

Ethylamine (2 M in THF, 1.5 mL, 3 mmol) was added portionwise to a solution of 3-(2,6,8-trichloro-pyrimido[5,4-d]pyrimidin-4-ylamino)-propan-1-ol (65) (300 mg, 0.97 mmol) in n-butanol (3 mL) and chloroform (3 mL) at 0° C. The mixture was stirred at room temperature for 2h. After this time, a saturated NaHCO$_3$ solution (20 mL) was added and the resulting suspension was extracted with chloroform (3×20 mL). The combined organic extracts were washed with water and dried over solid anhydrous MgSO$_4$. After filtration, the solvent was removed and the residue was purified by flash column chromatography using gradient elution from CH$_2$Cl$_2$ to CH$_2$Cl$_2$/MeOH (97:3) to give 3-(2,6-dichloro-8-ethylamino-pyrimido[5,4-d]pyrimidin-4-ylamino)-propan-1-ol (66) (275 mg, 89% yield). 300 MHz $^1$H NMR (CDCl$_3$, ppm): 7.17 (1H, t, J=5.9 Hz) 6.87 (1H, t, J=5.3 Hz) 3.80-3.72 (2H, m) 3.72-3.66 (2H, m) 3.64 (2H, qd, J=7.3, 5.9 Hz) 3.00 (1H, s) 1.93-1.83 (2H, m) 1.33 (3H, t, J—7.3 Hz). ESI-MS (m/z): 317, 319, 321 [M+H]$^+$.

(c) 3-(8-Ethylamino-2,6-bis-methylamino-pyrimido[5,4-d]-pyrimidin-4-ylamino)-propan-1-ol (67)

3-(2,6-Dichloro-8-ethylamino-pyrimido[5,4-d]pyrimidin-4-ylamino)-propan-1-ol (66) (270 mg, 0.85 mmol) and methylamine (40% water solution) were reacted in n-butanol using the procedure described for compound (4) to give 3-(8-ethylamino-2,6-bis-methylamino-pyrimido[5,4-d]-pyrimidin-4-ylamino)-propan-1-ol (67) (165 mg, 63% yield). 300 MHz $^1$H NMR (CDCl$_3$, ppm): 6.74 (1H, t, J=6.3 Hz)) 6.46 (1H, t, J=5.8 Hz) 5.2-4.4 (1H, br s) 4.75-4.64 (1H, m) 4.63-4.52 (1H, m) 3.74-3.66 (2H, m) 3.62-3.55 (2H, m) 3.54 (2H, qd, J=7.2, 5.8 Hz) 2.97 (3H, d, J=4.9 Hz) 2.95 (3H, d, J=4.9 Hz) 1.84-1.74 (2H, m) 1.29 (3H, t, J=7.2 Hz). ESI-MS (m/z): 307 [M+H]$^+$.

(b) 3-(8-Ethylamino-2,6-bis-methylamino-pyrimido[5,4-d]-pyrimidin-4-ylamino)-propan-1-ol Hydrochloride (67a)

3-(8-Ethylamino-2,6-bis-methylamino-pyrimido[5,4-d]-pyrimidin-4-ylamino)-propan-1-ol (67) (170 mg, 0.55 mmol) and 2M HCl/diethyl ether were reacted in diethyl ether/EtOH (4/1) using the procedure described for compound (14a) to produce 3-(8-ethylamino-2,6-bis-methylamino-pyrimido[5,4-d]-pyrimidin-4-ylamino)-propan-1-ol hydrochloride (67a) (185 mg, 98% yield). 300 MHz $^1$H NMR (CD$_3$OD, ppm): 3.80-3.49 (4H, m) 3.69 (2H, t, J=6.1 Hz) 3.11-2.87 (6H, m) 1.98-1.86 (2H, m) 1.31 (3H, t, J=7.2 Hz). ESI-MS (m/z): 307 [M+H]$^+$; MP: 179-181° C.

Example 36: 1-(2,6-Bis-methylamino-8-propylamino-pyrimido[5,4-d]pyrimidin-4-yl)-pyrrolidin-3-ol (71) and Corresponding Hydrochloride Salt (71a)

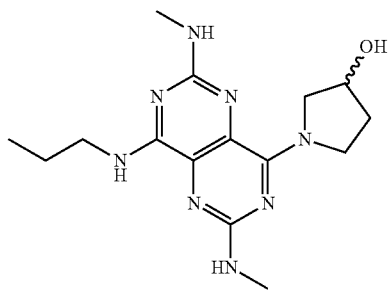

71

(a) 2,6,8-Trichloro-pyrimido[5,4-d]pyrimidin-4-ol (68)

A mixture of 2,4,6,8-tetrachloro-pyrimido[5,4-d]pyrimidine (1) (10.00 g, 37.05 mmol), water (60 mL) and THF (120 mL) was stirred at room temperature for 24h. The volatiles were removed in vacuo. Water (200 mL) was added and the resulting suspension was filtered. The collected solid were washed with water (2×50 mL) and dried over $P_2O_5$ in vacuo at 60° C. for 48h to give 2,6,8-trichloro-pyrimido[5,4-d]pyrimidin-4-ol (68) (8.47 g, 91% yield).

(b) 2,6-Dichloro-8-propylamino-pyrimido[5,4-d]pyrimidin-4-ol (69)

To a suspension of 2,6,8-trichloro-pyrimido[5,4-d]pyrimidin-4-ol (68) (8.47 g, 33.68 mmol) in THF (120 mL) at 0° C., propylamine (7.20 mL, 101.05 mmol) in THF (20 mL) was added dropwise. The mixture was stirred at room temperature for 16h after which time, the volatiles were removed in vacuo and water (200 mL) was added. The resultant precipitate was filtered, washed with water (3×50 mL) and dried over $P_2O_5$ in vacuo at 60° C. for 16h to give 2,6-dichloro-8-propylamino-pyrimido[5,4-d]pyrimidin-4-ol (69) (9.00 g, 97% yield). 300 MHz $^1$H NMR ($CDCl_3$+TFA, ppm): 7.79 (1H, t, J=6.0 Hz) 3.79-3.69 (2H, m) 1.81 (2H, sextet, J=7.4 Hz) 1.06 (3H, t, J=7.4 Hz). ESI-MS (m/z): 274, 276, 278 [M+H]$^+$.

(c) 2,6-Bis-methylamino-8-propylamino-pyrimido[5,4-d]pyrimidin-4-ol (70)

2,6-Dichloro-8-propylamino-pyrimido[5,4-d]pyrimidin-4-ol (69) (9.00 g, 32.83 mmol) and methylamine (40% water solution) (23.00 mL) were reacted in n-butanol (50 mL) was heated at 105° C. for 96 h in a closed vial. After cooling, a saturated $NaHCO_3$ solution (100 mL) was added and the resulting suspension was extracted with $CHCl_3$ (3×150 mL). The combined organic extracts were washed with water (300 mL) and dried over solid anhydrous $MgSO_4$. After filtration, the solvent was removed and the residue was purified by flash column chromatography using gradient elution from $CHCl_3$/MeOH (98:2) to $CHCl_3$/MeOH (1:1) to give 2,6-bis-methylamino-8-propylamino-pyrimido[5,4-d]pyrimidin-4-ol (70) (6.18 g, 71% yield). 300 MHz $^1$H NMR (DMSO-$d_6$, ppm): 7.18 (1H, s) 6.23 (1H, q, J=4.7 Hz) 6.10 (1H, q, J=4.7 Hz) 3.48-3.26 (2H, m, overlapped with water) 3.16 (1H, s) 2.83 (3H, d, J=4.7 Hz) 2.75 (3H, d, J=4.7 Hz) 1.66-1.52 (2H, m) (3H, t, J=7.4 Hz). ESI-MS (m/z): 264 [M+1-1]$^+$.

(d) 1-(2,6-Bis-methylamino-8-propylamino-pyrimido[5,4-d]pyrimidin-4-yl)-pyrrolidin-3-ol (71)

A mixture of 2,6-bis-methylamino-8-propylamino-pyrimido[5,4-d]pyrimidin-4-ol (70) (250 mg, 0.95 mmol), (benzotriazol-1-yloxy)tris(dimethylamino)phosphonium hexafluorophosphate (BOP) (548 mg, 1.24 mmol) and 1,8-diazabicyclo[5.4.0]undec-7-ene (DBU) (214 µL, 1.43 mmol) in DMF (5 mL) was stirred at room temperature for 1 h. A mixture of pyrrolidin-3-ol hydrochloride (352 mg, 2.85 mmol) and DBU (426 µL, 2.85 mmol) in DMF (2 mL) was added, and the resulting reaction mixture was stirred at room temperature for 18 h. Water (50 mL) was added and the resulting suspension was extracted with EtOAc (3×50 mL). The combined organic extracts were washed with a brine solution (50 mL) and dried over solid anhydrous $Na_2SO_4$. After filtration, the solvent was removed and the residue was purified by flash column chromatography using gradient elution from PE/EtOAc (99:1) to PE/EtOAc (1:99) to give 1-(2,6-bis-methylamino-8-propylamino-pyrimido[5,4-d]pyrimidin-4-yl)-pyrrolidin-3-ol (71) (161 mg, 51% yield). 300 MHz $^1$H NMR ($CDCl_3$, ppm): 6.62-6.53 (1H, m) 4.65-4.44 (3H, m) 4.36-3.98 (5H, m) 3.47-3.39 (2H, m) 2.95-2.89 (6H, m) 2.07-1.98 (2H, m) 1.69 (2H, sextet, J=7.4 Hz) 1.00 (3H, t, J=7.4 Hz). ESI-MS (m/z): 333 [M+H]$^+$.

(c) 1-(2,6-Bis-methylamino-8-propylamino-pyrimido[5,4-d]pyrimidin-4-yl)-pyrrolidin-3-ol Hydrochloride (71a)

1-(2,6-Bis-methylamino-8-propylamino-pyrimido[5,4-d]pyrimidin-4-yl)-pyrrolidin-3-ol (71) (144 mg, 0.43 mmol) and 2M HCl/diethyl ether were reacted in $CH_2Cl_2$ using the procedure described for compound (14a) to produce 1-(2,6-bis-methylamino-8-propylamino-pyrimido[5,4-d]pyrimidin-4-yl)-pyrrolidin-3-ol hydrochloride (71a) (125 mg, 78% yield). 300 MHz $^1$H NMR ($CD_3OD$, ppm): 4.59-4.52 (1H, m) 4.39-4.04 (4H, m) 3.54 (2H, t, J=7.4 Hz) 3.02 (3H, s) 2.97 (3H, s) 2.16-2.0 (2H, m) 1.75 (2H, sextet, J=7.4 Hz) 1.03 (3H, t, J=7.4 Hz). ESI-MS (m/z): 333 [M+H]$^+$; MP: 202-204° C.

Example 37: 1-[(2,6-Bis-methylamino-8-propylamino-pyrimido[5,4-d]pyrimidin-4-ylamino)-methyl]-cyclobutanol (72) and Corresponding Hydrochloride Salt (72a)

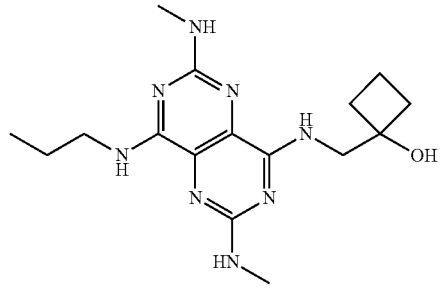

(a) 1-[(2,6-Bis-methylamino-8-propylamino-pyrimido[5,4-d]pyrimidin-4-ylamino)-methyl]-cyclobutanol (72)

A mixture of 2,6-bis-methylamino-8-propylamino-pyrimido[5,4-d]pyrimidin-4-ol (70) (250 mg, 0.95 mmol), BOP reagent (548 mg, 1.24 mmol and DBU (214 µL, 1.43 mmol) in DMF (5 mL) was stirred at room temperature for 1 h. 1-Aminomethyl-cyclobutanol (288 mg, 2.85 mmol) was added and the resulting reaction mixture was stirred at room temperature for 18 h. Water (50 mL) was added and the resulting suspension was extracted with EtOAc (3×50 mL). The combined organic extracts were washed with a brine solution (50 mL) and dried over solid anhydrous $Na_2SO_4$. After filtration the solvent was removed and the residue was purified by flash column chromatography using gradient elution from PE/EtOAc (99:1) to PE/EtOAc (1:99) to give 1-[(2,6-bis-methylamino-8-propylamino-pyrimido[5,4-d]pyrimidin-4-ylamino)-methyl]-cyclobutanol (72) (147 mg, 45% yield). 300 MHz $^1$H NMR ($CDCl_3$, ppm): 7.03-6.92 (1H, m) 6.53-6.44 (1H, m) 6.14-5.95 (1H, m) 4.67-4.60 (1H, m) 4.60-4.52 (1H, m) 3.68 (2H, d, J=6.2 Hz) 3.49-3.41 (2H, m) 2.97 (3H, d, J=5.1 Hz) 2.93 (3H, d, J=5.1 Hz) 2.18-2.02 (4H, m) 1.80-1.60 (3H, m) 1.58-1.41 (1H, m) 0.99 (3H, t, J=7.4 Hz). ESI-MS (m/z): 347 [M+H]$^+$.

(b) 1-[(2,6-Bis-methylamino-8-propylamino-pyrimido[5,4-d]pyrimidin-4-ylamino)-methyl]-cyclobutanol Hydrochloride (72a)

1-[(2,6-Bis-methylamino-8-propylamino-pyrimido[5,4-d]pyrimidin-4-ylamino)-methyl]-cyclobutanol (72) (113 mg, 0.33 mmol) and 2M HCl/diethyl ether were reacted in $CH_2Cl_2$ using procedures described elsewhere herein to produce 1-[(2,6-bis-methylamino-8-propylamino-pyrimido[5,4-d]pyrimidin-4-ylamino)-methyl]-cyclobutanol hydrochloride (72a) (95 mg, 76% yield). 300 MHz $^1$H NMR ($CD_3OD$, ppm): 3.85 (2H, s) 3.61 (2H, t, J=7.4 Hz) 3.04 (3H, s) 3.03 (3H, s) 2.22-2.04 (4H, m) 1.86-1.60 (2H, m) 1.77 (2H, sextet, J=7.4 Hz) 1.03 (3H, t, J=7.4 Hz). ESI-MS (m/z): 347 [M+H]$^+$; MP: 248-250° C.

Example 38: 1-[(2,6-Bis-methylamino-8-propylamino-pyrimido[5,4-d]-pyrimidin-4-yl)-methylamino]-propan-2-ol (73) and Corresponding Hydrochloride Salt (73a)

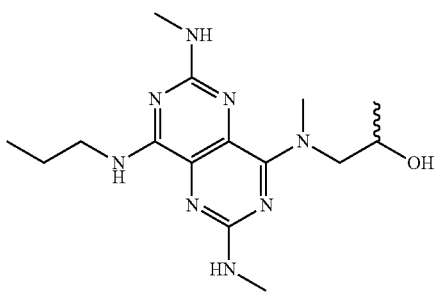

(a) 1-[(2,6-Bis-methylamino-8-propylamino-pyrimido[5,4-d]-pyrimidin-4-yl)-methyl-amino]-propan-2-ol (73)

2,6-Bis-methylamino-8-propylamino-pyrimido[5,4-d]pyrimidin-4-ol (70) (250 mg, 0.95 mmol) and 1-methylaminopropan-2-ol were reacted using procedures described elsewhere herein to obtain 1-[(2,6-bis-methylamino-8-propylamino-pyrimido[5,4-d]-pyrimidin-4-yl)-methylamino]-propan-2-ol (73) (170 mg, 54% yield). 300 MHz $^1$H NMR ($CDCl_3$, ppm): 7.0-6.4 (1H, br s) 6.79 (1H, t, J=5.7 Hz) 4.70 (1H, dd, J=14.5, 9.5 Hz) 4.61 (1H, q, J=5.1 Hz) 4.56 (1H, q, J=5.1 Hz) 4.24-4.10 (1H, m) 3.50-3.39 (2H, m) 3.30 (1H, dd, J=14.5, 2.5 Hz) 3.30 (3H, s) 2.97 (3H, d, J=5.1 Hz) 2.95 (3H, d, J=5.1 Hz) 1.76-1.61 (2H, m) 1.28 (3H, d, J=6.3 Hz) 1.00 (3H, t, J=7.4 Hz). ESI-MS (m/z): 335 [M+1-1]$^+$.

(b) 1-[(2,6-Bis-methylamino-8-propylamino-pyrimido[5,4-d]-pyrimidin-4-yl)-methyl-amino]-propan-2-ol Hydrochloride (73a)

1-[(2,6-Bis-methylamino-8-propylamino-pyrimido[5,4-d]-pyrimidin-4-yl)-methyl-amino]-propan-2-ol (73) (165 mg, 0.49 mmol) and 2M HCl/diethyl ether were reacted in diethyl ether using procedures described elsewhere herein to produce 1-[(2,6-bis-methylamino-8-propylamino-pyrimido[5,4-d]-pyrimidin-4-yl)-methyl-amino]-propan-2-ol hydrochloride (73a) (160 mg, 88% yield). 300 MHz $^1$H NMR ($CD_3OD$, ppm): 4.36-4.24 (1H, m) 3.85-3.67 (1H, m) 3.60 (2H, t, J=7.2 Hz) 3.28-3.11 (1H, m) 3.18 (3H, s) 3.03 (3H, s) 2.98 (3H, s) 1.83-1.67 (2H, m) 1.31 (3H, d, J=6.3 Hz) 1.01 (3H, t, J=7.4 Hz). ESI-MS (m/z): 335 [M+H]$^+$.

Example 39: 3-[(2,6-Bis-methylamino-8-propylamino-pyrimido[5,4-d]pyrimidin-4-ylamino)-methyl]-pentan-3-ol (74) and Corresponding Hydrochloride Salt (74a)

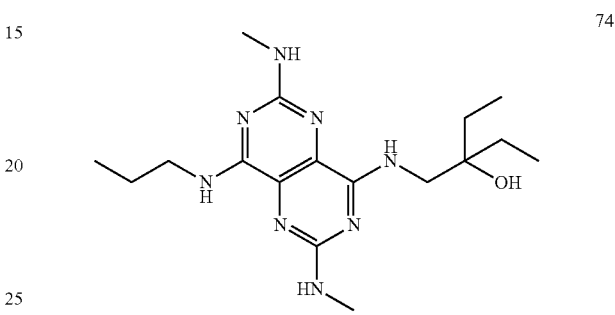

(a) 3-[(2,6-Bis-methylamino-8-propylamino-pyrimido[5,4-d]pyrimidin-4-ylamino)-methyl]-pentan-3-ol (74)

2,6-Bis-methylamino-8-propylamino-pyrimido[5,4-d]pyrimidin-4-ol (70) (300 mg, 1.14 mmol) and 3-aminomethyl-pentan-3-ol were reacted using the procedures described elsewhere herein to obtain 3-[(2,6-bis-methylamino-8-propylamino-pyrimido[5,4-d]pyrimidin-4-ylamino)-methyl]-pentan-3-ol (74) (134 mg, 32% yield). 300 MHz $^1$H NMR ($CDCl_3$, ppm): 6.81 (1H, t, J=6.3 Hz) 6.50 (1H, t, J=5.7 Hz) 5.09-4.73 (1H, br s) 4.69-4.53 (2H, m) 3.53 (2H, d, J=6.3 Hz) 3.49-3.42 (2H, m) 2.96 (3H, d, J=5.1 Hz) 2.94 (3H, d, J=5.1 Hz) 1.69 (2H, sextet, J=7.4 Hz) 1.58-1.51 (4H, m) 1.0 (3H, t, J=7.4 Hz) 0.92 (6H, t, J=7.6 Hz). ESI-MS (m/z): 363 [M+H]$^+$.

(b) 3-[(2,6-Bis-methylamino-8-propylamino-pyrimido[5,4-d]pyrimidin-4-ylamino)-methyl]-pentan-3-ol Hydrochloride (74a)

3-[(2,6-Bis-methylamino-8-propylamino-pyrimido[5,4-d]pyrimidin-4-ylamino)-methyl]-pentan-3-ol (74) (134 mg, 0.37 mmol) and 2M HCl/diethyl ether were reacted in diethyl ether using procedures described elsewhere herein to produce 3-[(2,6-bis-methylamino-8-propylamino-pyrimido[5,4-d]pyrimidin-4-ylamino)-methyl]-pentan-3-ol hydrochloride (74a) (137 mg, 93% yield). 400 MHz $^1$H NMR ($CD_3OD$, ppm): 3.69 (2H, s) 3.59 (2H, t, J=7.3 Hz) 3.02 (3H, s) 3.02 (3H, s) 1.76 (2H, sextet, J=7.4 Hz) 1.61-1.53 (4H, m) 1.03 (3H, t, J=7.4 Hz) 0.94 (6H, t, J=7.4 Hz). ESI-MS (m/z): 363 [M+H]$^+$; MP: 219-221° C.

Comparative Example 40: 3-(2,6-Bis-methylamino-8-propylamino-pyrimido[5,4-d]pyrimidin-4-ylamino)-propane-1,2-diol (75) and Corresponding Hydrochloride Salt (75a)

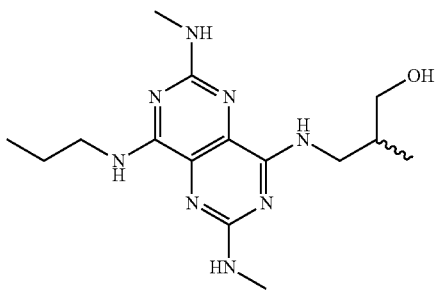

(a) 3-(2,6-Bis-methylamino-8-propylamino-pyrimido[5,4-d]pyrimidin-4-ylamino)-propane-1,2-diol (75)

2,6-Bis-methylamino-8-propylamino-pyrimido[5,4-d]pyrimidin-4-ol (70) (263 mg, 1.00 mmol) and 3-amino-propane-1,2-diol were reacted using the procedures described elsewhere herein. The crude product was purified by flash column chromatography using gradient elution from CH$_2$Cl$_2$ to CH$_2$Cl$_2$/EtOAc (4:1) as eluent to give pure 3-(2,6-bis-methylamino-8-propylamino-pyrimido[5,4-d]pyrimidin-4-ylamino)-propane-1,2-diol (75) (175 mg, 52% yield). 400 MHz $^1$H NMR (CDCl$_3$, ppm): 6.86 (1H, br s) 6.52 (1H, br s) 4.66 (1H, br s) 4.63-4.53 (1H, m) 3.98-3.81 (3H, m) 3.72-3.65 (2H, m) 3.61 (1H, dd, J=11.7, 4.0 Hz) 3.56 (1H, dd, J=11.7, 4.5 Hz) 3.51-3.42 (2H, m) 2.97 (3H, d, J=5.1 Hz) 2.95 (3H, J=5.1 Hz) 1.69 (2H, sextet, J=7.4 Hz) 1.00 (3H, t, J=7.4 Hz). ESI-MS (m/z): 337 [M+H]$^+$.

(b) 3-(2,6-Bis-methylamino-8-propylamino-pyrimido[5,4-d]pyrimidin-4-ylamino)-propane-1,2-diol Hydrochloride (75a)

3-(2,6-Bis-methylamino-8-propylamino-pyrimido[5,4-d]pyrimidin-4-ylamino)-propane-1,2-diol (75) (165 mg, 0.49 mmol) and 2M HCl/diethyl ether were reacted in diethyl ether/MeOH (6/1) using the procedure described for compound 6a to produce 3-(2,6-bis-methylamino-8-propylamino-pyrimido[5,4-d]pyrimidin-4-ylamino)-propane-1,2-diol hydrochloride (75a) (135 mg, 74% yield). 400 MHz $^1$H NMR (CD$_3$OD, ppm): 3.97-3.89 (1H, m) 3.83 (1H, dd, J=13.8, 4.1 Hz) 3.59 (2H, d, J=5.4 Hz) 3.63-3.51 (3H, m) 3.00 (6H, s) 1.74 (2H, sextet, J=7.4 Hz) 1.01 (3H, J=7.4 Hz). ESI-MS (m/z): 337 [M+H]$^+$; MP: 166-167° C.

Example 41: 1-[(2,6-Bis-methylamino-8-propylamino-pyrimido[5,4-d]pyrimidin-4-yl)-methyl-amino]-2-methyl-propan-2-ol (76) and Corresponding Hydrochloride Salt (76a)

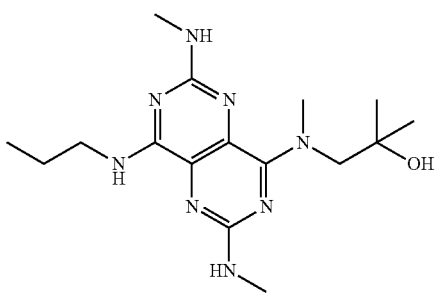

(a) 1-[(2,6-Bis-methylamino-8-propylamino-pyrimido[5,4-d]pyrimidin-4-yl)-methyl-amino]-2-methyl-propan-2-ol (76)

2,6-Bis-methylamino-8-propylamino-pyrimido[5,4-d]pyrimidin-4-ol (70) (300 mg, 1.14 mmol) and 2-methyl-1-methylamino-propan-2-ol were reacted using the procedures previously described to obtain 1-[(2,6-bis-methylamino-8-propylamino-pyrimido[5,4-d]pyrimidin-4-yl)-methyl-amino]-2-methyl-propan-2-ol (76) (235 mg, 59% yield). 300 MHz $^1$H NMR (CDCl$_3$, ppm): 6.79 (1H, t, J=5.0 Hz) 4.62-4.49 (2H, m) 4.06 (2H, s) 3.49-3.39 (2H, m) 3.41 (3H, s) 2.98-2.92 (6H, m) 1.68 (2H, sextet, J=7.4 Hz) 1.30 (6H, s) 0.99 (3H, t, J=7.4 Hz). ESI-MS (m/z): 349 [M+H]$^+$.

(b) 1-[(2,6-Bis-methylamino-8-propylamino-pyrimido[5,4-d]pyrimidin-4-yl)-methyl-amino]-2-methyl-propan-2-ol Hydrochloride (76a)

1-[(2,6-Bis-methylamino-8-propylamino-pyrimido[5,4-d]pyrimidin-4-yl)-methyl-amino]-2-methyl-propan-2-ol (76) (233 mg, 0.67 mmol) and 2M HCl/diethyl ether were reacted in diethyl ether using the procedure described for compound 6a to produce 1-[(2,6-bis-methylamino-8-propylamino-pyrimido[5,4-d]pyrimidin-4-yl)-methyl-amino]-2-methyl-propan-2-ol hydrochloride (76a) (160 mg, 62% yield). 400 MHz $^1$H NMR (CD$_3$OD, ppm): 3.71-3.63 (2H, br s) 3.60 (2H, t, J=7.4 Hz) 3.29-3.22 (3H, br s) 3.02 (3H, s) 2.97 (3H, s) 1.74 (2H, sextet, J=7.4 Hz) 1.41 (6H, s) 1.0 (3H, t, J=7.4 Hz). ESI-MS (m/z): 349 [M+H]$^+$; MP: 161-163° C.

Example 42: (1R,2S)-1-(2,6-Bis-methylamino-8-propylamino-pyrimido[5,4-d]-pyrimidin-4-ylamino)-indan-2-ol (77) and Corresponding Hydrochloride Salt (77a)

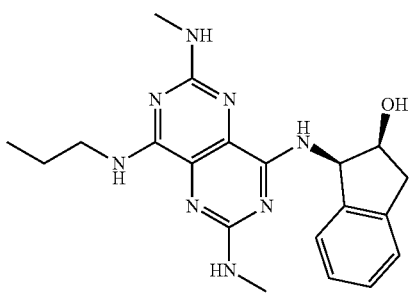

(a) (1R,2S)-1-(2,6-Bis-methylamino-8-propylamino-pyrimido[5,4-d]-pyrimidin-4-ylamino)-indan-2-ol (77)

2,6-Bis-methylamino-8-propylamino-pyrimido[5,4-d]pyrimidin-4-ol (70) (250 mg, 0.95 mmol) and (1R,2S)-1-amino-indan-2-ol were reacted using the procedure described for compound (71). The crude product was purified by flash column chromatography using gradient elution from CH$_2$Cl$_2$/MeOH (98:2) to CH$_2$Cl$_2$/MeOH (96:4) as eluent to give (1R,2S)-1-(2,6-bis-methylamino-8-propylamino-pyrimido[5,4-d]-pyrimidin-4-ylamino)-indan-2-ol (77) (180 mg, 48% yield). 300 MHz $^1$H NMR (CDCl$_3$, ppm): 7.38-7.33 (1H, m) 7.33-7.27 (2H, m) 7.25-7.19 (1H, m) 7.04 (1H, br s) 6.61 (1H, br s) 5.60 (1H, dd, J=7.4, 5.1 Hz) 4.87-4.54 (2H, m) 4.80 (1H, td, J=5.1, 2.8 Hz) 3.53-3.43 (2H, m) 3.23 (1H, dd, J=16.4, 5.3 Hz) 3.09 (1H, dd, J=16.4, 2.8 Hz) 2.97 (3H, d, J=5.1 Hz) 2.92 (3H, d, J=5.1 Hz) 1.78-1.63 (2H, m) 1.01 (3H, t, J=7.4 Hz). ESI-MS (m/z): 395 [M+H]⁺.

(b) (1R,2S)-1-(2,6-Bis-methylamino-8-propylamino-pyrimido[5,4-d]-pyrimidin-4-ylamino)-indan-2-ol Hydrochloride (77a)

(1R,2S)-1-(2,6-Bis-methylamino-8-propylamino-pyrimido[5,4-d]-pyrimidin-4-ylamino)-indan-2-ol (77) (145 mg, 0.37 mmol) and 2M HCl/diethyl ether were reacted in diethyl ether/MeOH (6/1) using procedures described elsewhere herein to produce (1R,2S)-1-(2,6-bis-methylamino-8-propylamino-pyrimido[5,4-d]-pyrimidin-4-ylamino)-indan-2-ol hydrochloride (77a) (155 mg, 98% yield). 300 MHz ¹H NMR (CD₃OD, ppm): 7.37-7.17 (4H, m) 5.83 (1H, d, J=5.1 Hz) 4.76 (1H, td, J=5.1, 1.8 Hz) 3.61 (2H, t, J=7.2 Hz) 3.24 (1H, dd, J=16.6, 5.1 Hz) 3.06-2.91 (1H, m) 3.01 (3H, s) 2.99 (3H, s) 1.84-1.68 (2H, m) 1.03 (3H, t, J=7.4 Hz). ESI-MS (m/z): 395 [M+1-1]⁺; MP: 281-283° C.

Using the procedures described herein, and variations readily available and known to those skilled in the art, the following pyrimido[5,4-d]-pyrimidinyl-amino cycloalkanols were prepared.

Example 43: (1S,2S)-1-(2,6-Bis-methylamino-8-propylamino-pyrimido[5,4-d]-pyrimidin-4-ylamino)-indan-2-ol (78) and Corresponding Hydrochloride Salt (78a)

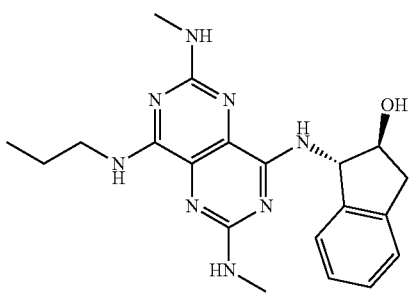

78

(a) (1S,2S)-1-(2,6-Bis-methylamino-8-propylamino-pyrimido[5,4-d]-pyrimidin-4-ylamino)-indan-2-ol (78)

2,6-Bis-methylamino-8-propylamino-pyrimido[5,4-d]pyrimidin-4-ol (70) (250 mg, 0.95 mmol) and (1S,2S)-1-amino-indan-2-ol were reacted using the procedure described for compound (71). The crude product was purified by flash column chromatography using gradient elution from CHCl₃ to CHCl₃/MeOH (99:1) as eluent to give (1S,2S)-1-(2,6-bis-methylamino-8-propylamino-pyrimido[5,4-d]-pyrimidin-4-ylamino)-indan-2-ol (78) (140 mg, 37% yield). 300 MHz ¹H NMR (CDCl₃, ppm) 7.42-7.35 (1H, m) 7.35-7.27 (3H, m) 7.12 (1H, s) 6.55 (1H, s) 6.27 (1H, br s) 5.30 (1H, t, J=5.9 Hz) 4.66 (2H, s) 4.58-4.47 (1H, m) 3.53-3.44 (2H, m) 3.37 (1H, dd, J=15.6, 7.9 Hz) 3.05-2.92 (1H, m) 2.98 (3H, d, J=5.1 Hz) 2.95 (3H, d, J=5.1 Hz) 1.78-1.63 (2H, m) 1.01 (3H, t, J=7.4 Hz). ESI-MS (m/z): 395 [M+H]⁺.

(b) (1S,2S)-1-(2,6-Bis-methylamino-8-propylamino-pyrimido[5,4-d]-pyrimidin-4-ylamino)-indan-2-ol Hydrochloride (78a)

(1S,2S)-1-(2,6-bis-methylamino-8-propyl amino-pyrimido[5,4-d]-pyrimidin-4-ylamino)-indan-2-ol (78) (140 mg, 0.35 mmol) and 2M HCl/diethyl ether were reacted in diethyl ether/MeOH (6/1) using the procedure described for compound 6a to produce (1S,2S)-1-(2,6-Bis-methylamino-8-propylamino-pyrimido[5,4-d]-pyrimidin-4-ylamino)-indan-2-ol hydrochloride (78a) (120 mg, 80% yield). 300 MHz ¹H NMR (CD₃OD, ppm): 7.32-7.25 (3H, m) 7.25-7.19 (1H, m) 5.67 (1H, d, J=5.5 Hz) 4.63-4.54 (1H, m) 3.62 (2H, t, J=7.1 Hz) 3.36 (1H, dd, J=15.9, 7.0 Hz) 3.01 (3H, s) 3.00 (3H, s) 2.91 (1H, dd, J=15.9, 6.3 Hz) 1.85-1.69 (2H, m) 1.03 (3H, t, J=7.4 Hz). ESI-MS (m/z): 395 [M+H]⁺; MP: 290-292° C.

Example 44: (1S,2R)-1-(2,6-Bis-methylamino-8-propylamino-pyrimido[5,4-d]pyrimidin-4-ylamino)-indan-2-ol (79) and Corresponding Hydrochloride Salt (79a)

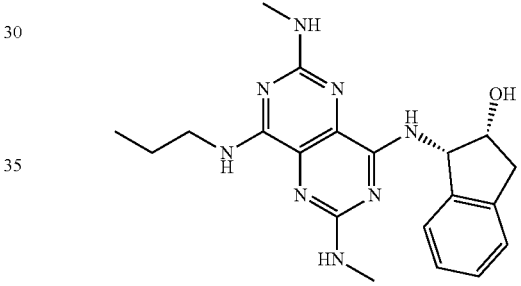

79

(a) (1S,2R)-1-(2,6-Bis-methylamino-8-propylamino-pyrimido[5,4-d]pyrimidin-4-ylamino)-indan-2-ol (79)

2,6-Bis-methylamino-8-propylamino-pyrimido[5,4-d]pyrimidin-4-ol (70) (300 mg, 1.14 mmol) and (1S,2R)-1-amino-indan-2-ol were reacted using procedures described above. The crude product was purified by flash column chromatography using gradient elution from CH₂Cl₂ to CH₂Cl₂/EtOAc (4:1) as eluent to give (1S,2R)-1-(2,6-bis-methylamino-8-propylamino-pyrimido[5,4-d]pyrimidin-4-ylamino)-indan-2-ol (79) (380 mg, 84% yield). 400 MHz ¹H NMR (CDCl₃, ppm): 7.36-7.32 (1H, m) 7.32-7.20 (3H, m) 7.01 (1H, d, J=7.1 Hz) 6.58-6.51 (1H, m) 5.59 (1H, dd, J=7.3, 5.3 Hz) 4.80 (1H, td, J=5.2, 2.6 Hz) 4.75-4.56 (2H, m) 3.54-3.40 (2H, m) 3.22 (1H, dd, J=16.4, 5.3 Hz) 3.06 (1H, dd, J=16.4, 2.5 Hz) 2.96 (3H, d, J=5.0 Hz) 2.91 (3H, d, J=5.0 Hz) 1.70 (2H, sextet, J=7.4 Hz) 1.01 (3H, t, J=7.4 Hz). ESI-MS (m/z): 395 [M+H]⁺.

(b) (1S,2R)-1-(2,6-Bis-methylamino-8-propylamino-pyrimido[5,4-d]pyrimidin-4-ylamino)-indan-2-ol Hydrochloride (79a)

(1S,2R)-1-(2,6-bis-methylamino-8-propylamino-pyrimido[5,4-d]-pyrimidin-4-ylamino)-indan-2-ol (79) (310 mg, 0.35 mmol) and 2M HCl/diethyl ether were reacted in diethyl ether/MeOH (1/1) using the procedure described for compound 6a to produce (1S,2R)-1-(2,6-bis-methylamino-8-propylamino-pyrimido[5,4-d]pyrimidin-4-ylamino)-indan-2-ol hydrochloride (79a) (300 mg, 88% yield). 300 MHz $^1$H NMR (CD$_3$OD, ppm): 7.40-7.15 (4H, m) 5.87-5.75 (1H, m) 4.78-4.70 (1H, m) 3.68-3.50 (2H, m) 3.33-3.16 (1H, m) 3.10-2.85 (7H, m) 1.76 (2H, sextet, J=7.4 Hz) 1.03 (3H, J=7.4 Hz). ESI-MS (m/z): 395 [M+H]$^+$; MP: 286° C. (dec.).

Example 45: (1R,2R)-1-(2,6-Bis-methylamino-8-propylamino-pyrimido[5,4-d]-pyrimidin-4-ylamino)-indan-2-ol (80) and Corresponding Hydrochloride Salt (80a)

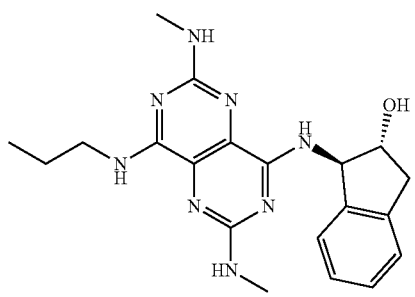

(a) (1R,2R)-1-(2,6-Bis-methylamino-8-propylamino-pyrimido[5,4-d]-pyrimidin-4-ylamino)-indan-2-ol (80)

2,6-Bis-methylamino-8-propylamino-pyrimido[5,4-d]pyrimidin-4-ol (70) (250 mg, 0.95 mmol) and (1R,2R)-1-amino-indan-2-ol were reacted using procedures described elsewhere herein. The crude product was purified by flash column chromatography using gradient elution from CH$_2$Cl$_2$/EtOH (99:1) to CH$_2$Cl$_2$/EtOH (9:1) to obtain (1R,2R)-1-(2,6-bis-methylamino-8-propylamino-pyrimido[5,4-d]-pyrimidin-4-ylamino)-indan-2-ol (80) (144 mg, 38% yield). 300 MHz $^1$H NMR (CDCl$_3$, ppm): 7.42-7.35 (1H, m) 7.35-7.26 (3H, m) 7.08 (1H, d, J=4.6 Hz) 6.57-6.45 (1H, m) 6.28 (1H, s) 5.33-5.24 (1H, m) 4.71-4.58 (2H, m) 4.58-4.47 (1H, m) 3.53-3.43 (2H, m) 3.37 (1H, dd, J=15.7, 7.9 Hz) 3.05-2.95 (1H, m) 2.98 (3H, d, J=5.1 Hz) 2.95 (3H, d, J=5.1) 1.78-1.61 (2H, m) 1.01 (3H, t, J=7.4 Hz). ESI-MS (m/z): 395 [M+H]$^+$.

(b) (1R,2R)-1-(2,6-Bis-methylamino-8-propylamino-pyrimido[5,4-d]-pyrimidin-4-ylamino)-indan-2-ol Hydrochloride (80a)

(1R,2R)-1-(2,6-bis-methylamino-8-propylamino-pyrimido[5,4-d]-pyrimidin-4-ylamino)-indan-2-ol (80) (130 mg, 0.33 mmol) and 2M HCl/diethyl ether were reacted in diethyl ether using the procedure described for compound 6a to produce (1R,2R)-1-(2,6-bis-methylamino-8-propylamino-pyrimido[5,4-d]-pyrimidin-4-ylamino)-indan-2-ol hydrochloride (80a) (120 mg, 84% yield). 300 MHz $^1$H NMR (CD$_3$OD, ppm): 7.32-7.24 (3H, m) 7.24-7.16 (1H, m) 5.65 (1H, d, J=5.5 Hz) 4.62-4.50 (1H, m) 3.61 (2H, t, J=7.0 Hz) 3.35 (1H, dd, J=16.0, 7.0 Hz) 2.99 (3H, s) 2.98 (3H, s) 2.90 (1H, dd, J=16.0, 6.4 Hz) 1.84-1.68 (2H, m) 1.02 (3H, t, J=7.4 Hz). ESI-MS (m/z): 395 [M+H]$^+$.

Example 46: rac-2-(2,6-Bis-methylamino-8-propylamino-pyrimido[5,4-d]-pyrimidin-4-ylamino)-indan-1-ol (81) and Corresponding Hydrochloride Salt (81a)

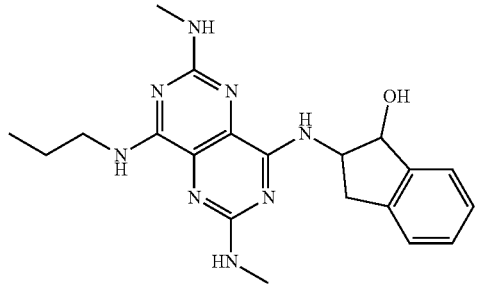

(a) 2-(2,6-Bis-methylamino-8-propylamino-pyrimido[5,4-d]-pyrimidin-4-ylamino)-indan-1-ol (81)

2,6-Bis-methylamino-8-propylamino-pyrimido[5,4-d]pyrimidin-4-ol (70) (220 mg, 0.84 mmol) and 2-amino-indan-1-ol were reacted using procedures described elsewhere herein. The crude product was purified by flash column chromatography using gradient elution from CH$_2$Cl$_2$/EtOH (99:1) to CH$_2$Cl$_2$/EtOH (9:1) to obtain (2-(2,6-bis-methylamino-8-propylamino-pyrimido[5,4-d]-pyrimidin-4-ylamino)-indan-1-ol (81) (200 mg, 61% yield). 300 MHz $^1$H NMR (CDCl$_3$, ppm): 7.48-7.39 (1H, m) 7.34-7.20 (3H, m) 7.00-6.90 (1H, m) 6.85 (1H, br s) 6.53 (1H, t, J=5.5 Hz) 5.19 (1H, d, J=6.7 Hz) 4.72-4.55 (2H, m) 4.49-4.35 (1H, m) 3.56-3.40 (3H, m) 3.06 (1H, dd, J=15.5, 10.2 Hz) 2.98 (3H, d, J=5.1 Hz) 2.97 (3H, d, J=5.1 Hz) 1.78-1.63 (2H, m) 1.01 (3H, t, J=7.4 Hz). ESI-MS (m/z): 395 [M+H]$^+$.

(b) 2-(2,6-Bis-methylamino-8-propylamino-pyrimido[5,4-d]-pyrimidin-4-ylamino)-indan-1-ol Hydrochloride (81a)

2-(2,6-bis-methylamino-8-propylamino-pyrimido[5,4-d]-pyrimidin-4-ylamino)-indan-1-ol (81) (200 mg, 0.51 mmol) and 2M HCl/diethyl ether were reacted in diethyl ether using the procedure described elsewhere herein to produce 2-(2,6-bis-methylamino-8-propylamino-pyrimido[5,4-d]-pyrimidin-4-ylamino)-indan-1-ol hydrochloride (81a) (200 mg, 91% yield). 300 MHz $^1$H NMR (CD$_3$OD, ppm): 7.44-7.37 (1H, m) 7.33-7.22 (3H, m) 5.26 (1H, d, J=5.8 Hz) 4.80-4.68 (1H, m) 3.60 (2H, t, J=7.2 Hz) 3.54 (1H, dd, J=15.8, 7.9 Hz) 3.02 (3H, s) 2.98 (3H, s) 2.92 (1H, dd, J=15.8, 7.2 Hz) 1.83-1.67 (2H, m) 1.02 (3H, t, J=7.4 Hz). ESI-MS (m/z): 395 [M+H]$^+$; MP: 181-183° C.

Example 47: (1R,2S)-2-(2,6-Bis-methylamino-8-propylamino-pyrimido[5,4-d]pyrimidin-4-ylamino)-cyclohexanol (82) and Corresponding Hydrochloride Salt (82a)

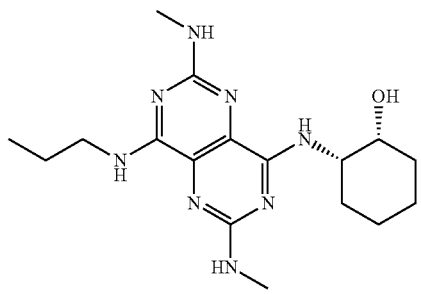

82

(a) (1R,2S)-2-(2,6-Bis-methylamino-8-propylamino-pyrimido[5,4-d]pyrimidin-4-ylamino)-cyclohexanol (82)

2,6-Bis-methylamino-8-propylamino-pyrimido[5,4-d]pyrimidin-4-ol (70) (250 mg, 0.95 mmol) and (1R,2S)-2-aminocyclohexanol hydrochloride were reacted using procedures described elsewhere herein to obtain (1R,2S)-2-(2,6-bis-methylamino-8-propylamino-pyrimido[5,4-d]pyrimidin-4-ylamino)-cyclohexanol (82) (190 mg, 56% yield). 300 MHz $^1$H NMR (CDCl$_3$, ppm): 6.76 (1H, d, J=6.7 Hz) 6.50 (1H, t, J=5.2 Hz) 4.76-4.63 (1H, m) 4.58 (1H, q, J=5.2 Hz) 4.25-4.16 (1H, m) 4.05-3.99 (1H, m) 3.50-3.41 (2H, m) 2.97 (3H, d, J=5.2 Hz) 2.94 (3H, d, J=5.2 Hz) 1.95-1.35 (10H, m) 0.99 (3H, J=7.4 Hz). ESI-MS (m/z): 361 [M+H]$^+$.

(b) (1R,2S)-2-(2,6-Bis-methylamino-8-propylamino-pyrimido[5,4-d]pyrimidin-4-ylamino)-cyclohexanol Hydrochloride (82a)

(1R,2S)-2-(2,6-Bis-methylamino-8-propylamino-pyrimido[5,4-d]pyrimidin-4-ylamino)-cyclohexanol (82) (190 mg, 0.53 mmol) and 2M HCl/diethyl ether were reacted in diethyl ether using the procedure described for compound 6a to produce (1R,2S)-2-(2,6-bis-methylamino-8-propylamino-pyrimido[5,4-d]pyrimidin-4-ylamino)-cyclohexanol hydrochloride (82a) (165 mg, 79% yield). 400 MHz $^1$H NMR (CD$_3$OD, ppm): 4.28-4.21 (1H, m) 4.13-4.08 (1H, m) 3.58 (2H, t, J=7.4 Hz) 3.01 (3H, s) 2.99 (3H, s) 1.93-1.58 (8H, m) 1.53-1.37 (2H, m) 1.02 (3H, t, J=7.4 Hz). ESI-MS (m/z): 361 [M+H]$^+$; MP: 249-251° C.

Example 48: (1S,2S)-2-(2,6-Bis-methylamino-8-propylamino-pyrimido[5,4-d]pyrimidin-4-ylamino)-(83) and Corresponding Cyclohexanol Hydrochloride Salt (83a)

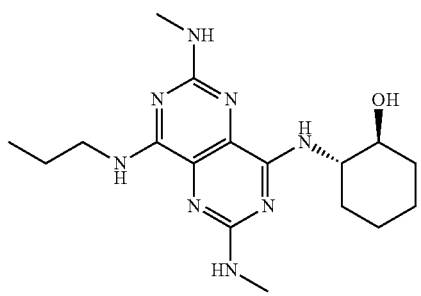

83

(a) (1S,2S)-2-(2,6-Bis-methylamino-8-propylamino-pyrimido[5,4-d]pyrimidin-4-ylamino)-cyclohexanol (83)

2,6-Bis-methylamino-8-propylamino-pyrimido[5,4-d]pyrimidin-4-ol (70) (300 mg, 1.14 mmol) and (1S,2S)-2-aminocyclohexanol were reacted using procedures described elsewhere herein. The crude product was purified by flash column chromatography using gradient elution from CH$_2$Cl$_2$ to CH$_2$Cl$_2$/EtOAc (4:1) as eluent to give (1S,2S)-2-(2,6-bis-methylamino-8-propylamino-pyrimido[5,4-d]pyrimidin-4-ylamino)-cyclohexanol (83) (269 mg, 65% yield). 300 MHz $^1$H NMR (CDCl$_3$, ppm): 6.6-6.3 (2H, br s) 5.42 (1H, s) 4.7-4.4 (2H, br s) 3.84-3.66 (1H, m) 3.58-3.38 (3H, m) 3.06-2.85 (6H, m) 2.18-2.02 (2H, m) 1.84-1.62 (2H, m) 1.69 (2H, sextet, J=7.4 Hz) 1.51-1.17 (4H, m) 1.00 (3H, t, J=7.4 Hz). ESI-MS (m/z): 361 [M+H]$^+$.

(b) (1S,2S)-2-(2,6-Bis-methylamino-8-propylamino-pyrimido[5,4-d]pyrimidin-4-ylamino)-cyclohexanol Hydrochloride (83a)

(1S,2S)-2-(2,6-bis-methylamino-8-propylamino-pyrimido[5,4-d]pyrimidin-4-ylamino)-cyclohexanol (83) (230 mg, 0.64 mmol) and 2M HCl/diethyl ether were reacted in diethyl ether using the procedure described for compound 6a to produce (1S,2S)-2-(2,6-bis-methylamino-8-propylamino-pyrimido[5,4-d]pyrimidin-4-ylamino)-cyclohexanol hydrochloride (83a) (215 mg, 85% yield). 300 MHz $^1$H NMR (CD$_3$OD, ppm): 4.15-4.00 (1H, m) 3.69-3.51 (1H, m) 3.59 (2H, t, J=7.4 Hz) 3.02 (3H, s) 2.99 (3H, s) 2.20-2.03 (2H, m) 1.86-1.68 (2H, m) 1.75 (2H, sextet, J=7.4 Hz) 1.49-1.29 (4H, m) 1.02 (3H, t, J=7.4 Hz). ESI-MS (m/z): 361 [M+H]$^+$; MP: 236-238° C.

Example 49: (1S,2R)-2-(2,6-Bis-methylamino-8-propylamino-pyrimido[5,4-d]pyrimidin-4-ylamino)-cyclohexanol (84) and Corresponding Hydrochloride Salt (84a)

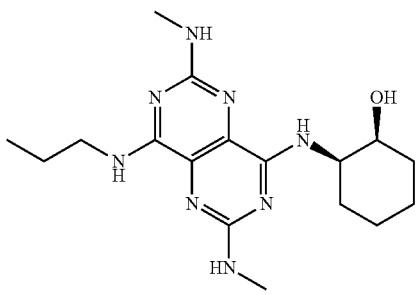

84

(a) (1S,2R)-2-(2,6-Bis-methylamino-8-propylamino-pyrimido[5,4-d]pyrimidin-4-ylamino)-cyclohexanol (84)

2,6-Bis-methylamino-8-propylamino-pyrimido[5,4-d]pyrimidin-4-ol (70) (250 mg, 0.95 mmol) and (1S,2R)-2-aminocyclohexanol hydrochloride were reacted procedures described elsewhere herein to obtain (1S,2R)-2-(2,6-bis-methylamino-8-propylamino-pyrimido[5,4-d]pyrimidin-4-ylamino)-cyclohexanol (84) (190 mg, 63% yield). 300 MHz $^1$H NMR (CDCl$_3$, ppm): 6.75 (1H, d, J=7.0 Hz) 6.50

(1H, t, J=5.2 Hz) 4.72-4.62 (1H, m) 4.58 (1H, q, J=5.2 Hz) 4.25 (1H, m) 4.06-3.98 (1H, m) 3.50-3.41 (2H, m) 2.96 (3H, d, J=5.2 Hz) 2.94 (3H, d, J=5.2) 1.94-1.58 (8H, m) 1.57-1.36 (2H, m) 0.99 (3H, t, J=7.4 Hz). ESI-MS (m/z): 361 [M+H]$^+$.

(b) (1S,2R)-2-(2,6-Bis-methylamino-8-propylamino-pyrimido[5,4-d]pyrimidin-4-ylamino)-cyclohexanol Hydrochloride (84a)

(1S,2R)-2-(2,6-bis-methylamino-8-propylamino-pyrimido[5,4-d]pyrimidin-4-ylamino)-cyclohexanol (84) (215 mg, 0.60 mmol) and 2M HCl/diethyl ether were reacted in diethyl ether using the procedure described for compound 6a to produce (1S,2R)-2-(2,6-bis-methylamino-8-propylamino-pyrimido[5,4-d]pyrimidin-4-ylamino)-cyclohexanol hydrochloride (84a) (180 mg, 76% yield). 300 MHz $^1$H NMR (CD$_3$OD, ppm): 4.30-4.19 (1H, m) 4.13-4.06 (1H, m) 3.58 (2H, t, J=7.4 Hz) 3.0 (3H, s) 2.99 (3H, s) 1.95-1.55 (8H, m) 1.54-1.34 (2H, m) 1.02 (3H, t, J=7.4 Hz). ESI-MS (m/z): 361 [M+H]$^+$; MP: 242-244° C.

Example 50: (1R,2R)-2-(2,6-Bis-methylamino-8-propylamino-pyrimido[5,4-d]pyrimidin-4-ylamino)-cyclohexanol (85) and Corresponding Hydrochloride Salt (85a)

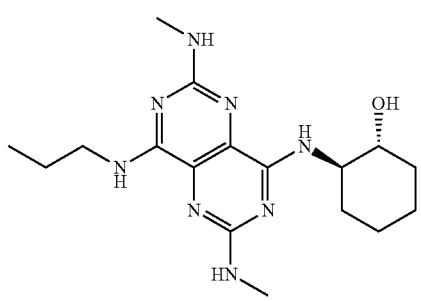

85

(a) (1R,2R)-2-(2,6-Bis-methylamino-8-propylamino-pyrimido[5,4-d]pyrimidin-4-ylamino)-cyclohexanol (85)

2,6-Bis-methylamino-8-propylamino-pyrimido[5,4-d]pyrimidin-4-ol (70) (300 mg, 1.14 mmol) and (1R,2R)-2-aminocyclohexanol were reacted using procedures described elsewhere herein. The crude product was purified by flash column chromatography using gradient elution from CH$_2$Cl$_2$ to CH$_2$Cl$_2$/EtOAc (4:1) as eluent to give (1R,2R)-2-(2,6-bis-methylamino-8-propylamino-pyrimido[5,4-d]pyrimidin-4-ylamino)-cyclohexanol (85) (205 mg, 55% yield). 300 MHz $^1$H NMR (CDCl$_3$, ppm): 6.59-6.40 (2H, m) 4.70-4.53 (2H, m) 3.82-3.71 (1H, m) 3.57-3.41 (3H, m) 2.98-2.91 (6H, m) 2.16-2.05 (2H, m) 1.82-1.72 (2H, m) 1.69 (2H, sextet, J=7.4 Hz) 1.51-1.24 (4H, m) 1.00 (3H, t, J=7.4 Hz). ESI-MS (m/z): 361 [M+H]$^+$.

(b) (1R,2R)-2-(2,6-Bis-methylamino-8-propylamino-pyrimido[5,4-d]pyrimidin-4-ylamino)-cyclohexanol Hydrochloride (85a)

(1R,2R)-2-(2,6-bis-methylamino-8-propylamino-pyrimido[5,4-d]pyrimidin-4-yl amino)-cyclohexanol (85) (195 mg, 0.54 mmol) and 2M HCl/diethyl ether were reacted in diethyl ether using the procedure described for compound 6a to produce (1R,2R)-2-(2,6-bis-methylamino-8-propylamino-pyrimido[5,4-d]pyrimidin-4-ylamino)-cyclohexanol hydrochloride (85a) (200 mg, 93% yield). 400 MHz $^1$H NMR (CD$_3$OD, ppm): 4.12-4.01 (1H, m) 3.67-3.54 (1H, m) 3.58 (2H, t, J=7.4 Hz) 3.02 (3H, s) 2.99 (3H, s) 2.19-2.06 (2H, m) 1.84-1.70 (2H, m) 1.74 (2H, sextet, J=7.4 Hz) 1.46-1.32 (4H, m) 1.01 (3H, t, J=7.4 Hz). ESI-MS (m/z): 361 [M+H]$^+$; MP: 212-213° C.

Example 51: (1S,2S)-2-(2,6-Bis-methylamino-8-propylamino-pyrimido[5,4-d]pyrimidin-4-ylamino)-cyclopentanol (86) and Corresponding Hydrochloride Salt (86a)

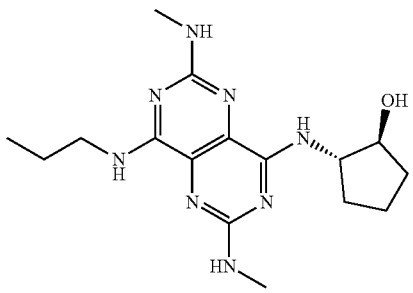

86

(a) (1S,2S)-2-(2,6-Bis-methylamino-8-propylamino-pyrimido[5,4-d]pyrimidin-4-ylamino)-cyclopentanol (86)

2,6-Bis-methylamino-8-propylamino-pyrimido[5,4-d]pyrimidin-4-ol (70) (300 mg, 1.14 mmol) and (1S,2S)-2-aminocyclopentanol hydrochloride were reacted using procedures previously. The crude product was purified by flash column chromatography using gradient elution from CH$_2$Cl$_2$ to CH$_2$Cl$_2$/EtOAc (4:1) as eluent to obtain (1S,2S)-2-(2,6-bis-methylamino-8-propylamino-pyrimido[5,4-d]pyrimidin-4-ylamino)-cyclopentanol (86) (275 mg, 73% yield). 300 MHz $^1$H NMR (CDCl$_3$, ppm): 6.68-6.59 (1H, m) 6.57-6.44 (1H, m) 6.2-6.0 (1H, br s) 4.75-4.47 (2H, m) 4.13-3.91 (2H, m) 3.53-3.40 (2H, m) 2.97 (3H, d, J=5.2 Hz) 2.95 (3H, d, J=5.2 Hz) 2.36-2.22 (1H, m) 2.20-2.04 (1H, m) 1.94-1.51 (4H, m) 1.69 (2H, sextet, J=7.4 Hz) 1.00 (3H, t, J=7.4 Hz). ESI-MS (m/z): 347 [M+H]$^+$.

(b) (1S,2S)-2-(2,6-Bis-methylamino-8-propylamino-pyrimido[5,4-d]pyrimidin-4-ylamino)-cyclopentanol Hydrochloride (86a)

(1S,2S)-2-(2,6-bis-methylamino-8-propylamino-pyrimido[5,4-d]pyrimidin-4-ylamino)-cyclopentanol (86) (235 mg, 0.68 mmol) and 2M HCl/diethyl ether were reacted in diethyl ether/MeOH (15/1) using the procedure described for compound 6a to produce (1S,2S)-2-(2,6-bis-methylamino-8-propylamino-pyrimido[5,4-d]pyrimidin-4-ylamino)-cyclopentanol hydrochloride (86a) (230 mg, 88% yield). 300 MHz $^1$H NMR (CD$_3$OD, ppm): 4.38-4.26 (1H, m) 4.24-4.13 (1H, m) 3.60 (2H, t, J=7.4 Hz) 3.03 (3H, s) 3.01 (3H, s) 2.37-2.22 (1H, m) 2.11-1.97 (1H, m) 1.92-1.58 (4H, m) 1.75 (2H, sextet, J=7.4 Hz) 1.02 (3H, t, J=7.4 Hz). ESI-MS (m/z): 347 [M+H]$^+$; MP: 257-259° C.

Example 52: (1R,2R)-2-(2,6-Bis-methylamino-8-propylamino-pyrimido[5,4-d]pyrimidin-4-ylamino)-cyclopentanol (87) and Corresponding Hydrochloride Salt (87a)

Example 53: 2-[6-(Cyclopropylmethyl-amino)-4,8-bis-methylamino-pyrimido[5,4-d]pyrimidin-2-ylamino]-ethanol (90) and Corresponding Hydrochloride Salt (90a)

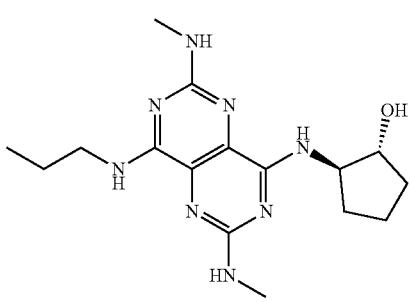

87

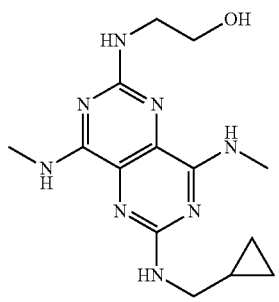

90

(a) (1R,2R)-2-(2,6-Bis-methylamino-8-propylamino-pyrimido[5,4-d]pyrimidin-4-ylamino)-cyclopentanol (87)

2,6-Bis-methylamino-8-propylamino-pyrimido[5,4-d]pyrimidin-4-ol (70) (300 mg, 1.14 mmol) and (1R,2R)-2-aminocyclopentanol hydrochloride were reacted using procedures described elsewhere herein. The crude product was purified by flash column chromatography using gradient elution from $CH_2Cl_2$ to $CH_2Cl_2$/EtOAc (4:1) as eluent to obtain (1R,2R)-2-(2,6-bis-methylamino-8-propylamino-pyrimido[5,4-d]pyrimidin-4-ylamino)-cyclopentanol (87) (210 mg, 55% yield). 300 MHz $^1$H NMR (CDCl$_3$, ppm): 6.68-6.57 (1H, m) 6.55-6.43 (1H, m) 6.2-6.1 (1H, br s) 4.67-4.49 (2H, m) 4.12-3.91 (2H, m) 3.51-3.42 (2H, m) 2.96 (3H, d, J=5.1 Hz) 2.95 (3H, d, J=5.0 Hz) 2.36-2.22 (1H, m) 2.20-2.04 (1H, m) 1.94-1.51 (4H, m) 1.69 (2H, sextet, J=7.4 Hz) 1.00 (3H, t, J=7.4 Hz). ESI-MS (m/z): 347 [M+H]$^+$.

(b) (1R,2R)-2-(2,6-Bis-methylamino-8-propylamino-pyrimido[5,4-d]pyrimidin-4-ylamino)-cyclopentanol Hydrochloride (87a)

(1R,2R)-2-(2,6-bis-methylamino-8-propylamino-pyrimido[5,4-d]pyrimidin-4-ylamino)-cyclopentanol (87) (235 mg, 0.68 mmol) and 2M HCl/diethyl ether were reacted in diethyl ether/MeOH (15/1) using procedure described for compound 6a to produce (1R,2R)-2-(2,6-bis-methylamino-8-propylamino-pyrimido[5,4-d]pyrimidin-4-ylamino)-cyclopentanol hydrochloride (87a) (160 mg, 80% yield). 300 MHz $^1$H NMR (CD$_3$OD, ppm): 4.38-4.26 (1H, m) 4.24-4.13 (1H, m) 3.60 (2H, t, J=7.4 Hz) 3.03 (3H, s) 3.00 (3H, s) 2.38-2.22 (1H, m) 2.11-1.97 (1H, m) 1.92-1.56 (4H, m) 1.75 (2H, sextet, J=7.4 Hz) 1.02 (3H, t, J=7.4 Hz). ESI-MS (m/z): 347 [M+H]$^+$; MP: 255-257° C.

(a) 2,6-Dichloro-N,N'-dimethyl-pyrimido[5,4-d]pyrimidine-4,8-diamine (88)

2M Methylamine/THF (42 mL, 84.00 mmol) was added dropwise to a solution of 2,4,6,8-tetrachloro-pyrimido[5,4-d]pyrimidine (1) (5.00 g, 18.52 mmol) in THF (300 mL) at 0° C. The reaction mixture was stirred at room temperature for 2 h and then the volatiles were removed. The residue was suspended in water (50 mL) and the precipitate was filtered, washed with water (2×30 mL) and dried over solid anhydrous P$_2$O$_5$ to give 2,6-dichloro-N,N'-dimethyl-pyrimido[5,4-d]pyrimidine-4,8-diamine (88) (4.61 g, 96% yield). 400 MHz $^1$H NMR (CDCl$_3$, ppm): 6.90 (2H, br s) 3.16 (6H, d, J=5.0 Hz). ESI-MS (m/z): 259, 261, 263 [M+H]$^+$.

(b) 2-(6-Chloro-4,8-bis-methylamino-pyrimido[5,4-d]pyrimidin-2-ylamino)-ethanol (89)

A mixture of 2,6-dichloro-N,N'-dimethyl-pyrimido[5,4-d]pyrimidine-4,8-diamine (88) (600 mg, 2.32 mmol) and 2-amino-ethanol (700 µL, 11.60 mmol) in 1,4-dioxane (5 mL) was heated at 100° C. for 18h in a closed vial. After cooling, a saturated NaHCO$_3$ solution (20 mL) was added and the resulting suspension was extracted with EtOAc (3×30 mL). The combined organic extracts were dried over solid anhydrous Na$_2$SO$_4$. After filtration, the volatiles were evaporated, and the residue was crystallized from EtOAc/petroleum ether (1/1) to give 2-(6-chloro-4,8-bis-methylamino-pyrimido[5,4-d]pyrimidin-2-ylamino)-ethanol (89) (500 mg, 76% yield). 300 MHz $^1$H NMR (CDCl$_3$, ppm): 6.68-6.54 (2H, m) 5.36 (1H, t, J=5.7 Hz) 3.87-3.82 (2H, m) 3.62 (2H, dt, J=5.7, 4.6 Hz) 3.46 (1H, br s) 3.13 (3H, d, J=5.2 Hz) 3.04 (3H, d, J=5.2 Hz). ESI-MS (m/z): 284, 286 [M+H]$^+$.

(c) 2-[6-(Cyclopropylmethyl-amino)-4,8-bis-methylamino-pyrimido[5,4-d]pyrimidin-2-ylamino]-ethanol (90)

A mixture of 2-(6-chloro-4,8-bis-methylamino-pyrimido[5,4-d]pyrimidin-2-ylamino)-ethanol (89) (250 mg, 0.81 mmol) and cyclopropylmethanamine (176 µL, 3.53 mmol) in n-butanol (4.0 mL) was heated at 125° C. for 72 h in a closed vial. The reaction mixture was cooled, and a saturated NaHCO$_3$ solution (20 mL) was added. The resulting suspension was extracted with EtOAc (3×30 mL). The combined organic extracts were washed with a brine solution (50 mL) and dried over solid anhydrous $Na_2SO_4$. After filtration, the solvent was removed and the residue was purified by flash column chromatography using gradient elution from PE/i-PrOH (2/1) to PE/i-PrOH (1/1) to give 2-[6-(cyclopropylmethyl-amino)-4,8-bis-methylamino-pyrimido[5,4-d]pyrimidin-2-ylamino]-ethanol (90) (159 mg, 57% yield). 400 MHz $^1$H NMR (CDCl3, ppm): 6.62-6.54 (1H, m) 6.27-6.19 (1H, m) 5.10 (1H, t, J=6.0 Hz) 4.84 (1H, t, J=5.0 Hz) 4.56 (1H, s) 3.85-3.81 (2H, m) 3.60-3.55 (2H, m) 3.24 (2H, dd, J=7.0, 5.2 Hz) 3.06 (3H, d, J=5.2 Hz) 3.05 (3H, d, J=5.2 Hz) 1.14-1.03 (1H, m) 0.55-0.49 (2H, m) 0.26-0.22 (2H, m). ESI-MS (m/z): 319 [M+H]$^+$.

(d) 2-[6-(Cyclopropylmethyl-amino)-4,8-bis-methyl-amino-pyrimido[5,4-d]pyrimidin-2-ylamino]-ethanol Hydrochloride (90a)

2-[6-(Cyclopropylmethyl-amino)-4,8-bis-methylamino-pyrimido[5,4-d]pyrimidin-2-ylamino]-ethanol (90) (159 mg, 0.50 mmol) was treated with 2M HCl/diethyl ether in dichloromethane using procedures described elsewhere herein to produce 2-[6-(cyclopropylmethyl-amino)-4,8-bis-methylamino-pyrimido[5,4-d]pyrimidin-2-ylamino]-ethanol hydrochloride (90a) (177 mg, 87% yield). 300 MHz $^1$H NMR (D$_2$O, ppm): 3.78 (2H, t, J=5.5 Hz) 3.55 (2H, t, J=5.5 Hz) 3.26 (2H, d, J=7.0 Hz) 3.05 (3H, s) 3.01 (3H, s) 1.19-1.08 (1H, m) 0.62-0.53 (2H, m) 0.34-0.26 (2H, m). ESI-MS (m/z): 319 [M+H]$^+$; MP: 214-216° C.

Example 54: 2-(4,8-Bis-methylamino-6-propylamino-pyrimido[5,4-d]pyrimidin-2-ylamino)-ethanol (91) and Corresponding Hydrochloride (91a)

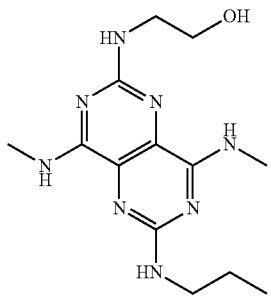

(a) 2-(4,8-Bis-methylamino-6-propylamino-pyrimido[5,4-d]pyrimidin-2-ylamino)-ethanol (91)

2-(6-Chloro-4,8-bis-methylamino-pyrimido[5,4-d]pyrimidin-2-ylamino)-ethanol (89) (250 mg, 0.81 mmol) and propylamine were reacted in n-butanol using procedure described for compound (90) to obtain 2-(4,8-bis-methylamino-6-propylamino-pyrimido[5,4-d]pyrimidin-2-ylamino)-ethanol (91) (129 mg, 48% yield). 400 MHz $^1$H NMR (CDCl$_3$, ppm): 6.64-6.54 (1H, m) 6.26-6.18 (1H, m) 5.09 (1H, t, J=6.0 Hz) 4.75-4.65 (1H, m) 4.64-4.48 (1H, br s) 3.85-3.81 (2H, m) 3.60-3.55 (2H, m) 3.38-3.32 (2H, m) 3.06 (3H, d, J=6.5 Hz) 3.05 (3H, d, J=6.5 Hz) 1.63 (2H, sextet, J=7.4 Hz) 0.99 (3H, t, J=7.4 Hz). ESI-MS (m/z): 307 [M+1-1]$^+$.

(b) 2-(4,8-Bis-methylamino-6-propylamino-pyrimido[5,4-d]pyrimidin-2-ylamino)-ethanol Hydrochloride (91a)

2-(4,8-Bis-methylamino-6-propylamino-pyrimido[5,4-d]pyrimidin-2-ylamino)-ethanol (91) (125 mg, 0.41 mmol) was treated with 2M HCl/diethyl ether in dichloromethane using procedures described elsewhere herein to produce 2-(4,8-bis-methylamino-6-propylamino-pyrimido[5,4-d]pyrimidin-2-ylamino)-ethanol hydrochloride (91a) (128 mg, 92% yield). 300 MHz $^1$H NMR (D$_2$O, ppm): 3.78 (2H, t, J=5.5 Hz) 3.55 (2H, t, J=5.5 Hz) 3.35 (2H, t, J=7.0 Hz) 3.05 (3H, s) 3.01 (3H, s) 1.64 (2H, sextet, J=7.3 Hz) 0.96 (3H, t, J=7.3 Hz). ESI-MS (m/z): 307 [M+H]$^+$; MP: 224-226° C.

Example 55: 2-(6-Dimethylamino-4,8-bis-methylamino-pyrimido[5,4-d]-pyrimidin-2-ylamino)-ethanol (92) and Corresponding Hydrochloride Salt (92a)

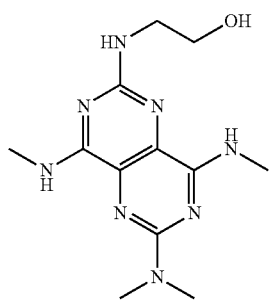

(a) 2-(6-Dimethylamino-4,8-bis-methylamino-pyrimido[5,4-d]-pyrimidin-2-ylamino)-ethanol (92)

A mixture of 2-(6-chloro-4,8-bis-methylamino-pyrimido[5,4-d]pyrimidin-2-ylamino)-ethanol (89) (300 mg, 1.06 mmol) and dimethylamine (40% water solution) (1.00 mL) in n-butanol (3.0 mL) was heated at 110° C. for 18h in a closed vial. The reaction mixture was cooled, the precipitate was filtered, washed with water (2×10 mL) and dried over solid anhydrous $P_2O_5$ to give 2-(6-dimethylamino-4,8-bis-methylamino-pyrimido[5,4-d]-pyrimidin-2-ylamino)-ethanol (92) (200 mg, 65% yield). 300 MHz $^1$H NMR (CDCl$_3$-d6, ppm): 6.68-6.51 (1H, m) 6.22-6.04 (1H, m) 5.06 (1H, t, J=6.1 Hz) 4.75 (1H, s) 3.88-3.78 (2H, m) 3.62-3.51 (2H, m) 3.16 (6H, s) 3.08 (3H, d, J=5.1 Hz) 3.07 (3H, d, J=5.1 Hz). ESI-MS (m/z): 293 [M+1-1]$^+$.

(b) 2-(6-Dimethylamino-4,8-bis-methylamino-pyrimido[5,4-d]-pyrimidin-2-ylamino)-ethanol Hydrochloride (92a)

2-(6-Dimethylamino-4,8-bis-methylamino-pyrimido[5,4-d]-pyrimidin-2-yl amino)-ethanol (92) (140 mg, 0.48 mmol) was treated with 2M HCl/diethyl ether in diethyl ether/MeOH (4/1) using procedure described for compound 6a to produce 2-(6-dimethylamino-4,8-bis-methylamino-pyrimido[5,4-d]-pyrimidin-2-ylamino)-ethanol hydrochloride (92a) (145 mg, 92% yield). 300 MHz $^1$H NMR (CD$_3$OD, ppm): 3.81-3.70 (2H, m) 3.68-3.55 (2H, m) 3.19 (6H, s) 3.15 (3H, s) 3.07 (3H, s). ESI-MS (m/z): 293 [M+H]$^+$; MP: 264-266° C.

Example 56: 1-(4,8-Bis-methylamino-6-propylamino-pyrimido[5,4-d]pyrimidin-2-ylamino)-2-methyl-propan-2-ol (94) and Corresponding Hydrochloride Salt (94a)

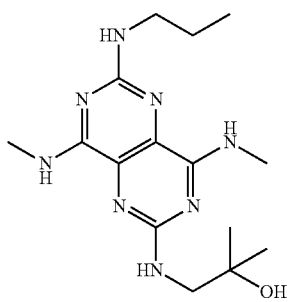

94

(a) 6-Chloro-N⁴,N⁸-dimethyl-N²-propylpyrimido[5,4-d]pyrimidine-2,4,8-triamine (93)

A mixture of 2,6-dichloro-N,N'-dimethyl-pyrimido[5,4-d]pyrimidine-4,8-diamine (88) (4.00 g, 15.44 mmol) and propylamine (5.1 mL, 61.75 mmol) in n-butanol (40 mL) was heated at 90° C. for 20 h. After cooling, a saturated NaHCO₃ solution (200 mL) was added and the resulting suspension was extracted with EtOAc (3×100 mL). The combined organic extracts were washed with water (200 mL), then with a brine solution (200 mL) and dried over solid anhydrous Na₂SO₄. After filtration, the solvent was removed to give 6-chloro-N⁴,N⁸-dimethyl-N²-propylpyrimido[5,4-d]pyrimidine-2,4,8-triamine (93) (4.32 g, 99% yield). 400 MHz $^1$H NMR (CDCl₃, ppm): 6.72 (1H, br s) 6.49 (1H, br s) 4.97 (1H, t, J=5.4 Hz) 3.42-3.35 (2H, m) 3.14 (3H, d, J=5.2 Hz) 3.04 (3H, d, J=5.1 Hz) 1.69-1.59 (2H, m) 0.99 (3H, t, J=7.4 Hz). ESI-MS (m/z): 282, 284 [M+H]⁺.

(b) 1-(4,8-Bis-methylamino-6-propylamino-pyrimido[5,4-d]pyrimidin-2-ylamino)-2-methyl-propan-2-ol (94)

A mixture of 6-chloro-N⁴,N⁸-dimethyl-N²-propylpyrimido[5,4-d]pyrimidine-2,4,8-triamine (93) (253 mg, 0.90 mmol) and 1-amino-2-methyl-propan-2-ol (340 µL, 3.60 mmol) in n-butanol (4.0 mL) was heated at 125° C. for 48h in a closed vial. A second portion of 1-amino-2-methyl-propan-2-ol (340 µL, 3.60 mmol) was added and the mixture was heated for 100 h. The reaction mixture was cooled and a saturated NaHCO₃ solution (20 mL) was added. The resulting suspension was extracted with EtOAc (3×30 mL). The combined organic extracts were washed with brine (50 mL) and dried over solid anhydrous Na₂SO₄. After filtration, the solvent was removed and the residue was purified by flash column chromatography using gradient elution from PE/EtOAc (1/1) to PE/EtOAc (1/99) to give 1-(4,8-bis-methylamino-6-propylamino-pyrimido[5,4-d]pyrimidin-2-ylamino)-2-methyl-propan-2-ol (94) (263 mg, 87% yield). 300 MHz $^1$H NMR (CDCl₃, ppm): 6.65-6.53 (1H, m) 6.19-6.11 (1H, m) 5.33 (1H, br s) 5.09 (1H, t, J=5.1 Hz) 4.69 (1H, t, J=5.1 Hz) 3.43-3.31 (2H, m) 3.39 (2H, d, J=6.4 Hz) 3.06 (3H, d, J=5.1 Hz) 3.04 (3H, d, J=5.1 Hz) 1.62 (2H, sextet, J=7.4 Hz) 1.27-1.24 (6H, m) 0.98 (3H, t, J=7.4 Hz). ESI-MS (m/z): 335 [M+H]⁺.

(c) 1-(4,8-Bis-methylamino-6-propylamino-pyrimido[5,4-d]pyrimidin-2-ylamino)-2-methyl-propan-2-ol Hydrochloride (94a)

1-(4,8-Bis-methylamino-6-propylamino-pyrimido[5,4-d]pyrimidin-2-ylamino)-2-methyl-propan-2-ol (94) (207 mg, 0.62 mmol) was treated with 2M HCl/diethyl ether in dichloromethane using procedures previously to produce 1-(4,8-bis-methylamino-6-propyl amino-pyrimido[5,4-d]pyrimidin-2-ylamino)-2-methyl-propan-2-ol hydrochloride (94a) (200 mg, 87% yield). 400 MHz $^1$H NMR (CD₃OD, ppm): 3.52 (2H, s) 3.46 (2H, t, J=7.1 Hz) 3.15 (3H, s) 3.13 (3H, s) 1.69 (2H, sextet, J=7.4 Hz) 1.27 (6H, s) 1.01 (3H, t, J=7.4 Hz). ESI-MS (m/z): 335 [M+H]⁺; MP: 191-193° C.

Example 57: 1-(4,8-Bis-methylamino-6-propylamino-pyrimido[5,4-d]-pyrimidin-2-ylamino)-propan-2-ol (95) and Corresponding Hydrochloride Salt (95a)

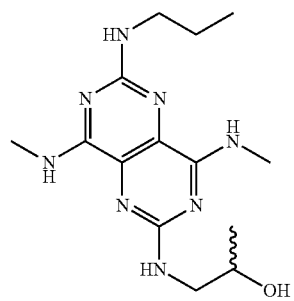

95

(a) 1-(4,8-Bis-methylamino-6-propylamino-pyrimido[5,4-d]-pyrimidin-2-ylamino)-propan-2-ol (95)

6-Chloro-N⁴,N⁸-dimethyl-N²-propylpyrimido[5,4-d]pyrimidine-2,4,8-triamine (93) (200 mg, 0.71 mmol) and 1-amino-propan-2-ol were reacted in n-butanol using procedure described for compound (94) to obtain 1-(4,8-bis-methylamino-6-propylamino-pyrimido[5,4-d]-pyrimidin-2-ylamino)-propan-2-ol (95) (110 mg, 48% yield). 400 MHz $^1$H NMR (CDCl₃, ppm): 6.57 (1H, s) 6.18 (1H, s) 5.10-4.90 (2H, m) 4.75-4.61 (1H, m) 4.08-3.99 (1H, m) 3.50 (1H, ddd, J=14.4, 6.3, 2.3 Hz) 3.41-3.30 (3H, m) 3.07 (3H, d, J=5.2 Hz) 3.05 (3H, d, J=5.2 Hz) 1.68-1.56 (2H, m) 1.22 (3H, d, J=6.3 Hz) 0.99 (3H, t, J=7.4 Hz). ESI-MS (m/z): 321 [M+H]⁺.

(b) 1-(4,8-Bis-methylamino-6-propylamino-pyrimido[5,4-d]-pyrimidin-2-ylamino)-propan-2-ol Hydrochloride (95a)

1-(4,8-Bis-methylamino-6-propylamino-pyrimido[5,4-d]-pyrimidin-2-ylamino)-propan-2-ol (95) (105 mg, 0.33 mmol) was treated with 2M HCl/diethyl ether in dichloromethane using procedures described elsewhere herein to produce 1-(4,8-bis-methylamino-6-propylamino-pyrimido[5,4-d]-pyrimidin-2-ylamino)-propan-2-ol hydrochloride (95a) (110 mg, 94% yield). 400 MHz $^1$H NMR (CD₃OD, ppm): 4.03-3.93 (1H, m) 3.53 (1H, dd, J=13.7, 4.6 Hz) 3.48-3.37 (3H, m) 3.13 (3H, s) 3.11 (3H, s) 1.74-1.63 (2H, m) 1.23 (3H, d, J=6.3 Hz) 1.01 (3H, t, J=7.4 Hz). ESI-MS (m/z): 321 [M+H]⁺; MP: 217-219° C.

Example 58: 1-[(4,8-Bis-methylamino-6-propylamino-pyrimido[5,4-d]pyrimidin-2-yl)-methyl-amino]-2-methyl-propan-2-ol (96) and Corresponding Hydrochloride Salt (96a)

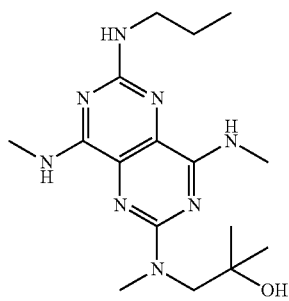

(a) 1-[(4,8-Bis-methylamino-6-propylamino-pyrimido[5,4-d]pyrimidin-2-yl)-methyl-amino]-2-methyl-propan-2-ol (96)

A mixture of 6-chloro-N⁴,N⁸-dimethyl-N²-propylpyrimido[5,4-d]pyrimidine-2,4,8-triamine (93) (285 mg, 1.01 mmol) and 2-methyl-1-methylamino-propan-2-ol (238 µL, 2.02 mmol) in n-butanol (4.0 mL) was heated at 125° C. for 120 h in a closed vial. The reaction mixture was cooled and a saturated NaHCO₃ solution (20 mL) was added. The resulting suspension was extracted with EtOAc (3×20 mL). The combined organic extracts were washed with a brine solution (50 mL) and then dried over solid anhydrous Na₂SO₄. After filtration, the solvent was removed and the residue was purified by flash column chromatography using gradient elution from PE/EtOAc (9/1) to PE/EtOAc (1/99) to give 1-[(4,8-bis-methylamino-6-propylamino-pyrimido[5,4-d]pyrimidin-2-yl)-methyl-amino]-2-methyl-propan-2-ol (96) (250 mg, 71% yield). 400 MHz ¹H NMR (CDCl₃, ppm): 6.8-6.5 (1H, br s) 6.55 (1H, s) 6.27 (1H, s) 4.70-4.63 (1H, m) 3.56 (2H, s) 3.38-3.31 (2H, m) 3.22 (3H, s) 3.07 (3H, d, J=5.2 Hz) 3.07 (3H, d, J=5.2 Hz) 1.63 (2H, sextet, J=7.4 Hz) 1.27 (6H, s) 0.99 (3H, t, J=7.4 Hz). ESI-MS (m/z): 349 [M+H]⁺.

(b) 1-[(4,8-Bis-methylamino-6-propylamino-pyrimido[5,4-d]pyrimidin-2-yl)-methyl-amino]-2-methyl-propan-2-ol Hydrochloride (96a)

1-[(4,8-Bis-methylamino-6-propylamino-pyrimido[5,4-d]pyrimidin-2-yl)-methyl-amino]-2-methyl-propan-2-ol (96) (182 mg, 0.52 mmol) was treated with 2M HCl/diethyl ether in diethyl ether using procedure described for compound 6a to produce 1-[(4,8-bis-methylamino-6-propylamino-pyrimido[5,4-d]pyrimidin-2-yl)-methyl-amino]-2-methyl-propan-2-ol hydrochloride (96a) (191 mg, 95% yield). 400 MHz ¹H NMR: (CD₃OD, ppm) 3.74 (2H, s) 3.46 (2H, t, J=7.4 Hz) 3.30 (3H, s) 3.15 (3H, s) 3.09 (3H, s) 1.70 (2H, sextet, J=7.4 Hz) 1.25 (6H, s) 1.01 (3H, t, J=7.4 Hz). ESI-MS (m/z): 349 [M+H]⁺; MP: 213-215° C.

Example 59: 1-[(4,8-Bis-methylamino-6-propylamino-pyrimido[5,4-d]pyrimidin-2-yl)-methyl-amino]-propan-2-ol (97) and Corresponding Hydrochloride Salt (97a)

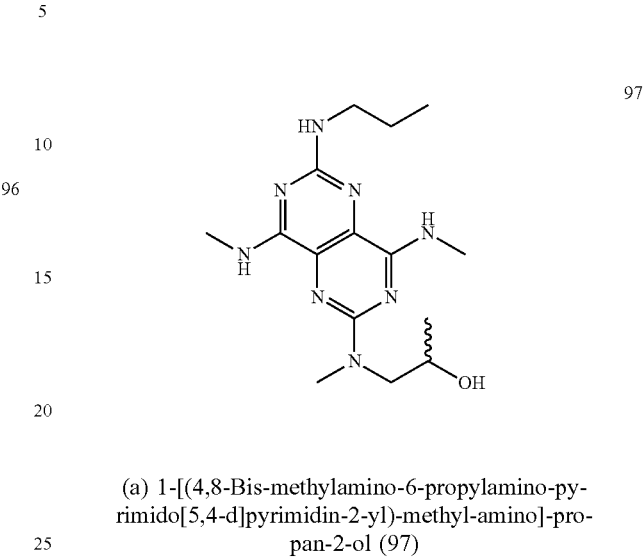

(a) 1-[(4,8-Bis-methylamino-6-propylamino-pyrimido[5,4-d]pyrimidin-2-yl)-methyl-amino]-propan-2-ol (97)

6-Chloro-N⁴,N⁸-dimethyl-N²-propylpyrimido[5,4-d]pyrimidine-2,4,8-triamine (93) (280 mg, 0.99 mmol) and 1-methylamino-propan-2-ol were reacted in n-butanol using procedure described for compound (94) to obtain 1-[(4,8-bis-methylamino-6-propylamino-pyrimido[5,4-d]pyrimidin-2-yl)-methyl-amino]-propan-2-ol (97) (215 mg, 64% yield). 400 MHz ¹H NMR (CDCl₃, ppm): 6.54 (1H, br s) 6.29 (1H, br s) 5.65 (1H, br s) 4.66 (1H, s) 4.18-4.07 (1H, m) 3.74 (1H, dd, J=14.7, 7.4 Hz) 3.47 (1H, d, J=14.7 Hz) 3.41-3.30 (2H, m) 3.21 (3H, s) 3.11-3.01 (6H, m) 1.63 (2H, sextet, J=7.4 Hz) 1.23 (3H, d, J=6.1 Hz) 0.99 (3H, t, J=7.4 Hz). ESI-MS (m/z): 349 [M+H]⁺. ESI-MS (m/z): 335 [M+H]⁺.

(b) 1-[(4,8-Bis-methylamino-6-propylamino-pyrimido[5,4-d]pyrimidin-2-yl)-methyl-amino]-propan-2-ol Hydrochloride (97a)

1-[(4,8-Bis-methylamino-6-propylamino-pyrimido[5,4-d]pyrimidin-2-yl)-methyl-amino]-propan-2-ol (97) (175 mg, 0.52 mmol) was treated with 2M HCl/diethyl ether in diethyl ether using procedure described for compound 6a to produce 1-[(4,8-bis-methylamino-6-propylamino-pyrimido[5,4-d]pyrimidin-2-yl)-methyl-amino]-propan-2-ol hydrochloride (97a) (159 mg, 82% yield). 400 MHz ¹H NMR (CD₃OD, ppm): 4.17-4.07 (1H, m) 3.64 (2H, s) 3.46 (2H, t, J=7.4 Hz) 3.25 (3H, s) 3.16 (3H, s) 3.07 (3H, s) 1.70 (2H, sextet, J=7.4 Hz) 1.20 (3H, d, J=6.1 Hz) 1.01 (3H, t, J=7.4 Hz). ESI-MS (m/z): 335 [M+H]⁺; MP: 236-237° C. Anal. Calcd for C₁₅H₂₇ClN₈O: C, 48.58; H, 7.34; N, 30.21. Found: C, 48.47; H, 7.33; N, 30.22.

Example 60: 1-[6-((R)-sec-Butylamino)-4,8-bis-methylamino-pyrimido[5,4-d]-pyrimidin-2-ylamino]-2-methyl-propan-2-ol (99) and Corresponding Hydrochloride Salt (99a)

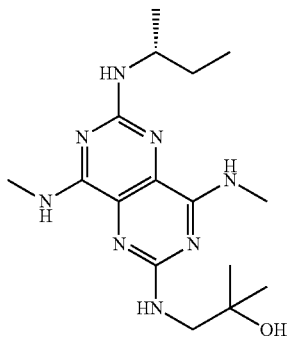

99

(a) (R)—N²-sec-butyl-6-chloro-N⁴,N⁸-dimethylpyrimido[5,4-d]pyrimidine-2,4,8-triamine (98)

A mixture of 2,6-dichloro-N,N'-dimethyl-pyrimido[5,4-d]pyrimidine-4,8-diamine (88) (350 mg, 1.35 mmol), (R)-(−)-sec-butylamine (216 μL, 2.16 mmol) and N-diisopropyl ethylamine (234 μL, 1.35 mmol) in n-butanol (5 mL) was heated at 80° C. for 72h. After cooling, a saturated NaHCO₃ solution (20 mL) was added and the resulting suspension was extracted with EtOAc (3×20 mL). The combined organic extracts were washed with water (30 mL), then with a brine solution (30 mL) and dried over solid anhydrous MgSO₄. After filtration, the solvent was removed and the residue was purified by flash column chromatography using gradient elution from PE/EtOAc (9/1) to PE/EtOAc (2/1) to give (R)—N²-sec-butyl-6-chloro-N⁴,N⁸-dimethyl pyrimido [5,4-d]pyrimidine-2,4,8-triamine (98) (330 mg, 83% yield). 300 MHz ¹H NMR (CDCl₃, ppm) 6.77-6.63 (1H, m) 6.54-6.41 (1H, m) 4.79 (1H, d, J=8.2 Hz) 4.09-3.94 (1H, m) 3.14 (3H, d, J=5.1 Hz) 3.04 (3H, d, J=5.1 Hz) 1.63-1.49 (2H, m) 1.21 (3H, d, J=6.6 Hz) 0.96 (3H, t, J=7.5 Hz). ESI-MS (m/z): 296, 298 [M+H]⁺.

(b) 1-[6-((R)-sec-Butylamino)-4,8-bis-methylamino-pyrimido[5,4-d]-pyrimidin-2-ylamino]-2-methyl-propan-2-ol (99)

(R)—N²-sec-Butyl-6-chloro-N⁴,N⁸-dimethylpyrimido[5,4-d]pyrimidine-2,4,8-triamine (98) (330 mg, 1.12 mmol) and 1-amino-2-methyl-propan-2-ol were reacted in n-butanol using procedure described for compound (94) to 1-[6-((R)-sec-butylamino)-4,8-bis-methyl amino-pyrimido[5,4-d]-pyrimidin-2-ylamino]-2-methyl-propan-2-ol (99) (160 mg, 41% yield). 300 MHz ¹H NMR (CDCl₃, ppm): 6.62-6.49 (1H, m) 6.20-6.06 (1H, m) 5.6-5.2 (1H, br s) 5.07 (1H, t, J=6.3 Hz) 4.52 (1H, d, J=8.3 Hz) 4.04-3.89 (1H, m) 3.39 (2H, d, J=6.3 Hz) 3.06 (3H, d, J=5.2 Hz) 3.04 (3H, d, J=5.2 Hz) 1.66-1.43 (2H, m) 1.26 (6H, s) 1.19 (3H, d, J=6.5 Hz) 0.96 (3H, t, J=7.4 Hz). ESI-MS (m/z): 349 [M+H]⁺.

(c) 1-[6-((R)-sec-Butylamino)-4,8-bis-methylamino-pyrimido[5,4-d]-pyrimidin-2-ylamino]-2-methyl-propan-2-ol Hydrochloride (99a)

1-[6-((R)-sec-Butylamino)-4,8-bis-methylamino-pyrimido[5,4-d]-pyrimidin-2-ylamino]-2-methyl-propan-2-ol (99) (140 mg, 0.40 mmol) was treated with 2M HCl/diethyl ether in diethyl ether using procedure described for compound 6a to produce 1-[6-((R)-sec-butylamino)-4,8-bis-methylamino-pyrimido[5,4-d]-pyrimidin-2-ylamino]-2-methyl-propan-2-ol hydrochloride (99a) (145 mg, 94% yield). 300 MHz ¹H NMR (CD₃OD, ppm): 4.19-4.06 (1H, m) 3.51 (2H, s) 3.13 (3H, s) 3.12 (3H, s) 1.70-1.55 (2H, m) 1.26 (6H, s) 1.25 (3H, d, J=6.4 Hz) 0.98 (3H, t, J=7.4 Hz). ESI-MS (m/z): 349 [M+H]⁺: MP: 174-176° C.

Example 61: (R)-1-[6-((R)-sec-Butylamino)-4,8-bis-methylamino-pyrimido[5,4-d]pyrimidin-2-ylamino]-propan-2-ol (100) and Corresponding Hydrochloride Salt (100a)

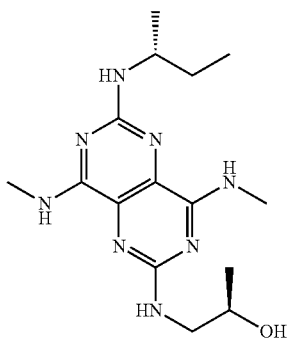

100

(a) (R)-1-[6-((R)-sec-Butylamino)-4,8-bis-methylamino-pyrimido[5,4-d]pyrimidin-2-ylamino]-propan-2-ol (100)

(R)—N²-sec-butyl-6-chloro-N⁴,N⁸-dimethylpyrimido[5,4-d]pyrimidine-2,4,8-triamine (98) (168 mg, 0.57 mmol) and (R)-1-amino-propan-2-ol were reacted in n-butanol using procedures described elsewhere herein to obtain (R)-1-[6-((R)-sec-butylamino)-4,8-bis-methylamino-pyrimido[5,4-d]pyrimidin-2-ylamino]-propan-2-ol (100) (109 mg, 67% yield). 300 MHz ¹H NMR (CDCl₃, ppm): 6.61-6.51 (1H, m) 6.24-6.14 (1H, m) 5.07 (1H, t, J=5.8 Hz) 4.54 (1H, d, J=8.3 Hz) 4.09-3.90 (2H, m) 3.49 (1H, ddd, J=14.4, 6.3, 2.5 Hz) 3.35 (1H, ddd, J=14.4, 6.9, 6.2 Hz) 3.06 (3H, d, J=5.1 Hz) 3.04 (3H, d, J=5.1 Hz) 1.69-1.46 (2H, m) 1.22 (3H, d, J=6.3 Hz) 1.19 (3H, d, J=6.5 Hz) 0.95 (3H, t, J=7.4 Hz). ESI-MS (m/z): 335 [M+H]⁺.

(b) (R)-1-[6-((R)-sec-Butylamino)-4,8-bis-methylamino-pyrimido[5,4-d]pyrimidin-2-ylamino]-propan-2-ol Hydrochloride (100a)

(R)-1-[6-((R)-sec-Butylamino)-4,8-bis-methylamino-pyrimido[5,4-d]pyrimidin-2-ylamino]-propan-2-ol (100) (109 mg, 0.33 mmol) was treated with 2M HCl/diethyl ether in diethyl ether using procedure described for compound 6a to produce (R)-1-[6-((R)-sec-butylamino)-4,8-bis-methylamino-pyrimido[5,4-d]pyrimidin-2-ylamino]-propan-2-ol hydrochloride (100a) (95 mg, 78% yield). 400 MHz ¹H NMR (CD₃OD, ppm): 4.17-4.06 (1H, m) 4.02-3.93 (1H, m) 3.51 (1H, dd, J=13.7, 4.5 Hz) 3.40 (1H, dd, J=13.7, 6.9 Hz) 3.12 (3H, s) 3.10 (3H, s) 1.62 (2H, pentet, J=7.4 Hz) 1.25 (3H, d, J=6.6 Hz) 1.22 (3H, d, J=6.3 Hz) 0.98 (3H, t, J=7.4 Hz). ESI-MS (m/z): 335 [M+H]⁺; MP: 186-188° C.

Example 62: (S)-1-[6-((R)-sec-Butylamino)-4,8-bis-methylamino-pyrimido[5,4-d]pyrimidin-2-ylamino]-propan-2-ol (101) and Corresponding Hydrochloride Salt (101a)

Example 63: 1-[6-((S)-sec-Butylamino)-4,8-bis-methylamino-pyrimido[5,4-d]-pyrimidin-2-ylamino]-2-methyl-propan-2-ol (103) and Corresponding Hydrochloride Salt (103a)

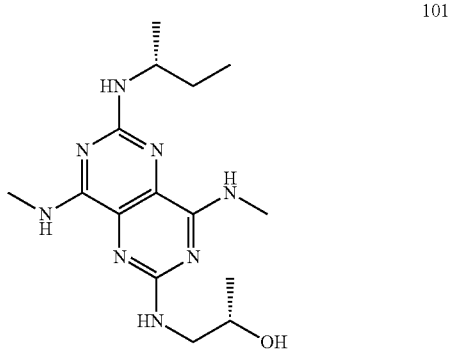 [SMILES: CC[C@@H](C)Nc1nc(NC)c2nc(NC[C@H](C)O)nc(NC)c2n1]

101

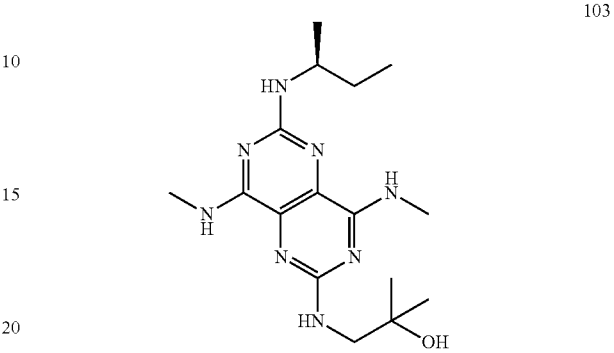

103

(a) (S)-1-[6-((R)-sec-Butylamino)-4,8-bis-methylamino-pyrimido[5,4-d]pyrimidin-2-ylamino]-propan-2-ol (101)

(S)—$N^2$-sec-butyl-6-chloro-$N^4$,$N^8$-dimethylpyrimido[5,4-d]pyrimidine-2,4,8-triamine (98) (168 mg, 0.57 mmol) and (S)-1-amino-propan-2-ol were reacted in n-butanol using procedures described elsewhere herein to obtain (S)-1-[6-((R)-sec-butylamino)-4,8-bis-methylamino-pyrimido[5,4-d]pyrimidin-2-ylamino]-propan-2-ol (101) (100 mg, 52% yield). 300 MHz $^1$H NMR (CDCl$_3$, ppm): 6.61-6.51 (1H, m) 6.24-6.14 (1H, m) 5.07 (1H, t, J=5.8 Hz) 4.54 (1H, d, J=8.3 Hz) 4.09-3.90 (2H, m) 3.49 (1H, ddd, J=14.4, 6.3, 2.5 Hz) 3.35 (1H, ddd, J=14.4, 6.9, 6.2 Hz) 3.06 (3H, d, J=5.1 Hz) 3.04 (3H, d, J=5.1 Hz) 1.69-1.46 (2H, m) 1.22 (3H, d, J=6.3 Hz) 1.19 (3H, d, J=6.5 Hz) 0.95 (3H, t, J=7.4 Hz). ESI-MS (m/z): 335 [M+H]$^+$.

(b) (S)-1-[6-((R)-sec-Butylamino)-4,8-bis-methylamino-pyrimido[5,4-d]pyrimidin-2-yl amino]-propan-2-ol Hydrochloride (101a)

(S)-1-[6-((R)-sec-Butylamino)-4,8-bis-methylamino-pyrimido[5,4-d]pyrimidin-2-ylamino]-propan-2-ol (101) (90 mg, 0.27 mmol) was treated with 2M HCl/diethyl ether in diethyl ether using procedure described for compound 6a to produce (S)-1-[6-((R)-sec-butylamino)-4,8-bis-methylamino-pyrimido[5,4-d]pyrimidin-2-ylamino]-propan-2-ol hydrochloride (101a) (85 mg, 85% yield). 400 MHz $^1$H NMR (CD$_3$OD, ppm): 4.16-4.06 (1H, m) 4.02-3.93 (1H, m) 3.51 (1H, dd, J=13.7, 4.6 Hz) 3.40 (1H, dd, J=13.7, 6.9 Hz) 3.12 (3H, s) 3.10 (3H, s) 1.62 (2H, pentet, J=7.4 Hz) 1.25 (3H, d, J=6.6 Hz) 1.22 (3H, d, J=6.3 Hz) 0.98 (3H, t, J=7.4 Hz). ESI-MS (m/z): 335 [M+H]$^+$; MP: 167-169° C.

(a) (S)—$N^2$-sec-butyl-6-chloro-$N^4$,$N^8$-dimethylpyrimido[5,4-d]pyrimidine-2,4,8-triamine (102)

2,6-Dichloro-N,N'-dimethyl-pyrimido[5,4-d]pyrimidine-4,8-diamine (88) (350 mg, 1.35 mmol) and (S)-(+)-sec-butylamine were reacted in n-butanol using procedures described elsewhere herein to obtain (S)—$N^2$-sec-butyl-6-chloro-$N^4$,$N^8$-dimethylpyrimido[5,4-d]pyrimidine-2,4,8-triamine (102) (250 mg, 63% yield). 300 MHz $^1$H NMR (CDCl$_3$, ppm): 6.77-6.63 (1H, m) 6.54-6.41 (1H, m) 4.79 (1H, d, J=8.2 Hz) 4.09-3.94 (1H, m) 3.14 (3H, d, J=5.1 Hz) 3.04 (3H, d, J=5.1 Hz) 1.65-1.49 (2H, m) 1.21 (3H, d, J=6.5 Hz) 0.96 (3H, t, J=7.5 Hz). ESI-MS (m/z): 296, 298 [M+H]$^+$.

(b) 1-[6-((S)-sec-Butylamino)-4,8-bis-methylamino-pyrimido[5,4-d]-pyrimidin-2-ylamino]-2-methyl-propan-2-ol (103)

(S)—$N^2$-sec-Butyl-6-chloro-$N^4$,$N^8$-dimethylpyrimido[5,4-d]pyrimidine-2,4,8-triamine (102) (250 mg, 0.85 mmol) and 1-amino-2-methyl-propan-2-ol were reacted in n-butanol using procedures described elsewhere herein to obtain 1-[6-((S)-sec-butylamino)-4,8-bis-methylamino-pyrimido[5,4-d]-pyrimidin-2-ylamino]-2-methyl-propan-2-ol (103) (180 mg, 61% yield). 300 MHz $^1$H NMR (CDCl$_3$, ppm): 6.62-6.49 (1H, m) 6.20-6.06 (1H, m) 5.41 (1H, s) 5.06 (1H, t, J=6.3 Hz) 4.51 (1H, d, J=8.3 Hz) 4.04-3.89 (1H, m) 3.39 (2H, d, J=6.3 Hz) 3.07 (3H, d, J=5.2 Hz) 3.04 (3H, d, J=5.2 Hz) 1.66-1.43 (2H, m) 1.26 (6H, s) 1.19 (3H, d, J=6.5 Hz) 0.96 (3H, t, J=7.4 Hz). ESI-MS (m/z): 349 [M+H]$^+$.

(c) 1-[6-((S)-sec-Butylamino)-4,8-bis-methylamino-pyrimido[5,4-d]-pyrimidin-2-ylamino]-2-methyl-propan-2-ol Hydrochloride (103a)

1-[6-((S)-sec-Butylamino)-4,8-bis-methylamino-pyrimido[5,4-d]-pyrimidin-2-ylamino]-2-methyl-propan-2-ol (103) (140 mg, 0.40 mmol) was treated with 2M HCl/diethyl ether in diethyl ether using procedure described for compound 6a to produce 1-[6-((S)-sec-butylamino)-4,8-bis-methylamino-pyrimido[5,4-d]-pyrimidin-2-ylamino]-2-methyl-propan-2-ol hydrochloride (103a) (140 mg, 91% yield). 300 MHz $^1$H NMR (CD$_3$OD, ppm): 4.19-4.06 (1H, m) 3.50 (2H, s) 3.12 (3H, s) 3.11 (3H, s) 1.70-1.55 (2H, m)

1.26 (6H, s) 1.25 (3H, d, J=6.5 Hz) 0.98 (3H, t, J=7.4 Hz). ESI-MS (m/z): 349 [M+H]⁺: MP: 182-184° C.

Example 64: (R)-1-[6-((S)-sec-Butylamino)-4,8-bis-methylamino-pyrimido[5,4-d]pyrimidin-2-ylamino]-propan-2-ol (104) and Corresponding Hydrochloride Salt (104a)

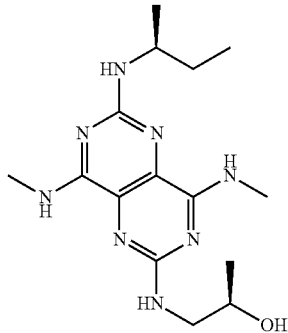

104

(a) (R)-1-[6-((S)-sec-Butylamino)-4,8-bis-methyl-amino-pyrimido[5,4-d]pyrimidin-2-ylamino]-propan-2-ol (104)

(S)—N²-sec-Butyl-6-chloro-N⁴,N⁸-dimethylpyrimido[5,4-d]pyrimidine-2,4,8-triamine (102) (185 mg, 0.63 mmol) and (R)-1-amino-propan-2-ol were reacted in n-butanol using procedures described elsewhere herein to obtain (R)-1-[6-((S)-sec-butylamino)-4,8-bis-methylamino-pyrimido[5,4-d]pyrimidin-2-ylamino]-propan-2-ol (104) (95 mg, 45% yield). 300 MHz ¹H NMR (CDCl₃, ppm): 6.56 (1H, s) 6.18 (1H, s) 5.20-4.85 (2H, m) 4.63-4.42 (1H, m) 4.10-3.90 (2H, m) 3.50 (1H, ddd, J=14.4, 6.3, 2.5 Hz) 3.35 (1H, ddd, J=14.4, 6.9, 6.2 Hz) 3.09-3.02 (6H, m) 1.67-1.48 (2H, m) 1.22 (3H, d, J=6.3 Hz) 1.20 (3H, d, J=6.5 Hz) 0.96 (3H, t, J=7.4 Hz). ESI-MS (m/z): 335 [M+H]⁺.

(b) (R)-1-[6-((S)-sec-Butylamino)-4,8-bis-methyl-amino-pyrimido[5,4-d]pyrimidin-2-ylamino]-propan-2-ol Hydrochloride (104a)

(R)-1-[6-((S)-sec-Butylamino)-4,8-bis-methylamino-pyrimido[5,4-d]pyrimidin-2-ylamino]-propan-2-ol (104) (95 mg, 0.28 mmol) was treated with 2M HCl/diethyl ether in diethyl ether using procedure described for compound 6a to produce (R)-1-[6-((S)-sec-butylamino)-4,8-bis-methyl-amino-pyrimido[5,4-d]pyrimidin-2-ylamino]-propan-2-ol hydrochloride (104a) (70 mg, 66% yield). 300 MHz ¹H NMR (CD₃OD, ppm): 4.20-4.06 (1H, m) 4.05-3.92 (1H, m) 3.53 (1H, dd, J=13.7, 4.6 Hz) 3.41 (1H, dd, J=13.7, 6.9 Hz) 3.13 (3H, s) 3.12 (3H, s) 1.69-1.56 (2H, m) 1.26 (3H, d, J=6.6 Hz) 1.23 (3H, d, J=6.3 Hz) 0.99 (3H, t, J=7.4 Hz). ESI-MS (m/z): 335 [M+H]⁺.

Example 65: (S)-1-[6-((S)-sec-Butylamino)-4,8-bis-methylamino-pyrimido[5,4-d]pyrimidin-2-ylamino]-propan-2-ol (105) and Corresponding Hydrochloride Salt (105a)

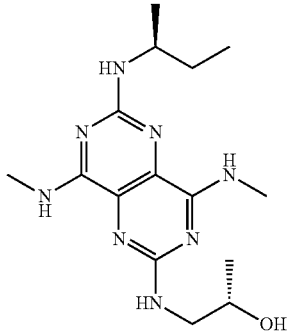

105

(a) (S)-1-[6-((S)-sec-Butylamino)-4,8-bis-methyl-amino-pyrimido[5,4-d]pyrimidin-2-ylamino]-propan-2-ol (105)

(S)—N²-sec-Butyl-6-chloro-N⁴,N⁸-dimethylpyrimido[5,4-d]pyrimidine-2,4,8-triamine (102) (185 mg, 0.63 mmol) and (S)-1-amino-propan-2-ol were reacted in n-butanol using procedures described elsewhere herein to afford (S)-1-[6-((S)-sec-butylamino)-4,8-bis-methylamino-pyrimido[5,4-d]pyrimidin-2-ylamino]-propan-2-ol (105) (110 mg, 52% yield). 300 MHz ¹H NMR (CDCl₃, ppm): 6.56 (1H, s) 6.18 (1H, s) 5.16-4.90 (2H, m) 4.60-4.45 (1H, m) 4.10-3.90 (2H, m) 3.50 (1H, ddd, J=14.4, 6.3, 2.5 Hz) 3.35 (1H, ddd, J=14.4, 6.9, 6.2 Hz) 3.06 (3H, d, J=5.1 Hz) 3.05 (3H, d, J=5.1 Hz) 1.66-1.45 (2H, m) 1.22 (3H, d, J=6.3 Hz) 1.19 (3H, d, J=6.5 Hz) 0.96 (3H, t, J=7.4 Hz). ESI-MS (m/z): 335 [M+H]⁺.

(b) (S)-1-[6-((S)-sec-Butylamino)-4,8-bis-methyl-amino-pyrimido[5,4-d]pyrimidin-2-ylamino]-propan-2-ol Hydrochloride (105a)

(S)-1-[6-((S)-sec-Butylamino)-4,8-bis-methylamino-pyrimido[5,4-d]pyrimidin-2-ylamino]-propan-2-ol (105) (110 mg, 0.33 mmol) was treated with 2M HCl/diethyl ether in diethyl ether using procedure described for compound 6a to produce (S)-1-[6-((S)-sec-butylamino)-4,8-bis-methyl-amino-pyrimido[5,4-d]pyrimidin-2-ylamino]-propan-2-ol hydrochloride (105a) (85 mg, 69% yield). 300 MHz ¹H NMR (CD₃OD, ppm): 4.20-4.08 (1H, m) 4.05-3.91 (1H, m) 3.54 (1H, dd, J=13.7, 4.6 Hz) 3.41 (1H, dd, J=13.7, 6.9 Hz) 3.14 (3H, s) 3.12 (3H, s) 1.69-1.56 (2H, m) 1.26 (3H, d, J=6.6 Hz) 1.23 (3H, d, J=6.3 Hz) 0.99 (3H, t, J=7.4 Hz). ESI-MS (m/z): 335 [M+H]⁺; MP: 178-180° C.

Example 66: 1-[6-(2,2-Difluoro-ethylamino)-4,8-bis-methylamino-pyrimido[5,4-d]pyrimidin-2-ylamino]-2-methyl-propan-2-ol (107) and Corresponding Hydrochloride Salt (107a)

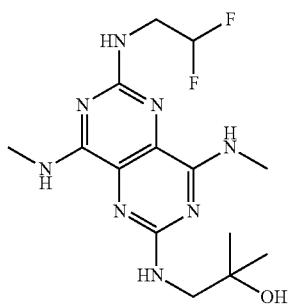

107

(a) 6-Chloro-N²-(2,2-difluoro-ethyl)-N″,1\r-dimethyl-pyrimido[5,4-d]pyrimidine-2,4,8-triamine (106)

A mixture of 2,6-dichloro-N,N'-dimethyl-pyrimido[5,4-d]pyrimidine-4,8-diamine (88) (250 mg, 0.96 mmol) and 2,2-difluoro-ethylamine (157 mg, 1.93 mmol) in 1,4-dioxane (4 mL) was heated at 100° C. for 18h in a closed vial. After cooling, a saturated NaHCO₃ solution (20 mL) was added and the resulting suspension was extracted with EtOAc (3×30 mL). The combined organic extracts were dried over solid anhydrous Na₂SO₄. After filtration, the volatiles were evaporated and the residue was purified by flash column chromatography using gradient elution from PE/EtOAc (9/1) to PE/EtOAc (1/2) to give 6-chloro-N²-(2,2-difluoro-ethyl)-N⁴,N⁸-dimethyl-pyrimido[5,4-d]pyrimidine-2,4,8-triamine (106) (105 mg, 36% yield). ESI-MS (m/z): 304, 306 [M+H]⁺.

(b) 1-[6-(2,2-Difluoro-ethylamino)-4,8-bis-methyl-amino-pyrimido[5,4-d]pyrimidin-2-yl amino]-2-methyl-propan-2-ol (107)

A mixture of 6-chloro-N²-(2,2-difluoro-ethyl)-N⁴,N⁸-dimethyl-pyrimido[5,4-d]pyrimidine-2,4,8-triamine (106) (105 mg, 0.35 mmol) and 1-amino-2-methyl-propan-2-ol (340 µl, 3.60 mmol) in n-butanol (4.0 mL) was heated at 125° C. for 48 h in a closed vial. The reaction mixture was cooled, and a saturated NaHCO₃ solution (20 mL) was added. The resulting suspension was extracted with EtOAc (3×30 mL). The combined organic extracts were washed with a brine solution (50 mL) and dried over solid anhydrous Na₂SO₄. After filtration, the solvent was removed; the residue was purified by flash column chromatography using gradient elution from PE/EtOAc (9/1) to PE/EtOAc (1/99) to give 1-[6-(2,2-difluoro-ethylamino)-4,8-bis-methylamino-pyrimido[5,4-d]pyrimidin-2-ylamino]-2-methyl-propan-2-ol (107) (95 mg, 76% yield). 300 MHz ¹H NMR (CDCl₃, ppm): 6.54-6.43 (1H, m) 6.30-6.20 (1H, m) 5.97 (1H, tt, J=57.0, 4.5 Hz) 5.12 (1H, t, J=6.4 Hz) 4.88 (1H, t, J=6.4 Hz) 3.86-3.71 (2H, m) 3.41 (2H, d, J=6.4 Hz) 3.07 (3H, d, J=5.2 Hz) 3.05 (3H, d, J=5.2 Hz) 1.27 (6H, s). ESI-MS (m/z): 357 [M+H]⁺.

(c) 1-[6-(2,2-Difluoro-ethylamino)-4,8-bis-methyl-amino-pyrimido[5,4-d]pyrimidin-2-ylamino]-2-methyl-propan-2-ol Hydrochloride (107a)

1-[6-(2,2-Difluoro-ethylamino)-4,8-bis-methylamino-pyrimido[5,4-d]pyrimidin-2-ylamino]-2-methyl-propan-2-ol (107) (95 mg, 0.27 mmol) was treated with 2M HCl/diethyl ether in dichloromethane using procedures described elsewhere herein to produce 1-[6-(2,2-difluoro-ethylamino)-4,8-bis-methylamino-pyrimido[5,4-d]pyrimidin-2-ylamino]-2-methyl-propan-2-ol hydrochloride (107a) (90 mg, 85% yield). 400 MHz ¹H NMR (CD₃OD, ppm): 6.02 (1H, tt, J=57.0, 4.2 Hz) 3.84 (2H, dd, J=14.7, 4.2 Hz) 3.52 (2H, s) 3.16 (3H, s) 3.09 (3H, s) 1.28 (6H, s). ESI-MS (m/z): 357 [M+H]⁺; MP: 223-225° C.

Example 67: 1-{4,8-Bis-methylamino-6-[(pyrimidin-2-ylmethyl)-amino]-pyrimido[5,4-d]pyrimidin-2-ylamino}-2-methyl-propan-2-ol (109) and Corresponding Hydrochloride Salt (109a)

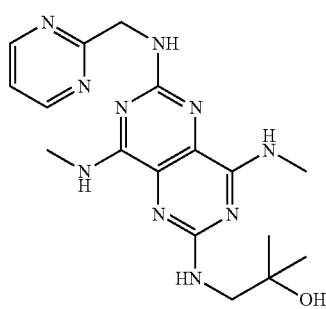

109

(a) 6-Chloro-N⁴,N⁸-dimethyl-N²-pyrimidin-2-ylmethyl-pyrimido[5,4-d]pyrimidine-2,4,8-triamine (109)

A mixture of 2,6-dichloro-N,N'-dimethyl-pyrimido[5,4-d]pyrimidine-4,8-diamine (88) (259 mg, 1.00 mmol), pyrimidin-2-ylmethanamine hydrochloride (218 mg, 1.50 mmol) and N,N-diisopropylethylamine (435 µL, 2.50 mmol) in n-butanol (3 mL) was heated at 90° C. for 72 h. The reaction mixture was cooled, the precipitate were filtered, washed with water (2×10 mL) and dried over P₂O₅ to afford 6-chloro-N⁴,N⁸-dimethyl-N²-pyrimidin-2-ylmethyl-pyrimido[5,4-d]pyrimidine-2,4,8-triamine (108) (260 mg, 79% yield). 300 MHz ¹H NMR (DMSO-d₆+TFA, ppm): 8.76 (2H, d, J=4.8 Hz) 7.92 (1H, q, J=4.9 Hz) 7.77 (1H, q, J=4.9 Hz) 7.38 (1H, t, J=4.8 Hz) 7.02 (1H, br s) 4.83 (2H, s) 2.91 (3H, d, J=4.9 Hz) 2.90-2.80 (3H, m). ESI-MS (m/z): 332, 334 [M+H]⁺.

(b) 1-{4,8-Bis-methylamino-6-[(pyrimidin-2-ylmethyl)-amino]-pyrimido[5,4-d]pyrimidin-2-ylamino}-2-methyl-propan-2-ol (109)

A mixture of 6-chloro-N⁴,N⁸-dimethyl-N²-pyrimidin-2-ylmethyl-pyrimido[5,4-d]pyrimidine-2,4,8-triamine (108) (125 mg, 0.38 mmol) and 1-amino-2-methyl-propan-2-ol (180 µL, 1.90 mmol) in DMSO (1.5 mL) was heated at 115° C. for 48 h. After cooling, the reaction mixture was cooled and water (20 mL) was added. The resulting suspension was extracted with CH$_2$Cl$_2$ (3×15 mL). The combined organic extracts were washed with water (20 mL) and dried over solid anhydrous Na$_2$SO$_4$. After filtration, the solvent was removed and the residue was purified by flash column chromatography using gradient elution from CH$_2$Cl$_2$ to CH$_2$Cl$_2$/EtOAc (4/1) to give 1-{4,8-bis-methylamino-6-[(pyrimidin-2-ylmethyl)-amino]-pyrimido[5,4-d]pyrimidin-2-ylamino}-2-methyl-propan-2-ol (109) (70 mg, 48% yield). 300 MHz $^1$H NMR (CDCl$_3$, ppm): 8.72 (2H, d, J=4.9 Hz) 7.18 (1H, t, J=4.9 Hz) 6.60 (1H, br s) 6.17 (1H, br s) 5.95-5.77 (1H, m) 5.34 (1H, br s) 5.09 (1H, br s) 4.87 (2H, d, J=5.2 Hz) 3.39 (2H, d, J=6.2 Hz) 3.06 (3H, d, J=5.1 Hz) 3.05 (3H, d, J=5.1 Hz) 1.26 (6H, s). ESI-MS (m/z): 385 [M+H]$^+$.

(c) 1-{4,8-Bis-methylamino-6-[(pyrimidin-2-ylmethyl)-amino]-pyrimido[5,4-d]pyrimidin-2-ylamino}-2-methyl-propan-2-ol Hydrochloride (109a)

1-{4,8-Bis-methylamino-6-[(pyrimidin-2-ylmethyl)-amino]-pyrimido[5,4-d]pyrimidin-2-ylamino}-2-methyl-propan-2-ol (109) (65 mg, 0.17 mmol) was treated with 2M HCl/diethyl ether in diethyl ether/MeOH (2/1) using procedures described elsewhere herein to produce 1-{4,8-bis-methylamino-6-[(pyrimidin-2-ylmethyl)-amino]-pyrimido[5,4-d]pyrimidin-2-ylamino}-2-methyl-propan-2-ol hydrochloride (109a) (63 mg, 88% yield). 400 MHz $^1$H NMR (CD$_3$OD, ppm): 8.80 (2H, d, J=5.0 Hz) 7.44 (1H, t, J=5.0 Hz) 4.87 (2H, s) 3.50 (2H, s) 3.13 (3H, s) 3.00 (3H, s) 1.27 (6H, s). ESI-MS (m/z): 385 [M+H]$^+$; MP: 159-160° C.

Example 68: 3-(4,8-Bis-methylamino-6-propylamino-pyrimido[5,4-d]pyrimidin-2-ylamino)-1,1,1-trifluoro-propan-2-ol (111) and Corresponding Hydrochloride Salt (111a)

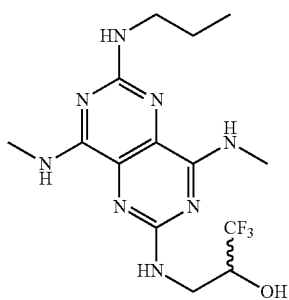

111

(a) 3-(6-Chloro-4,8-bis-methylamino-pyrimido[5,4-d]pyrimidin-2-ylamino)-1,1,1-trifluoro-propan-2-ol (110)

A mixture of 2,6-dichloro-N,N'-dimethyl-pyrimido[5,4-d]pyrimidine-4,8-diamine (88) (250 mg, 0.96 mmol), 3-amino-1,1,1-trifluoropropan-2-ol (249 mg, 1.93 mmol) and N,N-diisopropylethylamine (166 μL, 0.96 mmol) in 1,4-dioxane (4 mL) was heated at 90° C. for 18 h. After cooling, a saturated NaHCO$_3$ solution (20 mL) was added and the resulting suspension was extracted with EtOAc (3×20 mL). The combined organic extracts were washed with brine (30 mL) and dried over solid anhydrous Na$_2$SO$_4$. After filtration, the solvent was removed and the residue was purified by flash column chromatography using gradient elution from PE/EtOAc (9/1) to PE/EtOAc (1/4) to give 3-(6-chloro-4,8-bis-methylamino-pyrimido[5,4-d]pyrimidin-2-ylamino)-1,1,1-trifluoro-propan-2-ol (110) (151 mg, 45% yield). 400 MHz $^1$H NMR (CDCl$_3$, ppm): 6.75 (1H, q, J=5.2 Hz) 6.45 (1H, s) 5.90 (1H, br s) 5.39-5.29 (1H, m) 4.25-4.17 (1H, m) 3.83 (1H, ddd, J=15.0, 6.8, 2.6 Hz) 3.72 (1H, ddd, J=15.0, 7.4, 6.0 Hz) 3.15 (3H, d, J=5.2 Hz) 3.07 (3H, d, J=5.2 Hz). ESI-MS (m/z): 352, 354 [M+H]$^+$.

(b) 3-(4,8-Bis-methylamino-6-propylamino-pyrimido[5,4-d]pyrimidin-2-ylamino)-1,1,1-trifluoro-propan-2-ol (111)

3-(6-Chloro-4,8-bis-methylamino-pyrimido[5,4-d]pyrimidin-2-ylamino)-1,1,1-trifluoro-propan-2-ol (110) (151 mg, 0.43 mmol) and propylamine (212 μL, 2.58 mmol) in n-butanol (4.0 mL) was heated at 120° C. for 100 h in a closed vial. After cooling, the reaction mixture was cooled, and a saturated NaHCO$_3$ solution (20 mL) was added. The resulting suspension was extracted with EtOAc (3×30 mL). The combined organic extracts were washed with a brine solution (50 mL) and dried over solid anhydrous Na$_2$SO$_4$. After filtration, the solvent was removed and the residue was purified by flash column chromatography using gradient elution from PE/EtOAc (9/1) to PE/EtOAc (1/9) to give 3-(4,8-bis-methylamino-6-propylamino-pyrimido[5,4-d]pyrimidin-2-ylamino)-1,1,1-trifluoro-propan-2-ol (111) (150 mg, 93% yield). 300 MHz $^1$H NMR (CDCl$_3$, ppm): 6.73-6.63 (1H, m) 6.09-5.99 (1H, m) 5.04 (1H, t, J=5.3 Hz) 4.73 (1H, t, J=5.3 Hz) 4.22-4.11 (1H, m) 3.75-3.69 (2H, m) 3.40-3.31 (2H, m) 3.08 (3H, d, J=5.3 Hz) 3.06 (3H, d, J=5.3 Hz) 1.63 (2H, sextet, J=7.4 Hz) 0.99 (3H, t, J=7.4 Hz). ESI-MS (m/z): 375 [M+H]$^+$.

(c) 3-(4,8-Bis-methylamino-6-propylamino-pyrimido[5,4-d]pyrimidin-2-ylamino)-1,1,1-trifluoro-propan-2-ol Hydrochloride (111)

3-(4,8-Bis-methylamino-6-propylamino-pyrimido[5,4-d]pyrimidin-2-ylamino)-1,1,1-trifluoro-propan-2-ol (111) (150 mg, 0.40 mmol) was treated with 2M HCl/diethyl ether in diethyl ether to produce 3-(4,8-bis-methylamino-6-propylamino-pyrimido[5,4-d]pyrimidin-2-ylamino)-1,1,1-trifluoro-propan-2-ol hydrochloride (111a) (110 mg, 67% yield). 400 MHz $^1$H NMR (CD$_3$OD, ppm): 4.28-4.19 (1H, m) 3.88 (1H, dd, J=4.2, 14.3 Hz) 3.56-3.49 (1H, m) 3.46 (2H, t, J=7.10 Hz) 3.14 (3H, s) 3.09 (3H, s) 1.70 (2H, sextet, J=7.4 Hz) 1.01 (3H, t, J=7.4 Hz). ESI-MS (m/z): 375 [M+H]$^+$; MP: 236-240° C.

Example 69: (S)-1-(4,8-Bis-methylamino-6-propylamino-pyrimido[5,4-d]pyrimidin-2-ylamino)-propan-2-ol (113) and Corresponding Hydrochloride Salt (113a)

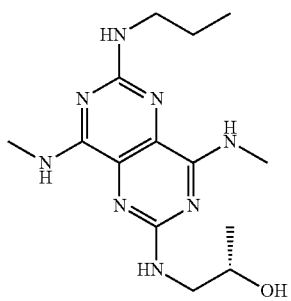

113

(a) (S)-1-(6-Chloro-4,8-bis(methylamino)pyrimido[5,4-d]pyrimidin-2-ylamino)propan-2-ol (112)

A mixture of 2,6-dichloro-N,N'-dimethyl-pyrimido[5,4-d]pyrimidine-4,8-diamine (88) (1.50, 5.79 mmol) and (S)-1-amino-propan-2-ol (869 mg, 11.78 mmol) in n-butanol (20 mL) was heated at 100° C. for 18 h in a closed vial. After cooling, a saturated NaHCO$_3$ solution (20 mL) was added and the resulting suspension was extracted with EtOAc (3×30 mL). The combined organic extracts were dried over solid anhydrous Na$_2$SO$_4$. After filtration, the volatiles were evaporated and the residue was purified by flash column chromatography using gradient elution from PE/acetone (5/1) to PE/acetone (1/1) to give (S)-1-(6-chloro-4,8-bis(methylamino)pyrimido[5,4-d]pyrimidin-2-ylamino)propan-2-ol (112) (1.33 g, 77% yield). 300 MHz $^1$H NMR (CDCl$_3$, ppm): 6.69-6.49 (2H, m) 5.35 (1H, t, J=6.0 Hz) 4.05 (1H, dqd, J=7.2, 6.3, 2.8 Hz) 3.77 (1H, br s) 3.56 (1H, ddd, J=14.2, 6.5, 2.8 Hz) 3.38 (1H, ddd, J=14.2, 7.2, 6.0 Hz) 3.13 (3H, d, J=5.2 Hz) 3.05 (3H, d, J=5.2 Hz) 1.24 (3H, d, J=6.3 Hz). ESI-MS (m/z): 298, 300 [M+H]$^+$.

(b) (S)-1-(4,8-Bis-methylamino-6-propylamino-pyrimido[5,4-d]pyrimidin-2-ylamino)-propan-2-ol (113)

(S)-1-(6-Chloro-4,8-bis(methylamino)pyrimido[5,4-d]pyrimidin-2-ylamino) propan-2-ol (112) (213 mg, 0.72 mmol) and propylamine were reacted in n-butanol as described above to afford (S)-1-(4,8-bis-methylamino-6-propylamino-pyrimido[5,4-d]pyrimidin-2-yl amino)-propan-2-ol (113) (108 mg, 47% yield). 300 MHz $^1$H NMR (CDCl$_3$, ppm): 6.63-6.52 (1H, m) 6.23-6.12 (1H, m) 5.04 (1H, br s) 5.04 (1H, t, J=5.3 Hz) 4.69 (1H, t, J=5.3 Hz) 4.09-3.96 (1H, m) 3.50 (1H, ddd, J=14.4, 6.3, 2.5 Hz) 3.41-3.30 (3H, m) 3.07 (3H, d, J=5.3 Hz) 3.05 (3H, d, J=5.3 Hz) 1.63 (2H, sextet, J=7.4 Hz) 1.22 (3H, d, J=6.3 Hz) 0.99 (3H, t, J=7.4 Hz). ESI-MS (m/z): 321 [M+H]$^+$.

(c) (S)-1-(4,8-Bis-methylamino-6-propylamino-pyrimido[5,4-d]pyrimidin-2-ylamino)-propan-2-ol Hydrochloride (113a)

(S)-1-(4,8-Bis-methylamino-6-propylamino-pyrimido[5,4-d]pyrimidin-2-yl amino)-propan-2-ol (113) (108 mg, 0.34 mmol) was treated with 2M HCl/diethyl ether in dichloromethane using procedures described elsewhere herein to produce (S)-1-(4,8-bis-methylamino-6-propylamino-pyrimido[5,4-d]pyrimidin-2-ylamino)-propan-2-ol hydrochloride (113a) (90 mg, 75% yield). 300 MHz $^1$H NMR (CD$_3$OD, ppm): 4.03-3.89 (1H, m) 3.59-3.34 (4H, m) 3.21-2.93 (6H, m) 1.75-1.58 (2H, m) 1.22 (3H, d, J=6.3 Hz) 1.0 (3H, t, J=7.4 Hz). ESI-MS (m/z): 321 [M+H]$^+$; MP: 218-220° C.

Example 70: (R)-1-(4,8-Bis-methylamino-6-propylamino-pyrimido[5,4-d]pyrimidin-2-ylamino)-propan-2-ol (115) and Corresponding Hydrochloride Salt (115a)

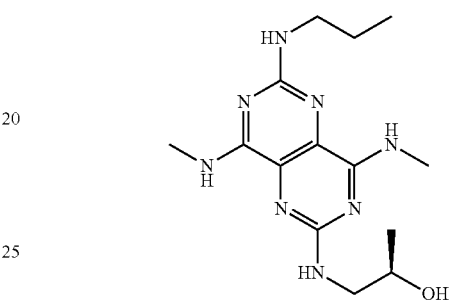

115

(a) (R)-1-(6-Chloro-4,8-bis(methylamino)pyrimido[5,4-d]pyrimidin-2-ylamino)propan-2-ol (114)

2,6-Dichloro-N,N'-dimethyl-pyrimido[5,4-d]pyrimidine-4,8-diamine (88) (250 mg, 0.96 mmol) and (R)-1-amino-propan-2-ol were reacted in 1,4-dioxane using procedures described elsewhere herein. The crude product was purified by flash column chromatography using gradient elution from PE/EtOAc (9/1) to PE/EtOAc (1/2) to afford the desired (R)-1-(6-chloro-4,8-bis(methylamino)pyrimido[5,4-d]pyrimidin-2-ylamino)propan-2-ol (114) (224 mg, 78% yield). 300 MHz $^1$H NMR (CDCl$_3$, ppm): 6.69-6.49 (2H, m) 5.37-5.28 (1H, m) 4.11-4.00 (1H, m) 3.77 (1H, br s) 3.56 (1H, ddd, J=14.2, 6.5, 2.8 Hz) 3.38 (1H, ddd, J=14.2, 7.2, 6.0 Hz) 3.13 (3H, d, J=5.2 Hz) 3.05 (3H, d, J=5.2 Hz) 1.25 (3H, d, J=6.3 Hz). ESI-MS (m/z): 298, 300 [M+H]$^+$.

(b) (R)-1-(4,8-Bis-methylamino-6-propylamino-pyrimido[5,4-d]pyrimidin-2-ylamino)-propan-2-ol (115)

(R)-1-(6-Chloro-4,8-bis(methylamino)pyrimido[5,4-d]pyrimidin-2-ylamino) propan-2-ol (114) (224 mg, 0.75 mmol) and propylamine were reacted in n-butanol using procedures described elsewhere herein to afford (R)-1-(4,8-bis-methylamino-6-propylamino-pyrimido[5,4-d]pyrimidin-2-ylamino)-propan-2-ol (115) (88 mg, 37% yield). 400 MHz $^1$H NMR (CDCl$_3$, ppm): 6.57 (1H, br s) 6.18 (1H, br s) 5.04 (1H, br s) 4.96 (1H, br s) 4.68 (1H, br s) 4.08-4.0 (1H, m) 3.50 (1H, ddd, J=14.3, 6.2, 2.4 Hz) 3.40-3.32 (3H, m) 3.07 (3H, d, J=5.3 Hz) 3.05 (3H, d, J=5.3 Hz) 1.63 (2H, sextet, J=7.4 Hz) 1.23 (3H, d, J=6.2 Hz) 0.99 (3H, t, J=7.4 Hz). ESI-MS (m/z): 321 [M+H]$^+$.

(c) (R)-1-(4,8-Bis-methylamino-6-propylamino-pyrimido[5,4-d]pyrimidin-2-ylamino)-propan-2-ol Hydrochloride (115a)

(R)-1-(4,8-Bis-methylamino-6-propylamino-pyrimido[5,4-d]pyrimidin-2-ylamino)-propan-2-ol (115) (69 mg, 0.22 mmol) was treated with 2M HCl/diethyl ether in dichloromethane using procedures described elsewhere herein to produce (R)-1-(4,8-bis-methylamino-6-propylamino-pyrimido[5,4-d]pyrimidin-2-ylamino)-propan-2-ol hydrochloride (115a) (75 mg, 97% yield). 400 MHz $^1$H NMR (CD$_3$OD, ppm): 4.02-3.93 (1H, m) 3.51 (1H, dd, J=13.7, 4.6 Hz) 3.47-3.40 (2H, m) 3.41 (1H, dd, J=13.7, 6.9 Hz) 3.13 (3H, s) 3.10 (3H, s) 1.68 (2H, sextet, J=7.4 Hz) 1.22 (3H, d, J=6.3 Hz) 1.01 (3H, t, J=7.4 Hz). ESI-MS (m/z): 321 [M+H]$^+$; MP: 215-217° C.

Example 71: 1-(4,8-Bis-methylamino-6-propylamino-pyrimido[5,4-d]pyrimidin-2-ylamino)-butan-2-ol (117) and Corresponding Hydrochloride Salt (117a)

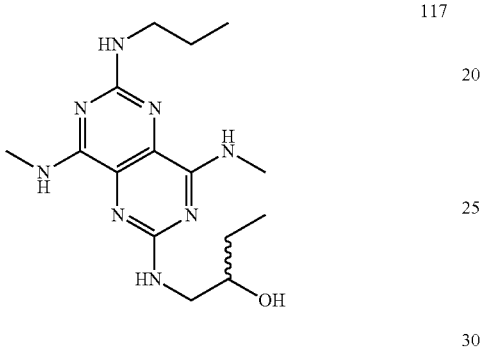

(a) 1-(6-Chloro-4,8-bis-methylamino-pyrimido[5,4-d]pyrimidin-2-ylamino)-butan-2-ol (116)

2,6-Dichloro-N,N'-dimethyl-pyrimido[5,4-d]pyrimidine-4,8-diamine (88) (1.40, 5.40 mmol) and 1-aminobutan-2-ol were reacted in n-butanol as described elsewhere herein. The crude product was purified by flash column chromatography using gradient elution from CH$_2$Cl$_2$/EtOAc (9/1) to CH$_2$Cl$_2$/EtOAc (1/2) to afford 1-(6-chloro-4,8-bis-methylamino-pyrimido[5,4-d]pyrimidin-2-ylamino)-butan-2-ol (116) (1.48 g, 88% yield). 300 MHz $^1$H NMR (CDCl$_3$, ppm): 6.67-6.50 (2H, m) 5.37-5.27 (1H, m) 3.81-3.71 (1H, m) 3.69 (1H, br s) 3.62 (1H, ddd, J=14.3, 6.5, 2.4 Hz) 3.44-3.33 (1H, m) 3.13 (3H, d, J=5.2 Hz) 3.05 (3H, d, J=5.2 Hz) 1.63-1.50 (2H, m) 1.00 (3H, t, J=7.4 Hz). ESI-MS (m/z): 312, 314 [M+H]$^+$.

(b) 1-(4,8-Bis-methylamino-6-propylamino-pyrimido[5,4-d]pyrimidin-2-ylamino)-butan-2-ol (117)

1-(6-Chloro-4,8-bis-methylamino-pyrimido[5,4-d]pyrimidin-2-ylamino)-butan-2-ol (116) (325 mg, 1.04 mmol) and propylamine were reacted in n-butanol as described elsewhere herein. The crude product was purified by flash column chromatography using gradient elution from CH$_2$Cl$_2$/EtOAc (9/1) to CH$_2$Cl$_2$/EtOAc (1/2) to afford 1-(4,8-bis-methylamino-6-propylamino-pyrimido[5,4-d]pyrimidin-2-ylamino)-butan-2-ol (117) (230 mg, 66% yield). 300 MHz $^1$H NMR (CDCl$_3$, ppm): 6.56 (1H, s) 6.18 (1H, s) 5.08-4.94 (1H, m) 4.94-4.81 (1H, m) 4.74-4.58 (1H, m) 3.79-3.68 (1H, m) 3.62-3.51 (1H, m) 3.43-3.30 (3H, m) 3.07 (3H, d, J=5.2 Hz) 3.05 (3H, d, J=5.2 Hz) 1.74-1.43 (4H, m) 0.99 (6H, t, J=7.4 Hz). ESI-MS (m/z): 335 [M+H]$^+$.

(c) 1-(4,8-Bis-methylamino-6-propylamino-pyrimido[5,4-d]pyrimidin-2-ylamino)-butan-2-ol Hydrochloride (117a)

1-(4,8-Bis-methylamino-6-propylamino-pyrimido[5,4-d] pyrimidin-2-ylamino)-butan-2-ol (117) (220 mg, 0.66 mmol) was treated with 2M HCl/diethyl ether in diethyl ether/MeOH (10/1) to produce 1-(4,8-bis-methylamino-6-propylamino-pyrimido[5,4-d]pyrimidin-2-ylamino)-butan-2-ol hydrochloride (117a) (190 mg, 78% yield). 400 MHz $^1$H NMR (CD$_3$OD, ppm): 3.75-3.66 (1H, m) 3.59 (1H, dd, J=13.8, 4.0 Hz) 3.48-3.40 (2H, m) 3.40 (1H, dd, J=13.8, 7.2 Hz) 3.13 (3H, s) 3.11 (3H, s) 1.68 (2H, sextet, J=7.2 Hz) 1.64-1.54 (1H, m) 1.54-1.43 (1H, m) 1.01 (3H, t, J=7.4 Hz) 1.00 (3H, t, J=7.4 Hz). ESI-MS (m/z): 335 [M+H]$^+$; MP: 189-190° C.

Example 72: 3-(4,8-Bis-methylamino-6-propylamino-pyrimido[5,4-d]pyrimidin-2-ylamino)-butan-2-ol (119) and Corresponding Hydrochloride Salt (119a)

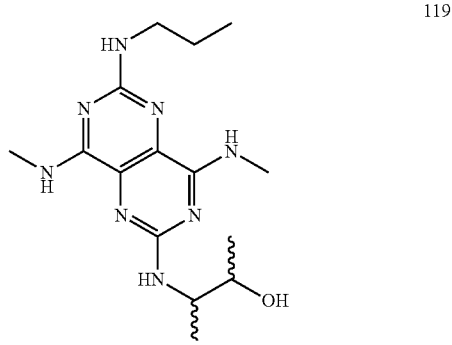

(a) 3-(6-Chloro-4,8-bis(methylamino)pyrimido[5,4-d]pyrimidin-2-ylamino)butan-2-ol (118)

A mixture of 2,6-dichloro-N$^4$,N$^8$-dimethyl-pyrimido[5,4-d]pyrimidine-4,8-diamine (88) (300 mg, 1.16 mmol) and 3-amino-butan-2-ol (206 mg, 2.32 mmol) in n-butanol (4 mL) was heated at 100° C. for 120 h. After cooling, a saturated NaHCO$_3$ solution (20 mL) was added and the resulting suspension was extracted with EtOAc (3×30 mL). The combined organic extracts were dried over solid anhydrous Na$_2$SO$_4$. After filtration, the volatiles were evaporated and the residue was purified by flash column chromatography using gradient elution from PE/EtOAc (9/1) to PE/EtOAc (1/2) to afford 3-(6-chloro-4,8-bis(methylamino) pyrimido[5,4-d]pyrimidin-2-ylamino)butan-2-ol (118) (251 mg, 69% yield). 400 MHz $^1$H NMR (CDCl$_3$, ppm): 6.67-6.53 (2H, m) 5.03 (1H, d, J=8.3 Hz) 4.06-3.96 (1H, m) 3.80 (1H, pentet, J=6.2 Hz) 3.4-3.1 (1H, br s) 3.13 (3H, d, J=5.2 Hz) 3.05 (3H, d, J=5.1 Hz) 1.25 (3H, d, J=6.2 Hz) 1.24 (3H, d, J=6.6 Hz). ESI-MS (m/z): 312, 314 [M+H]$^+$.

(b) 3-(4,8-Bis-methylamino-6-propylamino-pyrimido[5,4-d]pyrimidin-2-ylamino)-butan-2-ol (119)

3-(6-Chloro-4,8-bis(methylamino)pyrimido[5,4-d]pyrimidin-2-ylamino)butan-2-ol (118) (251 mg, 0.81 mmol) and propylamine were reacted in n-butanol as described elsewhere herein to afford 3-(4,8-Bis-methylamino-6-propylamino-pyrimido[5,4-d]pyrimidin-2-ylamino)-butan-2-ol (119) (80 mg, 30% yield). 300 MHz $^1$H NMR (CDCl$_3$, ppm): 6.54 (1H, q, J=5.2 Hz) 6.24 (1H, q, J=5.2 Hz) 4.75-4.60 (2H, m) 4.42 (1H, br s) 3.88 (1H, sextet, J=7.1 Hz) 3.73 (1H, pentet, J=6.4 Hz) 3.40-3.31 (2H, m) 3.06 (3H, d, J=5.1 Hz) 3.04 (3H, d, J=5.1 Hz) 1.62 (2H, sextet, J=7.4 Hz) 1.25-1.20 (6H, m) 0.98 (3H, t, J=7.4 Hz). ESI-MS (m/z): 335 [M+H]⁺.

(c) 3-(4,8-Bis-methylamino-6-propylamino-pyrimido[5,4-d]pyrimidin-2-ylamino)-butan-2-ol Hydrochloride (119a)

3-(4, 8-Bis-methylamino-6-propylamino-pyrimido[5,4-d]pyrimidin-2-ylamino)-butan-2-ol (119) (80 mg, 0.24 mmol) was treated with 2M HCl/diethyl ether in diethyl ether/EtOH (2/1 to produce 3-(4,8-bis-methylamino-6-propylamino-pyrimido[5,4-d]pyrimidin-2-ylamino)-butan-2-ol hydrochloride (119a) (85 mg, 96% yield). 400 MHz ¹H NMR (CD₃OD, ppm): 4.21-4.13 (1H, m) 3.88-3.82 (1H, m) 3.49-3.44 (2H, m) 3.15 (3H, s) 3.14 (3H, s) 1.69 (2H, sextet, J=7.4 Hz) 1.26 (3H, d, J=6.8 Hz) 1.20 (3H, d, J=6.4 Hz) 1.01 (3H, t, J=7.4 Hz). ESI-MS (m/z): 335 [M+H]⁺; MP: 179-181° C.

Comparative Example 73: 3-(4,8-Bis-methylamino-6-propylamino-pyrimido[5,4-d]pyrimidin-2-ylamino)-propane-1,2-diol (121) and Corresponding Hydrochloride Salt (121a)

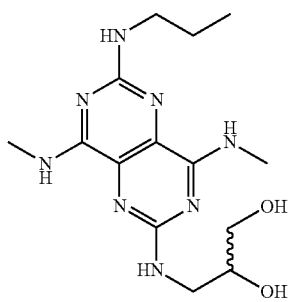

121

(a) 3-(6-Chloro-4,8-bis-methylamino-pyrimido[5,4-d]pyrimidin-2-ylamino)-propane-1,2-diol (120)

2,6-Dichloro-N,N'-dimethyl-pyrimido[5,4-d]pyrimidine-4,8-diamine (88) (300 mg, 1.16 mmol) and 3-aminopropane-1,2-diol were reacted in n-butanol using the procedures described elsewhere herein. The crude product was purified by flash column chromatography using gradient elution from CH₂Cl₂/EtOAc (9/1) to CH₂Cl₂/EtOAc (1/2) to afford 3-(6-chloro-4,8-bis-methylamino-pyrimido[5,4-d]pyrimidin-2-ylamino)-propane-1,2-diol (120) (260 mg, 71% yield). 400 MHz ¹H NMR (CDCl₃, ppm): 6.67 (1H, br s) 6.50 (1H, br s) 5.34-5.25 (1H, m) 3.95-3.88 (1H, m) 3.66 (2H, d, J=5.0 Hz) 3.65-3.60 (2H, m) 3.15 (3H, d, J=5.2 Hz) 3.06 (3H, d, J=5.2 Hz). ESI-MS (m/z): 314, 316 [M+H]⁺.

(b) 3-(4,8-Bis-methylamino-6-propylamino-pyrimido[5,4-d]pyrimidin-2-ylamino)-propane-1,2-diol (121)

3-(6-Chloro-4,8-bis-methylamino-pyrimido[5,4-d]pyrimidin-2-ylamino)-propane-1,2-diol (120) (260 mg, 0.83 mmol) and propylamine were reacted in n-butanol as described elsewhere herein. The crude product was purified by flash column chromatography using gradient elution from CH₂Cl₂/EtOAc (9/1) to CH₂Cl₂/EtOAc (1/2) to afford 3-(4,8-bis-methylamino-6-propylamino-pyrimido[5,4-d]pyrimidin-2-ylamino)-propane-1,2-diol (121) (119 mg, 43% yield). 400 MHz ¹H NMR (CDCl₃, ppm): 6.65 (1H, br s) 6.13 (1H, br s) 5.02 (1H, t, J=6.4 Hz) 4.78-4.67 (1H, m) 3.89-3.83 (1H, m) 3.66 (1H, dd, J=11.3, 4.9 Hz) 3.61 (1H, dd, J=11.3, 5.0 Hz) 3.61-3.56 (2H, m) 3.39-3.31 (2H, m) 3.07 (3H, d, J=5.2 Hz) 3.05 (3H, d, J=5.1 Hz) 1.63 (2H, sextet, J=7.4 Hz) 0.99 (3H, t, J=7.4 Hz). ESI-MS (m/z): 337 [M+H]⁺.

(c) 3-(4,8-Bis-methylamino-6-propylamino-pyrimido[5,4-d]pyrimidin-2-ylamino)-propane-1,2-diol Hydrochloride (121a)

3-(4,8-Bis-methylamino-6-propylamino-pyrimido[5,4-d]pyrimidin-2-ylamino)-propane-1,2-diol (121) (115 mg, 0.34 mmol) was treated with 2M HCl/diethyl ether in diethyl ether to produce 3-(4,8-bis-methylamino-6-propylamino-pyrimido[5,4-d]pyrimidin-2-ylamino)-propane-1,2-diol hydrochloride (121a) (120 mg, 94% yield). 400 MHz ¹H NMR (CD₃OD, ppm): 3.89-3.81 (1H, m) 3.66 (1H, dd, J=14.0, 4.5 Hz) 3.60-3.57 (2H, m) 3.47 (1H, dd, J=14.0, 6.8 Hz) 3.47-3.41 (2H, m) 3.12 (3H, s) 3.10 (3H, s) 1.68 (2H, sextet, J=7.4 Hz) 1.01 (3H, J=7.4 Hz). ESI-MS (m/z): 337 [M+H]⁺; MP: 232-234° C.

Example 74: (1R,2S)-1-(4,8-Bis-methylamino-6-propylamino-pyrimido[5,4-d]-pyrimidin-2-ylamino)-indan-2-ol (123) and Corresponding Hydrochloride Salt (123a)

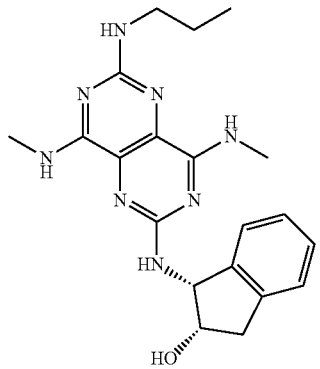

123

(a) (1R,2S)-1-(6-Chloro-4,8-bis(methylamino)pyrimido[5,4-d]pyrimidin-2-ylamino)-indan-2-ol (122)

A mixture of 2,6-dichloro-N⁴,N⁸-dimethyl-pyrimido[5,4-d]pyrimidine-4,8-diamine (88) (250 mg, 0.96 mmol), (1R,2S)-1-amino-indan-2-ol (215 mg, 1.44 mmol) and N,N-diisopropylethylamine (166 μL, 0.96 mmol) in n-butanol (3 mL) was heated at 100° C. for 72 h. The reaction mixture was cooled, the precipitate was filtered, washed with water (2×10 mL) and dried over solid P₂O₅ to afford (1R,2S)-1-(6-chloro-4,8-bis(methylamino)pyrimido[5,4-d]pyrimidin-2-ylamino)-indan-2-ol (122) (260 mg, 73% yield). 300 MHz ¹H NMR (CDCl₃, ppm): 7.38-7.32 (1H, m) 7.32-7.18 (3H, m) 6.72-6.56 (2H, m) 5.58-5.45 (2H, m) 4.81-4.73 (1H, m) 3.23 (1H, dd, J=16.5, 5.3 Hz) 3.14 (3H, d, J=5.2 Hz) 3.06 (3H, d, J=5.1 Hz) 3.04 (1H, dd, J=16.5, 2.5 Hz) 2.56 (1H, br s). ESI-MS (m/z): 372, 374 [M+H]⁺.

(b) (1R,2S)-1-(4,8-Bis-methylamino-6-propylamino-pyrimido[5,4-d]-pyrimidin-2-ylamino)-indan-2-ol (123)

(1R,2S)-1-(6-chloro-4,8-bis(methylamino)pyrimido[5,4-d]pyrimidin-2-ylamino)-indan-2-ol (122) (250 mg, 0.67 mmol) and propylamine were reacted in n-butanol as described elsewhere herein. The crude product was purified by flash column chromatography using gradient elution from PE/acetone (5/1) to PE/acetone (1/1) to obtain (1R,2S)-1-(4,8-bis-methylamino-6-propylamino-pyrimido[5,4-d]-pyrimidin-2-ylamino)-indan-2-ol (123) (140 mg, 53% yield). 300 MHz $^1$H NMR (CDCl$_3$, ppm): 7.38-7.32 (1H, m) 7.30-7.25 (2H, m) 7.25-7.17 (1H, m) 6.58 (1H, br s) 6.36 (1H, br s) 5.46 (1H, ddd, J=7.0, 5.1, 0.8 Hz) 5.14 (1H, br s) 4.84-4.63 (2H, m) 3.43-3.33 (2H, m) 3.19 (1H, dd, J=16.5, 5.4 Hz) 3.08-3.01 (1H, m) 3.07 (3H, d, J=5.1 Hz) 3.06 (3H, d, J=5.1 Hz) 1.72-1.56 (2H, m) 1.00 (3H, t, J=7.4 Hz). ESI-MS (m/z): 395 [M+H]$^+$.

(c) (1R,2S)-1-(4,8-Bis-methylamino-6-propylamino-pyrimido[5,4-d]-pyrimidin-2-ylamino)-indan-2-ol Hydrochloride (123a)

(1R,2S)-1-(4,8-Bis-methylamino-6-propylamino-pyrimido[5,4-d]-pyrimidin-2-ylamino)-indan-2-ol (123) (130 mg, 0.33 mmol) was treated with 2M HCl/diethyl ether in diethyl ether to produce (1R,2S)-1-(4,8-bis-methylamino-6-propylamino-pyrimido[5,4-d]-pyrimidin-2-ylamino)-indan-2-ol hydrochloride (123a) (110 mg, 77% yield). 300 MHz $^1$H NMR (CD$_3$OD, ppm): 7.33-7.26 (2H, m) 7.26-7.16 (2H, m) 5.68 (1H, d, J=4.9 Hz) 4.70 (1H, td, J=5.0, 1.5 Hz) 3.48 (2H, t, J=7.1 Hz) 3.22 (1H, dd, J=16.5, 4.9 Hz) 3.14 (3H, s) 3.13 (3H, s) 2.98 (1H, d, J=16.5 Hz) 1.78-1.63 (2H, m) 1.02 (3H, t, J=7.4 Hz). ESI-MS (m/z): 395 [M+H]$^+$.

Using the procedures described herein, and variations readily available and known to those skilled in the art, the following pyrimido[5,4-d]-pyrimidinyl-amino cycloalkanols were prepared.

Example 75: (1S,2S)-1-(4,8-Bis-methylamino-6-propylamino-pyrimido[5,4-d]-pyrimidin-2-ylamino)-indan-2-ol (125) and Corresponding Hydrochloride Salt (125a)

125

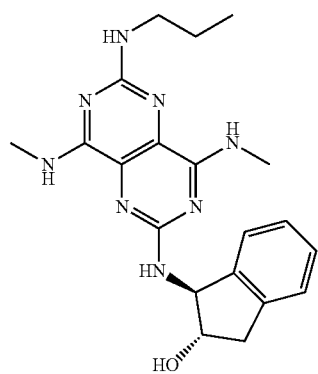

(a) (1S,2S)-1-(6-Chloro-4,8-bis(methylamino)pyrimido[5,4-d]pyrimidin-2-ylamino)-2,3-dihydro-1H-indan-2-ol (124)

2,6-Dichloro-N,N'-dimethyl-pyrimido[5,4-d]pyrimidine-4,8-diamine (88) (250 mg, 0.96 mmol) and (1S,2S)-1-amino-indan-2-ol were reacted in n-butanol using procedures described elsewhere herein. The crude product was purified by flash column chromatography using gradient elution from PE/EtOAc (3/1) to PE/EtOAc (1/1) to afford (1S,2S)-1-(6-chloro-4,8-bis(methylamino)pyrimido[5,4-d]pyrimidin-2-ylamino)-2indan-2-ol (124) (230 mg, 64% yield). 300 MHz $^1$H NMR (CDCl$_3$, ppm): 7.35-7.23 (4H, m) 6.74 (1H, s) 6.51 (1H, br s) 5.7-5.1 (1H, br s) 5.46 (1H, d, J=6.0 Hz) 5.39-5.31 (1H, m) 4.55-4.45 (1H, m) 3.34 (1H, dd, J=15.5, 7.7 Hz) 3.15 (3H, d, J=5.2 Hz) 3.09 (3H, d, J=5.2 Hz) 2.96 (1H, dd, J=15.5, 8.7 Hz). ESI-MS (m/z): 372, 374 [M+H]$^+$.

(b) (1S,2S)-1-(4,8-Bis-methylamino-6-propylamino-pyrimido[5,4-d]-pyrimidin-2-ylamino)-indan-2-ol (125)

(1S,2S)-1-(6-chloro-4,8-bis(methylamino)pyrimido[5,4-d]pyrimidin-2-ylamino)-indan-2-ol (124) (225 mg, 0.61 mmol) and propylamine were reacted in n-butanol using procedures described elsewhere herein. The crude product was purified by flash column chromatography using gradient elution from PE/acetone (5/1) to PE/acetone (2/1) to obtain (1S,2S)-1-(4,8-bis-methylamino-6-propylamino-pyrimido[5,4-d]-pyrimidin-2-ylamino)-indan-2-ol (125) (125 mg, 52% yield). 300 MHz $^1$H NMR (CDCl$_3$, ppm): 7.38-7.31 (1H, m) 7.31-7.22 (3H, m) 6.78-6.60 (1H, m) 6.49-6.04 (2H, m) 5.31-5.19 (2H, m) 4.73 (1H, t, J=5.7 Hz) 4.53-4.42 (1H, m) 4.42-3.27 (3H, m) 3.10 (3H, d, J=5.2 Hz) 3.07 (3H, d, J=5.2 Hz) 2.95 (1H, dd, J=15.3, 8.9 Hz) 1.72-1.56 (2H, m) 1.00 (3H, t, J=7.4 Hz). ESI-MS (m/z): 395 [M+H]$^+$.

(c) (1S,2S)-1-(4,8-Bis-methylamino-6-propylamino-pyrimido[5,4-d]-pyrimidin-2-ylamino)-indan-2-ol Hydrochloride (125a)

(1S,2S)-1-(4,8-bis-methylamino-6-propylamino-pyrimido[5,4-d]-pyrimidin-2-ylamino)-indan-2-ol (125) (125 mg, 0.32 mmol) was treated with 2M HCl/diethyl ether to produce (1S,2S)-1-(4,8-bis-methylamino-6-propylamino-pyrimido[5,4-d]-pyrimidin-2-ylamino)-indan-2-ol hydrochloride (125a) (115 mg, 84% yield). 300 MHz $^1$H NMR (CD$_3$OD, ppm): 7.28-7.14 (4H, m) 5.47 (1H, d, J=5.9 Hz) 4.51-4.38 (1H, m) 3.47 (2H, t, J=7.0 Hz) 3.35-3.23 (1H, m, overlapped with methanol) 3.14 (3H, s) 3.06 (3H, s) 2.86 (1H, dd, J=15.6, 6.7 Hz) 1.79-1.61 (2H, m) 1.02 (3H, t, J=7.4 Hz). ESI-MS (m/z): 395 [M+H]$^+$.

Example 76: (1S,2R)-1-(4,8-Bis-methylamino-6-propylamino-pyrimido[5,4-d]-pyrimidin-2-ylamino)-indan-2-ol (127) and Corresponding Hydrochloride Salt (127a)

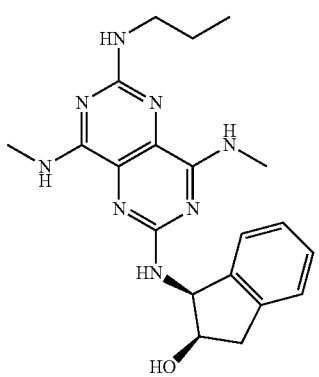

127

(a) (1S,2R)-1-(6-Chloro-4,8-bis(methylamino)pyrimido[5,4-d]pyrimidin-2-ylamino)-indan-2-ol (126)

2,6-Dichloro-N,N'-dimethyl-pyrimido[5,4-d]pyrimidine-4,8-diamine (88) (300 mg, 1.16 mmol) and (1S,2R)-1-amino-indan-2-ol were reacted in n-butanol using procedures described elsewhere herein. The crude product was purified by flash column chromatography using gradient elution from CH$_2$Cl$_2$/EtOAc (99/1) to CH$_2$Cl$_2$/EtOAc (1/4) to afford (1S,2R)-1-(6-chloro-4,8-bis(methylamino)pyrimido[5,4-d]pyrimidin-2-ylamino)-indan-2-ol (126) (300 mg, 70% yield). 300 MHz $^1$H NMR (CDCl$_3$, ppm): 7.37-7.31 (1H, m) 7.31-7.19 (3H, m) 6.73-6.55 (2H, m) 5.58-5.49 (2H, m) 4.83-4.73 (1H, s) 3.23 (1H, dd, J=16.4, 5.3 Hz) 3.13 (3H, d, J=5.2 Hz) 3.05 (3H, d, J=5.2 Hz) 3.04 (1H, dd, J=16.4, 2.2 Hz) 2.66 (1H, br s). ESI-MS (m/z): 372, 374 [M+H]$^+$.

(b) (1S,2R)-1-(4,8-Bis-methylamino-6-propylamino-pyrimido[5,4-d]-pyrimidin-2-ylamino)-indan-2-ol (127)

(1S,2R)-1-(6-Chloro-4,8-bis(methylamino)pyrimido[5,4-d]pyrimidin-2-ylamino)-indan-2-ol (126) (300 mg, 0.81 mmol) and propylamine were reacted in n-butanol using procedures described elsewhere herein. The crude product was purified by flash column chromatography using gradient elution from CH$_2$Cl$_2$/EtOAc (99/1) to CH$_2$Cl$_2$/EtOAc (1/4) to produce (1S,2R)-1-(4,8-bis-methylamino-6-propylamino-pyrimido[5,4-d]-pyrimidin-2-ylamino)-indan-2-ol (127) (170 mg, 53% yield). 300 MHz $^1$H NMR (CDCl$_3$, ppm): 7.38-7.33 (1H, m) 7.30-7.18 (3H, m) 6.61-6.47 (1H, m) 6.39-6.27 (1H, m) 5.49-5.42 (1H, m) 5.10 (1H, d, J=6.4 Hz) 4.80-4.65 (1H, m) 4.77 (1H, td, J=5.2, 3.3 Hz) 3.42-3.32 (2H, m) 3.19 (1H, dd, J=16.4, 5.4 Hz) 3.07 (3H, d, J=5.1 Hz) 3.05 (3H, d, J=5.0 Hz) 3.05 (1H, dd, J=16.4, 3.3 Hz) 1.64 (2H, sextet, J=7.4 Hz) 1.00 (3H, t, J=7.4 Hz). ESI-MS (m/z): 395 [M+H]$^+$.

(c) (1S,2R)-1-(4,8-Bis-methylamino-6-propylamino-pyrimido[5,4-d]-pyrimidin-2-ylamino)-indan-2-ol Hydrochloride (127a)

(1S,2R)-1-(4,8-Bis-methylamino-6-propylamino-pyrimido[5,4-d]-pyrimidin-2-ylamino)-indan-2-ol (146) (167 mg, 0.42 mmol) was treated with 2M HCl/diethyl ether in diethyl ether/MeOH (10/1) produce (1S,2R)-1-(4,8-bis-methylamino-6-propylamino-pyrimido[5,4-d]-pyrimidin-2-ylamino)-indan-2-ol hydrochloride (127a) (130 mg, 71% yield). 300 MHz $^1$H NMR (CD$_3$OD, ppm): 7.35-7.15 (4H, m) 5.69 (1H, d, J=4.2 Hz) 4.73-4.67 (1H, m) 3.47 (2H, t, J=7.0 Hz) 3.22 (1H, dd, J=16.5, 4.7 Hz) 3.14 (3H, s) 3.12 (3H, s) 2.98 (1H, d, J=16.5 Hz) 1.71 (2H, sextet, J=7.4 Hz) 1.03 (3H, J=7.4 Hz). ESI-MS (m/z): 395 [M+H]$^+$; MP: 210-211° C.

Example 77: (1R,2R)-1-(4,8-Bis-methylamino-6-propylamino-pyrimido[5,4-d]-pyrimidin-2-ylamino)-indan-2-ol (129) and Corresponding Hydrochloride Salt (129a)

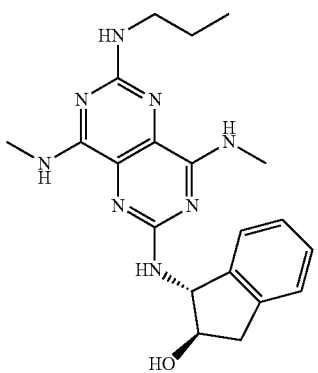

129

(a) (1R,2R)-1-(6-Chloro-4,8-bis(methylamino)pyrimido[5,4-d]pyrimidin-2-ylamino)-indan-2-ol (128)

2,6-Dichloro-N,N'-dimethyl-pyrimido[5,4-d]pyrimidine-4,8-diamine (88) (250 mg, 0.96 mmol) and (1R,2R)-1-amino-indan-2-ol were reacted in n-butanol using procedures described elsewhere herein to afford (1R,2R)-1-(6-chloro-4,8-bis (methylamino)pyrimido[5,4-d]pyrimidin-2-ylamino)-indan-2-ol (128) (230 mg, 64% yield). 300 MHz $^1$H NMR (CDCl$_3$, ppm): 7.35-7.23 (4H, m) 6.74 (1H, s) 6.50 (1H, br s) 5.6-5.1 (1H, br s) 5.46 (1H, d, J=6.1 Hz) 5.39-5.31 (1H, m) 4.55-4.45 (1H, m) 3.34 (1H, dd, J=15.6, 7.7 Hz) 3.15 (3H, d, J=5.2 Hz) 3.09 (3H, d, J=5.2 Hz) 2.96 (1H, dd, J=15.6, 8.7 Hz). ESI-MS (m/z): 372, 374 [M+H]$^+$.

(b) (1R,2R)-1-(4,8-Bis-methylamino-6-propylamino-pyrimido[5,4-d]-pyrimidin-2-ylamino)-indan-2-ol (129)

(1R,2R)-1-(6-Chloro-4,8-bis(methylamino)pyrimido[5,4-d]pyrimidin-2-ylamino)-indan-2-ol (128) (230 mg, 0.62 mmol) and propylamine were reacted in n-butanol using procedures described elsewhere herein. The crude product was purified by flash column chromatography using gradient elution from PE/acetone (5/1) to PE/acetone (2/1) to obtain (1R,2R)-1-(4,8-bis-methylamino-6-propylamino-pyrimido[5,4-d]-pyrimidin-2-ylamino)-indan-2-ol (129) (120 mg, 49% yield). 300 MHz $^1$H NMR (CDCl$_3$, ppm): 7.40-7.32 (1H, m) 7.32-7.22 (3H, m) 6.74-6.59 (1H, m) 6.24 (1H, br s) 6.18-6.06 (1H, m) 5.31-5.25 (1H, m) 5.22 (1H, d, J=5.9 Hz) 4.72 (1H, t, J=5.5 Hz) 4.47 (1H, ddd, J=9.0, 7.7, 6.8 Hz) 3.41-3.33 (2H, m) 3.33 (1H, dd, J=15.5, 7.7 Hz) 3.10 (3H, d, J=5.1 Hz) 3.07 (3H, d, J=5.1 Hz) 2.95 (1H, dd, J=15.5, 9.0 Hz) 1.72-1.57 (2H, m) 1.00 (3H, t, J=7.4 Hz). ESI-MS (m/z): 395 [M+H]$^+$.

(c) (1R,2R)-1-(4,8-Bis-methylamino-6-propylamino-pyrimido[5,4-d]-pyrimidin-2-ylamino)-indan-2-ol hydrochloride (129a)

(1R,2R)-1-(4,8-Bis-methylamino-6-propylamino-pyrimido[5,4-d]-pyrimidin-2-ylamino)-indan-2-ol (129) (115 mg, 0.29 mmol) was treated with 2M HCl/diethyl ether in diethyl to produce (1R,2R)-1-(4,8-bis-methylamino-6-propylamino-pyrimido[5,4-d]-pyrimidin-2-ylamino)-indan-2-ol hydrochloride (129a) (110 mg, 88% yield). 300 MHz $^1$H NMR (CD$_3$OD, ppm): 7.30-7.14 (4H, m) 5.47 (1H, d, J=6.1 Hz) 4.50-4.37 (1H, m) 3.47 (2H, t, J=7.1 Hz) 3.35-3.24 (1H, m, overlapped with methanol) 3.14 (3H, s) 3.07 (3H, s) 2.86 (1H, dd, J=15.6, 6.7 Hz) 1.79-1.62 (2H, m) 1.02 (3H, t, J=7.4 Hz). ESI-MS (m/z): 395 [M+H]$^+$.

Example 78: (1R,2S)-2-(4,8-Bis-methylamino-6-propylamino-pyrimido[5,4-d]pyrimidin-2-ylamino)-cyclohexanol (131) and Corresponding Hydrochloride Salt (131a)

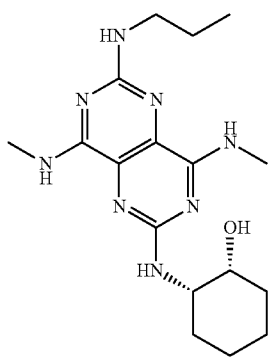

131

(a) (1R,2S)-2-(6-Chloro-4,8-bis(methylamino)pyrimido[5,4-d]pyrimidin-2-ylamino) cyclohexanol (130)

A mixture of 2,6-dichloro-N,N'-dimethyl-pyrimido[5,4-d]pyrimidine-4,8-diamine (88) (250 mg, 0.96 mmol), (1R,2S)-2-aminocyclohexanol hydrochloride (146 mg, 0.96 mmol) and N,N-diisopropylethylamine (319 µL, 1.92 mmol) in n-butanol (4 mL) was heated at 110° C. for 100h. The mixture was cooled, and a saturated NaHCO$_3$ solution (20 mL) was added. The resulting suspension was extracted with EtOAc (3×30 mL). The combined organic extracts were washed with a brine solution (50 mL) and dried over solid anhydrous Na$_2$SO$_4$. The solvent was removed and the residue was purified by flash column chromatography using gradient elution from PE/EtOAc (9/1) to PE/EtOAc (1/99) to afford (1R,2S)-2-(6-chloro-4,8-bis(methylamino)pyrimido[5,4-d]pyrimidin-2-ylamino)cyclohexanol (130)(140 mg, 43% yield). 300 MHz $^1$H NMR (CDCl$_3$, ppm): 6.63-6.52 (2H, m) 5.20 (1H, d, J=7.1 Hz) 4.19-4.08 (1H, m) 4.06-3.98 (1H, m) 3.3-3.0 (1H, br s) 3.14 (3H, d, J=5.2 Hz) 3.05 (3H, d, J=5.1 Hz) 1.84-1.57 (6H, m) 1.57-1.36 (2H, m). ESI-MS (m/z): 338, 340 [M+H]$^+$.

(b) (1R,2S)-2-(4,8-Bis-methylamino-6-propylamino-pyrimido[5,4-d]pyrimidin-2-ylamino)-cyclohexanol (131)

(1R,2S)-2-(6-Chloro-4,8-bis(methylamino)pyrimido[5,4-d]pyrimidin-2-ylamino) cyclohexanol (130) (140 mg, 0.41 mmol) and propylamine were reacted in n-butanol using procedures described elsewhere herein to obtain (1R,2S)-2-(4,8-bis-methylamino-6-propylamino-pyrimido[5,4-d]pyrimidin-2-ylamino)-cyclohexanol (131) (121 mg, 81% yield). 300 MHz $^1$H NMR (CDCl$_3$, ppm): 6.60-6.50 (1H, m) 6.36-6.21 (1H, m) 4.90 (1H, d, J=5.6 Hz) 4.76 (1H, t, J=5.2 Hz) 4.17-4.09 (1H, m) 3.99-3.92 (1H, m) 3.39-3.30 (2H, m) 3.06 (3H, d, J=5.2 Hz) 3.04 (3H, d, J=5.2 Hz) 1.86-1.34 (10H, m) 0.98 (3H, t, J=7.4 Hz). ESI-MS (m/z): 361 [M+H]$^+$.

(c) (1R,2S)-2-(4,8-Bis-methylamino-6-propylamino-pyrimido[5,4-d]pyrimidin-2-ylamino)-cyclohexanol Hydrochloride (131a)

(1R,2S)-2-(4,8-Bis-methylamino-6-propylamino-pyrimido[5,4-d]pyrimidin-2-ylamino)-cyclohexanol (130) (121 mg, 0.34 mmol) was treated with 2M HCl/diethyl ether in diethyl ether produce (1R,2S)-2-(4,8-bis-methylamino-6-propylamino-pyrimido[5,4-d]pyrimidin-2-ylamino)-cyclohexanol hydrochloride (131a) (85 mg, 64% yield). 300 MHz $^1$H NMR (CD$_3$OD, ppm): 4.15-4.06 (1H, m) 4.03-3.97 (1H, m) 3.43 (2H, t, J=7.4 Hz) 3.11 (3H, s) 3.11 (3H, s) 1.90-1.57 (8H, m) 1.53-1.36 (2H, m) 1.0 (3H, t, J=7.4 Hz). ESI-MS (m/z): 361 [M+H]$^+$.

Example 79: (1S,2S)-2-(4,8-Bis-methylamino-6-propylamino-pyrimido[5,4-d]pyrimidin-2-ylamino)-cyclohexanol (133) and Corresponding Hydrochloride Salt (133a)

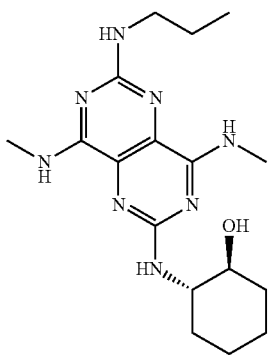

133

(a) (1S,2S)-2-(6-Chloro-4,8-bis(methylamino)pyrimido[5,4-d]pyrimidin-2-ylamino)cyclohexanol (132)

2,6-Dichloro-N$^4$,N$^8$-dimethyl-pyrimido[5,4-d]pyrimidine-4,8-diamine (88) (300 mg, 1.16 mmol) and (1S,2S)-2-aminocyclohexanol were reacted in n-butanol using procedures described elsewhere herein. The crude product was purified by flash column chromatography using gradient elution from CH$_2$Cl$_2$/EtOAc (99/1) to CH$_2$Cl$_2$/EtOAc (1/4) to afford (1S,2S)-2-(6-chloro-4,8-bis(methylamino)pyrimido[5,4-d]pyrimidin-2-ylamino)cyclohexanol (132) (290 mg, 74% yield). 300 MHz $^1$H NMR (CDCl$_3$, ppm): 6.69-6.59 (1H, m) 6.57-6.47 (1H, m) 4.93 (1H, d, J=6.7 Hz) 4.76 (1H, s) 3.79-3.65 (1H, m) 3.52-3.41 (1H, m) 3.14 (3H, d, J=5.2 Hz) 3.06 (3H, d, J=5.1 Hz) 2.16-1.99 (2H, m) 1.82-1.70 (2H, m) 1.48-1.18 (4H, m). ESI-MS (m/z): 338, 340 [M+H]$^+$.

(b) (1S,2S)-2-(4,8-Bis-methylamino-6-propylamino-pyrimido[5,4-d]pyrimidin-2-ylamino)-cyclohexanol (133)

(1S,2S)-2-(6-chloro-4,8-bis(methylamino)pyrimido[5,4-d]pyrimidin-2-ylamino) cyclohexanol (132) (290 mg, 0.86 mmol) and propylamine were reacted in n-butanol using procedures described elsewhere herein. The crude product was purified by flash column chromatography using gradient elution from CH$_2$Cl$_2$/EtOAc (99/1) to CH$_2$Cl$_2$/EtOAc (1/4) to obtain (1S,2S)-2-(4,8-bis-methylamino-6-propylamino-pyrimido[5,4-d]pyrimidin-2-ylamino)-cyclohexanol (133) (180 mg, 58% yield). 300 MHz $^1$H NMR (CDCl$_3$, ppm): 6.66-6.49 (1H, m) 6.23-6.06 (1H, m) 5.89-5.69 (1H, m) 4.75-4.57 (2H, m) 3.69-3.55 (1H, m) 3.50-3.40 (1H, m) 3.39-3.30 (2H, m) 3.07 (3H, d, J=5.2 Hz) 3.05 (3H, d, J=5.2 Hz) 2.16-1.95 (2H, m) 1.81-1.68 (2H, m) 1.63 (2H, sextet, J=7.4 Hz) 1.43-1.19 (4H, m) 0.99 (3H, t, J=7.4 Hz). ESI-MS (m/z): 361 [M+H]$^+$.

(c) (1S,2S)-2-(4,8-Bis-methylamino-6-propylamino-pyrimido[5,4-d]pyrimidin-2-ylamino)-cyclohexanol hydrochloride (133a)

(1S,2S)-2-(4,8-Bis-methylamino-6-propylamino-pyrimido[5,4-d]pyrimidin-2-ylamino)-cyclohexanol (133) (142 mg, 0.39 mmol) was treated with 2M HCl/diethyl ether in diethyl ether produce (1S,2S)-2-(4,8-bis-methylamino-6-propylamino-pyrimido[5,4-d]pyrimidin-2-ylamino)-cyclohexanol hydrochloride (133a) (135 mg, 86% yield). 300 MHz $^1$H NMR (CD$_3$OD, ppm): 3.89-3.75 (1H, m) 3.56-3.39 (1H, m) 3.44 (2H, t, J=7.4 Hz) 3.13 (3H, s) 3.12 (3H, s) 2.12-1.98 (2H, m) 1.84-1.72 (2H, m) 1.67 (2H, sextet, J=7.4 Hz) 1.52-1.25 (4H, m) 1.00 (3H, t, J=7.4 Hz). ESI-MS (m/z): 361 [M+H]$^+$; MP: 163-165° C.

Example 80: (1S,2R)-2-(4,8-Bis-methylamino-6-propylamino-pyrimido[5,4-d]pyrimidin-2-ylamino)-cyclohexanol (135) and Corresponding Hydrochloride Salt (135a)

(a) (1S,2R)-2-(6-Chloro-4,8-bis(methylamino)pyrimido[5,4-d]pyrimidin-2-ylamino) cyclohexanol (134)

2,6-Dichloro-N,N'-dimethyl-pyrimido[5,4-d]pyrimidine-4,8-diamine (88) (250 mg, 0.96 mmol) and (1S,2R)-2-aminocyclohexanol hydrochloride were reacted in n-butanol to afford (1S,2R)-2-(6-chloro-4,8-bis(methylamino)pyrimido[5,4-d]pyrimidin-2-ylamino) cyclohexanol (134) (221 mg, 68% yield). 300 MHz $^1$H NMR (CDCl$_3$, ppm): 6.64-6.50 (2H, m) 5.20 (1H, d, J=7.3 Hz) 4.19-4.09 (1H, m) 4.05-3.98 (1H, m) 3.3-3.0 (1H, br s) 3.14 (3H, d, J=5.2 Hz) 3.05 (3H, d, J=5.1 Hz) 1.84-1.36 (8H, m). ESI-MS (m/z): 338, 340 [M+H]$^+$.

(b) (1S,2R)-2-(4,8-Bis-methylamino-6-propylamino-pyrimido[5,4-d]pyrimidin-2-ylamino)-cyclohexanol (135)

(1S,2R)-2-(6-Chloro-4,8-bis(methylamino)pyrimido[5,4-d]pyrimidin-2-ylamino) cyclohexanol (134) (221 mg, 0.65 mmol) and propylamine were reacted in n-butanol to obtain (1S,2R)-2-(4,8-bis-methylamino-6-propylamino-pyrimido[5,4-d]pyrimidin-2-ylamino)-cyclohexanol (135) (155 mg, 66% yield). 300 MHz $^1$H NMR (CDCl$_3$, ppm): 6.60-6.49 (1H, m) 6.28-6.16 (1H, m) 4.83 (1H, d, J=6.0 Hz) 4.68 (1H, t, J=6.0 Hz) 4.18-4.10 (1H, m) 3.99-3.93 (1H, m) 3.39-3.30 (2H, m) 3.07 (3H, d, J=5.2 Hz) 3.05 (3H, d, J=5.2 Hz) 1.87-1.32 (8H, m) 1.63 (2H, sextet, J=7.4 Hz) 0.99 (3H, t, J=7.4 Hz). ESI-MS (m/z): 361 [M+H]$^+$.

(c) (1S,2R)-2-(4,8-Bis-methylamino-6-propylamino-pyrimido[5,4-d]pyrimidin-2-ylamino)-cyclohexanol Hydrochloride (134a)

(1S,2R)-2-(4,8-Bis-methylamino-6-propylamino-pyrimido[5,4-d]pyrimidin-2-ylamino)-cyclohexanol (135) (131 mg, 0.36 mmol) was treated with 2M HCl/diethyl ether in diethyl ether to produce (1S,2R)-2-(4,8-bis-methylamino-6-propylamino-pyrimido[5,4-d]pyrimidin-2-ylamino)-cyclohexanol hydrochloride (135a) (110 mg, 76% yield). 300 MHz $^1$H NMR (CD$_3$OD, ppm) 4.19-4.09 (1H, m) 4.03-3.96 (1H, m) 3.47 (2H, t, J=7.1 Hz) 3.15 (6H, s) 1.88-1.59 (8H, m) 1.53-1.37 (2H, m) 1.01 (3H, t, J=7.4 Hz). ESI-MS (m/z): 361 [M+H]$^+$.

Example 81: (1R,2R)-2-(4,8-Bis-methylamino-6-propylamino-pyrimido[5,4-d]pyrimidin-2-ylamino)-cyclohexanol (137) and Corresponding Hydrochloride Salt (137a)

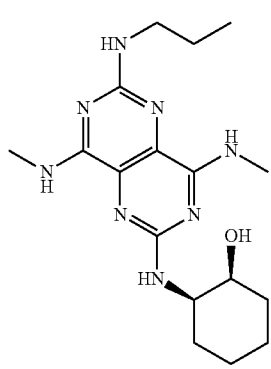

135

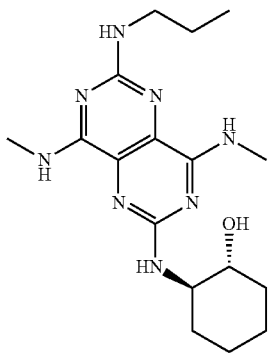

137

(a) (1R,2R)-2-(6-Chloro-4,8-bis(methylamino)pyrimido[5,4-d]pyrimidin-2-ylamino) cyclohexanol (136)

2,6-Dichloro-N,N'-dimethyl-pyrimido[5,4-d]pyrimidine-4,8-diamine (88) (300 mg, 1.16 mmol) and (1R,2R)-2-aminocyclohexanol were reacted in n-butanol and the crude product was purified by flash column chromatography using gradient elution from $CH_2Cl_2$/EtOAc (99/1) to $CH_2Cl_2$/EtOAc (1/4) to afford (1R,2R)-2-(6-chloro-4,8-bis(methylamino) pyrimido[5,4-d]pyrimidin-2-ylamino)cyclohexanol (136) (225 mg, 58% yield). 300 MHz $^1$H NMR (CDCl$_3$, ppm): 6.65 (1H, s) 6.53 (1H, s) 5.1-4.6 (1H, br s) 5.00-4.88 (1H, m) 3.80-3.62 (1H, m) 3.53-3.38 (1H, m) 3.14 (3H, d, J=5.2 Hz) 3.05 (3H, d, J=5.1 Hz) 2.17-1.98 (2H, m) 1.83-1.70 (2H, m) 1.45-1.18 (4H, m). ESI-MS (m/z): 338, 340 [M+H]$^+$.

(b) (1R,2R)-2-(4,8-Bis-methylamino-6-propylamino-pyrimido[5,4-d]pyrimidin-2-ylamino)-cyclohexanol (137)

(1R,2R)-2-(6-Chloro-4,8-bis(methylamino)pyrimido[5,4-d]pyrimidin-2-ylamino) cyclohexanol (136) (220 mg, 0.65 mmol) and propylamine were reacted in n-butanol and the crude product was purified by flash column chromatography using gradient elution from $CH_2Cl_2$/EtOAc (99/1) to $CH_2Cl_2$/EtOAc (1/4) to afford (1R,2R)-2-(4,8-bis-methylamino-6-propylamino-pyrimido[5,4-d]pyrimidin-2-ylamino)-cyclohexanol (137) (165 mg, 70% yield). 300 MHz $^1$H NMR (CDCl$_3$, ppm): 6.59 (1H, br s) 6.15 (1H, br s) 5.79 (1H, br s) 4.74-4.60 (2H, m) 3.69-3.55 (1H, m) 3.50-3.40 (1H, m) 3.39-3.30 (2H, m) 3.07 (3H, d, J=5.2 Hz) 3.05 (3H, d, J=5.2 Hz) 2.16-1.95 (2H, m) 1.81-1.68 (2H, m) 1.63 (2H, sextet, J=7.4 Hz) 1.47-1.19 (4H, m) 0.99 (3H, t, J=7.4 Hz). ESI-MS (m/z): 361 [M+H]$^+$.

(c) (1R,2R)-2-(4,8-Bis-methylamino-6-propylamino-pyrimido[5,4-d]pyrimidin-2-ylamino)-cyclohexanol Hydrochloride (137a)

(1R,2R)-2-(4,8-Bis-methylamino-6-propylamino-pyrimido[5,4-d]pyrimidin-2-ylamino)-cyclohexanol (137) (160 mg, 0.44 mmol) was treated with 2M HCl/diethyl ether in diethyl ether/MeOH (20/1) to produce (1R,2R)-2-(4,8-bis-methylamino-6-propylamino-pyrimido[5,4-d]pyrimidin-2-ylamino)-cyclohexanol hydrochloride (137a) (140 mg, 79% yield). 300 MHz $^1$H NMR (CD$_3$OD, ppm): 3.87-3.75 (1H, m) 3.53-3.37 (1H, m) 3.43 (2H, t, J=7.4 Hz) 3.11 (3H, s) 3.10 (3H, s) 2.11-1.98 (2H, m) 1.84-1.72 (2H, m) 1.67 (2H, sextet, J=7.4 Hz) 1.50-1.25 (4H, m) 1.00 (3H, t, J=7.4 Hz). ESI-MS (m/z): 361 [M+H]$^+$; MP: 170-171° C.

Example 82: (1S,2S)-2-(4,8-Bis-methylamino-6-propylamino-pyrimido[5,4-d]pyrimidin-2-ylamino)-cyclopentanol (139) and Corresponding Hydrochloride Salt (139a)

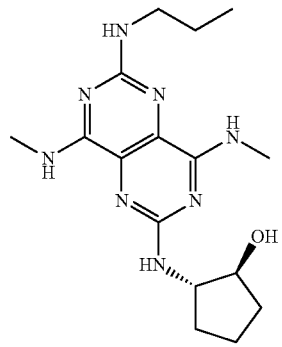

139

(a) (1S,2S)-2-((6-Chloro-4,8-bis(methylamino)pyrimido[5,4-d]pyrimidin-2-yl)amino)-cyclopentanol (138)

2,6-Dichloro-N,N'-dimethyl-pyrimido[5,4-d]pyrimidine-4,8-diamine (88) (300 mg, 1.16 mmol) and (1S,2S)-2-aminocyclopentanol hydrochloride were reacted in n-butanol and the crude product was purified by flash column chromatography using gradient elution from $CH_2Cl_2$/EtOAc (99/1) to $CH_2Cl_2$/EtOAc (1/4) to afford (1S,2S)-2-((6-chloro-4,8-bis(methylamino)pyrimido[5,4-d]pyrimidin-2-yl)amino)-cyclopentanol (138) (310 mg, 83% yield). 300 MHz $^1$H NMR (CDCl$_3$, ppm): 6.75-6.61 (1H, m) 6.47 (1H, br s) 5.30 (1H, br s) 5.14 (1H, d, J=3.8 Hz) 4.14-3.95 (2H, m) 3.12 (3H, d, J=5.2 Hz) 3.05 (3H, d, J=5.2 Hz) 2.28-2.02 (2H, m) 1.94-1.61 (3H, m) 1.61-1.43 (1H, m). ESI-MS (m/z): 324, 326 [M+H]$^+$.

(b) (1S,2S)-2-(4,8-Bis-methylamino-6-propylamino-pyrimido[5,4-d]pyrimidin-2-ylamino)-cyclopentanol (139)

(1S,2S)-2-((6-Chloro-4,8-bis(methylamino)pyrimido[5,4-d]pyrimidin-2-yl)amino)-cyclopentanol (138) (310 mg, 0.96 mmol) and propylamine were reacted in n-butanol and the crude product was purified by flash column chromatography using gradient elution from $CH_2Cl_2$/EtOAc (99/1) to $CH_2Cl_2$/EtOAc (1/4) to obtain (1S,2S)-2-(4,8-bis-methylamino-6-propylamino-pyrimido[5,4-d]pyrimidin-2-ylamino)-cyclopentanol (139) (135 mg, 41% yield). 300 MHz $^1$H NMR (CDCl$_3$, ppm): 6.69-6.55 (1H, m) 6.4-6.2 (1H, br s) 6.13-5.98 (1H, m) 4.86 (1H, d, J=3.6 Hz) 4.69 (1H, t, J=5.4 Hz) 4.08-3.86 (2H, m) 3.41-3.29 (2H, m) 3.07 (3H, d, J=5.2 Hz) 3.04 (3H, d, J=5.1 Hz) 2.24-2.03 (2H, m) 1.90-1.44 (6H, m) 0.99 (3H, t, J=7.4 Hz). ESI-MS (m/z): 347 [M+H]$^+$.

(c) (1S,2S)-2-(4,8-Bis-methylamino-6-propylamino-pyrimido[5,4-d]pyrimidin-2-ylamino)-cyclopentanol Hydrochloride (139a)

(1S,2S)-2-(4,8-Bis-methylamino-6-propylamino-pyrimido[5,4-d]pyrimidin-2-ylamino)-cyclopentanol (139) (134 mg, 0.39 mmol) was treated with 2M HCl/diethyl ether in diethyl ether/MeOH (6/1) to produce (1S,2S)-2-(4,8-bis-methylamino-6-propylamino-pyrimido[5,4-d]pyrimidin-2-ylamino)-cyclopentanol hydrochloride (139a) (85 mg, 57% yield). 300 MHz $^1$H NMR (CD$_3$OD, ppm) 4.21-4.04 (2H, m) 3.46 (2H, t, J=7.4 Hz) 3.16 (3H, s) 3.13 (3H, s) 2.31-2.14 (1H, m) 2.07-1.92 (1H, m) 1.92-1.74 (2H, m) 1.74-1.52 (4H, m) 1.01 (3H, t, J=7.4 Hz). ESI-MS (m/z): 347 [M+H]$^+$; MP: 215-217° C.

Example 83: (1R,2R)-2-(4,8-Bis-methylamino-6-propylamino-pyrimido[5,4-d]pyrimidin-2-ylamino)-cyclopentanol (141) and Corresponding Hydrochloride Salt (141a)

141

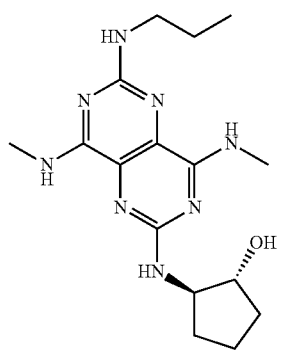

(a) (1R,2R)-2-((6-Chloro-4,8-bis(methylamino)pyrimido[5,4-d]pyrimidin-2-yl)amino)-cyclopentanol (140)

2,6-Dichloro-N,N'-dimethyl-pyrimido[5,4-d]pyrimidine-4,8-diamine (88) (300 mg, 1.16 mmol) and (1R,2R)-2-aminocyclopentanol hydrochloride were reacted in n-butanol and the crude product was purified by flash column chromatography using gradient elution from CH$_2$Cl$_2$/EtOAc (99/1) to CH$_2$Cl$_2$/EtOAc (1/4) to afford (1R,2R)-2-((6-chloro-4,8-bis(methyl amino)pyrimido[5,4-d]pyrimidin-2-yl)amino)-cyclopentanol (140) (270 mg, 72% yield). 300 MHz $^1$H NMR (CDCl$_3$, ppm): 6-76-6.62 (1H, m) 6.45 (1H, br s) 5.31 (1H, br s) 5.17-5.08 (1H, m) 4.12-3.95 (2H, m) 3.13 (3H, d, J=5.2 Hz) 3.06 (3H, d, J=5.2 Hz) 2.28-2.02 (2H, m) 1.94-1.62 (3H, m) 1.62-1.45 (1H, m). ESI-MS (m/z): 324, 326 [M+H]$^+$.

(b) (1R,2R)-2-(4,8-Bis-methylamino-6-propylamino-pyrimido[5,4-d]pyrimidin-2-ylamino)-cyclopentanol (141)

(1R,2R)-2-((6-Chloro-4,8-bis(methylamino)pyrimido[5,4-d]pyrimidin-2-yl) amino)-cyclopentanol (140) (270 mg, 0.83 mmol) and propylamine were reacted in n-butanol and the crude product was purified by flash column chromatography using gradient elution from CH$_2$Cl$_2$/EtOAc (99/1) to CH$_2$Cl$_2$/EtOAc (1/4) to obtain (1R,2R)-2-(4,8-bis-methyl-amino-6-propylamino-pyrimido[5,4-d]pyrimidin-2-ylamino)-cyclopentanol (141) (160 mg, 55% yield). 300 MHz $^1$H NMR (CDCl$_3$, ppm): 6.69-6.55 (1H, m) 6.31 (1H, s) 6.14-5.98 (1H, m) 4.87 (1H, d, J=3.6 Hz) 4.69 (1H, t, J=5.4 Hz) 4.08-3.98 (1H, m) 3.98-3.86 (1H, m) 3.41-3.30 (2H, m) 3.07 (3H, d, J=5.2 Hz) 3.04 (3H, d, J=5.1 Hz) 2.24-2.04 (2H, m) 1.92-1.44 (6H, m) 0.99 (3H, t, J=7.4 Hz). ESI-MS (m/z): 347 [M+H]$^+$.

(c) (1R,2R)-2-(4,8-Bis-methylamino-6-propylamino-pyrimido[5,4-d]pyrimidin-2-ylamino)-cyclopentanol hydrochloride (141a)

(1R,2R)-2-(4,8-Bis-methylamino-6-propylamino-pyrimido[5,4-d]pyrimidin-2-ylamino)-cyclopentanol (141) (160 mg, 0.46 mmol) was treated with 2M HCl/diethyl ether in diethyl ether/MeOH (6/1) to produce (1R,2R)-2-(4,8-bis-methylamino-6-propylamino-pyrimido[5,4-d]pyrimidin-2-ylamino)-cyclopentanol hydrochloride (141a) (115 mg, 65% yield). 300 MHz $^1$H NMR (CD$_3$OD, ppm): 4.22-4.03 (2H, m) 3.43 (2H, t, J=7.4 Hz) 3.15 (3H, s) 3.12 (3H, s) 2.30-2.14 (1H, m) 2.07-1.91 (1H, m) 1.91-1.74 (2H, m) 1.74-1.52 (4H, m) 1.01 (3H, t, J=7.4 Hz). ESI-MS (m/z): 347 [M+H]$^+$; MP: 209-210° C.

Example 84: (S)-1-[6-(Cyclopropylmethyl-amino)-4,8-bis-methylamino-pyrimido[5,4-d]pyrimidin-2-ylamino]-propan-2-ol (142) and Corresponding Hydrochloride Salt (142a)

142

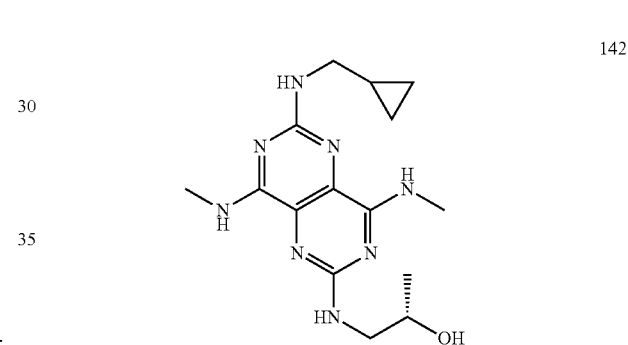

(a) (S)-1-[6-(Cyclopropylmethyl-amino)-4,8-bis-methylamino-pyrimido[5,4-d]pyrimidin-2-ylamino]-propan-2-ol (142)

(S)-1-(6-Chloro-4,8-bis(methylamino)pyrimido[5,4-d] pyrimidin-2-ylamino) propan-2-ol (112) (220 mg, 0.74 mmol) and cyclopropylmethanamine were reacted in n-butanol obtain (S)-1-[6-(cyclopropylmethyl-amino)-4,8-bis-methylamino-pyrimido[5,4-d]pyrimidin-2-ylamino]-propan-2-ol (142) (130 mg, 53% yield). 300 MHz $^1$H NMR (CDCl$_3$, ppm): 6.63-6.51 (1H, m) 6.25-6.14 (1H, m) 5.08-4.99 (1H, m) 4.86-4.76 (1H, m) 4.07-4.0 (1H, m) 3.55-3.44 (1H, m) 3.41-3.30 (1H, m) 3.28-3.21 (2H, m) 3.09-3.06 (6H, m) 1.22 (3H, d, J=6.3 Hz) 1.15-1.01 (1H, m) 0.56-0.48 (2H, m) 0.29-0.19 (2H, m). ESI-MS (m/z): 333 [M+H]$^+$.

(b) (S)-1-[6-(Cyclopropylmethyl-amino)-4,8-bis-methylamino-pyrimido[5,4-d]pyrimidin-2-ylamino]-propan-2-ol Hydrochloride (142a)

(S)-1-[6-(Cyclopropylmethyl-amino)-4,8-bis-methyl-amino-pyrimido[5,4-d]pyrimidin-2-ylamino]-propan-2-ol (142) (126 mg, 0.38 mmol) was treated with 2M HCl/diethyl ether in diethyl ether/EtOH (2/1) to produce (S)-1-[6-(cyclopropylmethyl-amino)-4,8-bis-methylamino-pyrimido[5,4-d]pyrimidin-2-ylamino]-propan-2-ol hydrochloride (142a) (90 mg, 64% yield). 300 MHz $^1$H NMR (CD$_3$OD, ppm): 4.06-3.92 (1H, m) 3.56-3.49 (1H, m) 3.46-3.37 (1H, m) 3.31 (2H, d, J=7.1 Hz) 3.14 (3H, s) 3.12 (3H, s) 1.23 (3H, d, J=6.4 Hz) 1.22-1.10 (1H, m) 0.60-0.51 (2H, m) 0.36-0.27 (2H, m). ESI-MS (m/z): 333 [M+H]$^+$; MP: 211-213° C.

Example 85: (S)-1-(6-Allylamino-4,8-bis-methyl-amino-pyrimido[5,4-d]pyrimidin-2-ylamino)-propan-2-ol (143) and Corresponding Hydrochloride Salt (143a)

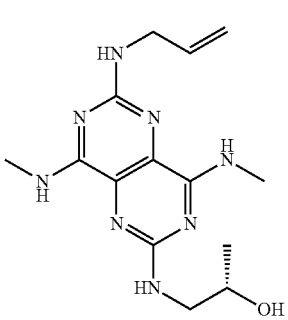

143

(a) (S)-1-(6-Allylamino-4,8-bis-methylamino-pyrimido[5,4-d]pyrimidin-2-yl amino)-propan-2-ol (143)

(S)-1-(6-Chloro-4,8-bis(methylamino)pyrimido[5,4-d]pyrimidin-2-ylamino) propan-2-ol (112) (1.33 g, 4.47 mmol) and allylamine (2.0 mL. 26.80 mmol) were heated in n-butanol at 105° C. for 8 days. The mixture was cooled, and a saturated NaHCO$_3$ solution (40 mL) was added. The resulting suspension was extracted with EtOAc (3×30 mL). The combined organic extracts were washed with a brine solution (50 mL) and dried over solid anhydrous MgSO$_4$. After filtration, the solvent was removed and the residue was purified by flash column chromatography using gradient elution from PE/EtOAc (1/1) to PE/EtOAc (99/1) to afford (S)-1-(6-allylamino-4,8-bis-methylamino-pyrimido[5,4-d]pyrimidin-2-ylamino)-propan-2-ol (143) (820 mg, 58% yield). 300 MHz $^1$H NMR (CDCl$_3$, ppm): 6.62-6.48 (1H, m) 6.26-6.14 (1H, m) 5.99 (1H, ddt, J=17.2, 10.2, 5.5 Hz) 5.25 (1H, ddt, J=17.2, 1.6, 1.6 Hz) 5.12 (1H, ddt, J=10.2, 1.6, 1.6 Hz) 5.04 (1H, t, J=6.3 Hz) 4.90 (1H, br s) 4.74 (1H, t, J=5.9 Hz) 4.09-3.98 (3H, m) 3.50 (1H, ddd, J=14.4, 6.3, 2.4 Hz) 3.36 (1H, ddd, J=14.4, 7.0, 6.3 Hz) 3.06 (3H, d, J=5.1 Hz) 3.05 (3H, d, J=5.1 Hz) 1.23 (3H, d, J=6.3 Hz). ESI-MS (m/z): 319 [M+H]$^+$.

(b) (S)-1-(6-Allylamino-4,8-bis-methylamino-pyrimido[5,4-d]pyrimidin-2-ylamino)-propan-2-ol Hydrochloride (143a)

(S)-1-(6-Allylamino-4,8-bis-methylamino-pyrimido[5,4-d]pyrimidin-2-ylamino)-propan-2-ol (143) (820 mg, 2.58 mmol) was treated with 2M HCl/diethyl ether in diethyl ether/MeOH (2/1) to produce (S)-1-(6-allylamino-4,8-bis-methylamino-pyrimido[5,4-d]pyrimidin-2-ylamino)-propan-2-ol hydrochloride (143a) (870 mg, 95% yield). 400 MHz $^1$H NMR (CD$_3$OD, ppm): 5.97 (1H, ddd, J=17.2, 10.3, 5.4 Hz) 5.29 (1H, ddt, J=17.2, 1.6, 1.6 Hz) 5.16 (1H, ddt, J=10.3, 1.6, 1.6 Hz) 4.13 (2H, dt, J=5.4, 1.6 Hz) 4.00 (1H, dqd, J=7.0, 6.3, 4.3 Hz) 3.56 (1H, dd, J=13.8, 4.3 Hz) 3.42 (1H, dd, J=13.8, 7.0 Hz) 3.14 (3H, s) 3.13 (3H, s) 1.23 (3H, d, J=6.3 Hz). ESI-MS (m/z): 319 [M+H]$^+$; MP: 192-193° C.

Example 86: (R)-1-[6-(Cyclopropylmethyl-amino)-4,8-bis-methylamino-pyrimido[5,4-d]pyrimidin-2-ylamino]-propan-2-ol (144) and Corresponding Hydrochloride Salt (144a)

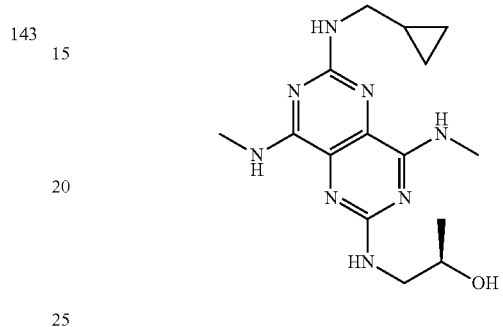

144

(a) (R)-1-[6-(Cyclopropylmethyl-amino)-4,8-bis-methylamino-pyrimido[5,4-d]pyrimidin-2-ylamino]-propan-2-ol (144)

(R)-1-(6-Chloro-4,8-bis(methylamino)pyrimido[5,4-d]pyrimidin-2-ylamino) propan-2-ol (114) (210 mg, 0.71 mmol) and cyclopropylmethanamine were reacted in n-butanol and the crude product was purified by flash column chromatography using gradient elution from PE/acetone (10/1) to PE/acetone (1/1) to afford (R)-1-[6-(cyclopropylmethyl-amino)-4,8-bis-methylamino-pyrimido[5,4-d]pyrimidin-2-ylamino]-propan-2-ol (144) (110 mg, 47% yield). 300 MHz $^1$H NMR (CDCl$_3$, ppm): 6.63-6.49 (1H, m) 6.24-6.12 (1H, m) 5.04 (1H, t, J=6.0 Hz) 4.93 (1H, s) 4.82 (1H, t, J=5.6 Hz) 4.09-3.98 (1H, m) 3.56-3.44 (1H, m) 3.42-3.29 (1H, m) 3.28-3.21 (2H, m) 3.07 (3H, d, J=5.2 Hz) 3.06 (3H, d, J=5.2 Hz) 1.23 (3H, d, J=6.3 Hz) 1.16-1.02 (1H, m) 0.56-0.46 (2H, m) 0.28-0.20 (2H, m). ESI-MS (m/z): 333 [M+H]$^+$.

(b) (R)-1-[6-(Cyclopropylmethyl-amino)-4,8-bis-methylamino-pyrimido[5,4-d]pyrimidin-2-ylamino]-propan-2-ol Hydrochloride (144a)

(R)-1-[6-(Cyclopropylmethyl-amino)-4,8-bis-methyl-amino-pyrimido[5,4-d]pyrimidin-2-ylamino]-propan-2-ol (144) (110 mg, 0.33 mmol) was treated with 2M HCl/diethyl ether in diethyl ether/MeOH (2/1) to produce (R)-1-[6-(cyclopropylmethyl-amino)-4,8-bis-methylamino-pyrimido[5,4-d]pyrimidin-2-ylamino]-propan-2-ol hydrochloride (144a) (120 mg, 98% yield). 300 MHz $^1$H NMR (CD$_3$OD, ppm): 4.05-3.91 (1H, m) 3.58-3.45 (1H, m) 3.45-3.34 (1H, m) 3.34-3.27 (2H, m, overlapped with methanol) 3.11 (3H, s) 3.09 (3H, s) 1.22 (3H, d, J=6.2 Hz) 1.19-1.07 (1H, m) 0.61-0.49 (2H, m) 0.35-0.24 (2H, m). ESI-MS (m/z): 333 [M+H]$^+$; MP: 224-226° C.

Example 87: (R)-1-(6-Allylamino-4,8-bis-methyl-amino-pyrimido[5,4-d]pyrimidin-2-ylamino)-propan-2-ol (145) and Corresponding Hydrochloride Salt (145a)

Example 88: 1-[6-(Cyclopropylmethyl-amino)-4,8-bis-methylamino-pyrimido[5,4-d]pyrimidin-2-ylamino]-butan-2-ol (146) and Corresponding Hydrochloride Salt (146a)

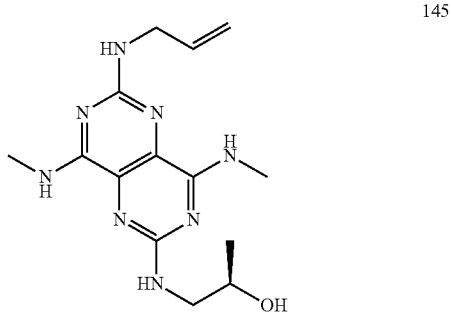 [SMILES: C=CCNc1nc(NC)c2nc(NC[C@@H](C)O)nc(NC)c2n1]

145

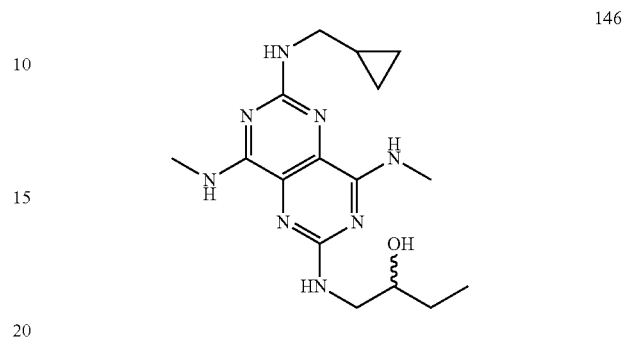

146

(a) (R)-1-(6-Allylamino-4,8-bis-methylamino-pyrimido[5,4-d]pyrimidin-2-ylamino)-propan-2-ol (145)

(R)-1-(6-Chloro-4,8-bis(methylamino)pyrimido[5,4-d]pyrimidin-2-ylamino) propan-2-ol (114) (210 mg, 0.71 mmol) and allylamine were reacted in n-butanol to obtain (R)-1-(6-allylamino-4,8-bis-methylamino-pyrimido[5,4-d]pyrimidin-2-ylamino)-propan-2-ol (145) (125 mg, 55% yield). 300 MHz $^1$H NMR (CDCl$_3$, ppm): 6.63-6.48 (1H, m) 6.27-6.13 (1H, m) 5.99 (1H, ddt, J=17.2, 10.2, 5.6 Hz) 5.25 (1H, ddt, J=17.2, 1.6, 1.6 Hz) 5.11 (1H, ddt, J=10.2, 1.6, 1.4 Hz) 5.05 (1H, t, J=6.0 Hz) 4.90 (1H, s) 4.74 (1H, t, J=6.0 Hz) 4.10-3.98 (3H, m) 3.50 (1H, ddd, J=14.4, 6.3, 2.4 Hz) 3.42-3.29 (1H, m) 3.06 (3H, d, J=5.1 Hz) 3.05 (3H, d, J=5.1 Hz) 1.23 (3H, d, J=6.3 Hz). ESI-MS (m/z): 319 [M+H]$^+$.

(b) (R)-1-(6-Allylamino-4,8-bis-methylamino-pyrimido[5,4-d]pyrimidin-2-ylamino)-propan-2-ol Hydrochloride (145a)

(R)-1-(6-Allylamino-4,8-bis-methylamino-pyrimido[5,4-d]pyrimidin-2-ylamino)-propan-2-ol (145) (120 mg, 0.38 mmol) was treated with 2M HCl/diethyl ether in diethyl ether/MeOH (2/1) to produce (R)-1-(6-allylamino-4,8-bis-methylamino-pyrimido[5,4-d]pyrimidin-2-ylamino)-propan-2-ol hydrochloride (145a) (120 mg, 90% yield). 400 MHz $^1$H NMR (CD$_3$OD, ppm): 5.97 (1H, ddt, J=17.2, 10.3, 5.4 Hz) 5.28 (1H, ddt, J=17.2, 1.6, 1.6 Hz) 5.15 (1H, ddt, J=10.3, 1.6, 1.5 Hz) 4.12 (2H, dt, J=5.4, 1.6 Hz) 4.04-3.95 (1H, m) 3.54 (1H, dd, J=13.7, 4.4 Hz) 3.42 (1H, dd, J=13.7, 7.0 Hz) 3.13 (3H, s) 3.12 (3H, s) 1.23 (3H, d, J=6.3 Hz). ESI-MS (m/z): 319 [M+H]$^+$; MP: 205-207° C.

(a) 1-[6-(Cyclopropylmethyl-amino)-4,8-bis-methyl-amino-pyrimido[5,4-d]pyrimidin-2-ylamino]-butan-2-ol (146)

1-(6-Chloro-4,8-bis-methylamino-pyrimido[5,4-d]pyrimidin-2-ylamino)-butan-2-ol (116) (350 mg, 1.12 mmol) and cyclopropylmethanamine were reacted in n-butanol and the crude product was purified by flash column chromatography using gradient elution from CH$_2$Cl$_2$/EtOAc (9/1) to CH$_2$Cl$_2$/EtOAc (1/4) to afford 1-[6-(cyclopropylmethyl-amino)-4,8-bis-methylamino-pyrimido[5,4-d]pyrimidin-2-ylamino]-butan-2-ol (146) (210 mg, 54% yield). 400 MHz $^1$H NMR (CDCl$_3$, ppm): 6.66-6.50 (1H, m) 6.28-6.15 (1H, m) 5.04 (1H, t, J=6.0 Hz) 4.90 (1H, s) 4.87-4.77 (1H, m) 3.77-3.69 (1H, m) 3.57 (1H, ddd, J=14.4, 6.3, 2.4 Hz) 3.41-3.32 (1H, m) 3.24 (2H, dd, J=7.0, 5.5 Hz) 3.06 (3H, d, J=5.1 Hz) 3.05 (3H, d, J=5.1 Hz) 1.64-1.47 (2H, m) 1.15-1.03 (1H, m) 0.99 (3H, t, J=7.4 Hz) 0.54-0.48 (2H, m) 0.27-0.21 (2H, m). ESI-MS (m/z): 347 [M+H]$^+$.

(b) 1-[6-(Cyclopropylmethyl-amino)-4,8-bis-methyl-amino-pyrimido[5,4-d]pyrimidin-2-ylamino]-butan-2-ol Hydrochloride (146a)

1-[6-(Cyclopropylmethyl-amino)-4,8-bis-methylamino-pyrimido[5,4-d]pyrimidin-2-ylamino]-butan-2-ol (146) (150 mg, 0.43 mmol) was treated with 2M HCl/diethyl ether in diethyl ether/MeOH (4/1) to produce 1-[6-(cyclopropylmethyl-amino)-4,8-bis-methylamino-pyrimido[5,4-d]pyrimidin-2-ylamino]-butan-2-ol hydrochloride (146a) (145 mg, 87% yield). 400 MHz $^1$H NMR (CD$_3$OD, ppm): 3.75-3.66 (1H, m) 3.60 (1H, dd, J=13.8, 3.9 Hz) 3.40 (1H, dd, J=13.8, 7.2 Hz) 3.35 (2H, d, J=7.0 Hz) 3.13 (3H, s) 3.11 (3H, s) 1.67-1.54 (1H, m) 1.54-1.42 (1H, m) 1.21-1.09 (1H, m) 1.01 (3H, t, J=7.4 Hz) 0.59-0.52 (2H, m) 0.34-0.28 (2H, m). ESI-MS (m/z): 347 [M+H]$^+$; MP: 208-209° C.

Example 89: 1-(6-Ethylamino-4,8-bis-methylamino-pyrimido[5,4-d]pyrimidin-2-ylamino)-butan-2-ol (147) and Corresponding Hydrochloride Salt (147a)

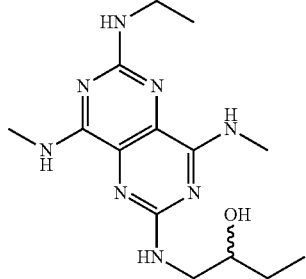

147

(a) 1-(6-Ethylamino-4,8-bis-methylamino-pyrimido[5,4-d]pyrimidin-2-ylamino)-butan-2-ol (147)

1-(6-Chloro-4,8-bis-methylamino-pyrimido[5,4-d]pyrimidin-2-ylamino)-butan-2-ol (116) (325 mg, 1.04 mmol) and ethylamine (70% water solution) (0.8 mL) were reacted in n-butanol and the crude product was purified by flash column chromatography using gradient elution from $CH_2Cl_2$/EtOAc (9/1) to $CH_2Cl_2$/EtOAc (1/4) to afford 1-(6-ethylamino-4,8-bis-methylamino-pyrimido[5,4-d]pyrimidin-2-ylamino)-butan-2-ol (147) (150 mg, 45% yield). 400 MHz $^1$H NMR (CDCl$_3$, ppm): 6.62 (1H, s) 6.25 (1H, s) 5.14-4.98 (1H, m) 4.97-4.53 (1H, m) 4.68 (1H, s) 3.77-3.70 (1H, m) 3.57 (1H, ddd, J=14.5, 6.3, 2.4 Hz) 3.43 (2H, qd, J=7.2, 5.7 Hz) 3.41-3.33 (1H, m) 3.07 (3H, d, J=5.2 Hz) 3.05 (3H, d, J=5.2 Hz) 1.64-1.47 (2H, m) 1.23 (3H, t, J=7.2 Hz) 0.99 (3H, t, J=7.5 Hz). ESI-MS (m/z): 321 [M+1-1]$^+$.

(b) 1-(6-Ethylamino-4,8-bis-methylamino-pyrimido[5,4-d]pyrimidin-2-ylamino)-butan-2-ol Hydrochloride (147a)

1-(6-Ethylamino-4,8-bis-methylamino-pyrimido[5,4-d]pyrimidin-2-ylamino)-butan-2-ol (147) (140 mg, 0.44 mmol) was treated with 2M HCl/diethyl ether in diethyl ether/MeOH (3/1) to produce 1-(6-ethylamino-4,8-bis-methylamino-pyrimido[5,4-d]pyrimidin-2-ylamino)-butan-2-ol hydrochloride (147a) (120 mg, 77% yield). 400 MHz $^1$H NMR (CD$_3$OD, ppm): 3.76-3.64 (1H, m) 3.64-3.34 (4H, m) 3.11 (3H, s) 3.09 (3H, s) 1.67-1.54 (1H, m) 1.54-1.42 (1H, m) 1.26 (3H, t, J=6.5 Hz) 1.01 (3H, t, J=7.4 Hz). ESI-MS (m/z): 321 [M+H]$^+$; MP: 190-191° C.

Example 90: 2-Methyl-1-(4,6,8-tris-methylamino-pyrimido[5,4-d]pyrimidin-2-ylamino)-propan-2-ol (148) and Corresponding Hydrochloride Salt (148a)

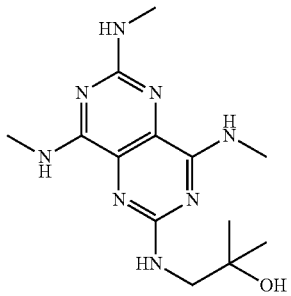

149

(a) 1-(6-Chloro-4,8-bis-methylamino-pyrimido[5,4-d]pyrimidin-2-ylamino)-2-methyl-propan-2-ol (148)

A mixture of 2,6-dichloro-N,N'-dimethyl-pyrimido[5,4-d]pyrimidine-4,8-diamine (88) (1.50 g, 5.79 mmol) and 1-amino-2-methyl-propan-2-ol (1.65 mL, 17.37 mmol) in n-butanol (10 mL) was heated at 90° C. for 40 h in a closed vial. Water (20 mL) was added and the resulting suspension was extracted with EtOAc (3×30 mL). The combined organic extracts were dried over solid anhydrous Na$_2$SO$_4$. After filtration, the solvent was removed and the residue was purified by flash column chromatography using gradient elution from $CH_2Cl_2$/EtOAc (9/1) to $CH_2Cl_2$/EtOAc (1/4) to afford 1-(6-chloro-4,8-bis-methylamino-pyrimido[5,4-d]pyrimidin-2-ylamino)-2-methyl-propan-2-ol (148) (1.47 g, 81% yield). 300 MHz $^1$H NMR (CDCl$_3$, ppm): 6.69-6.58 (1H, m) 6.58-6.46 (1H, m) 5.36 (1H, t, J=6.4 Hz) 4.02 (1H, s) 3.45 (2H, d, J=6.4 Hz) 3.13 (3H, d, J=5.2 Hz) 3.05 (3H, d, J=5.1 Hz) 1.28 (6H, s). ESI-MS (m/z): 312, 314 [M+H]$^+$.

(b) 2-Methyl-1-(4,6,8-tris-methylamino-pyrimido[5,4-d]pyrimidin-2-ylamino)-propan-2-ol (149)

A mixture of 1-(6-chloro-4,8-bis-methylamino-pyrimido[5,4-d]pyrimidin-2-yl amino)-2-methyl-propan-2-ol (148) (312 mg, 1.00 mmol) and methylamine (40% water solution) (2.30 mL) in n-butanol (7 mL) was heated at 120° C. for 48 h in a closed vial. Water (20 mL) was added and the resulting suspension was extracted with EtOAc (3×15 mL). Combined organic extracts were washed with water (30 mL), brine (30 mL) and dried over solid anhydrous Na$_2$SO$_4$. After filtration, the solvent was removed; the residue was purified by flash column chromatography using gradient elution from $CH_2Cl_2$/EtOAc (9/1) to $CH_2Cl_2$/EtOAc (1/4) to afford 2-methyl-1-(4,6,8-tris-methylamino-pyrimido[5,4-d]pyrimidin-2-ylamino)-propan-2-ol (149) (230 mg, 75% yield). 400 MHz $^1$H NMR (CDCl$_3$, ppm): 6.71-6.55 (1H, m) 6.24-6.09 (1H, m) 5.37 (1H, s) 5.09 (1H, t, J=6.3 Hz) 4.72-4.61 (1H, m) 3.40 (2H, d, J=6.3 Hz) 3.07 (3H, d, J=5.1 Hz) 3.04 (3H, d, J=5.1 Hz) 2.96 (3H, d, J=5.1 Hz) 1.26 (6H, s). ESI-MS (m/z): 307 [M+H]$^+$.

(c) 2-Methyl-1-(4,6,8-tris-methylamino-pyrimido[5,4-d]pyrimidin-2-ylamino)-propan-2-ol Hydrochloride (149a)

2-Methyl-1-(4,6,8-tris-methylamino-pyrimido[5,4-d]pyrimidin-2-ylamino)-propan-2-ol (149) (180 mg, 0.59 mmol)

was treated with 2M HCl/diethyl ether in diethyl ether/MeOH (10/1) to produce 2-methyl-1-(4,6,8-tris-methyl-amino-pyrimido[5,4-d]pyrimidin-2-ylamino)-propan-2-ol hydrochloride (149a) (145 mg, 72% yield). 400 MHz $^1$H NMR (CD$_3$OD, ppm): 3.51 (2H, s) 3.14 (3H, s) 3.13 (3H, s) 3.04 (3H, s) 1.26 (6H, s). ESI-MS (m/z): 307 [M+H]$^+$; MP: 214-215° C.

Comparative Example 91: (R)-1-(6-Amino-4,8-bis-methylamino-pyrimido[5,4-d]-pyrimidin-2-ylamino)-propan-2-ol (151) and Corresponding Hydrochloride Salt (151a)

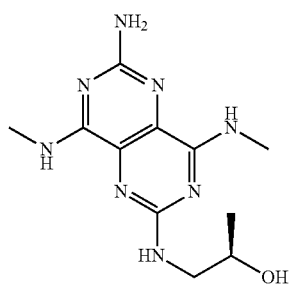

151

(a) 6-Chloro-N$^4$,N$^8$-dimethyl-pyrimido[5,4-d]py-rimidine-2,4,8-triamine (150)

A mixture of 2,6-dichloro-N,N'-dimethyl-pyrimido[5,4-d]pyrimidine-4,8-diamine (88) (800 mg, 3.09 mmol) and aqueous ammonia (25% solution) (1.00 mL) in n-butanol (10 mL) was heated at 100° C. for 48 h in a closed vial. An additional portion of aqueous ammonia (25% solution) (1.00 mL) was added and the heating was continued for another 48 h. The reaction mixture was cooled, and the precipitate were filtered, washed with water (2×30 mL) and dried over solid P$_2$O$_5$ to give 6-chloro-N$^4$,N$^8$-dimethyl-pyrimido[5,4-d]py-rimidine-2,4,8-triamine (150) (590 mg, 80% yield). 300 MHz $^1$H NMR (CDCl$_3$, ppm): 6.69 (1H, s) 6.59 (1H, s) 4.83 (2H, s) 3.13 (3H, d, J=5.2 Hz) 3.06 (3H, d, J=5.1 Hz). ESI-MS (m/z): 240, 242 [M+1-1]$^+$.

(b) (R)-1-(6-Amino-4,8-bis-methylamino-pyrimido[5,4-d]-pyrimidin-2-ylamino)-propan-2-ol (151)

6-Chloro-N$^4$,N$^8$-dimethyl-pyrimido[5,4-d]pyrimidine-2,4,8-triamine (150) (280 mg, 1.17 mmol) and (R)-1-amino-propan-2-ol were reacted in n-butanol and the crude product was purified by flash column chromatography using gradient elution from CHCl$_3$/EtOH (98/2) to CHCl$_3$/EtOH (96/4) to afford (R)-1-(6-amino-4,8-bis-methylamino-pyrimido[5,4-d]-pyrimidin-2-ylamino)-propan-2-ol (151) (170 mg, 52% yield). 300 MHz $^1$H NMR (CDCl$_3$, ppm): 6.61-6.46 (1H, m) 6.39-6.21 (1H, m) 5.31 (1H, t, J=5.9 Hz) 4.9-4.4 (1H, br s) 4.60 (2H, s) 4.04 (1H, dqd, J=7.1, 6.3, 2.5 Hz) 3.51 (1H, ddd, J=14.3, 6.3, 2.5 Hz) 3.36 (1H, ddd, J=14.3, 7.1, 6.1 Hz) 3.06 (3H, d, J=5.1 Hz) 3.04 (3H, d, J=5.1 Hz) 1.23 (3H, d, J=6.3 Hz). ESI-MS (m/z): 279 [M+H]$^+$.

(c) (R)-1-(6-Amino-4,8-bis-methylamino-pyrimido[5,4-d]-pyrimidin-2-ylamino)-propan-2-ol Hydrochloride (151a)

(R)-1-(6-Amino-4,8-bis-methylamino-pyrimido[5,4-d]-pyrimidin-2-ylamino)-propan-2-ol (151) (170 mg, 0.61 mmol) was treated with 2M HCl/diethyl ether in diethyl ether/MeOH (10/1) to produce (R)-1-(6-amino-4,8-bis-methylamino-pyrimido[5,4-d]-pyrimidin-2-ylamino)-propan-2-ol hydrochloride (151a) (150 mg, 78% yield). 300 MHz $^1$H NMR (CD$_3$OD, ppm): 4.03-3.90 (1H, m) 3.51 (1H, dd, J=13.7, 4.7 Hz) 3.40 (1H, dd, J=13.7, 6.9 Hz) 3.14 (3H, s) 3.09 (3H, s) 1.22 (3H, d, J=6.3 Hz). ESI-MS (m/z): 279 [M+H]$^+$; MP: 229-231° C.

Comparative Example 92: (S)-1-(6-Amino-4,8-bis-methylamino-pyrimido[5,4-d]-pyrimidin-2-ylamino)-propan-2-ol (152) and Corresponding Hydrochloride Salt (152a)

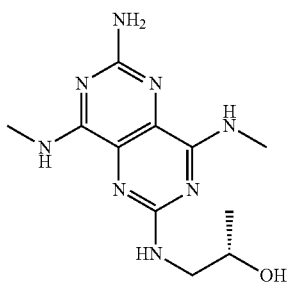

152

(a) (S)-1-(6-Amino-4,8-bis-methylamino-pyrimido[5,4-d]-pyrimidin-2-ylamino)-propan-2-ol (152)

6-Chloro-N$^4$,N$^8$-dimethyl-pyrimido[5,4-d]pyrimidine-2,4,8-triamine (150) (280 mg, 1.17 mmol) and (S)-1-amino-propan-2-ol were reacted in n-butanol and the crude product was purified by flash column chromatography using gradient elution from CH$_2$Cl$_2$/EtOH (99/1) to CH$_2$Cl$_2$/EtOH (9/1) to afford (S)-1-(6-amino-4,8-bis-methylamino-pyrimido[5,4-d]-pyrimidin-2-ylamino)-propan-2-ol (152) (165 mg, 51% yield). 300 MHz $^1$H NMR (CDCl$_3$, ppm): 6.59-6.48 (1H, m) 6.38-6.25 (1H, m) 5.16-5.04 (1H, m) 4.72 (1H, br s) 4.58 (2H, s) 4.09-3.98 (1H, m) 3.51 (1H, ddd, J=14.4, 6.3, 2.5 Hz) 3.36 (1H, ddd, J=14.4, 7.1, 6.1 Hz) 3.06 (3H, d, J=5.1 Hz) 3.04 (3H, d, J=5.1 Hz) 1.23 (3H, d, J=6.3 Hz). ESI-MS (m/z): 279 [M+H]$^+$.

(b) (S)-1-(6-Amino-4,8-bis-methylamino-pyrimido[5,4-d]-pyrimidin-2-ylamino)-propan-2-ol Hydrochloride (152a)

(S)-1-(6-Amino-4,8-bis-methylamino-pyrimido[5,4-d]-pyrimidin-2-ylamino)-propan-2-ol (152) (165 mg, 0.59 mmol) was treated with 2M HCl/diethyl ether in diethyl ether/MeOH (10/1) to produce (S)-1-(6-amino-4,8-bis-methylamino-pyrimido[5,4-d]-pyrimidin-2-ylamino)-propan-2-ol hydrochloride (152a) (150 mg, 80% yield). 400 MHz $^1$H NMR (CD$_3$OD, ppm): 4.00 (1H, dqd, J=7.0, 6.3, 4.3 Hz) 3.58 (1H, dd, J=13.7, 4.3 Hz) 3.44 (1H, dd, J=13.7, 7.0 Hz) 3.17 (3H, s) 3.16 (3H, s) 1.24 (3H, d, J=6.3 Hz). ESI-MS (m/z): 279 [M+H]$^+$; MP: 227-230° C.

Example 93: 2-(6-Allylamino-4,8-bis-methylamino-pyrimido[5,4-d]pyrimidin-2-ylamino)-ethanol (154) and Corresponding Hydrochloride Salt (154a)

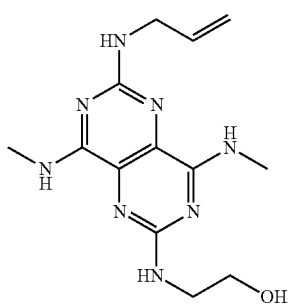

(a) $N^2$-Allyl-6-chloro-$N^4$,$N^8$-dimethyl-pyrimido[5,4-d]pyrimidine-2,4,8-triamine (153)

A mixture of 2,6-dichloro-N,N'-dimethyl-pyrimido[5,4-d]pyrimidine-4,8-diamine (88) (750 mg, 2.89 mmol) and allylamine (433 µL, 5.78 mmol) in 1,4-dioxane (5 mL) was heated at 100° C. for 18 h in a closed vial. After cooling, a saturated NaHCO$_3$ solution (20 mL) was added and the resulting suspension was extracted with EtOAc (3×30 mL). The combined organic extracts were dried over solid anhydrous Na$_2$SO$_4$. After filtration, the volatiles were evaporated, and the residue was purified by flash column chromatography using gradient elution from PE/EtOAc (9/1) to PE/EtOAc (1/2) to give $N^2$-allyl-6-chloro-$N^4$,$N^8$-dimethyl-pyrimido[5,4-d]pyrimidine-2,4,8-triamine (153) (760 mg, 94% yield). 300 MHz $^1$H NMR (CDCl$_3$, ppm): 6.79-6.65 (1H, m) 6.58-6.45 (1H, m) 5.97 (1H, ddt, J=17.2, 10.3, 5.4 Hz) 5.26 (1H, ddt, J=17.2, 1.6, 1.6 Hz) 5.14 (1H, ddt, J=10.3, 1.4, 1.4 Hz) 5.04 (1H, t, J=5.4 Hz) 4.11-4.04 (2H, m) 3.14 (3H, d, J=5.2 Hz) 3.04 (3H, d, J=5.1 Hz). ESI-MS (m/z): 280, 282 [M+H]$^+$.

(b) 2-(6-Allylamino-4,8-bis-methylamino-pyrimido[5,4-d]pyrimidin-2-ylamino)-ethanol (154)

$N^2$-Allyl-6-chloro-$N^4$,$N^8$-dimethyl-pyrimido[5,4-d]pyrimidine-2,4,8-triamine (153) (250 mg, 0.89 mmol) and 2-amino-ethanol were reacted in n-butanol to afford 2-(6-allylamino-4,8-bis-methylamino-pyrimido[5,4-d]pyrimidin-2-ylamino)-ethanol (154) (120 mg, 44% yield). 300 MHz $^1$H NMR (CDCl$_3$, ppm): 6.62-6.51 (1H, m) 6.31-6.17 (1H, m) 5.99 (1H, ddt, J=17.1, 10.3, 5.7 Hz) 5.25 (1H, ddt, J=17.1, 1.7, 1.7 Hz) 5.15-5.05 (2H, m) 4.76 (1H, t, J=5.7 Hz) 4.08-4.02 (2H, m) 3.86-3.80 (2H, m) 3.62-3.54 (2H, m) 3.06 (3H, d, J=5.2 Hz) 3.05 (3H, d, J=5.2 Hz). ESI-MS (m/z): 305 [M+1-1]$^+$.

(c) 2-(6-Allylamino-4,8-bis-methylamino-pyrimido[5,4-d]pyrimidin-2-ylamino)-ethanol Hydrochloride (154a)

2-(6-Allylamino-4,8-bis-methylamino-pyrimido[5,4-d]pyrimidin-2-ylamino)-ethanol (154) (120 mg, 0.39 mmol) was treated with 2M HCl/diethyl ether in diethyl ether/MeOH (1/1) to produce 2-(6-allylamino-4,8-bis-methylamino-pyrimido[5,4-d]pyrimidin-2-ylamino)-ethanol hydrochloride (154a) (110 mg, 83% yield). 300 MHz $^1$H NMR (CD$_3$OD, ppm): 5.98 (1H, ddt, J=17.1, 10.3, 5.7 Hz) 5.31-5.21 (1H, m) 5.17-5.10 (1H, m) 4.15-4.04 (2H, m) 3.77-3.71 (2H, m) 3.63-3.55 (2H, m) 3.09 (6H, s). ESI-MS (m/z): 305 [M+1-1]$^+$.

Example 94: (S)-1-[(6-Allylamino-4,8-bis-methyl-amino-pyrimido[5,4-d]-pyrimidin-2-yl)-propyl-amino]-propan-2-ol (155) and Corresponding Hydrochloride Salt (155a)

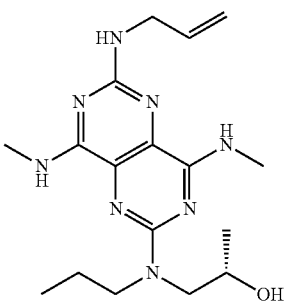

(a) (S)-1-(propylamino)propan-2-ol

Propionaldehyde (274 µL, 3.76 mmol) was added to the solution of (S)-1-amino-propan-2-ol in EtOH (5.0 mL) at 0° C., and the mixture was stirred at 0° C. for 45 min. After this time, NaBH$_4$ (259 mg, 6.84 mmol) was added in portions at 0° C. The reaction mixture was stirred for 18 h at room temperature. Water (4 mL) was added and the resulting suspension was extracted with EtOAc (3×10 mL). The combined organic extracts were washed with brine (20 mL) and dried over solid anhydrous Na$_2$SO$_4$. After filtration, the solvent was removed to give (S)-1-(propylamino)propan-2-ol (336 mg, 84% yield). 400 MHz $^1$H NMR (CDCl$_3$, ppm): 3.79-3.70 (1H, m) 3.21 (1H, br s) 2.70 (1H, dd, J=12.1, 3.2 Hz) 2.65-2.62 (1H, dt, J=11.6, 7.1 Hz) 2.55 (1H, dt, J=11.6, 7.1 Hz) 2.38 (1H, dd, J=12.1, 9.5 Hz) 1.49 (2H, sextet, J=7.4 Hz) 1.14 (3H, d, J=6.3 Hz) 0.92 (3H, t, J=7.4 Hz). ESI-MS (m/z): 118 [M+H]$^+$.

(b) (S)-1-[(6-Allylamino-4,8-bis-methylamino-pyrimido[5,4-d]-pyrimidin-2-yl)-propyl-amino]-propan-2-ol (155)

A mixture of $N^2$-allyl-6-chloro-$N^4$,$N^8$-dimethyl-pyrimido[5,4-d]pyrimidine-2,4,8-triamine (153) (250 mg, 0.89 mmol), (S)-1-(propylamino)propan-2-ol (313 mg, 2.67 mmol) and N,N-diisopropylethylamine (295 µL, 1.78 mmol) in n-butanol (5 mL) was heated at 125° C. for 100 h. After cooling, saturated NaHCO$_3$ solution (20 mL) was added and the resulting suspension was extracted with EtOAc (3×20 mL). The combined organic extracts were washed with water (30 mL), then with a brine solution (30 mL) and dried over solid anhydrous MgSO$_4$. After filtration, the solvent was removed and the residue was purified by flash column chromatography using gradient elution from PE/EtOAc (9/1) to PE/EtOAc (2/1) to obtain (S)-1-[(6-allylamino-4,8-bis-methylamino-pyrimido[5,4-d]-pyrimidin-2-yl)-propyl-amino]-propan-2-ol (155) (135 mg, 42% yield). 300 MHz $^1$H NMR (CDCl$_3$, ppm): 6.49 (1H, br s) 6.21 (1H, br s) 6.06-5.90 (2H, m) 5.30-5.20 (1H, m) 5.15-5.07 (1H, m) 4.76-4.66 (1H, m) 4.17-3.99 (3H, m) 3.78 (1H, dd, J=14.8, 7.9 Hz) 3.73-3.59 (1H, m) 3.54-3.42 (1H, m) 3.37 (1H, dd, J=14.8, 1.2 Hz) 3.07 (6H, d, J=5.1 Hz) 1.75-1.60 (2H, m) 1.22 (3H, d, J=6.3 Hz) 0.93 (3H, t, J=7.4 Hz). ESI-MS (m/z): 361 [M+H]$^+$.

(c) (S)-1-[(6-Allylamino-4,8-bis-methylamino-pyrimido[5,4-d]-pyrimidin-2-yl)-propyl-amino]-propan-2-ol Hydrochloride (155a)

(S)-1-[(6-Allylamino-4,8-bis-methylamino-pyrimido[5,4-d]-pyrimidin-2-yl)-propyl-amino]-propan-2-ol (155) (125 mg, 0.35 mmol) was treated with 2M HCl/diethyl ether in diethyl ether to produce (S)-1-[(6-allylamino-4,8-bis-methylamino-pyrimido[5,4-d]-pyrimidin-2-yl)-propyl-amino]-propan-2-ol hydrochloride (155a) (120 mg, 86% yield). 300 MHz $^1$H NMR (CD$_3$OD, ppm): 5.98 (1H, ddt, J=17.2, 10.4, 5.1 Hz) 5.29 (1H, ddt, J=17.2, 1.5, 1.5 Hz) 5.18 (1H, ddt, J=10.4, 1.5, 1.5 Hz) 4.22-4.08 (3H, m) 3.76-3.50 (4H, m) 3.15 (3H, s) 3.09 (3H, s) 1.78-1.61 (2H, m) 1.22 (3H, d, J=6.4 Hz) 0.95 (3H, t, J=7.4 Hz). ESI-MS (m/z): 361 [M+H]$^+$; MP: 198-200° C.

Example 95: (S)-1-[(6-Allylamino-4,8-bis-methyl-amino-pyrimido[5,4-d]pyrimidin-2-yl)-methyl-amino]-propan-2-ol (156) and Corresponding Hydrochloride Salt (156a)

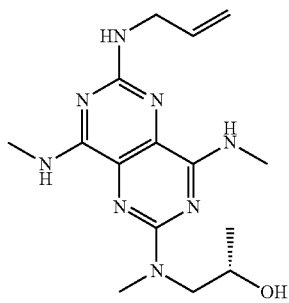

156

(a) (S)-ethyl 2-((2-hydroxypropyl)amino)acetate

To the solution of (S)-1-amino-propan-2-ol (414 μL, 5.26 mmol) in 1,4-dioxane (5.0 mL) 5M NaOH (1.18 mL, 5.92 mmol) and ethyl chloroformate (564 μL, 5.92 mmol) were added and the mixture was stirred at room temperature for 30 min. Water (15 mL) was added and the resulting suspension was extracted with EtOAc (3×10 mL). The combined organic extracts were washed with a brine solution (20 mL) and dried over solid anhydrous Na$_2$SO$_4$. After filtration, the solvent was removed to give (S)-ethyl 2-((2-hydroxypropyl)amino)acetate (734 mg, 95% yield). 300 MHz $^1$H NMR (CDCl$_3$, ppm): 5.12 (1H, br s) 4.16-4.06 (2H, m) 3.96-3.83 (1H, m) 3.31 (1H, ddd, J=14.0, 6.5, 3.1 Hz) 3.03 (1H, ddd, J=14.0, 7.5, 5.5 Hz) 2.7-2.2 (1H, br s) 1.28-1.20 (6H, m) 1.17 (3H, d, J=6.3 Hz). ESI-MS (m/z): 148 [M+1-1]$^+$.

(b) (S)-1-(methylamino)propan-2-ol

LiAlH$_4$ (379 mg, 9.97 mmol) was added to a solution of (S)-ethyl 2-((2-hydroxypropyl)-amino)acetate (734 mg, 4.99 mmol) in THF (10 mL). The mixture was refluxed for 2h and after cooling, a 15% NaOH water solution (1.2 mL) was added. The resultant precipitate was filtered and washed successively with THF, CH$_2$Cl$_2$ and diethyl ether (each 10 mL). The filtrate was evaporated to give (S)-1-(methyl-amino)propan-2-ol (289 mg, 65% yield). 300 MHz $^1$H NMR (CDCl$_3$, ppm): 3.86-3.74 (1H, m) 2.64 (1H, dd, J=12.0, 3.1 Hz) 2.44 (3H, s) 2.4 (1H, dd, J=12.0, 9.4 Hz) 1.16 (3H, d, J=6.3 Hz). ESI-MS (m/z): 90 [M+H]$^+$.

(c) (S)-1-[(6-Allylamino-4,8-bis-methylamino-pyrimido[5,4-d]pyrimidin-2-yl)-methyl-amino]-propan-2-ol (156)

$N^2$-Allyl-6-chloro-$N^4$,$N^8$-dimethyl-pyrimido[5,4-d]pyrimidine-2,4,8-triamine (153) (253 mg, 0.90 mmol) (S)-1-(methylamino)propan-2-ol were reacted in n-butanol to afford (5)-1-[(6-allylamino-4,8-bis-methylamino-pyrimido[5,4-d]pyrimidin-2-yl)-methyl-amino]-propan-2-ol (156) (130 mg, 43% yield). 300 MHz $^1$H NMR (CDCl$_3$, ppm): 6.68-6.46 (1H, br s) 6.43-6.27 (1H, br s) 5.98 (1H, ddt, J=17.4, 10.3, 5.6 Hz) 5.26 (1H, ddt, J=17.4, 1.7, 1.7 Hz) 5.12 (1H, ddt, J=10.3, 1.5, 1.5 Hz) 4.93-4.65 (1H, br s) 4.17-4.09 (1H, m) 4.08-4.03 (2H, m) 3.75 (1H, dd, J=14.7, 7.4 Hz) 3.47 (1H, dd, J=14.7, 2.2 Hz) 3.21 (3H, s) 3.07 (6H, d, J=5.1 Hz) 1.23 (3H, d, J=6.3 Hz). ESI-MS (m/z): 333 [M+H]$^+$.

(d) (S)-1-[(6-Allylamino-4,8-bis-methylamino-pyrimido[5,4-d]pyrimidin-2-yl)-methyl-amino]-propan-2-ol Hydrochloride (156a)

(S)-1-[(6-Allylamino-4,8-bis-methylamino-pyrimido[5,4-d]pyrimidin-2-yl)-methyl-amino]-propan-2-ol (156) (130 mg, 0.39 mmol) was treated with 2M HCl/diethyl ether in diethyl ether/ethanol (5/2) to produce (S)-1-[(6-allylamino-4,8-bis-methylamino-pyrimido[5,4-d]pyrimidin-2-yl)-methyl-amino]-propan-2-ol hydrochloride (156a) (110 mg, 76% yield). 300 MHz $^1$H NMR (CD$_3$OD, ppm): 5.98 (1H, ddt, J=17.2, 10.3, 5.4 Hz) 5.29 (1H, ddt, J=17.2, 1.7, 1.7 Hz) 5.18 (1H, ddt, J=10.3, 1.5, 1.5 Hz) 4.17-4.10 (3H, m) 3.71-3.61 (2H, m) 3.28 (3H, s) 3.15 (3H, s) 3.09 (3H, s) 1.22 (3H, d, J=6.3 Hz). ESI-MS (m/z): 333 [M+H]$^+$; MP: 218-220° C.

Example 96: (R)-1-[6-(2-Methyl-allylamino)-4,8-bis-methylamino-pyrimido[5,4-d]-pyrimidin-2-ylamino]-propan-2-ol (158) and Corresponding Hydrochloride Salt (158a)

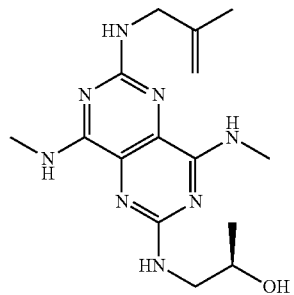

158

(a) 6-Chloro-$N^4$,$N^8$-dimethyl-$N^2$-(2-methylallyl) pyrimido[5,4-d]pyrimidine-2,4,8-triamine (157)

A mixture of 2,6-dichloro-N,N'-dimethyl-pyrimido[5,4-d] pyrimidine-4,8-diamine (88) (700 mg, 2.70 mmol), 2-methyl-allylamine (294 μL, 3.24 mmol) and N,N-diisopropyl ethylamine (560 μL, 3.24 mmol) in n-butanol (8 mL) was heated at 90° C. for 48 h. An additional portion of 2-methyl-allylamine (100 μL, 1.10 mmol) was added and the mixture was heated at 90° C. for 24 h. After cooling, water (30 mL) was added and the resulting suspension was extracted with EtOAc (3×30 mL). The combined organic extracts were washed with a brine solution (30 mL) and dried over solid anhydrous MgSO$_4$. After filtration, the solvent was removed; the residue filtered through silica gel using PE/EtOAc (1/1) to give 6-chloro-$N^4$,$N^8$-dimethyl-$N^2$-(2-methylallyl)pyrimido[5,4-d]pyrimidine-2,4,8-triamine (157) (650 mg, 82% yield). 300 MHz $^1$H NMR (CDCl$_3$, ppm): 6.77-6.63 (1H, m) 6.58-6.45 (1H, m) 5.06 (1H, t, J=6.0 Hz) 4.96-4.91 (1H, m) 4.87-4.83 (1H, m) 4.03-3.98 (2H, m) 3.14 (3H, d, J=5.2 Hz) 3.05 (3H, d, J=5.1 Hz) 1.81-1.78 (3H, m). ESI-MS (m/z): 294, 296 [M+H]$^+$.

(b) (R)-1-[6-(2-Methyl-allylamino)-4,8-bis-methyl-amino-pyrimido[5,4-d]-pyrimidin-2-ylamino]-propan-2-ol (158)

6-Chloro-$N^4$,$N^8$-dimethyl-$N^2$-(2-methylallyl)pyrimido[5,4-d]pyrimidine-2,4,8-triamine (157) (325 mg, 1.11 mmol) and (R)-1-amino-propan-2-ol were reacted in n-butanol and the crude product was purified by flash column chromatography using gradient elution from CHCl$_3$/MeOH (99/1) to CHCl$_3$/EtOH (97/3) to obtain (R)-1-[6-(2-methyl-allylamino)-4,8-bis-methylamino-pyrimido[5,4-d]-pyrimidin-2-ylamino]-propan-2-ol (158) (185 mg, 50% yield). 300 MHz $^1$H NMR (CDCl$_3$, ppm): 6.63-6.48 (1H, m) 6.29-6.12 (1H, m) 5.11-5.01 (1H, m) 4.96-4.91 (1H, m) 4.86-4.81 (1H, m) 4.81-4.73 (1H, m) 4.09-3.95 (1H, m) 3.98 (2H, d, J=6.0 Hz) 3.50 (1H, ddd, J=14.4, 6.3, 2.5 Hz) 3.41-3.30 (1H, m) 3.06 (3H, d, J=5.2 Hz) 3.05 (3H, d, J=5.2 Hz) 1.80 (3H, s) 1.22 (3H, d, J=6.3 Hz). ESI-MS (m/z): 333 [M+H]$^+$.

(c) (R)-1-[6-(2-Methyl-allylamino)-4,8-bis-methyl-amino-pyrimido[5,4-d]-pyrimidin-2-ylamino]-propan-2-ol Hydrochloride (158a)

(R)-1-[6-(2-Methyl-allylamino)-4,8-bis-methylamino-pyrimido[5,4-d]-pyrimidin-2-ylamino]-propan-2-ol (158) (180 mg, 0.54 mmol) was treated with 2M HCl/diethyl ether in diethyl ether/methanol (2/1) to produce (R)-1-[6-(2-methyl-allylamino)-4,8-bis-methylamino-pyrimido[5,4-d]-pyrimidin-2-ylamino]-propan-2-ol hydrochloride (158a) (175 mg, 88% yield). 300 MHz $^1$H NMR (D$_2$O, ppm): 4.97-4.90 (2H, m) 4.14-4.04 (1H, m) 4.04-3.99 (2H, m) 3.52 (1H, dd, J=14.0, 4.5 Hz) 3.44 (1H, dd, J=14.0, 7.0 Hz) 3.08 (3H, s) 3.07 (3H, s) 1.81 (3H, s) 1.25 (3H, d, J=6.4 Hz). ESI-MS (m/z): 333 [M+H]$^+$.

Example 97: (S)-1-[6-(2-Methyl-allylamino)-4,8-bis-methylamino-pyrimido[5,4-d]-pyrimidin-2-ylamino]-propan-2-ol (159) and Corresponding Hydrochloride Salt (159a)

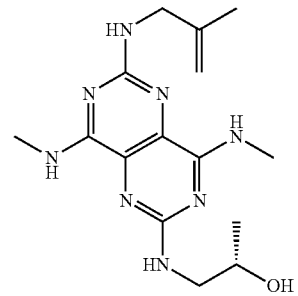

159

(a) (S)-1-[6-(2-Methyl-allylamino)-4,8-bis-methyl-amino-pyrimido[5,4-d]-pyrimidin-2-ylamino]-propan-2-ol (159)

6-Chloro-$N^4$,$N^8$-dimethyl-$N^2$-(2-methylallyl)pyrimido[5,4-d]pyrimidine-2,4,8-triamine (157) (325 mg, 1.11 mmol) and (S)-1-amino-propan-2-ol were reacted in n-butanol and the crude product was purified by flash column chromatography using gradient elution from CHCl$_3$/MeOH (99/1) to CHCl$_3$/EtOH (97/3) to afford (S)-1-[6-(2-methyl-allylamino)-4,8-bis-methylamino-pyrimido[5,4-d]-pyrimidin-2-ylamino]-propan-2-ol (159) (185 mg, 50% yield). 300 MHz $^1$H NMR (CDCl$_3$, ppm): 6.62-6.47 (1H, m) 6.26-6.13 (1H, m) 5.05 (1H, t, J=6.1 Hz) 4.96-4.91 (1H, m) 4.85-4.81 (1H, m) 4.78 (1H, t, J=5.9 Hz) 4.09-3.95 (1H, m) 3.98 (2H, d, J=6.1 Hz) 3.50 (1H, ddd, J=14.3, 6.3, 2.5 Hz) 3.41-3.30 (1H, m) 3.06 (3H, d, J=5.2 Hz) 3.05 (3H, d, J=5.2 Hz) 1.81-1.78 (3H, m) 1.22 (3H, d, J=6.3 Hz). ESI-MS (m/z): 333 [M+H]$^+$.

(b) (S)-1-[6-(2-Methyl-allylamino)-4,8-bis-methyl-amino-pyrimido[5,4-d]-pyrimidin-2-ylamino]-propan-2-ol Hydrochloride (159a)

(S)-1-[6-(2-Methyl-allylamino)-4,8-bis-methylamino-pyrimido[5,4-d]-pyrimidin-2-ylamino]-propan-2-ol (159) (180 mg, 0.54 mmol) was treated with 2M HCl/diethyl ether in diethyl ether/methanol (2/1) to produce (S)-1-[6-(2-methyl-allylamino)-4,8-bis-methylamino-pyrimido[5,4-d]-pyrimidin-2-ylamino]-propan-2-ol hydrochloride (159a) (185 mg, 93% yield). 300 MHz $^1$H NMR (D$_2$O, ppm): 4.97-4.90 (2H, s) 4.13-4.03 (1H, m) 4.03-3.95 (2H, m) 3.55-3.35 (2H, m) 3.05 (6H, s) 1.81 (3H, s) 1.25 (3H, d, J=6.3 Hz). ESI-MS (m/z): 333 [M+H]$^+$; MP: 201-203° C.

Example 98: 2-(4,8-Bis-ethylamino-6-propylamino-pyrimido[5,4-d]pyrimidin-2-ylamino)-ethanol (162) and Corresponding Hydrochloride Salt (162a)

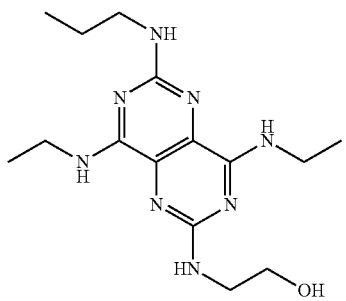

162

(a) 2,6-Dichloro-N,N'-diethyl-pyrimido[5,4-d]pyrimidine-4,8-diamine (160)

2M Ethylamine/THF (27 mL, 54.00 mmol) was added dropwise to a solution of 2,4,6,8-tetrachloro-pyrimido[5,4-d]pyrimidine (1) (3.00 g, 11.15 mmol) in THF (150 mL) at 0° C. The reaction mixture was stirred at room temperature for 2 h. The volatiles were removed and the residue was suspended in water (50 mL). The resultant the precipitate were filtered, washed with water (2×30 mL) and dried over solid $P_2O_5$ to give 2,6-dichloro-N,N'-diethyl-pyrimido[5,4-d]pyrimidine-4,8-diamine (160) (2.93 g, 92% yield). 300 MHz $^1$H NMR (DMSO-$d_6$, ppm): 8.68 (2H, t, J=5.9 Hz) 3.52-3.40 (4H, m) 1.16 (6H, t, J=7.1 Hz). ESI-MS (m/z): 287, 289, 291 [M+H]$^+$.

(b) 6-Chloro-N$^4$,N$^8$-diethyl-N$^2$-propyl-pyrimido[5,4-d]pyrimidine-2,4,8-triamine (161)

A mixture of 2,6-dichloro-N,N'-diethyl-pyrimido[5,4-d]pyrimidine-4,8-diamine (160) (420 mg, 1.46 mmol) and propylamine (720 µL, 8.76 mmol) in n-butanol (5 mL) was heated at 90° C. for 24 h. After cooling, a saturated NaHCO$_3$ solution (15 mL) was added and the resulting suspension was extracted with EtOAc (3×20 mL). The combined organic extracts were washed with water (30 mL), then with a brine (30 mL) solution and dried over solid anhydrous Na$_2$SO$_4$. After filtration, the solvent was removed to give 6-chloro-N$^4$,N$^8$-diethyl-N$^2$-propylpyrimido[5,4-d]pyrimidine-2,4,8-triamine (161) (450 mg, 99% yield). 300 MHz $^1$H NMR (CDCl$_3$, ppm): 6.66 (1H, t, J=5.9 Hz) 6.46 (1H, t, J=5.9 Hz) 4.93 (1H, t, J=6.0 Hz) 3.61 (2H, qd, J=7.3, 5.9 Hz) 3.52 (2H, qd, J=7.3, 5.9 Hz) 3.38 (2H, td, J=7.1, 6.0 Hz) 1.71-1.55 (2H, m) 1.32 (3H, t, J=7.3 Hz) 1.28 (3H, t, J=7.3 Hz) 1.00 (3H, t, J=7.5 Hz). ESI-MS (m/z): 310, 312 [M+H]$^+$.

(c) 2-(4,8-Bis-ethylamino-6-propylamino-pyrimido[5,4-d]pyrimidin-2-ylamino)-ethanol (162)

A mixture of 6-chloro-N$^4$,N$^8$-diethyl-N$^2$-propyl-pyrimido[5,4-d]pyrimidine-2,4,8-triamine (161) (225 mg, 0.73 mmol) and 2-amino-ethanol (176 µL, 2.92 mmol) in n-butanol (3 mL) was heated at 120° C. for 24h in a closed vial. An additional portion of 2-amino-ethanol (176 µL, 2.92 mmol) was added and heating was continued for another 24 h. After cooling, water (10 mL) and a saturated NaHCO$_3$ solution (10 mL) was added. The resulting suspension was extracted with EtOAc (3×20 mL). The combined organic extracts were washed with a brine solution (30 mL) and dried over solid anhydrous Na$_2$SO$_4$. After filtration, the solvent was removed and the residue was purified by flash column chromatography using gradient elution from CH$_2$Cl$_2$/EtOH (99/1) to CH$_2$Cl$_2$/EtOH (97/3) to give 2-(4,8-bis-ethylamino-6-propylamino-pyrimido[5,4-d]pyrimidin-2-ylamino)-ethanol (162) (165 mg, 68% yield). 300 MHz $^1$H NMR (CDCl$_3$, ppm): 6.53 (1H, br s) 6.18 (1H, br s) 5.04 (1H, t, J=5.0 Hz) 4.76-4.46 (2H, m) 3.86-3.80 (2H, m) 3.61-3.46 (6H, m) 3.36 (2H, td, J=7.0, 6.1 Hz) 1.70-1.55 (2H, m) 1.30 (3H, t, J=7.2 Hz) 1.28 (3H, t, J=7.2 Hz) 0.99 (3H, t, J=7.3 Hz). ESI-MS (m/z): 335 [M+H]$^+$.

(d) 2-(4,8-Bis-ethylamino-6-propylamino-pyrimido[5,4-d]pyrimidin-2-ylamino)-ethanol Hydrochloride (162a)

2-(4,8-Bis-ethylamino-6-propylamino-pyrimido[5,4-d]pyrimidin-2-ylamino)-ethanol (162) (155 mg, 0.46 mmol) was treated with 2M HCl/diethyl ether in diethyl ether/ethanol (2/1) to produce 2-(4,8-bis-ethylamino-6-propylamino-pyrimido[5,4-d]pyrimidin-2-ylamino)-ethanol hydrochloride (162a) (165 mg, 97% yield). 300 MHz $^1$H NMR (CD$_3$OD, ppm): 3.73 (2H, t, J=5.6 Hz) 3.69-3.56 (6H, m) 3.44 (2H, t, J=7.1 Hz) 1.68 (2H, sextet, J=7.4 Hz) 1.32 (6H, t, J=7.2 Hz) 1.00 (3H, t, J=7.4 Hz). ESI-MS (m/z): 335 [M+H]$^+$; MP: 183-184° C.

Example 99: 1-(4,8-Bis-ethylamino-6-propylamino-pyrimido[5,4-d]pyrimidin-2-ylamino)-2-methyl-propan-2-ol (163) and Corresponding Hydrochloride Salt (163a)

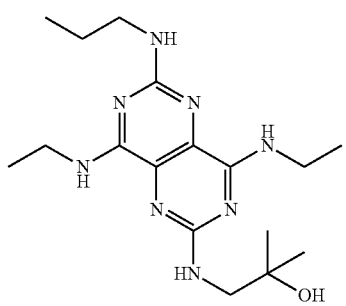

163

(a) 1-(4,8-Bis-ethylamino-6-propylamino-pyrimido[5,4-d]pyrimidin-2-ylamino)-2-methyl-propan-2-ol (163)

A mixture of 6-chloro-N$^4$,N$^8$-diethyl-N$^2$-propyl-pyrimido[5,4-d]pyrimidine-2,4,8-triamine (161) (200 mg, 0.65 mmol) and 1-amino-2-methyl-propan-2-ol (232 mg, 2.60 mmol) in n-butanol (4 mL) was heated at 120° C. for 48 h in a closed vial. An additional portion of 1-amino-2-methyl-propan-2-ol (232 mg, 2.60 mmol) was added and heating was continued for another 48 h. After cooling, a saturated NaHCO$_3$ solution (20 mL) was added and the resulting suspension was extracted with EtOAc (3×20 mL). The combined organic extracts were washed with a brine (30 mL) solution and dried over solid anhydrous Na$_2$SO$_4$. After filtration, the solvent was removed; the residue was purified by flash column chromatography using gradient elution from CH₂Cl₂ to CH₂Cl₂/EtOH (98/2) to obtain 1-(4,8-bis-ethyl-amino-6-propylamino-pyrimido[5,4-d]pyrimidin-2-ylamino)-2-methyl-propan-2-ol (163) (180 mg, 76% yield). 300 MHz ¹H NMR (CDCl₃, ppm): 6.53 (1H, s) 6.15 (1H, s) 5.24 (1H, br s) 5.09-4.97 (1H, m) 4.70-4.60 (1H, m) 3.58-3.46 (4H, m) 3.39 (2H, d, J=6.4 Hz) 3.39-3.31 (2H, m) 1.63 (2H, sextet, J=7.4 Hz) 1.34-1.23 (6H, m) 1.26 (6H, s) 0.99 (6H, t, J=7.4 Hz). ESI-MS (m/z): 363 [M+H]⁺.

(b) 1-(4,8-Bis-ethylamino-6-propylamino-pyrimido[5,4-d]pyrimidin-2-ylamino)-2-methyl-propan-2-ol Hydrochloride (163a)

1-(4,8-Bis-ethylamino-6-propylamino-pyrimido[5,4-d]pyrimidin-2-ylamino)-2-methyl-propan-2-ol (163) (170 mg, 0.47 mmol) was treated with 2M HCl/diethyl ether in diethyl ether/MeOH (20/1) to produce 1-(4,8-bis-ethylamino-6-propylamino-pyrimido[5,4-d]pyrimidin-2-ylamino)-2-methyl-propan-2-ol hydrochloride (163a) (145 mg, 77% yield). 300 MHz ¹H NMR (CD₃OD, ppm): 3.70-3.53 (4H, m) 3.48 (2H, s) 3.42 (2H, t, J=7.2 Hz) 1.75-1.60 (2H, m) 1.35-1.27 (6H, m) 1.25 (6H, s) 1.00 (3H, t, J=7.4 Hz). ESI-MS (m/z): 363 [M+H]⁺; MP: 182-183° C.

Example 100: (S)-1-(4,6,8-Tris-ethylamino-pyrimido[5,4-d]pyrimidin-2-ylamino)-propan-2-ol (165) and Corresponding Hydrochloride Salt (165a)

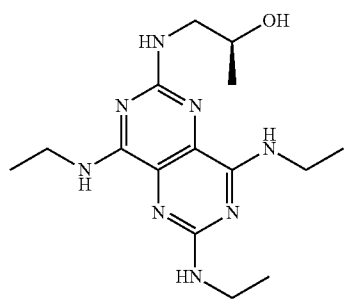

165

(a) (S)-1-((6-Chloro-4,8-bis(ethylamino)pyrimido[5,4-d]pyrimidin-2-yl)amino)propan-2-ol (164)

A mixture of 2,6-dichloro-N,N'-diethyl-pyrimido[5,4-d]pyrimidine-4,8-diamine (160) (500 mg, 1.74 mmol), (S)-1-amino-propan-2-ol (207 mg, 2.76 mmol) and N,N-diisopropyl ethylamine (301 µL, 1.74 mmol) in n-butanol (5 mL) was heated at 75° C. for 48 h. After cooling, a saturated NaHCO₃ solution (20 mL) was added and the resulting suspension was extracted with EtOAc (3×20 mL). The combined organic extracts were washed with a brine solution (30 mL) and dried over solid anhydrous MgSO₄. After filtration, the solvent was removed; the residue was purified by flash column chromatography using gradient elution from PE/acetone (9/1) to PE/acetone (3/1) to give (S)-1-((6-chloro-4,8-bis(ethylamino)pyrimido[5,4-d]pyrimidin-2-yl)amino)propan-2-ol (164) (330 mg, 58% yield). 300 MHz ¹H NMR (CDCl₃, ppm): 6.63-6.47 (2H, m) 5.30 (1H, t, J=6.1 Hz) 4.11-3.99 (1H, m) 3.70 (1H, br s) 3.60 (2H, qd, J=7.3, 5.9 Hz) 3.59-3.52 (1H, m) 3.52 (2H, qd, J=7.3, 5.8 Hz) 3.36 (1H, ddd, J=14.2, 7.2, 6.1 Hz) 1.31 (3H, t, J=7.3 Hz) 1.29 (3H, t, J=7.3 Hz) 1.25 (3H, d, J=6.3 Hz). ESI-MS (m/z): 326, 328 [M+1-1]⁺.

(b) (S)-1-(4,6,8-Tris-ethylamino-pyrimido[5,4-d]pyrimidin-2-ylamino)-propan-2-ol (165)

A mixture of (S)-1-((6-chloro-4,8-bis(ethylamino)pyrimido[5,4-d]pyrimidin-2-yl)amino)propan-2-ol (164) (160 mg, 0.49 mmol) and ethylamine (70% water solution) (0.8 mL) in n-butanol (3 mL) was heated at 120° C. for 48 h in a closed vial. After cooling, a saturated NaHCO₃ solution (10 mL) was added and the resulting suspension was extracted with EtOAc (3×20 mL). The combined organic extracts were washed with a brine solution (30 mL) and dried over solid anhydrous Na₂SO₄. After filtration, the solvent was removed; the residue was purified by flash column chromatography using gradient elution from PE/acetone (9/1) to PE/acetone (1/1) to obtain (S)-1-(4,6,8-Tris-ethylamino-pyrimido[5,4-d]pyrimidin-2-ylamino)-propan-2-ol (165) (95 mg, 58% yield). 300 MHz ¹H NMR (CDCl₃, ppm): 6.61-6.43 (1H, m) 6.25-6.10 (1H, m) 5.10-4.87 (2H, m) 4.67-4.53 (1H, m) 4.08-3.97 (1H, m) 3.59-3.27 (8H, m) 1.30 (3H, t, J=7.0 Hz) 1.27 (3H, t, J=7.0 Hz) 1.23 (3H, t, J=7.2 Hz) 1.22 (3H, d, J=6.3 Hz). ESI-MS (m/z): 335 [M+H]⁺.

(c) (S)-1-(4,6,8-Tris-ethylamino-pyrimido[5,4-d]pyrimidin-2-ylamino)-propan-2-ol Hydrochloride (165a)

(S)-1-(4,6,8-Tris-ethylamino-pyrimido[5,4-d]pyrimidin-2-ylamino)-propan-2-ol (165) (95 mg, 0.28 mmol) was treated with 2M HCl/diethyl ether in diethyl ether/EtOH (1/1) to produce (S)-1-(4,6,8-tris-ethylamino-pyrimido[5,4-d]pyrimidin-2-ylamino)-propan-2-ol hydrochloride (165a) (105 mg, 100% yield). 300 MHz ¹H NMR (CD₃OD, ppm): 4.04-3.91 (1H, m) 3.65 (2H, q, J=7.3 Hz), 3.63 (2H, q, J=7.3 Hz) 3.5.7-3.46 (3H, m) 3.40 (1H, dd, J=13.7, 7.0 Hz) 1.33 (6H, t, J=7.3 Hz) 1.27 (3H, t, J=7.2 Hz) 1.24 (3H, d, J=6.3 Hz). ESI-MS (m/z): 335 [M+H]⁺; MP: 193-195° C.

Example 101: (S)-1-(4,8-Bis-ethylamino-6-propylamino-pyrimido[5,4-d]-pyrimidin-2-ylamino)-propan-2-ol (166) and Corresponding Hydrochloride Salt (166a)

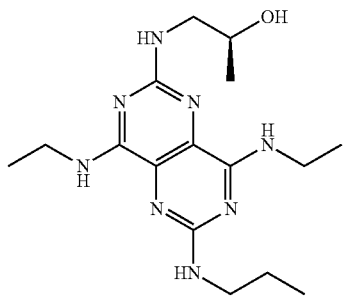

166

(a) (S)-1-(4,8-Bis-ethylamino-6-propylamino-pyrimido[5,4-d]-pyrimidin-2-ylamino)-propan-2-ol (166)

A mixture of (S)-1-((6-chloro-4,8-bis(ethylamino)pyrimido[5,4-d]pyrimidin-2-yl)amino)propan-2-ol (164) (160 mg, 0.49 mmol) and propylamine (403 µL, 4.90 mmol) in n-butanol (3 mL) was heated at 120° C. for 24h in a closed vial. An additional portion of propylamine (200 μL, 2.45 mmol) was added and heating was continued for another 24h. After cooling, a saturated NaHCO$_3$ solution (10 mL) was added and the resulting suspension was extracted with EtOAc (3×20 mL). The combined organic extracts were washed with a brine solution (30 mL) and dried over solid anhydrous Na$_2$SO$_4$. After filtration, the solvent was removed; the residue was purified by flash column chromatography using gradient elution from PE/acetone (9/1) to PE/acetone (1/1) to obtain (S)-1-(4,8-bis-ethylamino-6-propylamino-pyrimido[5,4-d]-pyrimidin-2-ylamino)-propan-2-ol (166) (110 mg, 64% yield). 300 MHz $^1$H NMR (CDCl$_3$, ppm): 6.60-6.46 (1H, m) 6.24-6.12 (1H, m) 5.10-4.90 (2H, m) 4.72-4.60 (1H, m) 4.10-3.96 (1H, m) 3.58-3.45 (5H, m) 3.40-3.25 (3H, m) 1.71-1.55 (2H, m) 1.30 (3H, t, J=7.2 Hz) 1.27 (3H, t, J=7.2 Hz) 1.22 (3H, d, J=6.3 Hz) 0.99 (3H, t, J=7.4 Hz). ESI-MS (m/z): 349 [M+H]$^+$.

(b) (S)-1-(4,8-Bis-ethylamino-6-propylamino-pyrimido[5,4-d]-pyrimidin-2-ylamino)-propan-2-ol Hydrochloride (166a)

(S)-1-(4,8-Bis-ethylamino-6-propylamino-pyrimido[5,4-d]-pyrimidin-2-ylamino)-propan-2-ol (166) (100 mg, 0.29 mmol) was treated with 2M HCl/diethyl ether in diethyl ether/EtOH (1/1) to produce (S)-1-(4,8-bis-ethylamino-6-propylamino-pyrimido[5,4-d]-pyrimidin-2-ylamino)-propan-2-ol hydrochloride (166a) (100 mg, 90% yield). 300 MHz $^1$H NMR (CD$_3$OD, ppm): 4.04-3.90 (1H, m) 3.69-3.55 (4H, m) 3.55-3.34 (4H, m) 1.76-1.59 (2H, m) 1.31 (6H, t, J=7.3 Hz) 1.22 (3H, d, J=6.4 Hz) 1.00 (3H, t, J=7.4 Hz). ESI-MS (m/z): 349 [M+H]$^+$.

Example 102: (R)-1-(4,6,8-Tris-ethylamino-pyrimido[5,4-d]pyrimidin-2-ylamino)-propan-2-ol (168) and Corresponding Hydrochloride Salt (168a)

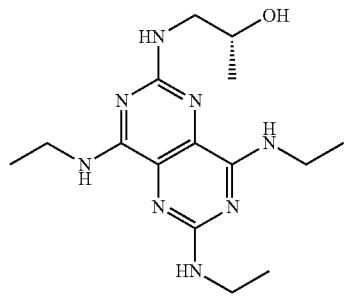

168

(a) (R)-1-((6-Chloro-4,8-bis(ethylamino)pyrimido[5,4-d]pyrimidin-2-yl)amino)propan-2-ol (167)

A mixture of 2,6-dichloro-N,N'-diethyl-pyrimido[5,4-d]pyrimidine-4,8-diamine (160) (300 mg, 1.04 mmol), (R)-1-amino-propan-2-ol (157 mg, 2.09 mmol) in n-butanol (5 mL) was heated at 100° C. for 18 h. After cooling, a saturated NaHCO$_3$ solution (20 mL) was added and the resulting suspension was extracted with EtOAc (3×20 mL). The combined organic extracts were washed with a brine solution (30 mL) and dried over solid anhydrous Na$_2$SO$_4$. After filtration, the solvent was removed; the residue was purified by flash column chromatography using gradient elution from PE/EtOAc (9/1) to PE/EtOAc (1/4) to give (R)-1-((6-chloro-4,8-bis(ethylamino)pyrimido[5,4-d]pyrimidin-2-yl)amino)propan-2-ol (167) (222 mg, 66% yield). 300 MHz $^1$H NMR (CDCl$_3$, ppm): 6.59 (1H, t, J=5.8 Hz) 6.54 (1H, t, J=5.8 Hz) 5.32 (1H, t, J=6.0 Hz) 4.05 (1H, dqd, J=7.2, 6.4, 2.8 Hz) 3.76 (1H, br s) 3.60 (2H, qd, J=7.3, 5.8 Hz) 3.59-3.53 (1H, m) 3.51 (2H, qd, J=7.3, 5.8 Hz) 3.36 (1H, ddd, J=14.2, 7.2, 6.0 Hz) 1.30 (3H, t, J=7.3 Hz) 1.28 (3H, J=7.3 Hz) 1.24 (3H, d, J=6.4 Hz). ESI-MS (m/z): 326, 328 [M+H]$^+$.

(b) (R)-1-(4,6,8-Tris-ethylamino-pyrimido[5,4-d]pyrimidin-2-ylamino)-propan-2-ol (168)

(R)-1-((6-Chloro-4,8-bis(ethylamino)pyrimido[5,4-d]pyrimidin-2-yl)amino)propan-2-ol (167) (222 mg, 0.68 mmol) and ethylamine (70% water solution) were reacted in n-butanol. The crude product was purified by flash column chromatography using gradient elution from PE/EtOAc (9/1) to PE/EtOAc (1/4) to obtain (R)-1-(4,6,8-tris-ethylamino-pyrimido[5,4-d]pyrimidin-2-ylamino)-propan-2-ol (168) (128 mg, 56% yield). 300 MHz $^1$H NMR (CDCl$_3$, ppm) 6.57-6.49 (1H, m) 6.23-6.14 (1H, m) 5.01 (1H, t, J=6.0 Hz) 4.90 (1H, br s) 4.60 (1H, t, J=5.0 Hz) 4.10-3.96 (1H, m) 3.58-3.27 (8H, m) 1.33-1.19 (12H, m). ESI-MS (m/z): 335 [M+H]$^+$.

(c) (R)-1-(4,6,8-Tris-ethylamino-pyrimido[5,4-d]pyrimidin-2-ylamino)-propan-2-ol Hydrochloride (168a)

(R)-1-(4,6,8-Tris-ethylamino-pyrimido[5,4-d]pyrimidin-2-ylamino)-propan-2-ol (168) (110 mg, 0.33 mmol) was treated with 2M HCl/diethyl ether in CH$_2$Cl$_2$ to produce (R)-1-(4,6,8-tris-ethylamino-pyrimido[5,4-d]pyrimidin-2-ylamino)-propan-2-ol hydrochloride (168a) (122 mg, 100% yield). 400 MHz $^1$H NMR (CD$_3$OD, ppm): 4.02-3.94 (1H, m) 3.65 (2H, q, J=7.3 Hz) 3.62 (2H, q, J=7.3 Hz) 3.55-3.48 (3H, m) 3.40 (1H, dd, J=13.7, 7.0 Hz) 1.32 (6H, t, J=7.3 Hz) 1.26 (3H, t, J=7.2 Hz) 1.22 (3H, d, J=6.3 Hz). ESI-MS (m/z): 335 [M+H]$^+$; MP: 194-196° C.

Example 103: (R)-1-(4,8-Bis-ethylamino-6-propylamino-pyrimido[5,4-d]-pyrimidin-2-ylamino)-propan-2-ol (169) and Corresponding Hydrochloride Salt (169a)

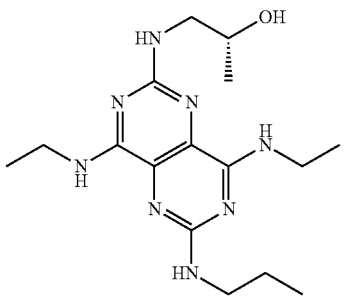

169

(a) (R)-1-(4,8-Bis-ethylamino-6-propylamino-pyrimido[5,4-d]-pyrimidin-2-ylamino)-propan-2-ol (169)

(R)-1-((6-Chloro-4,8-bis(ethylamino)pyrimido[5,4-d]pyrimidin-2-yl)amino)propan-2-ol (167) (160 mg, 0.49 mmol)

and propylamine were reacted in n-butanol using procedures described elsewhere herein. The crude product was purified by flash column chromatography using gradient elution from PE/EtOAc (9/1) to PE/EtOAc (1/4) to obtain (R)-1-(4,8-bis-ethylamino-6-propylamino-pyrimido[5,4-d]-pyrimidin-2-ylamino)-propan-2-ol (169) (123 mg, 72% yield). 400 MHz $^1$H NMR (CDCl$_3$, ppm): 6.53 (1H, br s) 6.18 (1H, br s) 5.04-4.97 (1H, m) 4.91 (1H, br s) 4.69-4.60 (1H, br s) 4.07-3.99 (1H, m) 3.56-3.47 (5H, m) 3.39-3.29 (3H, m) 1.63 (2H, sextet, J=7.4 Hz) 1.30 (3H, t, J=7.3 Hz) 1.28 (3H, t, J=7.3 Hz) 1.22 (3H, d, J=6.3 Hz) 0.99 (3H, t, J=7.4 Hz). ESI-MS (m/z): 349 [M+H]$^+$.

(b) (R)-1-(4,8-Bis-ethylamino-6-propylamino-pyrimido[5,4-d]-pyrimidin-2-ylamino)-propan-2-ol hydrochloride (169a)

(R)-1-(4,8-Bis-ethylamino-6-propylamino-pyrimido[5,4-d]-pyrimidin-2-ylamino)-propan-2-ol (169) (100 mg, 0.29 mmol) was treated with 2M HCl/diethyl ether in CH$_2$Cl$_2$ to produce (R)-1-(4,8-bis-ethylamino-6-propylamino-pyrimido[5,4-d]-pyrimidin-2-ylamino)-propan-2-ol hydrochloride (169a) (105 mg, 95% yield). 400 MHz $^1$H NMR (CD$_3$OD, ppm): 4.02-3.93 (1H, m) 3.67-3.57 (4H, m) 3.50 (1H, dd, J=13.7, 4.6 Hz) 3.46-3.39 (2H, m) 3.40 (1H, dd, J=13.7, 6.9) 1.68 (2H, sextet, J=7.4) 1.31 (6H, t, J=7.3 Hz) 1.22 (3H, d, J=6.3 Hz) 1.0 (3H, t, J=7.4 Hz). ESI-MS (m/z): 349 [M+H]$^+$.

Comparative Example 104: (R)-1-(6-Amino-4,8-bis-ethylamino-pyrimido[5,4-d]-pyrimidin-2-ylamino)-propan-2-ol (171) and Corresponding Hydrochloride Salt (171a)

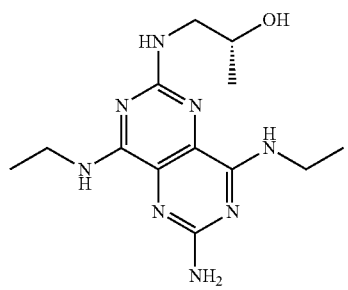

171

(a) 6-Chloro-N$^4$,N$^8$-diethyl-pyrimido[5,4-d]pyrimidine-2,4,8-triamine (170)

A mixture of 2,6-dichloro-N$^4$,N$^8$-diethyl-pyrimido[5,4-d]pyrimidine-4,8-diamine (160) (800 mg, 2.79 mmol) and ammonium hydroxide (NH$_3$, 25% water solution, 1.00 mL) in n-butanol (5 mL) was heated at 95° C. for 72 h. An additional portion of ammonium hydroxide (NH$_3$, 25% water solution, 1.00 mL) was added and heating was continued for 96 h. After cooling, a saturated NaHCO$_3$ solution (20 mL) was added and the resulting suspension was extracted with CHCl$_3$ (3×20 mL). The combined organic extracts were washed with water (30 mL) and dried over solid anhydrous MgSO$_4$. After filtration, the solvent was removed; the residue was purified by flash column chromatography using gradient elution from CHCl$_3$/MeOH (99/1) to CHCl$_3$/MeOH (95/5) to give 6-chloro-N$^4$,N$^8$-diethyl-pyrimido[5,4-d]pyrimidine-2,4,8-triamine (170) (380 mg, 51% yield). 300 MHz $^1$H NMR (CDCl$_3$, ppm): 6.70-6.60 (1H, m) 6.60-6.50 (1H, m) 4.80 (2H, s) 3.59 (2H, qd, J=7.2, 5.8 Hz) 3.53 (2H, qd, J=7.2, 5.8 Hz) 1.31 (3H, t, J=7.2 Hz) 1.28 (3H, t, J=7.2 Hz). ESI-MS (m/z): 268, 270 [M+1-1]$^+$.

(b) (R)-1-(6-Amino-4,8-bis-ethylamino-pyrimido[5,4-d]-pyrimidin-2-ylamino)-propan-2-ol (171)

A mixture of 6-chloro-N$^4$,N$^8$-diethyl-pyrimido[5,4-d]pyrimidine-2,4,8-triamine (170) (150 mg, 0.56 mmol) and (R)-1-amino-propan-2-ol (170 mg, 2.24 mmol) in n-butanol (3 mL) was heated at 110° C. for 120 h. After cooling, a saturated NaHCO$_3$ solution (20 mL) was added and the resulting suspension was extracted with EtOAc (3×20 mL). The combined organic extracts were washed with brine (30 mL) and dried over solid anhydrous MgSO$_4$. After filtration, the solvent was removed; the residue was purified by flash column chromatography using gradient elution from CH$_2$Cl$_2$/EtOH (99/1) to CH$_2$Cl$_2$/EtOH (9/1) to obtain (R)-1-(6-amino-4,8-bis-ethylamino-pyrimido[5,4-d]-pyrimidin-2-ylamino)-propan-2-ol (171) (115 mg, 67% yield). 300 MHz $^1$H NMR (CDCl$_3$, ppm): 6.55-6.41 (1H, m) 6.32-6.19 (1H, m) 5.05 (1H, t, J=5.8 Hz) 4.70 (1H, br s) 4.54 (2H, s) 4.09-3.98 (1H, m) 3.59-3.45 (5H, m) 3.34 (1H, ddd, J=14.2, 6.7, 6.2 Hz) 1.29 (3H, t, J=7.3 Hz) 1.28 (3H, t, J=7.3 Hz) 1.23 (3H, d, J=6.3 Hz). ESI-MS (m/z): 307 [M+1-1]$^+$.

(c) (R)-1-(6-Amino-4,8-bis-ethylamino-pyrimido[5,4-d]-pyrimidin-2-ylamino)-propan-2-ol Hydrochloride (171a)

(R)-1-(6-Amino-4,8-bis-ethylamino-pyrimido[5,4-d]-pyrimidin-2-ylamino)-propan-2-ol (171) (105 mg, 0.34 mmol) was treated with 2M HCl/diethyl ether in diethyl ether to produce (R)-1-(6-amino-4,8-bis-ethylamino-pyrimido[5,4-d]-pyrimidin-2-ylamino)-propan-2-ol hydrochloride (171a) (105 mg, 90% yield). 300 MHz $^1$H NMR (CD$_3$OD, ppm) 4.02-3.89 (1H, m) 3.64 (2H, q, J=7.2 Hz) 3.58 (2H, q, J=7.2 Hz) 3.52-3.34 (2H, m) 1.31 (3H, t, J=7.2 Hz) 1.30 (3H, t, J=7.2 Hz) 1.21 (3H, d, J=6.3 Hz). ESI-MS (m/z): 307 [M+H]$^+$; MP: 178-180° C.

Comparative Example 105: (S)-1-(6-Amino-4,8-bis-ethylamino-pyrimido[5,4-d]-pyrimidin-2-ylamino)-propan-2-ol (172) and Corresponding Hydrochloride Salt (172a)

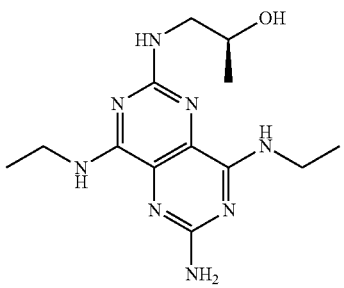

172

(a) (S)-1-(6-Amino-4,8-bis-ethylamino-pyrimido[5,4-d]-pyrimidin-2-ylamino)-propan-2-ol (193)

6-Chloro-N$^4$,N$^8$-diethyl-pyrimido[5,4-d]pyrimidine-2,4,8-triamine (170) (150 mg, 0.56 mmol) and (S)-1-aminopropan-2-ol were reacted in n-butanol to obtain (S)-1-(6-amino-4,8-bis-ethylamino-pyrimido[5,4-d]-pyrimidin-2-ylamino)-propan-2-ol (172) (115 mg, 67% yield). 300 MHz $^1$H NMR (CDCl$_3$, ppm): 6.48 (1H, s) 6.27 (1H, s) 5.05 (1H, t, J=5.8 Hz) 4.9-4.3 (1H, br s) 4.54 (2H, s) 4.09-3.98 (1H, m) 3.59-3.45 (5H, m) 3.41-3.25 (1H, m) 1.29 (3H, t, J=7.3 Hz) 1.28 (3H, t, J=7.3 Hz) 1.23 (3H, d, J=6.3 Hz). ESI-MS (m/z): 307 [M+H]$^+$.

(b) (S)-1-(6-Amino-4,8-bis-ethylamino-pyrimido[5,4-d]-pyrimidin-2-ylamino)-propan-2-ol Hydrochloride (172a)

(S)-1-(6-Amino-4,8-bis-ethylamino-pyrimido[5,4-d]-pyrimidin-2-ylamino)-propan-2-ol (172) (105 mg, 0.34 mmol) was treated with 2M HCl/diethyl ether in diethyl ether to produce (S)-1-(6-amino-4,8-bis-ethylamino-pyrimido[5,4-d]-pyrimidin-2-ylamino)-propan-2-ol hydrochloride (172a) (100 mg, 86% yield). 300 MHz $^1$H NMR (CD$_3$OD, ppm): 4.02-3.89 (1H, m) 3.64 (2H, q, J=7.2 Hz) 3.58 (2H, q, J=7.2 Hz) 3.48 (1H, dd, J=13.6, 4.6 Hz) 3.38 (1H, dd, J=13.6, 6.7 Hz) 1.31 (3H, t, J=7.2 Hz) 1.30 (3H, t, J=7.2 Hz) 1.21 (3H, d, J=6.3 Hz). ESI-MS (m/z): 307 [M+H]$^+$; MP: 180-182° C.

Example 106: (R)-1-[4,8-Bis-ethylamino-6-(2-methyl-allylamino)-pyrimido[5,4-d]-pyrimidin-2-ylamino]-propan-2-ol (174) and Corresponding Hydrochloride Salt (174a)

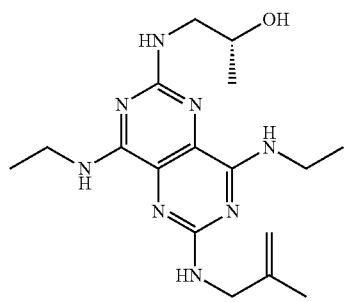

174

(a) 6-Chloro-N$^4$,N$^8$-diethyl-N$^2$-(2-methyl-allyl)-pyrimido[5,4-d]pyrimidine-2,4,8-triamine (173)

A mixture of 2,6-dichloro-N$^4$,N$^8$-diethyl-pyrimido[5,4-d]pyrimidine-4,8-diamine (160) (700 mg, 2.44 mmol), 2-methyl-allylamine (270 µL, 2.93 mmol) and N,N-diisopropyl ethylamine (334 µL, 2.93 mmol) in n-butanol (8 mL) was heated at 80° C. for 24 h. An additional portion of 2-methyl-allylamine (130 µL, 1.43 mmol) was added and the mixture was heated at 90° C. for 24 h. After cooling, water (30 mL) was added and the resulting suspension was extracted with CHCl$_3$ (3×30 mL). The combined organic extracts were washed with water (30 mL) and dried over solid anhydrous MgSO$_4$. After filtration, the solvent was removed; the residue was purified by flash column chromatography using gradient elution from PE/EtOAc (9/1) to PE/EtOAc (5/1) to give 6-chloro-N$^4$,N$^8$-diethyl-N$^2$-(2-methyl-allyl)-pyrimido[5,4-d]pyrimidine-2,4,8-triamine (173) (570 mg, 73% yield). 300 MHz $^1$H NMR (CDCl$_3$, ppm): 6.64 (1H, t, J=5.9 Hz) 6.49 (1H, t, J=5.9 Hz) 5.03 (1H, t, J=6.1 Hz) 4.96-4.91 (1H, m) 4.88-4.83 (1H, m) 4.01 (2H, d, J=6.1 Hz) 3.60 (2H, qd, J=7.2, 5.9 Hz) 3.53 (2H, qd, J=7.2, 5.9 Hz) 1.80 (3H, s) 1.31 (3H, t, J=7.2 Hz) 1.28 (3H, t, J=7.2 Hz). ESI-MS (m/z): 322, 324 [M+1-1]$^+$.

(b) (R)-1-[4,8-Bis-ethylamino-6-(2-methyl-allylamino)-pyrimido[5,4-d]-pyrimidin-2-ylamino]-propan-2-ol (174)

6-Chloro-N$^4$,N$^8$-diethyl-N$^2$-(2-methyl-allyl)-pyrimido[5,4-d]pyrimidine-2,4,8-triamine (173) (285 mg, 0.89 mmol) and (R)-1-amino-propan-2-ol were reacted in n-butanol and the crude product was purified by flash column chromatography using gradient elution from PE/EtOAc (5/1) to PE/EtOAc (1/1) to obtain (R)-1-[4,8-bis-ethylamino-6-(2-methyl-allylamino)-pyrimido[5,4-d]-pyrimidin-2-ylamino]-propan-2-ol (174) (150 mg, 47% yield). 300 MHz $^1$H NMR (CDCl$_3$, ppm): 6.50 (1H, t, J=5.6 Hz) 6.20 (1H, t, J=5.6 Hz) 5.01 (1H, t, J=6.0 Hz) 4.95-4.92 (1H, m) 4.90 (1H, br s) 4.85-4.81 (1H, m) 4.75 (1H, t, J=6.1 Hz) 4.07-3.94 (3H, m) 3.57-3.45 (5H, m) 3.33 (1H, ddd, J=14.4, 6.9, 6.1) 1.80 (3H, s) 1.29 (3H, t, J=7.2 Hz) 1.27 (3H, t, J=7.2 Hz) 1.22 (3H, d, J=6.3 Hz). ESI-MS (m/z): 361 [M+1-1]$^+$.

(c) (R)-1-[4,8-Bis-ethylamino-6-(2-methyl-allylamino)-pyrimido[5,4-d]-pyrimidin-2-ylamino]-propan-2-ol Hydrochloride (174a)

(R)-1-[4,8-Bis-ethylamino-6-(2-methyl-allylamino)-pyrimido[5,4-d]-pyrimidin-2-ylamino]-propan-2-ol (174) (150 mg, 0.42 mmol) was treated with 2M HCl/diethyl ether in diethyl ether to produce (R)-1-[4,8-bis-ethylamino-6-(2-methyl-allylamino)-pyrimido[5,4-d]-pyrimidin-2-ylamino]-propan-2-ol hydrochloride (174a) (145 mg, 88% yield). 300 MHz $^1$H NMR (CD$_3$OD, ppm): 4.92 (1H, s) 4.85 (1H, s, overlapped with water) 4.04 (2H, s) 4.02-3.92 (1H, m) 3.62 (2H, q, J=7.2 Hz) 3.61 (2H, q, J=7.2 Hz) 3.52 (1H, dd, J=13.7, 4.5 Hz) 3.39 (1H, dd, J=13.7, 6.9 Hz) 1.79 (3H, s) 1.31 (3H, t, J=7.2 Hz) 1.30 (3H, t, J=7.2 Hz) 1.22 (3H, d, J=6.3 Hz). ESI-MS (m/z): 361 [M+H]$^+$; MP: 148-150° C.

Example 107: (S)-1-[4,8-Bis-ethylamino-6-(2-methyl-allylamino)-pyrimido[5,4-d]-pyrimidin-2-ylamino]-propan-2-ol (175) and Corresponding Hydrochloride Salt (175a)

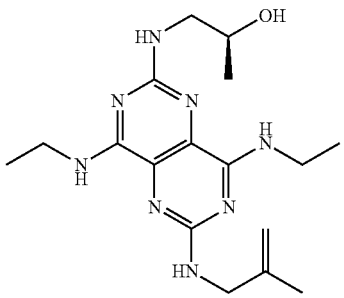

175

(a) (S)-1-[4,8-Bis-ethylamino-6-(2-methyl-allylamino)-pyrimido[5,4-d]-pyrimidin-2-ylamino]-propan-2-ol (175)

6-Chloro-N$^4$,N$^8$-diethyl-N$^2$-(2-methyl-allyl)-pyrimido[5,4-d]pyrimidine-2,4,8-triamine (173) (285 mg, 0.89 mmol) and (S)-1-amino-propan-2-ol were reacted in n-butanol. The crude product was purified by flash column chromatography using gradient elution from PE/EtOAc (5/1) to PE/EtOAc (1/1) to obtain (S)-1-[4,8-bis-ethylamino-6-(2-methyl-allylamino)-pyrimido[5,4-d]-pyrimidin-2-ylamino]-propan-2-ol (175) (160 mg, 50% yield). 300 MHz $^1$H NMR (CDCl$_3$, ppm): 6.50 (1H, t, J=5.6 Hz) 6.20 (1H, t, J=5.6 Hz) 5.01 (1H, t, J=6.0 Hz) 4.95-4.92 (1H, m) 4.90 (1H, br s) 4.85-4.81 (1H, m) 4.75 (1H, t, J=6.1 Hz) 4.07-3.94 (3H, m) 3.57-3.45 (5H, m) 3.33 (1H, ddd, J=14.4, 6.9, 6.1) 1.80 (3H, s) 1.29 (3H, t, J=7.2 Hz) 1.27 (3H, t, J=7.2 Hz) 1.22 (3H, d, J=6.3 Hz). ESI-MS (m/z): 361 [M+1-1]$^+$.

(b) (S)-1-[4,8-Bis-ethylamino-6-(2-methyl-allylamino)-pyrimido[5,4-d]-pyrimidin-2-ylamino]-propan-2-ol hydrochloride (175a)

(S)-1-[4,8-Bis-ethylamino-6-(2-methyl-allylamino)-pyrimido[5,4-d]-pyrimidin-2-ylamino]-propan-2-ol (175) (160 mg, 0.44 mmol) was treated with 2M HCl/diethyl ether in diethyl ether to produce (S)-1-[4,8-bis-ethylamino-6-(2-methyl-allylamino)-pyrimido[5,4-d]-pyrimidin-2-ylamino]-propan-2-ol hydrochloride (175a) (150 mg, 85% yield). 300 MHz $^1$H NMR (CD$_3$OD, ppm): 4.92 (1H, s) 4.85 (1H, s, overlapped with water) 4.04 (2H, s) 4.02-3.92 (1H, m) 3.62 (2H, q, J=7.2 Hz) 3.61 (2H, q, J=7.2 Hz) 3.52 (1H, dd, J=13.7, 4.5 Hz) 3.39 (1H, dd, J=13.7, 6.9 Hz) 1.79 (3H, s) 1.31 (3H, t, J=7.2 Hz) 1.30 (3H, t, J=7.2 Hz) 1.22 (3H, d, J=6.3 Hz). ESI-MS (m/z): 361 [M+H]$^+$; MP: 151-153° C.

Example 108: Salt Screen

The salt formers (i.e., acids) and solvents evaluated in a salt screen for 1-(2,6-bis-methylamino-8-propylamino-pyrimido[5,4-d]pyrimidin-4-ylamino)-2-methyl-propan-2-ol (31) are illustrated in FIG. 1. 1-(2,6-Bis-methylamino-8-propylamino-pyrimido[5,4-d]pyrimidin-4-ylamino)-2-methyl-propan-2-ol free base (31) was combined with 1 or 2 molar equivalents of salt former in a variety of solvents at room temperature and heated as necessary for form a clear solution. The solution was concentrated to dryness and the resulting solid was evaluated for solubility at room temperature and under reflux at 50 mg/mL in the solvents listed in FIG. 1. Any solutions which formed were allowed to cool to as low as 0° C. to induce crystallization. Mixtures from which solids were formed were noted. Only select salts were prepared in larger quantities (i.e., those in which solids were formed); however the lack of solid formation from any given experiment do not imply that a salt was not formed.

Example 109: General Procedure to Prepare Gram Quantities of Selected Salts of 31 (FIG. 2)

The indicated quantity 1-(2,6-bis-methylamino-8-propylamino-pyrimido[5,4-d]pyrimidin-4-ylamino)-2-methyl-propan-2-ol (31) free base was mixed with the indicated solvent and appropriate molar equivalents of salt former was added; the mixture was heated as needed to form a solution, cooled to room temperature in cases where heated to form a solution, then stirred overnight at room temperature. Crystallized product was collected by filtration, rinsed with diethyl ether (for salts formed from EtOH/Et$_2$O) or otherwise with the same solvent or solvent mixture as used to form the salt. The rinsed product was briefly dried on the filter, then in air at 65° C. Salts were characterized by melting point (SRS OptiMelt) or DSC endothermic behavior, LC/MS, $^1$H NMR, elemental analysis and XRPD. Elemental analysis and $^1$H NMR confirmed the stoichiometry for all initially obtained salts as prepared by combining free base and salt former in the column C solvent or solvent mixture.

For the XRPD spectrum, XRPD peaks listing and DSC spectrum for: Hydrochloride salts of 31a, see FIGS. 3A-3C; Bis-Hydrochloride salts of 31a, see FIGS. 4A-4C; Hydrogen Malonate salts of 31a, see FIGS. 5A-5C; Hydrogen Malonate Male-A salts of 31a, see FIGS. 6A-6C; Hydrogen Maleinate Male-B salts of 31a, see FIGS. 7A-7C; Hydrogen Fumarate salts of 31a, see FIGS. 8A-8C; Hydrogen-L(+) Tartrate salts of 31a, see FIGS. 9A-9C; D,L-Mandelate salts of 31a, see FIGS. 10A-10C; Tosylate salts of 31a, see FIGS. 11A-11C and 12A-12C; Mesylate salts of 31a, see FIGS. 13A-13C; Saccharinate salts of 31a, see FIGS. 14A-14C.

Example 110: Polymorphic Transformation by Exposure to Humidity

Approximately 10 mg of the solid as its initially obtained polymorphic form were placed in a 4 mL open vial. In a 20 mL vial, about 5 mL of distilled water were added and heated to about 50° C., then the vial was capped, and the contents were cooled for about 30 minutes at ambient temperature. Then the 20 mL vial was uncapped, the smaller vial was placed inside the bigger vial, the bigger vial was recapped, and the sample in the smaller vial was exposed and aged in an environment of approximately 80-95% relative humidity at ambient temperature for 3 days. Polymorphic transformation was confirmed by XRPD and DSC vs. that for the initially obtained polymorphic form.

The maleinate salt 31d was initially obtained as form Mal-A (31d-1) and was converted to form Mal-B (31d-2) after exposure to >80% humidity for three days at ambient temperature as described above.

The tosylate salt 31h was initially obtained as form Tos-A (31h-1) and was converted to form Tos-B (31h-2) after exposure to >80% humidity for three days at ambient temperature.

See FIG. 2 for a summary of the gram scale preparation of selected salts of 1-(2,6-bis-methylamino-8-propylamino-pyrimido[5,4-d]pyrimidin-4-ylamino)-2-methyl-propan-2-ol (31).

See FIGS. 3A-14C for XRPD spectra, XRPD peak listings and DSC spectra of the salts of 1-(2,6-bis-methylamino-8-propylamino-pyrimido[5,4-d]pyrimidin-4-ylamino)-2-methyl-propan-2-ol (31).

Analytical Characterization

X-ray powder diffraction patterns were obtained using a Bruker D8 Advance X-Ray Diffractometer equipped with a Cu Kα radiation source (λ=1.54060° Å) in locked/coupled mode. A 9-position sample changer and LYNXEYE high speed detector were used. Samples were placed on zero-background, silicon plate holders. The step was 0.05°. Count times were 1.3 second per step.

DSC data were collected using a TA Instruments Q1000 DSC equipped with auto-sampler. Typically, samples (~2-5 mg) were placed in hermetic alodined aluminum sample pans and scanned from 30 to 300° C. at a rate of 10° C./min under a nitrogen purge of 50 mL/min. Then the pan was cooled to 25° C. at a rate of 20° C./min.

Example 111: Effect on Respiratory Rate (RR), Tidal Volume (V$_T$), and Product Minute Volume (MV) Using an Anesthetized Rat Spirometry Screening Assay Anesthetized rats provide a quick method of screening compounds for respiratory and cardiovascular activity.

Method Outline:

Rats were initially anesthetized with 3% isoflurane (inhaled) and femoral artery and vein cannulas were surgically inserted. Once cannulated, the rats were transitioned to urethane anesthesia (1.5 g/kg; i.v.) and a tracheal cut-down was performed. After placing the tracheal cannula, it was connected to a pneumotachometer to record respiratory airflow from which respiratory rate (RR), tidal volume ($V_T$), and their product minute volume (MV, also termed $\dot{V}_E$) were derived. After the surgical preparation was complete, animals were allowed to stabilize for 30 minutes while respiratory rate, tidal volume, minute volume, blood pressure and heart rate were recorded continuously. Arterial blood gases (ABG) were obtained from arterial blood collected from the femoral artery. ABG measurements were taken before and 6 minutes after vehicle and each dose of compound administered. Compounds being screened were administered via bolus injections through the venous cannula followed by a saline flush (total time of administration is approximately 30 seconds), and the animal was monitored for at least 6 minutes for changes in cardiovascular efforts. Compounds were prepared in formulations identified to ensure optimal solubility. As such, vehicle controls were matched for the formulation of each compound tested. Dosing of the compounds being screened was conducted at 0.1 and/or 0.3 mg/kg and/or 3 mg/kg The next dose was not administered until all cardiovascular and respiratory measures had returned to baseline levels. The positive control compounds used were N-[4,6-di-(n-propylamino)-[1,3,5]triazin-2-yl]-N,O-dimethyl-hydroxylamine or N-[2,6-di-(n-propylamino)-[1,3]pyrimidin-4-yl]-N,O-dimethyl-hydroxylamine (both administered at the end of each screening experiment (0.3 mg/kg dose) to validate the experiment and also to serve as a measure with which the compound being screened could be compared.

Data Analysis:

Data were analyzed by collecting cardiovascular and respiratory data in 30 second averages (BINs). Data were plotted 2 minutes before challenge and then 6 minutes after challenge.

TABLE 1

Ventilatory activity.

| Compound No. | $V_E$ % Inc @ 0.3 mg/kg IV | Peak ratio @ 0.3 dose* | $V_E$ % Inc @ 3.0 mg/kg IV | Peak ratio @ 3.0 dose * |
|---|---|---|---|---|
| 4a | 90 | 0.55 | | |
| 6a | 37 | 0.29 | | |
| 8a | 31 | 0.22 | | |
| 10a | 93 | 0.47 | | |
| 12a | 114 | 0.70 | | |
| 14a | 88 | 0.46 | | |
| 16a | 80 | 0.53 | | |
| 18a | 50 | 0.38 | | |
| 20a | 107 | 0.68 | | |
| 22a | 102 | 0.85 | | |
| 24a | 100 | 0.87 | 121 | 1.05 |
| 26a | 39 | 0.26 | 143 | 0.95 |
| 27a | 110 | 0.87 | | |
| 28a | 16 | 0.12 | | |
| 31a | 69 | 0.58 | | |
| 32a | 201 | 0.69 | | |
| 33a | 23 | 0.14 | 115 | 0.71 |
| 34a | 2 | 0.01 | | |
| 36a | 34 | 0.20 | | |
| 38a | 18 | 0.14 | 27 | 0.22 |
| 40a | 79 | 0.64 | 158 | 1.28 |
| 42a | 76 | 0.60 | 149 | 1.17 |
| 44a | 122 | 0.95 | 132 | 1.02 |
| 46a | 79 | 0.34 | 203 | 0.88 |
| 47a | 31 | 0.25 | | |
| 48a | 20 | 0.12 | 78 | 0.45 |
| 49a | 127 | 0.73 | 183 | 1.05 |
| 52a | 26 | 0.16 | | |
| 54a | 165 | 0.96 | | |
| 56a | 2 | 0.02 | | |
| 58a | 10 | 0.08 | | |
| 60a | 15 | 0.10 | 119 | 0.79 |
| 62a | 40 | 0.25 | | |
| 64a | 32 | 0.17 | 157 | 0.83 |
| 67a | 7 | 0.04 | 136 | 0.74 |
| 71a | 17 | 0.16 | 84 | 0.78 |
| 72a | 132 | 0.94 | 150 | 1.07 |
| 73a | 16 | 0.11 | 79 | 0.53 |
| 74a | 153 | 0.77 | 208 | 1.05 |
| 75a | 158 | 0.79 | 180 | 0.90 |
| 76 | 37 | 0.22 | 71 | 0.42 |
| 77 | 135 | 0.55 | 170 | 0.77 |
| 78 | 173 | 0.79 | 180 | 0.82 |
| 79 | 56 | 0.30 | 162 | 0.89 |
| 80 | 71 | 0.36 | 95 | 0.48 |
| 81 | 50 | 0.41 | 72 | 0.60 |
| 82 | 102 | 0.70 | 132 | 0.90 |
| 83 | 176 | 0.86 | 153 | 0.75 |
| 84 | 169 | 1.04 | 184 | 1.13 |
| 85 | 69 | 0.62 | 83 | 0.74 |
| 86 | 26 | 0.20 | 92 | 0.78 |
| 87 | 39 | 0.17 | 129 | 0.57 |
| 90 | 26 | 0.16 | | |
| 91 | 16 | 0.12 | | |
| 92 | 49 | 0.36 | 148 | 1.10 |
| 94 | 18 | 0.13 | 130 | 0.91 |
| 95 | 138 | 0.90 | | |
| 96 | 70 | 0.43 | 96 | 0.58 |
| 97 | 49 | 0.26 | 140 | 0.75 |
| 99 | 25 | 0.13 | 61 | 0.32 |
| 100 | 33 | 0.20 | 139 | 0.86 |
| 101 | 20 | 0.08 | 129 | 0.52 |
| 103 | 5 | 0.03 | 99 | 0.52 |
| 104 | 33 | 0.17 | 98 | 0.50 |
| 105 | 14 | 0.07 | 120 | 0.63 |
| 107 | 14 | 0.11 | 95 | 0.74 |
| 109 | 21 | 0.10 | 10 | 0.05 |
| 111 | 18 | 0.15 | 105 | 0.90 |
| 113 | 111 | 0.49 | 190 | 0.84 |
| 115 | 60 | 0.33 | 151 | 0.83 |
| 117 | 150 | 0.82 | 162 | 0.88 |
| 119 | 10 | 0.05 | 151 | 0.82 |
| 121 | 0 | 0.00 | 38 | 0.20 |
| 123 | 11 | 0.07 | 129 | 0.87 |
| 125 | 38 | 0.26 | 84 | 0.57 |
| 127 | 81 | 0.48 | 108 | 0.64 |
| 129 | 2 | 0.01 | 68 | 0.48 |
| 131 | 18 | 0.08 | 142 | 0.62 |
| 133 | 35 | 0.18 | 111 | 0.58 |
| 135 | 22 | 0.11 | 142 | 0.68 |
| 137 | 22 | 0.10 | 103 | 0.48 |
| 139 | 90 | 0.41 | 114 | 0.51 |
| 141 | 71 | 0.32 | 146 | 0.67 |
| 142 | 2 | 0.01 | 62 | 0.45 |
| 143 | 81 | 0.51 | 150 | 0.94 |
| 144 | 14 | 0.08 | 98 | 0.50 |
| 145 | 47 | 0.22 | 156 | 0.75 |
| 146 | 9 | 0.06 | 121 | 0.76 |
| 147 | 31 | 0.20 | 147 | 0.93 |
| 149 | 16 | 0.10 | 49 | 0.30 |
| 151 | 0.00 | 0.00 | 95 | 0.44 |
| 152 | 7 | 0.04 | 89 | 0.52 |
| 154 | 40 | 0.35 | 103 | 0.90 |
| 155 | 14 | 0.05 | 79 | 0.30 |
| 156 | 16 | 0.11 | 97 | 0.68 |
| 158 | 68 | 0.44 | 120 | 0.78 |
| 159 | 61 | 0.36 | 160 | 0.95 |

TABLE 1-continued

Ventilatory activity.

| Compound No. | $V_E$ % Inc @ 0.3 mg/kg IV | Peak ratio @ 0.3 dose* | $V_E$ % Inc @ 3.0 mg/kg IV | Peak ratio @ 3.0 dose * |
|---|---|---|---|---|
| 162 | 187 | 0.88 | 216 | 1.01 |
| 163 | 88 | 0.49 | 144 | 0.80 |
| 165 | 66 | 0.61 | 101 | 0.93 |
| 166 | 88 | 0.84 | 91 | 0.87 |
| 186 | 37 | 0.26 | 90 | 0.62 |
| 169 | 113 | 0.88 | 142 | 1.10 |
| 171 | 17 | 0.08 | 175 | 0.84 |
| 172 | 5 | 0.03 | 155 | 0.90 |
| 174 | 72 | 0.47 | 114 | 0.75 |
| 175 | 75 | 0.40 | 134 | 0.71 |

*Ratio compared to N-(2,6-Bis-propylamino-pyrimidin-4-yl)-O,N-dimethyl-hydroxylamine hydrogen sulfate

Example 112: Effects on the Apnea Hypopnea Index and Ventilation During Sleep in Rats Receiving Chronic Morphine Central sleep apnea (CSA) and hypopnea are especially prevalent in people on chronic opioid therapy. Accordingly, a novel rodent model of chronic opioid-induced sleep disordered breathing that mimics many features of the condition in people was developed.

Morphine was administered chronically to rats in their drinking water at a dose and duration that elicited morphine tolerance. Morphine sulfate was added to the drinking water of individually housed rats beginning at 0.1 mg/ml morphine and increasing the concentration in increments so that a final concentration of 0.6 mg/ml was achieved within 2 weeks of beginning morphine exposure. During the first three weeks after starting morphine administration, rats were acclimated to whole body plethysmography chambers.

Respiratory rate (fR), tidal volume (VT), minute volume (VE), and CSA and hypopnea frequency and length (i.e., duration of each apnea) were measured continuously while animals were unrestrained in whole-body plethysmography chambers. Animals breathed room air for the duration of the study, except where indicated for the hyperoxia validation study. A bias chamber air flow of at least 2 L/min was generated by connecting the chambers to a constant flow vacuum source. A period of at least 1 hour was permitted for animals to acclimate to the chamber before data collection began. In general, most rats would enter into a normal sleep-wake cycle within that time frame. On occasion, more time was needed until the rat was restful.

A respiratory waveform was generated from the expansion and contraction of the air that was exchanged between the animal and the chamber. The cyclic change in air volume during the respiratory cycle elicited oscillating airflow across a calibrated pneumotachometer in the wall of the plethysmograph chamber. Each pneumotachometer was calibrated (5.0 mL volume delivered in triplicate) on each study day prior to placing the animals in the chambers. The airflow signal was amplified and continuously recorded using PowerLab and LabChart 7.0.

Respiratory pattern (tidal volume, respiratory rate) and minute volume (the product of tidal volume and respiratory rate), and the number and length of central sleep apneas and number of hypopneas were measured using whole-body plethysmography before and after administration of either vehicle or test compound (10 mg/kg PO) in a cross over design. The coefficient of variation for respiratory period, an index of ventilatory instability, was also calculated. Epochs of time were classified as either "sleep" or "awake" based on the presence or absence of movement artifact in the air flow waveform recorded from a pneumotachometer attached to the wall of the plethysmograph chamber. The total number of CSA and hypopneas were summed per hour to provide an apnea hypopnea index (AHI).

Methods:

All surgical and plethysmographic studies were approved by the IACUC committee of Galleon Pharmaceuticals. The study used rats implanted with dual biopotential electrodes that permitted continuous and simultaneous telemetric recordings of electroencephalogram (EEG) and electromyogram (EMG) waveforms. Three treatment conditions were assessed for their effects on sleep quantity, architecture, and quality: baseline (drug-naïve), (31a) (10 mg/kg PO) and vehicle (equal volume PO). Baseline and (31a) treatment study days were randomized. However, vehicle alone was assessed after each rat had completed drug nave and compound (31a) evaluations.

EEG, EMG and Temperature Implantation Surgeries:

Standard aseptic technique was used for all surgical procedures. Adult male Sprague Dawley rats were premedicated with dexmedetomidine (0.1 mg/kg subcutaneously) for sedation and analgesia, carprofen (5 mg/kg subcutaneously) for analgesia, and ceftriaxone (33 mg/kg subcutaneously or intravenously) as a prophylactic antibiotic. Anesthesia was induced and maintained with isoflurane in oxygen. The body of the telemetry implant was sutured to the parietal peritoneum via a midline laparotomy. The 4 electrode leads (each pair used as one biopotential) exited the abdomen via the midline incision and were tunneled subcutaneously to the dorsum of the neck. For EEG lead placement, the electrodes were attached to two screws that penetrated the thickness of the cranium (coordinates first electrode: at ~5 mm caudal to the bregma and ~5 mm to the left of the midline; second electrode: ~5 mm caudal to the bregma and ~2 mm to the right of the midline) and anchored with dental cement. For EMG lead placement, the electrodes were secured to neck muscles with nylon suture. Surgical wounds were closed using standard techniques. Buprenorphine (0.05 mg/kg subcutaneously or intravenously) was administered at the end of surgery and before recovery from anesthesia. Atipamezole (0.4 mg/kg subcutaneously or intravenously) was administered at the end of surgery to reverse the effects of dexmedetomidine. Antibiotics and analgesics were continued for 3 days post-surgery, as necessary. At least 1 week (7-10 days) was permitted post-surgery before animals were used in further studies.

EEG, EMG and Temperature Telemetry Data Collection:

Rats with implanted telemeters were allowed to remain in their home cages during data collection. Signals from the telemeters were wirelessly transmitted to receivers that were placed directly under the home cages. EEG and EMG waveforms were recorded between 8 am and 3 pm each study day. Only data collected between the hours of 10:00 am to 3:00 pm was used in the final analysis. For each rat, the three telemetry signals (EEG, EMG, and temperature) were routed from the receiver to the PowerLab and recorded using LabChart. EEG/EMG signal conditioning is described in the Data Analysis section.

Data Analysis and Statistical Methods:

Sleep Scoring:

EEG, EMG, and temperature signals were calibrated within LabChart software according to the telemeter manufacturer's recommendations. The sampling frequency for each signal was 1 K/s. The EEG signal was digitally band-pass filtered between 0.3 to 30 Hz. The EMG signal was filtered using a high pass filter of 25 Hz, rectified, and moving averaged (100 ms). All sleep scoring analysis was performed using Sleep Sign (Kissei Comtec). This software was developed and validated, and its ability to identify sleep states in rats is based on previous studies (www dot sleepsign dot com/bibliography dot html).

The principal aspects of these analyses were to quantify the magnitude of the EMG signal (i.e., the animals activity level) and the relative densities of EEG delta waves (0.5 to 4 Hz; predominant in NREM sleep) and EEG theta waves (6 to 10 Hz; predominant in REM sleep) during each 4-second epoch. The relative wave densities allowed one to template each sleep/awake state (NREM, REM & AWAKE) in the Sleep Sign analysis software as AWAKE (relatively high frequency and low amplitude EEG, with high EMG activity), NREM (low frequency and high amplitude EEG, with low EMG activity), and REM (high frequency and low amplitude EEG, with generally lower EMG activity than NREM sleep). Once templated the software automatically assigned a sleep/awake state to each 4 second epoch based on a minimum percentage of time the epoch spent in each state. After completing the automated analysis, each 4 second epoch for each file used in the final data analysis was visually assessed by the investigator to ensure accuracy of epoch scoring. Any epochs that were scored incorrectly by Sleep Sign were manually corrected by the same investigator. Hypnograms were then exported to Excel to permit analysis of relative time in NREM/REM/AWAKE per hour, awakening index, number of awake bouts/hour sleep, arousals/hour sleep, number of NREM/REM bouts/hr, number of NREM/REM epochs/hr, NREM/REM bout length, and NREM/REM epoch length.

Statistical Analysis

A sleep bout was defined as 3 or more continuous epochs (4-s periods) of NREM or REM sleep. Wake bouts were defined as 4 or more epochs of wakefulness preceded by one or more bouts of sleep. An arousal was defined as 3 or less epochs of wakefulness preceded by at least 3 epochs of sleep. For each animal, the sleep quantity, architecture and quality parameters were averaged between the periods of 10:00 am and 3:00 pm and compared between vehicle control and test compound treatment groups using two way ANOVA and Dunnett's post hoc tests (comparison to the drug naïve state).

Sleep architecture was assessed by quantifying: the percent time spent in awake, NREM sleep, and REM sleep, the number of awake bouts per hr sleep, the number of arousal per hr sleep, awakening index (sum of awake bouts and arousals per hour), number of NREM bouts per hr, number of NREM epochs per hr, NREM bout length, NREM epoch length, number of REM bouts per hr, number of REM epochs per hr, REM bout length, and REM epoch length.

Sleep quality was evaluated by measuring the EEG spectral power density ($\mu V^2/0.25$ Hz) and relative power density (across the 0.5-30 Hz spectrum) during NREM and REM sleep. See FIG. 24.

Figures 23, 24:
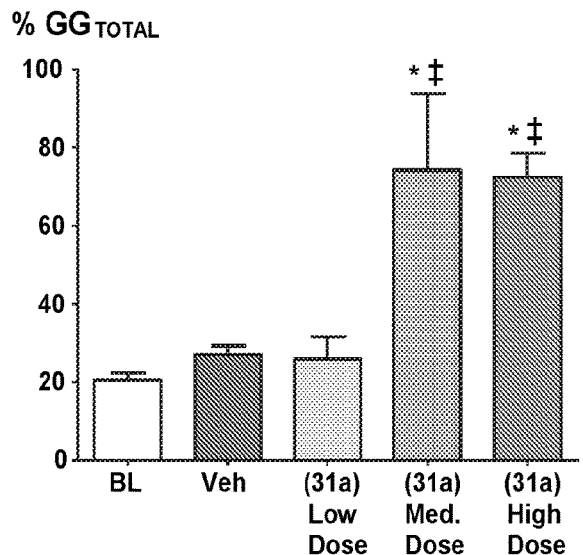
FIG. 23 depicts a graph illustrating that 1-(2,6-bis-methylamino-8-propylamino-pyrimido[5,4-d]pyrimidin-4-yl amino)-2-methyl-propan-2-ol hydrochloride salt (31a) administered by IV infusion dose-dependently increases the upper airway response (genioglossus activity) to spontaneous obstructive apneas in rats.
FIG. 24 is a table illustrating that 1-(2,6-bis-methylamino-8-propylamino-pyrimido[5,4-d]pyrimidin-4-yl amino)-2-methyl-propan-2-ol hydrochloride salt (31a) (10 mg/kg PO) does not produce effects on sleep architecture in rats.

Results:

The effects of vehicle and (31a) (10 mg/kg PO) on indices of sleep architecture. For each animal, these parameters were averaged between the periods of 10:00 am 3:00 pm and compared between vehicle and (31a) treatment groups using Student-Neuman-Keuls post hoc tests. No significant differences in sleep architecture were detected comparing baseline to the (31a) groups (FIG. 24).

Oral administration of 1-(2,6-Bis-methylamino-8-propylamino-pyrimido[5,4-d]pyrimidin-4-yl amino)-2-methyl-propan-2-ol hydrochloride salt (31a) at 10 mg/kg PO was not associated with any statistically significant effects on sleep quantity, architecture, or quality. A vehicle effect on REM sleep architecture was likely related to non-randomization of treatment study days and subsequent anticipation of oral gavage as an adverse stimulus.

Example 113: Effects on Obstructive Sleep Apnea

Two rodent models of obstructive apnea were used: one that modeled spontaneous obstructions (spontaneous obstructive apnea model) which become progressively worse over time, and another (evoked obstructive apnea model) where the investigator retained control over the variables that define OSA severity, such as apnea frequency (f OA) and apnea duration (OA t).

The majority of studies were conducted using the spontaneous obstructive apnea model, where rats were positioned in dorsal recumbency (supine), and permitted to breathe spontaneously on room air. Air flow was measured continuously by whole-body plethysmography. Most anesthetized and supine rats exhibit a eupneic breathing pattern, and to elicit spontaneous recurring obstructions, the neck of each rat was ventroflexed and maintained at 25° to 30° above the horizontal plane. OA were defined as periods of no air flow for more than 2 respiratory cycles accompanied by efforts to breathe (e.g., increased transthoracic esophageal inspiratory pressure). After neck flexion, eupnea became increasingly interrupted by clusters of upper airway obstructions (f OA $30\pm3$ $hr^{-1}$ (mean$\pm$SEM), range: 13 to 94 $hr^{-1}$; OA t $11\pm3$ s, range: 6 to 15 s). OA severity was further quantified by the peak change in hemoglobin oxygen saturation during an obstruction ($\Delta SpO_2$: $-20\pm1\%$, range: $-11$ to $-31\%$). Clustered OAs were often separated by long periods of eupneic breathing, which presumably returned when activation of a relevant afferent/effector reflex (e.g., chemoreceptor driven increased motor drive to the genioglossus muscle) reached a threshold necessary to reestablish a patent upper airway.

Methods:

All animal experiments were performed according to protocols approved by the Institutional Animal Care and Use Committee (IACUC) at Galleon Pharmaceuticals, Inc. All experimental procedures were performed under general anesthesia. All experiments were non-survival procedures and animals were euthanized at the conclusion of the experiment prior to the animal recovering from anesthesia. Two rodent models of obstructive apnea were used, one that modeled spontaneous obstructions that become progressively worse over time (Spontaneous Obstructive Apnea Model), and another where the investigator retained control over the parameters that defined OSA severity, such as f OA, and OA t, and by controlling these directly also controlling of the magnitude of oxy-hemoglobin desaturation (Evoked Obstructive Apnea Model).

Anesthesia Common to all Spontaneous Obstructive Apnea Models:

Rats were initially anesthetized in a rodent anesthesia induction chamber using 3% (dial setting) isoflurane in 97% oxygen ($O_2$) for surgical instrumentation. When rats had become recumbent they were removed from the chamber and placed in dorsal recumbency (supine) on a heating pad. Anesthesia was maintained with 2% isoflurane in 98% oxygen and rats were permitted to breathe spontaneously on room air. After instrumentation, isoflurane was slowly discontinued and urethane (1.5 to 1.8 g/kg, IV) administered to maintain anesthesia without interruption. Supplemental oxygen was discontinued at this time.

Instrumentation Common to all Models:

The femoral artery was cannulated to permit continuous recording of arterial blood pressure and intermittent sampling of blood for pH and blood gas analyses, and single time point quantification of test article plasma concentrations. The femoral vein was cannulated to permit test compound administration and fluid support. The arterial cannula was connected to a heparinized saline filled pressure transducer. The arterial pressure waveforms were sampled at 2K/second and band-pass filtered between 0-1000 Hz. The cyclic measurement function in LabChart was used to calculate heart rate and the average of the weighted ratio ⅓ max+⅔ min was used to calculate mean arterial blood pressure (MAP).

Spontaneous Obstructive Apnea Model:

After femoral vessel cannulation, rats were positioned in dorsal recumbency within a head-out plethysmography chamber to permit continuous recording of respiratory air flow waveforms. The arterial and venous lines were exteriorized by threading each line through a port in the chamber. The cervical segment of the esophagus was exposed by surgical cut down and gently dissociated away the surrounding tissue. A small incision was made into the esophagus to allow the insertion of saline filled PE-205 tubing and attached to a saline-filled pressure transducer. The tubing was advanced into the thoracic segment of the esophagus to a level that detected maximal inspiratory pressure fluctuations without affecting the respiratory pattern. Bipolar EMG electrodes were inserted into the genioglossus muscle immediately cranial to the hyoid bone and a ground lead was attached to nearby skin. $EMG_{GG}$ activity was digitized and sampled at 4 K/s, amplified, filtered (Band-pass: high cut-off frequency: 2500 Hz Low cut-off frequency 120 Hz), and rectified and moving time averaged (60 ms). An intravenous infusion of 50% Hetastarch/50% saline was administered at a rate of 5 mL/kg/min as fluid support.

One hour elapsed to allow physiological stabilization before starting the period of baseline data recording. Most anesthetized and supine rats exhibit a eupneic breathing pattern, so to elicit spontaneous recurring OA, the neck of each rat was slightly ventroflexed and maintained between 25° to 30° above the horizontal plane at the start of the stabilization period. OA were defined as periods of no air flow for more than 2 respiratory cycles accompanied by evidence that inspiratory efforts were occurring during the apnea (e.g. increased trans-esophageal inspiratory pressure (PTP) and EMGGG inspiratory burst amplitude).

Study Parameters to Quantify OA Severity:

OA severity was quantified by the number of OA per hour (f OA $hr^{-1}$), mean duration of each apnea (OA t, seconds), and mean decrease in hemoglobin oxygen saturation ($\Delta SpO_2$, %) associated with an apnea. The response to an obstruction was quantified by measuring the peak change in the moving time averaged (100 ms) EMGGG burst amplitude during an apnea ($\mu V \cdot s$).

Study Parameters to Assess Physiological State:

Study parameters that were measured to evaluate physiological state during and between apneic periods, but not quantitate OA severity, were arterial blood pressure (mmHg), respiratory air flow (L/s), PTP (mmHg), percutaneous hemoglobin oxygen saturation (Pulse oximetry, $SpO_2$, %). These parameters were recorded continuously as waveforms throughout each experiment. The study variables that were derived from these waveforms and also considered "continuously measured", were MAP, fH, f1R, VT, $\dot{V}_E$, and $\Delta$PTP during each inspiration. Intermittently measured study parameters were rectal temperature (° C.), and arterial pH, $PaCO_2$ (mmHg), $PaO_2$ (mmHg), $SpO_2$ (%) derived from arterial blood gas analyses.

Model Validation with Continuous Positive Airway Pressure (CPAP):

Continuous positive airway pressure (CPAP) is a first line treatment for patients with OSA and was administered to a subset of rats as a positive control. Rats were fitted with a custom made mask positioned to cover the nose without covering the mouth. Thus, a circuit for positive pressure flow was created with forced air entering the upper airway via the nares and exiting through the mouth. Constant positive pressure was applied throughout the respiratory cycle producing a steady state bias flow from which each rat ventilated using normal inspiratory pressures. The objectives for the first experiment were to validate the model as a tool with sufficient sensitivity to detect an incremental decrease in f OA while incrementally increasing the level of CPAP support. The level of CPAP was controlled using a custom made valve with a resolution of $\pm 0.1$ $cmH_2O$. CPAP pressure was slowly increased (0, 0.5, 1.0, 1.5, 2.0, and 4.0 $cmH_2O$). Rats was allowed to remain at each pressure for 30 minutes while the study parameters were recorded. In a second study, the objective was to determine if the positive effects of CPAP on OA severity were indeed temporary, as described for humans. The study parameters were recorded during baseline conditions, 30 minutes of CPAP support at 4 cm $H_2O$, then a final 30 minutes off CPAP support (FIGS. 18-25).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A compound that is 1-(2,6-Bis-methylamino-8-propylamino-pyrimido[5,4-d]pyrimidin-4-yl amino)-2-methyl-propan-2-ol (31) or at least one crystalline salt selected from the group consisting of:

(xiii) Crystalline hydrochloride salt (31a), with a XRPD spectrum as per FIG. 3A; XRPD peaks as per FIG. 3B; and/or DSC spectrum as per FIG. 3C;

(xiv) Crystalline bis-hydrochloride salt (31b), with a XRPD spectrum as per FIG. 4A; XRPD peaks as per FIG. 4B; and/or DSC spectrum as per FIG. 4C;

(xv) Crystalline hydrogen malonate salt (31c), with a XRPD spectrum as per FIG. 5A; XRPD peaks as per FIG. 5B; and/or DSC spectrum as per FIG. 5C;

(xvi) Crystalline hydrogen maleinate salt Form Male-A (31d-1), with a XRPD spectrum as per FIG. 6A; XRPD peaks as per FIG. 6B; and/or DSC spectrum as per FIG. 6C;

(xvii) Crystalline hydrogen maleinate salt Form Male-B (31d-2), with a XRPD spectrum as per FIG. 7A; XRPD peaks as per FIG. 7B; and/or DSC spectrum as per FIG. 7C;

(xviii) Crystalline hydrogen fumarate salt (31e), with a XRPD spectrum as per FIG. 8A; XRPD peaks as per FIG. 8B; and/or DSC spectrum as per FIG. 8C;

(xix) Crystalline hydrogen L(+)tartrate salt (31f), with a XRPD spectrum as per FIG. 9A; XRPD peaks as per FIG. 9B; DSC spectrum as per FIG. 9C;

(xx) Crystalline D,L-mandelate salt (31g), with a XRPD spectrum as per FIG. 10A; XRPD peaks as per FIG. 10B; and/or DSC spectrum as per FIG. 10C;
(xxi) Crystalline tosylate salt form Tos-A (31h-1), with a XRPD spectrum as per FIG. 11A; XRPD peaks as per FIG. 11B; and/or DSC spectrum as per FIG. 11C;
(xxii) Crystalline tosylate salt form Tos-B (31h-2), with a XRPD spectrum as per FIG. 12A; XRPD peaks as per FIG. 12B; and/or DSC spectrum as per FIG. 12C;
(xxiii) Crystalline mesylate salt (31i), with a XRPD spectrum as per FIG. 13A; XRPD peaks as per FIG. 13B; and/or DSC spectrum as per FIG. 13C;
(xxiv) Crystalline saccharinate salt (31j), with a XRPD spectrum as per FIG. 14A; XRPD peaks as per FIG. 14B; and/or DSC spectrum as per FIG. 14C; and any mixtures thereof.

2. A pharmaceutical composition comprising at least one compound of claim 1 and at least one pharmaceutically acceptable carrier or excipient.

3. The composition of claim 2, further comprising at least one additional agent selected from the group consisting of doxapram, enantiomers of doxapram, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, and armodafinil.

4. The composition of claim 3, wherein the compound and the additional agent are physically mixed or physically separated in the composition.

5. The composition of claim 2, further comprising at least one additional agent that causes changes in breathing control.

6. The composition in claim 5, wherein the additional agent is at least one selected from the group consisting of opioid narcotics, benzodiazepines, sedatives, sleeping aids, hypnotics, propofol, and any combinations thereof.

7. The composition of claim 3, wherein the compound and the additional agent are physically mixed or physically separated in the composition.

8. The composition of claim 2, wherein the composition allows for modified delivery of the compound following oral administration to a subject.

9. The composition of claim 8, wherein the composition minimizes delivery of the compound to the stomach of the subject and maximizes delivery of the compound to the intestine of the subject.

10. The composition of claim 2, wherein the composition includes an enteric coating.

11. The composition of claim 2, wherein the compound is contained in a pharmaceutically suitable capsule.

12. The composition of claim 11, wherein the capsule contains granules or powder of the compound, or an admixture of the compound with the carrier or excipient.

13. The composition of claim 12, wherein the excipient comprises a binder, disintegrant, diluent, buffer, lubricant, glidant, antioxidant, antimicrobial preservative, colorant, or flavorant.

14. The composition of claim 12, wherein the capsule is enterically coated but the granules or powders of the compound are not enterically coated.

15. The composition of claim 12, wherein the granules or powders of the compound are coated with an enteric coating before being placed into the capsule.

16. The composition of claim 15, wherein the granules or powders of the compound are coated with a plurality of enteric coatings, as to provide delivery of drug to different regions of the intestine of the subject.

17. The composition of claim 12, wherein at least a portion of the granules or powders of the compound are enterically coated.

18. The composition of claim 12, wherein the capsule is coated with an enteric coating that is different from the enteric coating that coats the granules or powders of the compound.

19. The composition of claim 2, wherein the compound is coated onto a base particle so as to form a core.

20. The composition of claim 19, wherein the base particle is not enterically coated and the composition is contained in a pharmaceutically acceptable capsule that is enterically coated.

21. The composition of claim 19, wherein the core is coated with an enteric coating, thereby forming an enterically coated bead.

22. The composition of claim 21, wherein the enterically coated bead is contained in a pharmaceutically acceptable capsule.

23. The composition of claim 22, wherein the capsule contains beads coated with a plurality of enteric coatings, so that the capsule provides delivery of the compound to different regions of the intestine of the subject.

24. The composition of claim 22, wherein the contents of the capsule are dissolved or suspended in a pharmaceutically acceptable liquid as to provide a liquid-filled capsule.

25. The composition of claim 24, wherein the capsule is enterically coated but the liquid formulation contained within does not comprise an enteric coating.

26. A method of inhibiting or treating a breathing control disorder or disease in a subject in need thereof, the method comprising administering to the subject an effective amount of at least one compound of claim 1 or a salt, solvate, enantiomer, diastereoisomer or tautomer thereof.

27. The method of claim 26, wherein the breathing control disorder or disease is at least one selected from the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), congenital central hypoventilation syndrome, Alzheimer's disease, Parkinson's disease, stroke, Duchenne muscular dystrophy, and brain and spinal cord traumatic injury.

28. The method of claim 27, wherein the respiratory depression is caused by an anesthetic, a sedative, a sleeping aid, an anxiolytic agent, a hypnotic agent, alcohol or a narcotic.

29. The method of claim 26, wherein the subject is further administered at least one agent useful for treating the breathing disorder or disease.

30. The method of claim 29, wherein the agent is at least one selected from the group consisting of doxapram, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, and armodafinil.

31. The method of claim 29, wherein the compound and the agent are separately administered to the subject.

32. The method of claim 29, wherein the compound and the agent are co-administered to the subject, further wherein the compound and the agent are physically mixed or physically separated when administered to the subject.

33. The method of claim 26, wherein the subject is further administered at least one additional therapeutic agent that changes normal breathing control in the subject.

34. The method of claim 33, wherein that at least one additional agent is selected from the group consisting of opioid narcotics, benzodiazepines, sedatives, sleeping aids, hypnotics, propofol, and any combinations thereof.

35. The method of claim 26, wherein the compound is administered in conjunction with the use of a mechanical ventilation device or positive airway pressure device on the subject.

36. The method of claim 26, wherein the subject is a mammal or bird.

37. The method of claim 36, wherein the mammal is a human.

38. The method of claim 26, wherein the compound is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes.

39. The method of claim 26, wherein the salt comprises an acid addition salt, and the acid is at least one selected from the group consisting of sulfuric, hydrochloric, hydrobromic, hydroiodic, nitric, carbonic, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, pamoic, methanesulfonic, ethanesulfonic, benzenesulfonic, pantothenic, sulfanilic, stearic, alginic, trifluoromethanesulfonic, 2-hydroxyethanesulfonic, p-toluenesulfonic, cyclohexylaminosulfonic, β-hydroxybutyric, salicylic, galactaric and galacturonic, and any combinations thereof.

40. A method of inhibiting destabilization or stabilizing breathing rhythm in a subject in need thereof, the method comprising administering to the subject an effective amount of at least one pharmaceutically acceptable carrier and at least one compound of any of claim 1, or a salt, solvate, enantiomer, diastereoisomer or tautomer thereof.

41. The method of claim 40, wherein the destabilization is associated with a breathing control disorder or disease selected from the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), congenital central hypoventilation syndrome, Alzheimer's disease, Parkinson's disease, stroke, Duchenne muscular dystrophy, and brain and spinal cord traumatic injury.

42. The method of claim 41, wherein the respiratory depression is caused by an anesthetic, a sedative, a sleeping aid, an anxiolytic agent, a hypnotic agent, alcohol or a narcotic.

43. The method of claim 40, wherein the subject is further administered at least one agent useful for treating the breathing disorder or disease.

44. The method of claim 43, wherein the agent is selected from the group consisting of doxapram, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, and armodafinil.

45. The method of claim 43, wherein the compound and the agent are separately administered to the subject.

46. The method of claim 43, wherein the compound and the agent are co-administered to the subject, further wherein the compound and the agent are physically mixed or physically separated when administered to the subject.

47. The method of claim 40, wherein the subject is further administered at least one additional therapeutic agent that changes normal breathing control in the subject.

48. The method of claim 47, wherein the additional agent is at least one selected from the group consisting of opioid narcotics, benzodiazepines, sedatives, sleeping aids, hypnotics, propofol, and any combinations thereof.

49. The method of claim 40, wherein the compound is administered in conjunction with the use of a mechanical ventilation device or positive airway pressure device on the subject.

50. The method of claim 40, wherein the subject is a mammal or bird.

51. The method of claim 40, wherein the compound is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes.

52. The method of claim 40, wherein the salt comprises an acid addition salt, and the acid is at least one selected from the group consisting of sulfuric, hydrochloric, hydrobromic, hydroiodic, nitric, carbonic, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, pamoic, methanesulfonic, ethanesulfonic, benzenesulfonic, pantothenic, sulfanilic, stearic, alginic, trifluoromethanesulfonic, 2-hydroxyethanesulfonic, p-toluenesulfonic, cyclohexylaminosulfonic, β-hydroxybutyric, salicylic, galactaric and galacturonic, and any combinations thereof.

\* \* \* \* \*